(12) United States Patent
Celanire et al.

(10) Patent No.: US 7,943,605 B2
(45) Date of Patent: May 17, 2011

(54) COMPOUNDS COMPRISING A LACTAM OR A LACTAM DERIVATIVE MOIETY, PROCESSES FOR MAKING THEM, AND THEIR USES

(75) Inventors: Sylvain Celanire, Feigeres (FR); Luc Quere, Sombreffe (BE); Frédéric Denonne, Brussels (BE); Laurent Provins, Soignies (BE)

(73) Assignee: UCB Pharma S.A., Brussels (BE)

( * ) Notice: Subject to any disclaimer, the term of this patent is extended or adjusted under 35 U.S.C. 154(b) by 344 days.

(21) Appl. No.: 12/091,380

(22) PCT Filed: Oct. 25, 2006

(86) PCT No.: PCT/EP2006/010294
§ 371 (c)(1),
(2), (4) Date: Sep. 2, 2008

(87) PCT Pub. No.: WO2007/048595
PCT Pub. Date: May 3, 2007

(65) Prior Publication Data
US 2009/0023708 A1    Jan. 22, 2009

(30) Foreign Application Priority Data

Oct. 27, 2005   (EP) .................................... 05023486

(51) Int. Cl.
| | |
|---|---|
| *A61K 31/395* | (2006.01) |
| *A61K 31/55* | (2006.01) |
| *A61K 31/541* | (2006.01) |
| *A61K 31/5355* | (2006.01) |
| *A61K 31/496* | (2006.01) |
| *A61K 31/438* | (2006.01) |
| *A61K 31/4439* | (2006.01) |
| *A61K 31/4025* | (2006.01) |
| *C07D 401/14* | (2006.01) |
| *C07D 403/14* | (2006.01) |
| *C07D 417/14* | (2006.01) |
| *C07D 413/14* | (2006.01) |
| *C07D 221/20* | (2006.01) |
| *C07D 215/06* | (2006.01) |
| *C07D 209/54* | (2006.01) |
| *C07D 207/12* | (2006.01) |

(52) U.S. Cl. ................ 514/183; 514/217.08; 514/227.8; 514/235.5; 514/253.09; 514/254.01; 514/278; 514/307; 514/314; 514/326; 514/409; 514/422; 540/481; 540/602; 544/60; 544/141; 544/364; 544/372; 546/16; 546/148; 546/164; 546/208; 548/408; 548/523

(58) Field of Classification Search ........................ None
See application file for complete search history.

(56) References Cited

U.S. PATENT DOCUMENTS
4,642,307 A * 2/1987 Aoyagi et al. ........... 514/253.12

FOREIGN PATENT DOCUMENTS
| | | | |
|---|---|---|---|
| GB | 1 456 253 | A | 11/1976 |
| GB | 1456253 | * | 11/1976 |
| WO | 02/12214 | A | 2/2002 |
| WO | 2004/035556 | A | 4/2004 |
| WO | 2004/056369 | A | 7/2004 |
| WO | 2004/089373 | A | 10/2004 |

OTHER PUBLICATIONS

Santa, Z. et al., "Synthesis of Enantiomerically Pure 2-Isoxycephems", Monatshefte Fur Chemie, 135(6), 2004, 671-684.

* cited by examiner

*Primary Examiner* — Rebecca L Anderson
*Assistant Examiner* — Alicia L Otton
(74) *Attorney, Agent, or Firm* — McDonnell Boehnen Hulbert & Berghoff LLP

(57) ABSTRACT

The present invention relates to compounds of formula (I) comprising a lactam or a lactam derivative moiety, processes for preparing them, pharmaceutical compositions comprising said compounds and their uses as pharmaceuticals.

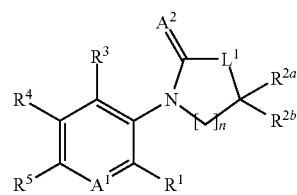

(I)

17 Claims, No Drawings

COMPOUNDS COMPRISING A LACTAM OR A LACTAM DERIVATIVE MOIETY, PROCESSES FOR MAKING THEM, AND THEIR USES

This application is a U.S. national phase of International Application No. PCT/EP2006/010294 filed on Oct. 25, 2006, the disclosure of which is incorporated herein by reference.

The present invention relates to compounds comprising a lactam or a lactam derivative moiety, processes for preparing them, pharmaceutical compositions comprising said compounds and their uses as pharmaceuticals.

The histamine $H_3$ receptor has been known for several years and identified pharmacologically in 1983 by Arrang, J. M. et al. (Nature 1983, 302, 832). Since the cloning of the human histamine $H_3$ receptor in 1999, histamine $H_3$ receptors have been successively cloned by sequence homology from a variety of species, including rat, guinea pig, mouse and monkey.

Histamine $H_3$-receptor agonists, antagonists and inverse agonists have shown potential therapeutic applications as described in the literature, for example by Stark, H. in Exp. Opin. Ther. Patents 2003, 13, 851.

The histamine $H_3$ receptor is predominantly expressed in the mammalian central nervous system but can also be found in the autonomic nervous system. Evidence has been shown that the histamine $H_3$ receptor displays high constitutive activity, which activity occurs in the absence of endogenous histamine or of a $H_3$-receptor agonist. Thus, a histamine $H_3$-receptor antagonist and/or inverse agonist could inhibit this activity.

The general pharmacology of histamine $H_3$ receptor, including $H_3$-receptor subtypes, has been reviewed by Hancock, A. A in Life Sci. 2003, 73, 3043. The histamine $H_3$ receptor is not only considered as a presynaptic autoreceptor on histaminergic neurons, but also as a heteroreceptor on non-histaminergic neurons (Barnes, W. et al., Eur. J. Pharmacol. 2001, 431, 215). Indeed, the histamine $H_3$ receptor has been shown to regulate the release of histamine but also of other important neurotransmitters, including acetylcholine, dopamine, serotonin, norepinephrin and γ-aminobutyric acid (GABA).

Thus, the histamine $H_3$ receptor is of current interest for the development of new therapeutics and the literature suggests that novel histamine $H_3$-receptor antagonists or inverse agonists may be useful for the treatment and prevention of diseases or pathological conditions of the central nervous system including Mild Cognitive Impairment (MCI), Alzheimer's disease, learning and memory disorders, cognitive disorders, attention deficit disorder (ADD), attention-deficit hyperactivity disorder (ADHD), Parkinson's disease, schizophrenia, dementia, depression, epilepsy, seizures or convulsions, sleep/wake disorders, narcolepsy, and/or obesity.

$H_3$-receptor ligands alone or in combination with an acetylcholinesterase inhibitor may also be useful in the treatment of cholinergic-deficit disorders, Mild Cognitive Impairment and Alzheimer's disease as reported by Morisset, S. et al. in Eur. J. Pharmacol. 1996, 315, R1-R2.

$H_3$-receptor ligands, alone or in combination with a histamine $H_1$-receptor antagonist may be useful for the treatment of upper airway allergic disorders, as reported by McLeod, R. et al. in J. Pharmacol. Exp. Ther. 2003, 305, 1037.

As described in international patent application WO 02/072093, $H_3$-receptor ligands alone or in combination with a muscarinic receptor ligand and particularly with a muscarinic $M_2$-receptor antagonist, may be useful for the treatment of cognitive disorders, Alzheimer's disease, attention-deficit hyperactivity disorder.

$H_3$-receptor ligands may also be useful in the treatment of sleep/wake and arousal/vigilance disorders such as hypersomnia, and narcolepsy according to Passani, M. B. et al. in Trends Pharmacol. Sci. 2004, 25(12), 618-25.

In general, $H_3$-receptor ligands, and particularly $H_3$-receptor antagonists or inverse agonists may be useful in the treatment of all types of cognitive-related disorders as reviewed by Hancock, A. A and Fox, G. B. in Expert Opin. Invest. Drugs 2004, 13, 1237.

In particular, histamine $H_3$-receptor antagonists or inverse agonists may be useful in the treatment of cognitive dysfunctions in diseases such as mild cognitive impairment, dementia, Alzheimer's disease, Parkinson's disease, Down's syndrome as well as in the treatment of attention-deficit hyperactivity disorder (ADHD) as non-psychostimulant agents (see for example Witkin, J. M. et al., Pharmacol. Ther. 2004, 103(1), 1-20).

$H_3$-receptor antagonists or inverse agonists may also be useful in the treatment of psychotic disorders such as schizophrenia, migraine, eating disorders such as obesity, inflammation, pain disorders, anxiety, stress, depression and cardiovascular disorders, in particular acute myocardial infarction.

There is therefore a need to manufacture new compounds which can potentially act as $H_3$-receptor ligands.

Early literature reports (e.g. Ali, S. M. et al., J. Med. Chem. 1999, 42, 903 and Drugs Fut. 1996, 21, 507) describe that an imidazole function is essential for high affinity histamine $H_3$-receptor ligands; this is confirmed, for example, by U.S. Pat. Nos. 6,506,756B2, 6,518,287B2, 6,528,522B2 and 6,762,186B2 which relate to substituted imidazole compounds that have $H_3$ receptor antagonist or dual histamine $H_1$-receptor and $H_3$-receptor antagonist activity.

International patent application WO 02/12214 relates to non-imidazole aryloxyalkylamines for the treatment of disorders and conditions mediated by the histamine receptor.

International patent application WO 02/074758 relates to bicyclic heterocyclic derivatives comprising an amine moiety and reported as $H_3$-receptor ligands.

International patent application WO 2004/056369 relates to benzodiazepine derivatives for the treatment of neurological disorders.

International patent application WO 2005/007644 relates to heteroaryloxy nitrogenous saturated heterocyclic derivatives which exhibit histamine receptor $H_3$ antagonist or inverse agonist activity.

International patent application WO 03/089409 describes compounds comprising a lactam moiety and having affinity at $5HT_{2C}$ receptor.

Compounds comprising a lactam moiety, particularly 1-[4-[2-(pyrrolidin-1-yl)ethoxy]phenyl]pyrrolidin-2-one, are described as synthesis intermediates by J. L. Neumeyer et al. in J. Med. Chem. 1967, 10, 615-620.

Selvakumar N. et al. in Bioorg. Med. Chem. Lett. 2003, 13, 4169-4172 describe oxazolidinone derivatives as antibacterial agents.

1-[4-[2-[4-(2-methylphenyl)-1-piperazinyl]ethoxy]phenyl]-pyrrolidin-2-one is disclosed in British patent application GB 1456253.

3-(p-2-morpholinoethoxyphenyl)-oxazolidin-2-one is disclosed by H. Nayer et al. in Bull. Soc. Chim. Fr. 1957, 471-479.

It has now surprisingly been found that certain compounds comprising a lactam or a lactam derivative moiety may act as $H_3$-receptor ligands and therefore may demonstrate therapeutic properties for one or more pathologies that we have described above.

The present invention relates to compounds of formula (I), geometrical isomers, enantiomers, diastereoisomers, pharmaceutically acceptable salts and all possible mixtures thereof,

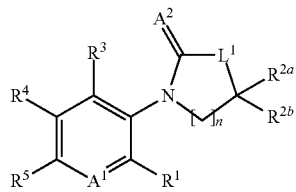

wherein
$A^1$ is CH, C-halogen or N;
$A^2$ is oxygen or sulfur;
$R^1$ is hydrogen;
$R^{2a}$ is hydrogen, aryl, $C_{1-6}$ alkoxy, amino, $C_{1-6}$ alkyl, $C_{2-6}$ alkenyl, heteroaryl, $C_{3-8}$ cycloalkyl, 3-8-membered heterocycloalkyl, acyl, $C_{1-6}$-alkyl aryl, $C_{1-6}$-alkyl heteroaryl, $C_{1-6}$-alkyl cycloalkyl, $C_{1-6}$-alkyl heterocycloalkyl, carboxy, alkoxycarbonyl, aminocarbonyl, $C_{1-6}$-alkyl carboxy, $C_{1-6}$-alkyl acyl, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{1-6}$-alkyl ureido, $C_{1-6}$-alkyl carbamate, $C_{1-6}$-alkyl amino, $C_{3-8}$-cycloalkyl amino, hydroxy, $C_{1-6}$ alkyl hydroxy, halogen or cyano;
$R^{2b}$ is hydrogen, halogen, $C_{1-8}$-alkyl or $C_{3-8}$ cycloalkyl;
or $R^{2a}$ and $R^{2b}$ are linked together to form a $C_{3-8}$ cycloalkyl, a 3-8-membered heterocycloalkyl or an oxo group;
$R^3$ is hydrogen, halogen, $C_{1-4}$ alkyl or $C_{1-4}$ alkoxy;
$R^4$ is hydrogen, halogen, $C_{1-4}$ alkyl, $C_{1-4}$ alkoxy or —O—$(CH_2)_t$—$NR^{7a}R^{7b}$;
$R^5$ is hydrogen or —O—$(CH_2)_w$—$NR^{8a}R^{8b}$;
$L^1$ is —$(O)_v$—$(CR^{9a}R^{9b})_m$—$(CH_2)_z$;
$R^{7a}$ and $R^{7b}$ are linked together to form with N a 3 to 8 membered heterocycloalkyl;
$R^{8a}$ and $R^{8b}$ are linked together to form with N a 3 to 8 membered heterocycloalkyl;
$R^{9a}$ is hydrogen or unsubstituted $C_{1-8}$ alkyl;
$R^{9b}$ is a $C_{1-6}$-alkyl aryl or unsubstituted $C_{1-8}$ alkyl;
n is an integer equal to 0, 1 or 2;
t is an integer equal to 2, 3 or 4;
w is an integer equal to 2, 3 or 4;
v is an integer equal to 0 or 1;
m is an integer equal to 0 or 1;
z is an integer equal to 0, 1, 2 or 3;
provided that
at least one of m and z is different from 0; and that
$R^4$ is —O—$(CH_2)_t$—$NR^{7a}R^{7b}$, when $R^5$ is hydrogen; and $R^5$ is —O—$(CH_2)_w$—$NR^{8a}R^{8b}$, when $R^4$ is hydrogen, halogen, $C_{1-4}$ alkyl or $C_{1-4}$ alkoxy; and
that compound of formula (I) is different from 1-[4-[2-(pyrrolidin-1-yl)ethoxy]phenyl]pyrrolidin-2-one, 1-[4-[2-[4-(2-methylphenyl)-1-piperazinyl]ethoxy]phenyl]-pyrrolidin-2-one and 3-(p-2-morpholinoethoxyphenyl)-oxazolidin-2-one.

The term "alkyl", as used herein, is a group which represents saturated, monovalent hydrocarbon radicals having straight (unbranched) or branched moieties, or combinations thereof, and containing 1-8 carbon atoms, preferably 1-6 carbon atoms; more preferably alkyl groups have 1-4 carbon atoms.

Usually, according to the present invention, alkyl groups are not substituted. Preferred such alkyl groups according to the present invention are methyl, ethyl, n-propyl and isopropyl.

Some alkyl groups may be substituted by 1 to 5 halogen atoms. Examples of such an alkyl groups are trifluoromethyl and trifluoroethyl.

The term "halogen", as used herein, represents an atom of fluorine, chlorine, bromine, or iodine. Preferred halogens are chlorine and fluorine.

The term "hydroxy", as used herein, represents a group of formula —OH.

The term "$C_{1-6}$-alkyl hydroxy", as used herein, refers to an alkyl as defined above substituted by a hydroxy. Preferred "$C_{1-6}$-alkyl hydroxy" groups according to the present invention are hydroxymethyl and 2-hydroxyethyl.

The term "$C_{3-8}$ cycloalkyl", as used herein, represents a monovalent group of 3 to 8 carbon atoms derived from a saturated cyclic hydrocarbon Preferred $C_{3-8}$ cycloalkyl groups according to the present invention are cyclopropyl, cyclobutyl, cyclopentyl and cyclohexyl.

The term "$C_{1-6}$-alkyl cycloalkyl", as used herein, refers to a $C_{1-6}$ alkyl having a cycloalkyl substitutent as defined here above. Examples of "$C_{1-6}$-alkyl cycloalkyl" according to the invention are cyclopropylmethyl, cyclopentylmethyl and cyclohexylmethyl.

The term "alkylene", as used herein, represents a group of formula —$(CH_2)_x$— in which x is comprised between 2 and 6, preferably comprised between 3 and 6.

The term "methylene" as used herein represents a group of formula —$CH_2$—.

The term "$C_{2-6}$ alkenyl" refers to alkenyl groups preferably having from 2 to 6 carbon atoms and having at least 1 or 2 sites of alkenyl unsaturation. Preferred alkenyl groups include ethenyl (vinyl, —CH=$CH_2$), n-2-propenyl (allyl, —$CH_2$—CH=$CH_2$) and the like.

The term "$C_{2-6}$ alkynyl" refers to alkynyl groups preferably having from 2 to 6 carbon atoms and having at least 1 to 2 sites of alkynyl unsaturation. Preferred alkynyl groups include ethynyl (—C≡CH), propargyl (—$CH_2$—C≡CH), and the like.

The term "aryl" as used herein, refers to an unsaturated aromatic carbocyclic group of from 6 to 14 carbon atoms having a single ring (e.g., phenyl) or multiple condensed rings (e.g., naphthyl). The "aryl" groups may be unsubstituted or substituted by 1 to 4 substituents independently selected from halogen, $C_{1-4}$ alkyl or $C_{1-4}$ alkoxy as defined herein. Preferred aryl groups according to the present invention are phenyl, 2-fluorophenyl, 3-fluorophenyl, 4-fluorophenyl, 2,4-difluorophenyl, 3,4-difluorophenyl, 3,5-difluorophenyl, 3-methoxyphenyl, 4-(trifluoromethyl)phenyl, 4-methylphenyl, 1,3-benzodioxol-5-yl, and 4-chlorophenyl.

The term "$C_{1-6}$-alkyl aryl", as used herein, refers to a group of formula —$R^e$-aryl in which $R^e$ is a $C_{1-6}$ alkyl. Examples of "$C_{1-6}$-alkyl aryl" according to the present invention are benzyl, 4-fluorobenzyl and 4-chlorobenzyl.

The term "heteroaryl" as used herein represents an aryl group as defined here above wherein one or more of the carbon atoms have been replaced by a heteroatom as defined herein. Examples of heteroaromatic groups are pyridyl, pyrrolyl, furyl, thienyl, imidazolyl, triazolyl and the like.

The term "$C_{1-6}$-alkyl heteroaryl" refers to a $C_{1-6}$ alkyl having a heteroaryl substituent as defined hereabove.

Examples include 2-furylmethyl, (2-methyl-1H-imidazol-1yl)methyl and (1H-1,2,4-triazol-1-yl)methyl.

The term "alkoxy", as used herein, represents a group of formula —OR$^a$ wherein R$^a$ is an alkyl or an aryl group, as defined above. Usually, according to the present invention, alkyl group of alkoxy group is not substituted. Examples of alkoxy group are methoxy, 4-fluorophenoxy and 3,4-difluorophenoxy.

The term "C$_{1-6}$-alkyl alkoxy", as used herein, refers to a C$_{1-6}$ alkyl group having an alkoxy substituent as defined here-above. Examples of "C$_{1-6}$-alkyl alkoxy" according to the present invention are (4-fluorophenoxy)methyl and (3,4-difluorophenoxy)methyl.

The term "carbonyl", as used herein represents a group of formula —(C=O)—.

The term "acyl", as used herein, represents a group of formula —C(=O)R$^b$ wherein R$^b$ is an alkyl, a C$_{3-8}$ cycloalkyl or an aryl group, as defined here above. Preferred acyl group is acetyl or cyclopropylcarbonyl. The term "arylcarbonyl" as used herein, represents an acyl group as defined here above wherein R$^b$ is an aryl group as defined here above.

The term "C$_{1-6}$-alkyl acyl" as used herein refers to a C$_{1-6}$ alkyl having an acyl substituent as defined here above, including 3-oxobutyl and the like.

The term "heterocycloalkyl" as used herein represents a cycloalkyl as defined here above wherein one, two or three carbon atoms are replaced by one, two or three O, S or N. Particularly, the heterocycloalkyl is a 3 to 8 membered heterocycloalkyl, i.e. a heterocycloalkyl wherein the cycloalkyl is a C$_{3-8}$ cycloalkyl. The heterocycloalkyl may be unsubstituted or substituted by any suitable group including, but not limited to, one or more moieties selected from alkyl, cycloalkyl, hydroxy, alkoxy, acyl, aryl and halogen. Examples of 3 to 8 membered heterocycloalkyl according to the present invention are azepanyl, morpholinyl, 4-(cyclohexylmethyl)piperazinyl, 4-(cyclopentyl)piperazinyl, 4-(isopropyl)piperazinyl, piperidinyl, 2,6-dimethylpiperidinyl, 2-methylpiperidinyl, (2S)-2-methylpyrrolidinyl, (2R)-2-methylpyrrolidinyl, 4-methylpiperidinyl, pyrrolidinyl, 2-methylpyrrolidinyl, 1-benzylpyrrolidinyl, 4-benzylpiperidinyl, 3-phenylpiperidinyl, (2-hydroxymethyl)pyrrolidinyl, (4aR,8aS)-octahydroisoquinolinyl, octahydroisoquinolinyl, 2,6-dimethylmorpholinyl, cis-2,6-dimethylmorpholinyl, thiomorpholinyl, 1,1-dioxidothiomorpholinyl, 1-acetylpyrrolidinyl, (2S)-2-(pyrrolidin-1-ylmethyl)pyrrolidinyl, azaspiro[4,4]nonyl, azaspiro[5,5]undecyl, azocanyl, 3,5-dimethylpiperidinyl and 4,4-difluoropiperidinyl.

The term "C$_{1-6}$-alkyl heterocycloalkyl", as used herein, refers to a C$_{1-6}$ alkyl substituted by a heterocycloalkyl as defined here above. Examples of "C$_{1-6}$-alkyl heterocycloalkyl" according to the present invention are azepan-1-ylmethyl, morpholin-4-ylmethyl, [4-(cyclohexylmethyl)piperazin-1-yl]methyl, [4-(cyclopentyl)piperazin-1-yl]methyl, 2-[4-(cyclopentyl)piperazin-1-yl]ethyl, (4-(isopropyl)piperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, (2,6-dimethylmorpholin-4-yl)methyl, [cis-2,6-dimethylmorpholin-4-yl]methyl, thiomorpholin-4-ylmethyl, (1,1-dioxidothiomorpholin-4-yl)methyl and (4,4-difluoropiperidin-1-yl)methyl.

The term "heterocycloalkyl acyl" refers to a heterocycloalkyl group having an acyl substituent as defined here above.

The term "amino", as used herein, represents a group of formula —NR$^c$R$^d$ wherein R$^c$ and R$^d$ are independently hydrogen, "C$_{1-6}$ alkyl", "C$_{2-6}$ alkenyl", "C$_{2-6}$ alkynyl", "C$_{3-8}$ cycloalkyl", "heterocycloalkyl", "aryl", "heteroaryl", "C$_{1-6}$-alkyl aryl", "C$_{1-6}$-alkyl heteroaryl", "C$_{1-6}$-alkyl cycloalkyl" or "C$_{1-6}$-alkyl heterocycloalkyl" groups; or R$^c$ and R$^d$ are linked together with N to form a 3 to 8 membered heterocycloalkyl.

Examples of "amino" groups according to the present invention are cyclohexylmethylamino, (cyclohexylmethyl)(cyclopropylmethyl)amino, (cyclopropylmethyl)(propyl)amino, cyclobutylamino, cyclohexylamino, cyclopentylamino, diethylamino, anilino, (4-fluorobenzyl)amino, (4-fluorophenyl)amino, (cyclohexylmethyl)(cyclopropylcarbonyl)amino, (2-fluorophenyl)amino, (3-fluorophenyl)amino, (2,4-difluorophenyl)amino, (3-methoxyphenyl)amino, [4-(trifluoromethyl)phenyl]amino, (4-methylphenyl)amino, (3,4-difluorophenyl)amino, (3,5-difluorophenyl)amino, (2,2,2-trifluoroethyl)amino, 1,3-benzodioxol-5-ylamino, (4-fluorophenyl)(methyl)amino, dibenzylamino, amino, acetylamino, azepan-1-yl, morpholin-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, (2S)-2-methylpyrrolidin-1-yl, (2R)-2-methylpyrrolidin-1-yl, 4-methylpiperidin-1-yl, pyrrolidin-1-yl, 2-methylpyrrolidin-1-yl, 4-benzylpiperidin-1-yl, 3-phenylpiperidin-1-yl, (2-hydroxymethyl)pyrrolidin-1-yl, (4aR,8aS)-octahydroisoquinolin-2(1H)-yl, octahydroisoquinolin-2(1H)-yl, 2,6-dimethylmorpholin-4-yl, cis-2,6-dimethylmorpholin-4-yl, thiomorpholin-4-yl, 1,1-dioxidothiomorpholin-4-yl, (2S)-2-(pyrrolidin-1-ylmethyl)pyrrolidin-1-yl, 1-azaspiro[4,4]non-1-yl, 2-azaspiro[5,5]undec-2-yl, azocan-1-yl, 3,5-dimethylpiperidin-1-yl and 4,4-difluoropiperidin-1-yl.

The term "C$_{1-6}$-alkyl amino", as used herein, represents a C$_{1-6}$ alkyl group substituted by an amino group as defined above. Examples of "C$_{1-6}$-alkyl amino" according to the present invention are [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclohexylmethylamino)methyl, (cyclopentylamino)methyl, (diethylamino)methyl, anilinomethyl, [(4-fluorobenzyl)amino]methyl, [(4-fluorophenyl)amino]methyl, [(cyclohexylmethyl)(cyclopropylcarbonyl)amino]methyl, [(2-fluorophenyl)amino]methyl, [(3-fluorophenyl)amino]methyl, [(2,4-difluorophenyl)amino]methyl, [(3-methoxyphenyl)amino]methyl, {[4-(trifluoromethyl)phenyl]amino}methyl, [(4-methylphenyl)amino]methyl, [(3,4-difluorophenyl)amino]methyl, [(3,5-difluorophenyl)amino]methyl, [(2,2,2-trifluoroethyl)amino]methyl, [1,3-benzodioxol-5-ylamino]methyl, [(4-fluorophenyl)(methyl)amino]methyl, (dibenzylamino)methyl, aminomethyl, (acetylamino)methyl, azepan-1-ylmethyl, morpholin-4-ylmethyl, [4-(cyclohexylmethyl)piperazin-1-yl]methyl, [4-(cyclopentyl)piperazin-1-yl]methyl, 2-[4-(cyclopentyl)piperazin-1-yl]ethyl, (4-(isopropyl)piperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, (2,6-dimethylmorpholin-4-yl)methyl, [cis-2,6-dimethylmorpholin-4-yl]methyl, thiomorpholin-4-ylmethyl, (1,1-dioxidothiomorpholin-4-yl)methyl and (4,4-difluoropiperidin-1-yl)methyl.

The term "aminocarbonyl" as used herein refers to a group of formula —C(O)N R$^c$R$^d$ wherein R$^c$ and R$^d$ are as defined here above for the amino group.

The term "$C_{1-6}$-alkyl aminocarbonyl" as used herein, refers to a $C_{1-6}$ alkyl substituted by an aminocarbonyl as defined hereabove.

The term "$C_{3-8}$-cycloalkyl amino", as used herein, represents a $C_{3-8}$ cycloalkyl group substituted by an amino group as defined above.

The term "acylamino", as used herein refers to a group of formula —$NR^cC(O)R^d$ wherein $R^c$ and $R^d$ are as defined hereabove for the amino group.

The term "$C_{1-6}$-alkyl acylamino", as used herein refers to a $C_{1-6}$ alkyl substituted by an acylamino as defined hereabove.

The term "carboxy", as used herein represents a group of formula —COOH.

The term "$C_{1-6}$-alkyl carboxy", as used herein refers to a $C_{1-6}$-alkyl substituted by a carboxy group including 2-carboxyethyl and the like.

The term "cyano", as used herein represents a group of formula —CN.

The term "alkoxycarbonyl" refers to the group —$C(O)OR^g$ wherein $R^g$ includes "$C_{1-6}$ alkyl", "$C_{2-6}$ alkenyl", "$C_{2-6}$ alkynyl", "$C_{3-8}$ cycloalkyl", "heterocycloalkyl", "aryl", "heteroaryl", "$C_{1-6}$-alkyl aryl" or "$C_{1-6}$-alkyl heteroaryl", "$C_{2-6}$-alkyl cycloalkyl", "$C_{1-6}$-alkyl heterocycloalkyl". Examples of alkoxycarbonyl are methoxycarbonyl and ethoxycarbonyl.

The term "$C_{1-6}$-alkyl alkoxycarbonyl" refers to a $C_{1-6}$ alkyl having an alkoxycarbonyl as defined here above as substituent.

The term "ureido" as used herein refers to a group of formula —$NR^iC(O)NR^cR^d$ wherein $R^i$ is as defined hereabove for $R^c$ or $R^d$, and $R^c$ and $R^d$ are as defined here above for the amino group.

The term "$C_{1-6}$-alkyl ureido" as used herein refers to a $C_{1-6}$ alkyl substituted by a ureido as defined here above.

The term "carbamate", as used herein, refers to a group of formula —$NR^cC(O)OR^d$ wherein $R^c$ and $R^d$ are as defined here above for the amino group.

The term "$C_{1-6}$-alkyl carbamate" as used herein refers to a $C_{1-6}$ alkyl substituted by a carbamate as defined here above.

The term "oxo" as used herein refers to =O.

In an embodiment, $A^1$ is CH, C—F or N.

In a more particular embodiment, $A^1$ is CH.

In a specific embodiment, $A^2$ is oxygen. In another specific embodiment, $A^2$ is sulfur.

Generally, $R^1$ is hydrogen.

In one embodiment, $R^{2a}$ is hydrogen; $C_{1-6}$ alkyl; aryl; $C_{1-6}$-alkyl alkoxy; $C_{1-6}$-alkyl hydroxy; $C_{1-6}$-alkyl aryl; or —$(CH_2)_r$—$NR^{6a}R^{6b}$; or $R^{2a}$ and $R^{2b}$ are linked together to form a $C_{2-6}$ alkylene, one methylene being optionally replaced by a nitrogen atom, said nitrogen atom being optionally substituted by a $C_{1-6}$-alkyl aryl or an acyl;

In another embodiment, $R^{2a}$ is hydrogen, n-propyl, isopropyl, hydroxymethyl, 2-hydroxyethyl, phenyl, benzyl, 4-chlorophenyl, (4-fluorophenoxy)methyl, (3,4-difluorophenoxy)methyl, 4-chlorobenzyl, cyclohexylmethyl, [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclopentylamino)methyl, (cyclohexylamino)methyl, (diethylamino)methyl, anilinomethyl, [(4-fluorobenzyl)amino]methyl, [(4-fluorophenyl)amino]methyl, azepan-1-ylmethyl, morpholin-4-ylmethyl, [4-(cyclohexylmethyl)piperazin-1-yl]methyl, (4-cyclopentylpiperazin-1-yl)methyl, 2-(4-cyclopentylpiperazin-1-yl)ethyl, (4-isopropylpiperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, [(cyclohexylmethyl)(cyclopropylcarbonyl)amino]methyl, [(2-fluorophenyl)amino]methyl, [(3-fluorophenyl)amino]methyl, [(2,4-difluorophenyl)amino]methyl, [(3-methoxyphenyl)amino]methyl, {[4-(trifluoromethyl)phenyl)]amino}methyl, [4-(methylphenyl)amino]methyl, [(3,4-difluorophenyl)amino]methyl, (2,6-dimethylmorpholin-4-yl)methyl, thiomorpholin-4-ylmethyl, [(3,5-difluorophenyl)amino]methyl, (4,4-difluoropiperidin-1-yl)methyl, [(2,2,2-trifluoroethyl)amino]methyl, (1,3-benzodioxol-5-ylamino)methyl, [(4-fluorophenyl)(methyl)amino]methyl, (cis-2,6-dimethylmorpholin-4-yl)methyl, (1,1-dioxidothiomorpholin-4-yl)methyl, (dibenzylamino)methyl, aminomethyl or (acetylamino)methyl; or $R^{2a}$ and $R^{2b}$ are linked together to form a —$CH_2$—N(benzyl)-$(CH_2)_2$—, —$CH_2$—N(acetyl)-$(CH_2)_2$—, or a —$(CH_2)_5$— group.

In a further embodiment, $R^{2a}$ is n-propyl, hydroxymethyl, phenyl, benzyl, 4-chlorophenyl, (4-fluorophenoxy)methyl, (3,4-difluorophenoxy)methyl, 4-chlorobenzyl, cyclohexylmethyl, [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclopentylamino)methyl, (cyclohexylamino)methyl, (diethylamino)methyl, anilinomethyl, [(4-fluorobenzyl)amino]methyl, [(4-fluorophenyl)amino]methyl, azepan-1-ylmethyl, morpholin-4-ylmethyl, [4-(cyclohexylmethyl)piperazin-1-yl]methyl, (4-cyclopentylpiperazin-1-yl)methyl, 2-(4-cyclopentylpiperazin-1-yl)ethyl, (4-isopropylpiperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, [(cyclohexylmethyl)(cyclopropylcarbonyl)amino]methyl, [(2-fluorophenyl)amino]methyl, [(3-fluorophenyl)amino]methyl, [(2,4-difluorophenyl)amino]methyl, [(3-methoxyphenyl)amino]methyl, {[4-(trifluoromethyl)phenyl)]amino}methyl, [4-(methylphenyl)amino]methyl, [(3,4-difluorophenyl)amino]methyl, (2,6-dimethylmorpholin-4-yl)methyl, thiomorpholin-4-ylmethyl, [(3,5-difluorophenyl)amino]methyl, (4,4-difluoropiperidin-1-yl)methyl, [(2,2,2-trifluoroethyl)amino]methyl, (1,3-benzodioxol-5-ylamino)methyl, [(4-fluorophenyl)(methyl)amino]methyl, [cis-2,6-dimethylmorpholin-4-yl]methyl, (1,1-dioxidothiomorpholin-4-yl) methyl, (dibenzylamino)methyl, aminomethyl; or $R^{2a}$ and $R^{2b}$ are linked together to form a —$CH_2$—N(benzyl)-$(CH_2)_2$—, —$CH_2$—N(acetyl)-$(CH_2)_2$—, or a —$(CH_2)_5$— group.

In a specific embodiment, $R^{2a}$ is benzyl, (4-fluorophenoxy)methyl, (3,4-difluorophenoxy)methyl, 4-chlorobenzyl, cyclohexylmethyl, [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclopentylamino)methyl, (cyclohexylamino)methyl, (diethylamino)methyl, anilinomethyl, [(4-fluorobenzyl)amino]methyl, [(4-fluorophenyl)amino]methyl, azepan-1-ylmethyl, morpholin-4-ylmethyl, [4-(cyclohexylmethyl)piperazin-1-yl]methyl, (4-cyclopentylpiperazin-1-yl)methyl, (4-isopropylpiperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, [(cyclohexylmethyl)(cyclopropylcarbonyl)amino]methyl, [(2-fluorophenyl)amino]methyl, [(2,4-difluorophenyl)amino]methyl, [(3,4-difluorophenyl)amino]methyl, (2,6-dimethylmorpholin-4-yl)methyl, thiomorpholin-4-ylmethyl, [(3,5-difluorophenyl)amino]methyl, (4,4-difluoropiperidin- 1-yl)methyl, [(2,2,2-trifluoroethyl)amino]methyl, [(4-fluorophenyl)(methyl)amino]methyl, [cis-2,6-dimethylmorpholin-4-yl]methyl, (1,1-dioxidothiomorpholin-4-yl)methyl, (dibenzylamino)methyl or aminomethyl; or $R^{2a}$ and $R^{2b}$ are linked together to form a $CH_2$—N(benzyl)-$(CH_2)_2$—.

In a particular embodiment, $R^{2a}$ is benzyl, (3,4-difluorophenoxy)methyl, cyclohexylmethyl, [(cyclohexylmethyl)amino]methyl, [(cyclopropylmethyl)(propyl)amino]methyl, (cyclobutylamino)methyl, (cyclopentylamino)methyl, (diethylamino)methyl, anilinomethyl, [(4-fluorophenyl)amino]methyl, azepan-1-ylmethyl, morpholin-4-ylmethyl, (4-isopropylpiperazin-1-yl)methyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, [(2,4-difluorophenyl)amino]methyl, [(3,4-difluorophenyl)amino]methyl, thiomorpholin-4-ylmethyl, (4,4-difluoropiperidin-1-yl)methyl, [cis-2,6-dimethylmorpholin-4-yl]methyl or (1,1-dioxidothiomorpholin-4-yl)methyl.

In one embodiment, $R^{2b}$ is hydrogen; or $R^{2a}$ and $R^{2b}$ are linked together to form a $C_{2-6}$ alkylene, one methylene being optionally replaced by a nitrogen atom, said nitrogen atom being optionally substituted by a $C_{1-6}$-alkyl aryl or an acyl.

In another embodiment, $R^{2b}$ is hydrogen; or $R^{2a}$ and $R^{2b}$ are linked together to form —$CH_2$—N(benzyl)-$(CH_2)_2$—, —$CH_2$—N(acetyl)-$(CH_2)_2$—, or a —$(CH_2)_5$— group.

In a specific embodiment, $R^{2b}$ is hydrogen; or $R^{2a}$ and $R^{2b}$ are linked together to form a —$CH_2$—N(benzyl)-$(CH_2)_2$ group.

In a particular embodiment, $R^{2b}$ is hydrogen.

In one embodiment, $R^3$ is hydrogen, halogen or $C_{1-4}$ alkoxy.

In another embodiment, $R^3$ is hydrogen, fluorine or methoxy.

In a further embodiment, $R^3$ is hydrogen or fluorine.

In a specific embodiment, $R^3$ is hydrogen.

In one embodiment, $R^4$ is hydrogen, $C_{1-4}$ alkyl, $C_{1-4}$ alkoxy, halogen or —O—$(CH_2)_t$—$NR^{7a}R^{7b}$.

In another embodiment, $R^4$ is hydrogen, methyl, fluorine or —O—$(CH_2)_t$—$NR^{7a}R^{7b}$.

In a specific embodiment, $R^4$ is hydrogen, methyl or fluorine.

In a particular embodiment, $R^4$ is hydrogen or fluorine.

In a specific embodiment, $R^5$ is —O—$(CH_2)_w$—$NR^{8a}R^{8b}$.

In one embodiment, $R^{6a}$ is hydrogen, $C_{1-8}$ alkyl, $C_{1-6}$-alkyl cycloalkyl, $C_{3-8}$ cycloalkyl, acyl, aryl or $C_{1-6}$-alkyl aryl; or $R^{6a}$ and $R^{6b}$ are linked together to form a $C_{3-6}$ alkylene, each methylene of the alkylene being optionally substituted by one or two halogen, or by one or two $C_{1-4}$ alkyl, optionally linked together to form with the carbon to which they are attached a $C_{3-8}$ cycloalkyl; or one methylene thereof being linked to a second methylene thereof to form a $C_{3-6}$ alkylene; or one methylene being optionally replaced by sulfur dioxide, an oxygen, a sulfur or a nitrogen atom, said nitrogen atom being optionally substituted by a $C_{1-8}$ alkyl or $C_{3-8}$ cycloalkyl.

In another embodiment, $R^{6a}$ is hydrogen, ethyl, cyclobutyl, cyclopentyl, cyclohexyl, cyclopropylmethyl, cyclohexylmethyl, 4-fluorobenzyl, phenyl, 4-fluorophenyl, cyclopropylcarbonyl, 2-fluorophenyl, 3-fluorophenyl, 2,4-difluorophenyl, 3-methoxyphenyl, 4-(trifluoromethyl)phenyl, 4-methylphenyl, 3,4-difluorophenyl, 3,5-difluorophenyl, 2,2,2-trifluoroethyl, 1,3-benzodioxol-5-yl, benzyl or acetyl; or $R^{6a}$ and $R^{6b}$ are linked together to form with N a 3-8 membered heterocycloalkyl selected from the group consisting of azepan-1-yl, morpholin-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, (4aR,8aS)-octahydroisoquinolin-2(1H)-yl, 2,6-dimethylmorpholin-4-yl, cis-2,6-dimethylmorpholin-4-yl, thiomorpholin-4-yl, 4,4-difluoropiperidin-1-yl and 1,1-dioxidothiomorpholin-4-yl.

In a further embodiment, $R^{6a}$ is hydrogen, ethyl, cyclobutyl, cyclopentyl, cyclohexyl, cyclopropylmethyl, cyclohexylmethyl, 4-fluorobenzyl, phenyl, 4-fluorophenyl, cyclopropylcarbonyl, 2-fluorophenyl, 3-fluorophenyl, 2,4-difluorophenyl, 3-methoxyphenyl, 4-(trifluoromethyl)phenyl, 4-methylphenyl, 3,4-difluorophenyl, 3,5-difluorophenyl, 2,2,2-trifluoroethyl, 1,3-benzodioxol-5-yl, benzyl; or $R^{6a}$ and $R^{6b}$ are linked together to form with N a 3-8 membered heterocycloalkyl selected from the group consisting of azepan-1-yl, morpholin-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, (4aR,8aS)-octahydroisoquinolin-2(1H)-yl, 2,6-dimethylmorpholin-4-yl, cis-2,6-dimethylmorpholin-4-yl, thiomorpholin-4-yl, 4,4-difluoropiperidin-1-yl and 1,1-dioxidothiomorpholin-4-yl.

In a specific embodiment, $R^{6a}$ is hydrogen, ethyl, cyclobutyl, cyclopentyl, cyclohexyl, cyclopropylmethyl, cyclohexylmethyl, 4-fluorobenzyl, phenyl, 4-fluorophenyl, cyclopropylcarbonyl, 2-fluorophenyl, 2,4-difluorophenyl, 3,4-difluorophenyl, 3,5-difluorophenyl, 2,2,2-trifluoroethyl, benzyl; or $R^{6a}$ and $R^{6b}$ are linked together to form with N a 3-8 membered heterocycloalkyl selected from the group consisting of azepan-1-yl, morpholin-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, (4aR,8aS)-octahydroisoquinolin-2(1H)-yl, 2,6-dimethylmorpholin-4-yl, cis-2,6-dimethylmorpholin-4-yl, thiomorpholin-4-yl, 4,4-difluoropiperidin-1-yl and 1,1-dioxidothiomorpholin-4-yl.

In a particular embodiment, $R^{6a}$ is hydrogen, ethyl, cyclobutyl, cyclopentyl, cyclopropylmethyl, cyclohexylmethyl, phenyl, 4-fluorophenyl, 3,4-difluorophenyl; or $R^{6a}$ and $R^{6b}$ are linked together to form with N a 3-8 membered heterocycloalkyl selected from the group consisting of azepan-1-yl, morpholin-4-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, cis-2,6-dimethylmorpholin-1-yl, thiomorpholin-4-yl, 4,4-difluoropiperidin-1-yl and 1,1-dioxidothiomorpholin-4-yl.

In one embodiment, $R^{6b}$ is hydrogen, $C_{1-4}$ alkyl, $C_{1-6}$-alkyl cycloalkyl or $C_{1-6}$-alkyl aryl; or $R^{6a}$ and $R^{6b}$ are linked together to form a $C_{3-6}$ alkylene, each methylene of the alkylene being optionally substituted by one or two halogen, or by one or two $C_{1-4}$ alkyl, optionally linked together to form with the carbon to which they are attached a $C_{3-8}$ cycloalkyl; or one methylene thereof being linked to a second methylene thereof to form a $C_{3-6}$ alkylene; or one methylene being optionally replaced by sulfur dioxide, an oxygen, a sulfur or a nitrogen atom, said nitrogen atom being optionally substituted by a $C_{1-8}$ alkyl or $C_{3-8}$ cycloalkyl.

In another embodiment, $R^{6b}$ is hydrogen, methyl, ethyl, n-propyl, cyclopropylmethyl, cyclohexylmethyl or benzyl; or $R^{6a}$ and $R^{6b}$ are linked together to form with N a 3-8 membered heterocycloalkyl selected from the group consisting of azepan-1-yl, morpholin-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, (4aR,8aS)-octahydroisoquinolin-2 (1H)-yl, 2,6-dimethyl-4-morpholin-1-yl, cis-2,6-dimethylmorpholin-4-yl, thiomorpholin-4-yl, 4,4-difluoropiperidin-1-yl and 1,1-dioxidothiomorpholin-4-yl.

In a further embodiment, $R^{6b}$ is hydrogen, methyl, ethyl, n-propyl, cyclopropylmethyl, cyclohexylmethyl or benzyl; or $R^{6a}$ and $R^{6b}$ are linked together to form with N a 3-8 membered heterocycloalkyl selected from the group consisting of azepan-1-yl, morpholin-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, (4aR,8aS)-octahydroisoquinolin-2 (1H)-yl, 2,6-dimethylmorpholin-4-yl, cis-2,6-dimethylmorpholin-4-yl, thiomorpholin-4-yl, 4,4-difluoropiperidin-1-yl and 1,1-dioxidothiomorpholin-4-yl.

In a specific embodiment, $R^{6b}$ is hydrogen, methyl, ethyl, n-propyl, cyclopropylmethyl, cyclohexylmethyl or benzyl; or $R^{6a}$ and $R^{6b}$ are linked together to form with N a 3-8 membered heterocycloalkyl selected from the group consisting of azepan-1-yl, morpholin-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, (4aR,8aS)-octahydroisoquinolin-2 (1H)-yl, 2,6-dimethylmorpholin-4-yl, cis-2,6-dimethylmorpholin-4-yl, thiomorpholin-4-yl, 4,4-difluoropiperidin-1-yl and 1,1-dioxidothiomorpholin-4-yl.

In a particular embodiment, $R^{6b}$ is hydrogen, ethyl, n-propyl; or $R^{6a}$ and $R^{6b}$ are linked together to form with N a 3-8 membered heterocycloalkyl selected from the group consisting of azepan-1-yl, morpholin-4-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, cis-2,6-dimethylmorpholin-1-yl, thiomorpholin-4-yl, 4,4-difluoropiperidin-1-yl and 1,1-dioxidothiomorpholin-4-yl.

In one embodiment, $R^{7a}$ and $R^{7b}$ are linked together to form a $C_{3-6}$ alkylene, each methylene of the alkylene being optionally substituted by one or two $C_{1-4}$ alkyl.

In another embodiment, $R^{7a}$ and $R^{7b}$ are linked together to form with N a 2-methylpyrrolidin-1-yl group.

In one embodiment, $R^{8a}$ and $R^{8b}$ are linked together to form a $C_{3-6}$ alkylene, each methylene of the alkylene being optionally substituted by one or two $C_{1-4}$ alkyl optionally linked together to form with the carbon to which they are attached a $C_{3-8}$ cycloalkyl, by $C_{1-6}$-alkyl hydroxy, by $C_{1-6}$-alkyl heterocycloalkyl, by aryl or by $C_{1-6}$-alkyl aryl; or one methylene thereof being linked to a second methylene thereof to form a $C_{3-6}$ alkylene; or one methylene of the alkylene being optionally replaced by a nitrogen, said nitrogen being substituted by a $C_{1-4}$ alkyl or $C_{3-8}$ cycloalkyl.

In another embodiment, $R^{8a}$ and $R^{8b}$ are linked together to form with N a 3-8 membered heterocycloalkyl selected from the group consisting of 4-cyclopentylpiperazin-1-yl, 4-isopropylpiperazin-1-yl, piperidin-1-yl, 2-methylpiperidin-1-yl, 2-methylpyrrolidin-1-yl, (2S)-2-methylpyrrolidin-2-yl, (2R)-2-methylpyrrolidin-2-yl, 2-(pyrrolidin-1-ylmethyl)pyrrolidin-1-yl, (2S)-2-(pyrrolidin-1-ylmethyl)pyrrolidin-1-yl, 1-azaspiro[4.4]non-1-yl, 4-methylpiperidin-1-yl, 3,5-dimethylpiperidin-1-yl, 3-octahydroquinolin-1(2H)-yl, 2-azaspiro[5.5]undec-2-yl, 4-benzylpiperidin-1-yl, 3-phenylpiperidin-1-yl, 2-(hydroxymethyl)pyrrolidin-1-yl, azepan-1-yl or azocan-1-yl.

In a further embodiment, $R^{8a}$ and $R^{8b}$ are linked together to form with N a 3-8 membered heterocycloalkyl selected from the group consisting of piperidin-1-yl, 2-methylpiperidin-1-yl, 2-methylpyrrolidin-1-yl, (2S)-2-methylpyrrolidin-1-yl, (2R)-2-methylpyrrolidin-1-yl, 1-azaspiro[4.4]non-1-yl, 4-methylpiperidin-1-yl, 3,5-dimethylpiperidin-1-yl, 2-azaspiro[5.5]undec-2-yl, 4-benzylpiperidin-1-yl, 3-phenylpiperidin-1-yl, azepan-1-yl or azocan-1-yl.

In a specific embodiment, $R^{8a}$ and $R^{8b}$ are linked together to form with N a 3-8 membered heterocycloalkyl selected from the group consisting of piperidin-1-yl, 2-methylpyrrolidin-1-yl, (2S)-2-methylpyrrolidin-1-yl, (2R)-2-methylpyrrolidin-1-yl, 1-azaspiro[4.4]non-1-yl, 3,5-dimethylpiperidin-1-yl, 2-azaspiro[5.5]undec-2-yl or azepan-1-yl.

In a particular embodiment, $R^{8a}$ and $R^{8b}$ are linked together to form with N a 3-8 membered heterocycloalkyl selected from the group consisting of piperidin-1-yl, 2-methylpyrrolidin-1-yl, (2S)-2-methylpyrrolidin-1-yl, (2R)-2-methylpyrrolidin-1-yl, 3,5-dimethylpiperidin-1-yl or azepan-1-yl.

In one embodiment, $R^{9a}$ is hydrogen or unsubstituted $C_{1-8}$ alkyl.

In another embodiment, $R^{9a}$ is methyl.
In one embodiment, $R^{9b}$ is unsubstituted $C_{1-4}$ alkyl.
In another embodiment, $R^{9b}$ is methyl.
In one embodiment, n is equal to 0 or 1.
In a particular embodiment, n is equal to 0.
In one embodiment, r is an integer equal to 1 or 2;
In a specific embodiment, r is equal to 1.
In one embodiment, t is equal to 3.
In a specific embodiment, w is equal to 3 or 4.
In another specific embodiment, w is equal to 3.
In a further embodiment, z is equal to 0, 1 or 2.
In a specific embodiment, z is equal to 1 or 2.

Each $CH_2$ of $-(CH_2)_r-NR^{6a}R^{6b}$, $-O-(CH_2)_t-NR^{7a}R^{7b}$, $-O-(CH_2)_w-NR^{8a}R^{8b}$ or $-(O)_v-(CR^{9a}R^{9b})_m-(CH_2)_z$ groups may be substituted by one or two $C_{1-4}$ alkyl. Generally, said $CH_2$ will be unsubstituted.

In one embodiment, the present invention relates to compounds of formula (I), geometrical isomers, enantiomers, diastereoisomers, pharmaceutically acceptable salts and all possible mixtures thereof,

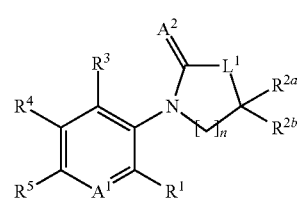

(I)

$A^1$ is CH, N or C-halogen;
$A^2$ is oxygen or sulfur;
$R^1$ is hydrogen;
$R^{2a}$ is hydrogen; $C_{1-6}$ alkyl; aryl; $C_{1-6}$-alkyl alkoxy; $C_{1-6}$-alkyl hydroxy or $C_{1-6}$-alkyl aryl; or $-(CH_2)_r-NR^{6a}R^{6b}$;
$R^{2b}$ is hydrogen;
or $R^{2a}$ and $R^{2b}$ are linked together to form a $C_{2-6}$ alkylene, one methylene being optionally replaced by a nitrogen atom, said nitrogen atom being optionally substituted by a $C_{1-6}$-alkyl aryl or an acyl;
$R^3$ is hydrogen, halogen or $C_{1-4}$ alkoxy;
$R^4$ is hydrogen, $C_{1-4}$ alkyl, $C_{1-4}$ alkoxy, halogen or $-O-(CH_2)_t-NR^{7a}R^{7b}$;
$R^5$ is hydrogen or $-O-(CH_2)_w-NR^{8a}R^{8b}$;
$L^1$ is $(O)_v-(CR^{9a}R^{9b})_m-(CH_2)_z-$;

$R^{6a}$ is hydrogen, $C_{1-8}$ alkyl, $C_{1-6}$-alkyl cycloalkyl, $C_{3-8}$ cycloalkyl, acyl, aryl or $C_{1-6}$-alkyl aryl;

$R^{6b}$ is hydrogen, $C_{1-4}$ alkyl, $C_{1-6}$-alkyl cycloalkyl or $C_{1-6}$-alkyl aryl;

or $R^{6a}$ and $R^{6b}$ are linked together to form a $C_{3-6}$ alkylene, each methylene of the alkylene being optionally substituted by one or two halogen, or by one or two $C_{1-4}$ alkyl, optionally linked together to form with the carbon to which they are attached a $C_{3-8}$ cycloalkyl; or one methylene thereof being linked to a second methylene thereof to form a $C_{3-6}$ alkylene; or one methylene being optionally replaced by sulfur dioxide, an oxygen, a sulfur or a nitrogen atom, said nitrogen atom being optionally substituted by a $C_{1-8}$ alkyl or $C_{3-8}$ cycloalkyl;

$R^{7a}$ and $R^{7b}$ are linked together to form a $C_{3-6}$ alkylene, each methylene of the alkylene being optionally substituted by one or two $C_{1-4}$ alkyl;

$R^{8a}$ and $R^{8b}$ are linked together to form a $C_{3-6}$ alkylene, each methylene of the alkylene being optionally substituted by one or two $C_{1-4}$ alkyl optionally linked together to form with the carbon to which they are attached a $C_{3-8}$ cycloalkyl, by $C_{1-6}$-alkyl hydroxy, $C_{1-6}$-alkyl heterocycloalkyl, by aryl or by $C_{1-6}$-alkyl aryl; or one methylene thereof being linked to a second methylene thereof to form a $C_{3-6}$ alkylene; or one methylene of the alkylene being optionally replaced by a nitrogen, said nitrogen being substituted by a $C_{1-4}$ alkyl or $C_{3-8}$ cycloalkyl;

$R^{9a}$ is hydrogen or an unsubstituted $C_{1-8}$ alkyl;

$R^{9b}$ is an unsubstituted $C_{1-8}$ alkyl;

n is an integer equal to 0 or 1;
r is an integer equal to 1 or 2;
t is an integer equal to 2, 3 or 4;
w is an integer equal to 2, 3 or 4;
v is an integer equal to 0 or 1;
m is an integer equal to 0 or 1;
z is an integer equal to 0, 1, 2 or 3;
provided that
at least one of m and z is different from 0; and that
$R^4$ is —O—$(CH_2)_t$—$NR^{7a}R^{7b}$, when $R^5$ is hydrogen;
$R^5$ is —O—$(CH_2)_w$—$NR^{8a}R^{8b}$, when $R^4$ is hydrogen, $C_{1-4}$ alkyl, $C_{1-4}$ alkoxy or halogen;
and that compound of formula (I) is different from 1-[4-[2-(pyrrolidin-1-yl)ethoxy]phenyl]pyrrolidin-2-one.

In a second embodiment, the present invention relates to compounds of formula (I), geometrical isomers, enantiomers, diastereoisomers, pharmaceutically acceptable salts and all possible mixtures thereof,

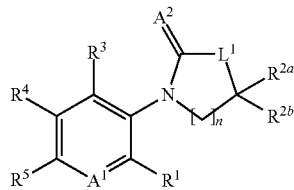

(I)

wherein
$A^1$ is CH;
$A^2$ is oxygen or sulfur;
$R^1$ is hydrogen;
$R^{2a}$ is hydrogen; aryl; $C_{1-8}$ alkyl optionally substituted by hydroxy or aryl; or —$(CH_2)_r$—$NR^{6a}R^{6b}$; or $R^{2a}$ and $R^{2b}$ are linked together to form a $C_{2-6}$ alkylene, one methylene being optionally replaced by a nitrogen atom, said nitrogen atom being optionally substituted by an arylalkyl;

$R^{2b}$ is hydrogen; or $R^{2a}$ and $R^{2b}$ are linked together to form a $C_{2-6}$ alkylene, one methylene being optionally replaced by a nitrogen atom, said nitrogen atom being optionally substituted by an arylalkyl;

$R^3$ is hydrogen;
$R^4$ is hydrogen or —O—$(CH_2)_t$—$NR^{7a}R^{7b}$;
$R^5$ is hydrogen or —O—$(CH_2)_w$—$NR^{8a}R^{8b}$;
$L^1$ is $(O)_v$—$(CR^{9a}R^{9b})_m$—$(CH_2)_z$—;
$R^{6a}$ is $C_{1-8}$ alkyl, aryl or arylalkyl; or $R^{6a}$ and $R^{6b}$ are linked together to form a $C_{3-6}$ alkylene, each methylene of the alkylene being optionally substituted by one or two $C_{1-4}$ alkyl, one methylene being optionally replaced by an oxygen atom or a nitrogen atom, said nitrogen atom being optionally substituted by a $C_{1-8}$ alkyl;

$R^{6b}$ is hydrogen or $C_{1-4}$ alkyl; or $R^{6a}$ and $R^{6b}$ are linked together to form a $C_{3-6}$ alkylene, each methylene of the alkylene being optionally substituted by one or two $C_{1-4}$ alkyl, one methylene being optionally replaced by an oxygen atom or a nitrogen atom, said nitrogen atom being optionally substituted by a $C_{1-8}$ alkyl;

$R^{7a}$ and $R^{7b}$ are linked together to form a $C_{3-6}$ alkylene, each methylene of the alkylene being optionally substituted by one or two $C_{1-4}$ alkyl;

$R^{8a}$ and $R^{8b}$ are linked together to form a $C_{3-6}$ alkylene, each methylene of the alkylene being optionally substituted by one or two $C_{1-4}$ alkyl; or one methylene of the alkylene being optionally replaced by a nitrogen, said nitrogen being substituted by a $C_{1-4}$ alkyl; or one methylene of the alkylene being optionally replaced by a $C_{3-6}$ cycloalkyl;

$R^{9a}$ is hydrogen or $C_{1-4}$ alkyl;
$R^{9b}$ is $C_{1-4}$ alkyl;
n is an integer equal to 0 or 1;
r is an integer equal to 1 or 2;
t is an integer equal to 2, 3 or 4;
w is an integer equal to 2, 3 or 4;
v is an integer equal to 0 or 1;
m is an integer equal to 0 or 1;
z is an integer equal to 0, 1, 2 or 3;
provided that
at least one of m and z is different from 0; and that
when $R^4$ is —O—$(CH_2)_t$—$NR^{7a}R^{7b}$, then $R^5$ is hydrogen;
when $R^5$ is —O—$(CH_2)_w$—$NR^{8a}R^{8b}$, then $R^4$ is hydrogen;
and
that compounds of formula (I) are different from 1-[4-[2-(pyrrolidin-1-yl)ethoxy]phenyl]pyrrolidin-2-one and (5R)-(hydroxymethyl)-3-[3-fluoro-4-[2-(1-piperidinyl)ethoxy]phenyl]-oxazolidin-2-one.

In another embodiment, the present invention relates to compounds of formula (I), geometrical isomers, enantiomers, diastereoisomers, pharmaceutically acceptable salts and all possible mixtures thereof,

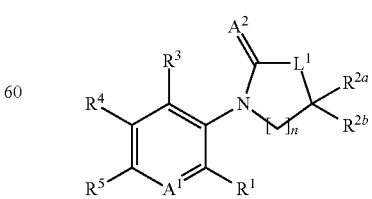

(I)

wherein
$A^1$ is CH, C—F or N;

A² is oxygen or sulfur;
R¹ is hydrogen;
R²ᵃ is hydrogen, n-propyl, isopropyl, hydroxymethyl, 2-hydroxyethyl, phenyl, benzyl, 4-chlorophenyl, (4-fluorophenoxy)methyl, (3,4-difluorophenoxy)methyl, 4-chlorobenzyl, cyclohexylmethyl, [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclopentylamino)methyl, (cyclohexylamino)methyl, (diethylamino)methyl, anilinomethyl, [(4-fluorobenzyl)amino]methyl, [(4-fluorophenyl)amino]methyl, azepan-1-ylmethyl, morpholin-4-ylmethyl, [4-(cyclohexylmethyl)piperazin-1-yl]methyl, (4-cyclopentylpiperazin-1-yl)methyl, 2-(4-cyclopentylpiperazin-1-yl)ethyl, (4-isopropylpiperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, [(cyclohexylmethyl)(cyclopropylcarbonyl)amino]methyl, [(2-fluorophenyl)amino]methyl, [(3-fluorophenyl)amino]methyl, [(2,4-difluorophenyl)amino]methyl, [(3-methoxyphenyl)amino]methyl, {[4-(trifluoromethyl)phenyl]amino}methyl, [4-(methylphenyl)amino]methyl, [(3,4-difluorophenyl)amino]methyl, (2,6-dimethylmorpholin-4-yl)methyl, thiomorpholin-4-ylmethyl, [(3,5-difluorophenyl)amino]methyl, (4,4-difluoropiperidin-1-yl)methyl, [(2,2,2-trifluoroethyl)amino]methyl, (1,3-benzodioxol-5-ylamino)methyl, [(4-fluorophenyl)methyl)amino]methyl, (cis-2,6-dimethylmorpholin-4-yl)methyl, (1,1-dioxidothiomorpholin-4-yl)methyl, (dibenzylamino)methyl, aminomethyl or (acetylamino)methyl;
R²ᵇ is hydrogen;
or R²ᵃ and R²ᵇ are linked together to form —CH₂—N(benzyl)-(CH₂)₂—, —CH₂—N(acetyl)-(CH₂)₂—, or a —(CH₂)₅— group;
R³ is hydrogen, fluorine or methoxy;
R⁴ is hydrogen, methyl, fluorine or —O—(CH₂)ₜ—NR⁷ᵃR⁷ᵇ;
R⁵ is hydrogen or —O—(CH₂)_w—NR⁸ᵃR⁸ᵇ;
L¹ is (O)_v—(CR⁹ᵃR⁹ᵇ)_m—(CH₂)_z—;
R⁷ᵃ and R⁷ᵇ are linked together to form with N a 2-methylpyrrolidin-1-yl group;
R⁸ᵃ and R⁸ᵇ are linked together to form with N a 3-8 membered heterocycloalkyl selected from the group consisting of 4-cyclopentylpiperazin-1-yl, 4-isopropylpiperazin-1-yl, piperidin-1-yl, 2-methylpiperidin-1-yl, 2-methylpyrrolidin-1-yl, (2S)-2-methylpyrrolidin-1-yl, (2R)-2-methylpyrrolidin-1-yl, 2-(pyrrolidin-1-ylmethyl)pyrrolidin-1-yl, (2S)-2-(pyrrolidin-1-ylmethyl)pyrrolidin-1-yl, 1-azaspiro[4.4]non-1-yl, 4-methylpiperidin-1-yl, 3,5-dimethylpiperidin-1-yl, 3-octahydroquinolin-2(1H)-yl, 2-azaspiro[5.5]undec-2-yl, 4-benzylpiperidin1-yl, 3-phenylpiperidin-1-yl, 2-(hydroxymethyl)pyrrolidin-1-yl, azepan 1-yl or azocan-1-yl;
R⁹ᵃ is methyl;
R⁹ᵇ is methyl;
n is an integer equal to 0 or 1;
t is an integer equal to 3;
w is an integer equal to 2, 3 or 4;
v is an integer equal to 0 or 1;
m is an integer equal to 0 or 1;
z is an integer equal to 0, 1, 2 or 3;
provided that
at least one of m and z is different from 0; and that
R⁴ is —O—(CH₂)ₜ—NR⁷ᵃR⁷ᵇ, when R⁵ is hydrogen;

R⁵ is —O—(CH₂)_w—NR⁸ᵃR⁸ᵇ, when R⁴ is hydrogen, methyl or fluorine.

In a further embodiment, the present invention relates to compounds of formula (I), geometrical isomers, enantiomers, diastereoisomers, pharmaceutically acceptable salts and all possible mixtures thereof,

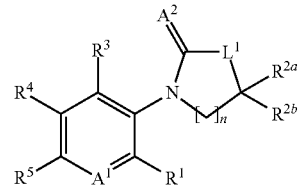

(I)

wherein
A¹ is CH, C—F or N;
A² is oxygen or sulfur;
R¹ is hydrogen;
R²ᵃ is n-propyl, hydroxymethyl, phenyl, benzyl, 4-chlorophenyl, (4-fluorophenoxy)methyl, (3,4-difluorophenoxy)methyl, 4-chlorobenzyl, cyclohexylmethyl, [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclopentylamino)methyl, (cyclohexylamino)methyl, (diethylamino)methyl, anilinomethyl, [(4-fluorobenzyl)amino]methyl, [(4-fluorophenyl)amino]methyl, azepan-1-ylmethyl, morpholin-4-ylmethyl, [4-(cyclohexylmethyl)piperazin-1-yl]methyl, (4-cyclopentylpiperazin-1-yl)methyl, 2-(4-cyclopentylpiperazin-1-yl)ethyl, (4-isopropylpiperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, [(cyclohexylmethyl)(cyclopropylcarbonyl)amino]methyl, [(2-fluorophenyl)amino]methyl, [(3-fluorophenyl)amino]methyl, [(2,4-difluorophenyl)amino]methyl, [(3-methoxyphenyl)amino]methyl, {[4-(trifluoromethyl)-phenyl]amino}methyl, [4-(methylphenyl)amino]methyl, [(3,4-difluorophenyl)amino]methyl, (2,6-dimethylmorpholin-4-yl)methyl, thiomorpholin-4-ylmethyl, [(3,5-difluorophenyl)amino]methyl, (4,4-difluoropiperidin-1-yl)methyl, [(2,2,2-trifluoroethyl)amino]methyl, (1,3-benzodioxol-5-ylamino)methyl, [(4-fluorophenyl)methyl)amino]methyl, (cis-2,6-dimethylmorpholin-4-yl)methyl, (1,1-dioxidothiomorpholin-4-yl)methyl, (dibenzylamino)methyl or aminomethyl;
R²ᵇ is hydrogen; or
R²ᵃ and R²ᵇ are linked together to form —CH₂—N(benzyl)-(CH₂)₂—, —CH₂—N(acetyl)-(CH₂)₂—, or a —(CH₂)₅— group;
R³ is hydrogen or fluorine;
R⁴ is hydrogen, methyl, fluorine or —O—(CH₂)ₜ—NR⁷ᵃR⁷ᵇ;
R⁵ is hydrogen or —O—(CH₂)_w—NR⁸ᵃR⁸ᵇ;
L¹ is —(O)_v—(CR⁹ᵃR⁹ᵇ)_m—(CH₂)_z—;
R⁷ᵃ and R⁷ᵇ are linked together to form with N a 2-methylpyrrolidin-1-yl group;
R⁸ᵃ and R⁸ᵇ are linked together to form with N a 3-8 membered heterocycloalkyl selected from the group consisting of piperidin-1-yl, 2-methylpiperidin-1-yl, 2-methylpyrrolidin-1-yl, (2S)-2-methylpyrrolidin-1-yl, (2R)-2-methylpyrrolidin-1-yl, 1-azaspiro[4.4]non-1-yl, 4-methylpiperidin-1-yl, 3,5-dimethylpiperidin-1-yl, 2-azaspiro[5.5]undec-2-yl, 4-benzylpiperidin-1-yl, 3-phenylpiperidin-1-yl, azepan-1-yl or azocan-1-yl;

$R^{9a}$ is methyl;
$R^{9b}$ is methyl;
n is an integer equal to 0 or 1;
t is an integer equal to 3;
w is an integer equal to 2, 3 or 4;
v is an integer equal to 0 or 1;
m is an integer equal to 0 or 1;
z is an integer equal to 0, 1 or 2;
provided that at least one of m and z is different from 0 and that
$R^4$ is $-O-(CH_2)_t-NR^{7a}R^{7b}$, when $R^5$ is hydrogen;
$R^5$ is $-O-(CH_2)_w-NR^{8a}R^{8b}$, when $R^4$ is hydrogen, methyl or fluorine.

In a specific embodiment, the present invention relates to compounds of formula (I), geometrical isomers, enantiomers, diastereoisomers, pharmaceutically acceptable salts and all possible mixtures thereof,

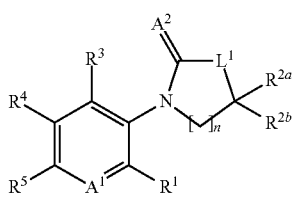
(I)

wherein
$A^1$ is CH, C—F or N;
$A^2$ is oxygen;
$R^1$ is hydrogen;
$R^{2a}$ is benzyl, (4-fluorophenoxy)methyl, (3,4-difluorophenoxy)methyl, 4-chlorobenzyl, cyclohexylmethyl, [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclopentylamino)methyl, (cyclohexylamino)methyl, (diethylamino)methyl, anilinomethyl, [(4-fluorobenzyl)amino]methyl, [(4-fluorophenyl)amino]methyl, azepan-1-ylmethyl, morpholin-4-ylmethyl, [4-(cyclohexylmethyl)piperazin-1-yl]methyl, (4-cyclopentylpiperazin-1-yl)methyl, (4-isopropylpiperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, (4aR,8aS)-octahydroisoquinolin-2(1H)-ylmethyl, [(cyclohexylmethyl)(cyclopropylcarbonyl)amino]methyl, [(2-fluorophenyl)amino]methyl, [(2,4-difluorophenyl)amino]methyl, [(3,4-difluorophenyl)amino]methyl, (2,6-dimethylmorpholin-4-yl)methyl, thiomorpholin-4-ylmethyl, [(3,5-difluorophenyl)amino]methyl, (4,4-difluoropiperidin-1-yl)methyl, [(2,2,2-trifluoroethyl)amino]methyl, [(4-fluorophenyl)methyl)amino]methyl, (cis-2,6-dimethylmorpholin-4-yl)methyl, (1,1-dioxidothiomorpholin-4-yl)methyl, (dibenzylamino)methyl or aminomethyl;
$R^{2b}$ is hydrogen; or
$R^{2a}$ and $R^{2b}$ are linked together to form a $CH_2-N$(benzyl)-$(CH_2)_2-$;
$R^3$ is hydrogen;
$R^4$ is hydrogen, methyl or fluorine;
$R^5$ is $-O-(CH_2)_w-NR^{8a}R^{8b}$;
$L^1$ is $-(O)_v-(CR^{9a}R^{9b})_m-(CH_2)_z-$;
$R^{8a}$ and $R^{8b}$ are linked together to form with N a 3-8 membered heterocycloalkyl selected from the group consisting of piperidin-1-yl, 2-methylpyrrolidin-1-yl, (2S)-2-methylpyrrolidin-1-yl, (2R)-2-methylpyrrolidin-1-yl, 1-azaspiro[4.4]non-1-yl, 3,5-dimethylpiperidin-1-yl, 2-azaspiro[5.5]undec-2-yl or azepan-1-yl;
$R^{9a}$ is methyl;
$R^{9b}$ is methyl;
n is an integer equal to 0 or 1;
w is an integer equal to 3 or 4;
v is an integer equal to 0 or 1;
m is an integer equal to 0 or 1;
z is an integer equal to 1 or 2.

In a particular embodiment, the present invention relates to compounds of formula (I), geometrical isomers, enantiomers, diastereoisomers, pharmaceutically acceptable salts and all possible mixtures thereof,

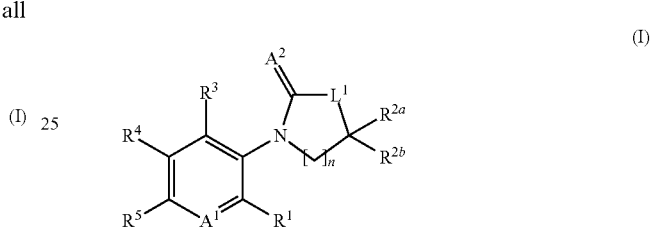
(I)

wherein
$A^1$ is CH, C—F or N;
$A^2$ is oxygen;
$R^1$ is hydrogen;
$R^{2a}$ is benzyl, (3,4-difluorophenoxy)methyl, cyclohexylmethyl, [(cyclohexylmethyl)amino]methyl, [(cyclopropylmethyl)(propyl)amino]methyl, (cyclobutylamino)methyl, (cyclopentylamino)methyl, (diethylamino)methyl, anilinomethyl, [(4-fluorophenyl)amino]methyl, azepan-1-ylmethyl, morpholin-4-ylmethyl, (4-isopropylpiperazin-1-yl)methyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, (2-methylpyrrolidin-1-yl)methyl, [(2,4-difluorophenyl)amino]methyl, [(3,4-difluorophenyl)amino]methyl, thiomorpholin-4-ylmethyl, (4,4-difluoropiperidin-1-yl)methyl, (cis-2,6-dimethylmorpholin-4-yl)methyl or (1,1-dioxidothiomorpholin-4-yl)methyl;
$R^{2b}$ is hydrogen;
$R^3$ is hydrogen;
$R^4$ is hydrogen or fluorine;
$R^5$ is $-O-(CH_2)_w-NR^{8a}R^{8b}$;
$L^1$ is $(O)_v-(CR^{9a}R^{9b})_m-(CH_2)_z-$;
$R^{8a}$ and $R^{8b}$ are linked together to form with N a 3-8 membered heterocycloalkyl selected from the group consisting of piperidin-1-yl, 2-methylpyrrolidin-1-yl, (2S)-2-methylpyrrolidin-1-yl, (2R)-2-methylpyrrolidin-1-yl, 3,5-dimethylpiperidin-1-yl or azepan-1-yl;
$R^{9a}$ is methyl;
$R^{9b}$ is methyl;
n is an integer equal to 0;
w is an integer equal to 3;
v is an integer equal to 0 or 1;
m is an integer equal to 0 or 1;
z is an integer equal to 1 or 2.

In an example of the present invention, $R^{2a}$ is $-(CH_2)_r-NR^{6a}R^{6b}$.

In an example of the present invention, m is equal to 0.

In another example of the present invention, the sum v+m+z+n is inferior or equal to 5.

In a further example of the present invention, the sum v+m+z+n is equal to 2, 3 or 4.

In a particular aspect, the present invention relates to compounds of formula (Ia) geometrical isomers, enantiomers, diastereoisomers, pharmaceutically acceptable salts and all possible mixtures thereof,

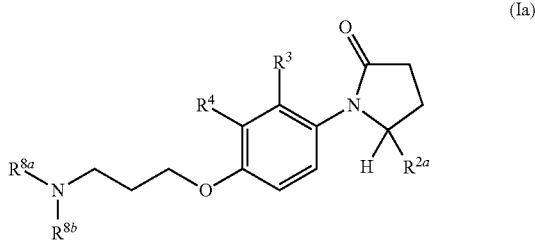

(Ia)

wherein
$R^{2a}$ is hydrogen, aryl, $C_{1-6}$ alkoxy, amino, $C_{1-6}$ alkyl, $C_{2-6}$ alkenyl, heteroaryl, $C_{3-8}$ cycloalkyl, 3-8-membered heterocycloalkyl, acyl, $C_{1-6}$-alkyl aryl, $C_{1-6}$-alkyl heteroaryl, $C_{1-6}$-alkyl cycloalkyl, $C_{1-6}$-alkyl heterocycloalkyl, carboxy, alkoxycarbonyl, aminocarbonyl, $C_{1-6}$-alkyl carboxy, $C_{1-6}$-alkyl acyl, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{1-6}$-alkyl ureido, $C_{1-6}$-alkyl carbamate, $C_{1-6}$-alkyl amino, $C_{3-8}$-cycloalkyl amino, hydroxy, $C_{1-6}$ alkyl hydroxy, halogen or cyano;
$R^3$ is hydrogen, halogen, $C_{1-4}$ alkyl or $C_{1-4}$ alkoxy;
$R^4$ is hydrogen, halogen, $C_{1-4}$ alkyl or $C_{1-4}$ alkoxy;
$R^{8a}$ and $R^{8b}$ are linked together to form with N a 3 to 8 membered heterocycloalkyl.

In another particular aspect, the present invention the present invention relates to compounds of formula (Ib) geometrical isomers, enantiomers, diastereoisomers, pharmaceutically acceptable salts and all possible mixtures thereof,

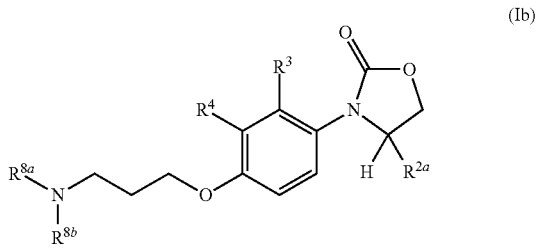

(Ib)

wherein
$R^{2a}$ is hydrogen, aryl, $C_{1-6}$ alkoxy, amino, $C_{1-6}$ alkyl, $C_{2-6}$ alkenyl, heteroaryl, $C_{3-8}$ cycloalkyl, 3-8-membered heterocycloalkyl, acyl, $C_{1-6}$-alkyl aryl, $C_{1-6}$-alkyl heteroaryl, $C_{1-6}$-alkyl cycloalkyl, $C_{1-6}$-alkyl heterocycloalkyl, carboxy, alkoxycarbonyl, aminocarbonyl, $C_{1-6}$-alkyl carboxy, $C_{1-6}$-alkyl acyl, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{1-6}$-alkyl ureido, $C_{1-6}$-alkyl carbamate, $C_{1-6}$-alkyl amino, $C_{3-8}$-cycloalkyl amino, hydroxy, $C_{1-6}$ alkyl hydroxy, halogen or cyano;
$R^3$ is hydrogen, halogen, $C_{1-4}$ alkyl or $C_{1-4}$ alkoxy;
$R^4$ is hydrogen, halogen, $C_{1-4}$ alkyl or $C_{1-4}$ alkoxy;
$R^{8a}$ and $R^{8b}$ are linked together to form with N a 3 to 8 membered heterocycloalkyl.

In a further particular aspect, the present invention relates to compounds of formula (Ia) and (Ib) as defined here above wherein
$R^{2a}$ is hydrogen; $C_{1-6}$ alkyl; aryl; $C_{1-6}$-alkyl alkoxy; $C_{1-6}$-alkyl hydroxy or $C_{1-6}$-alkyl aryl; or —$(CH_2)_r$—$NR^{6a}R^{6b}$;
$R^3$ is hydrogen, halogen or $C_{1-4}$ alkoxy;
$R^4$ is hydrogen, $C_{1-4}$ alkyl, $C_{1-4}$ alkoxy or halogen;
$R^{6a}$ is hydrogen, $C_{1-8}$ alkyl, $C_{1-6}$-alkyl cycloalkyl, $C_{3-8}$ cycloalkyl, acyl, aryl or $C_{1-6}$-alkyl aryl;
$R^{6b}$ is hydrogen, $C_{1-4}$ alkyl, $C_{1-6}$-alkyl cycloalkyl or $C_{1-6}$-alkyl aryl;
or $R^{6a}$ and $R^{6b}$ are linked together to form a $C_{3-6}$ alkylene, each methylene of the alkylene being optionally substituted by one or two halogen, or by one or two $C_{1-4}$ alkyl, optionally linked together to form with the carbon to which they are attached a $C_{3-8}$ cycloalkyl; or one methylene thereof being linked to a second methylene thereof to form a $C_{3-6}$ alkylene; or one methylene being optionally replaced by sulfur dioxide, an oxygen, a sulfur or a nitrogen atom, said nitrogen atom being optionally substituted by a $C_{1-8}$ alkyl or $C_{3-8}$ cycloalkyl;
$R^{8a}$ and $R^{8b}$ are linked together to form a $C_{3-6}$ alkylene, each methylene of the alkylene being optionally substituted by one or two $C_{1-4}$ alkyl optionally linked together to form with the carbon to which they are attached a $C_{3-8}$ cycloalkyl, by $C_{1-6}$-alkyl hydroxy, $C_{1-6}$-alkyl heterocycloalkyl, by aryl or by $C_{1-6}$-alkyl aryl; or one methylene thereof being linked to a second methylene thereof to form a $C_{3-6}$ alkylene; or one methylene of the alkylene being optionally replaced by a nitrogen, said nitrogen being substituted by a $C_{1-4}$ alkyl or $C_{3-8}$ cycloalkyl;
r is an integer equal to 1 or 2.

Particular embodiments described here above for $R^{2a}$, $R^3$, $R^4$, $R^{6a}$, $R^{6b}$, r, $R^{8a}$ and $R^{8b}$ in compounds of formula (I) also apply to $R^{2a}$, $R^3$, $R^4$, $R^{6a}$, $R^{6b}$, r, $R^{8a}$ and $R^{8b}$ in compounds of formula (Ia) and (Ib).

Examples of compounds according to the present invention are:
(5S)-5-{[(cyclohexylmethyl)amino]methyl}-1-{4-[3-(2-methylpyrrolidin-1-yl)propoxy]phenyl}pyrrolidin-2-one;
(5S)-5-{[(cyclohexylmethyl)amino]methyl}-1-[4-(3-piperidin-1-ylpropoxy)phenyl]pyrrolidin-2-one;
(5S)-5-{[(cyclohexylmethyl)(cyclopropylmethyl)amino] methyl}-1-{4-[3-(2-methylpyrrolidin-1-yl)propoxy] phenyl}pyrrolidin-2-one;
(5S)-5-{[(cyclopropylmethyl)(propyl)amino]methyl}-1-[4-(3-piperidin-1-ylpropoxy)phenyl]pyrrolidin-2-one;
(5S)-5-{[(cyclopropylmethyl)(propyl)amino]methyl}-1-{4-[3-(2-methylpyrrolidin-1-yl)propoxy]phenyl}pyrrolidin-2-one;
(5S)-5-[(cyclobutylamino)methyl]-1-[4-(3-piperidin-1-ylpropoxy)phenyl]pyrrolidin-2-one;
(5S)-5-[(cyclobutylamino)methyl]-1-{4-[3-(2-methylpyrrolidin-1-yl)propoxy]phenyl}pyrrolidin-2-one;
(5S)-5-[(cyclohexylamino)methyl]-1-{4-[3-(2-methylpyrrolidin-1-yl)propoxy]phenyl}pyrrolidin-2-one;
(5S)-5-[(cyclohexylamino)methyl]-1-[4-(3-piperidin-1-ylpropoxy)phenyl]pyrrolidin-2-one;
(5S)-5-[(cyclopentylamino)methyl]-1-{4-[3-(2-methylpyrrolidin-1-yl)propoxy]phenyl}pyrrolidin-2-one;
(5S)-5-[(cyclopentylamino)methyl]-1-[4-(3-piperidin-1-ylpropoxy)phenyl]pyrrolidin-2-one;
(5S)-5-[(diethylamino)methyl]-1-{4-[3-(2-methylpyrrolidin-1-yl)propoxy]phenyl}pyrrolidin-2-one;

(5S)-5-(anilinomethyl)-1-{4-[3-(2-methylpyrrolidin-1-yl)propoxy]phenyl}pyrrolidin-2-one;
(5S)-5-(anilinomethyl)-1-[4-(3-piperidin-1-ylpropoxy)phenyl]pyrrolidin-2-one;
(5S)-5-{[(4-fluorobenzyl)amino]methyl}-1-{4-[3-(2-methylpyrrolidin-1-yl)propoxy]phenyl}pyrrolidin-2-one;
(5S)-5-{[(4-fluorobenzyl)amino]methyl}-1-[4-(3-piperidin-1-ylpropoxy)phenyl]pyrrolidin-2-one;
(5S)-5-{[(4-fluorophenyl)amino]methyl}-1-[4-(3-piperidin-1-ylpropoxy)phenyl]pyrrolidin-2-one;
(5S)-5-{[(4-fluorophenyl)amino]methyl}-1-{4-[3-(2-methylpyrrolidin-1-yl)propoxy]phenyl}pyrrolidin-2-one;
(5S)-5-(azepan-1-ylmethyl)-1-{4-[3-(2-methylpyrrolidin-1-yl)propoxy]phenyl}pyrrolidin-2-one;
(5S)-5-(azepan-1-ylmethyl)-1-{4-[3-(2-methylpyrrolidin-1-yl)propoxy]phenyl}pyrrolidine-2-thione;
(4R)-4-benzyl-3-{4-[3-(2-methylpyrrolidin-1-yl)propoxy]phenyl}-1,3-oxazolidin-2-one;
1-{4-[3-(2-methylpiperidin-1-yl)propoxy]phenyl}pyrrolidin-2-one;
1-{4-[3-(2-methylpyrrolidin-1-yl)propoxy]phenyl}pyrrolidin-2-one;
1-{4-[3-(2-methylpyrrolidin-1-yl)propoxy]phenyl}piperidin-2-one;
1-{4-[3-(2-methylpyrrolidin-1-yl)propoxy]phenyl}azepan-2-one;
(5S)-5-(hydroxymethyl)-1-[4-(3-piperidin-1-ylpropoxy)phenyl]pyrrolidin-2-one;
(5S)-5-(hydroxymethyl)-1-{4-[3-(2-methylpyrrolidin-1-yl)propoxy]phenyl}pyrrolidin-2-one;
(4R)-4-isopropyl-3-{4-[3-(2-methylpyrrolidin-1-yl)propoxy]phenyl}-1,3-oxazolidin-2-one;
(5S)-1-{4-[3-(2-methylpyrrolidin-1-yl)propoxy]phenyl}-5-(morpholin-4-ylmethyl)pyrrolidin-2-one;
(5S)-1-{4-[3-(2-methylpyrrolidin-1-yl)propoxy]phenyl}-5-(morpholin-4-ylmethyl)pyrrolidin-2-one;
(4R)-1-{4-[3-(2-methylpiperidin-1-yl)propoxy]phenyl}-4-propylpyrrolidin-2-one;
(4S)-1-{4-[3-(2-methylpiperidin-1-yl)propoxy]phenyl}-4-propylpyrrolidin-2-one;
(4R)-1-[4-(3-piperidin-1-ylpropoxy)phenyl]-4-propylpyrrolidin-2-one;
1-{4-[3-(4-isopropylpiperazin-1-yl)propoxy]phenyl}-4-propylpyrrolidin-2-one;
4-(4-chlorophenyl)-3,3-dimethyl-1-[4-(3-piperidin-1-ylpropoxy)phenyl]pyrrolidin-2-one;
4-(4-chlorophenyl)-1-[4-(3-piperidin-1-ylpropoxy)phenyl]pyrrolidin-2-one;
5-(4-chlorophenyl)-1-[4-(3-piperidin-1-ylpropoxy)phenyl]piperidin-2-one;
4-(4-chlorophenyl)-1-{4-[3-(4-isopropylpiperazin-1-yl)propoxy]phenyl}pyrrolidin-2-one;
5-(4-chlorophenyl)-1-{4-[3-(4-isopropylpiperazin-1-yl)propoxy]phenyl}piperidin-2-one;
(5S)-5-{[4-(cyclohexylmethyl)piperazin-1-yl]methyl}-1-[4-(3-piperidin-1-ylpropoxy)phenyl]pyrrolidin-2-one;
(5S)-5-[(4-cyclopentylpiperazin-1-yl)methyl]-1-{4-[3-(2-methylpyrrolidin-1-yl)propoxy]phenyl}pyrrolidin-2-one;
(5S)-5-[(4-cyclopentylpiperazin-1-yl)methyl]-1-[4-(3-piperidin-1-ylpropoxy)phenyl]pyrrolidin-2-one;
4-[(4-cyclopentylpiperazin-1-yl)methyl]-1-{4-[3-(2-methylpyrrolidin-1-yl)propoxy]phenyl}pyrrolidin-2-one;
4-[2-(4-cyclopentylpiperazin-1-yl)ethyl]-1-{4-[3-(2-methylpyrrolidin-1-yl)propoxy]phenyl}pyrrolidin-2-one;
(5S)-5-[(4-isopropylpiperazin-1-yl)methyl]-1-{4-[3-(2-methylpyrrolidin-1-yl)propoxy]phenyl}pyrrolidin-2-one;
1-{4-[3-(2-methylpyrrolidin-1-yl)propoxy]phenyl}-4-(2-piperidin-1-ylethyl)pyrrolidin-2-one;
(5S)-1-{4-[3-(2-methylpyrrolidin-1-yl)propoxy]phenyl}-5-(piperidin-1-ylmethyl)pyrrolidin-2-one;
(5S)-5-(piperidin-1-ylmethyl)-1-[4-(3-piperidin-1-ylpropoxy)phenyl]pyrrolidin-2-one;
(4S)-4-(piperidin-1-ylmethyl)-1-[4-(3-piperidin-1-ylpropoxy)phenyl]azetidin-2-one;
(5S)-1-[4-(2-piperidin-1-ylethoxy)phenyl]-5-(piperidin-1-ylmethyl)pyrrolidin-2-one;
(5S)-1-{4-[2-(2-methylpyrrolidin-1-yl)ethoxy]phenyl}-5-(piperidin-1-ylmethyl)pyrrolidin-2-one;
(5R)-5-(piperidin-1-ylmethyl)-1-[4-(3-piperidin-1-ylpropoxy)phenyl]pyrrolidin-2-one;
(5S)-1-{3-[3-(2-methylpyrrolidin-1-yl)propoxy]phenyl}-5-(piperidin-1-ylmethyl)pyrrolidin-2-one;
(5S)-1-{4-[3-(4-cyclopentylpiperazin-1-yl)propoxy]phenyl}-5-(piperidin-1-ylmethyl)pyrrolidin-2-one;
(5S)-5-[(2,6-dimethylpiperidin-1-yl)methyl]-1-[4-(3-piperidin-1-ylpropoxy)phenyl]pyrrolidin-2-one;
(5S)-5-[(2,6-dimethylpiperidin-1-yl)methyl]-1-{4-[3-(2-methylpyrrolidin-1-yl)propoxy]phenyl}pyrrolidin-2-one;
(5S)-5-[(2-methylpiperidin-1-yl)methyl]-1-[4-(3-piperidin-1-ylpropoxy)phenyl]pyrrolidin-2-one;
(5S)-5-[(2-methylpiperidin-1-yl)methyl]-1-{4-[3-(2-methylpyrrolidin-1-yl)propoxy]phenyl}pyrrolidin-2-one;
(5S)-5-[(4-methylpiperidin-1-yl)methyl]-1-{4-[3-(2-methylpyrrolidin-1-yl)propoxy]phenyl}pyrrolidin-2-one;
(5S)-5-[(4-methylpiperidin-1-yl)methyl]-1-[4-(3-piperidin-1-ylpropoxy)phenyl]pyrrolidin-2-one;
(5S)-1-{4-[3-(2-methylpyrrolidin-1-yl)propoxy]phenyl}-5-(pyrrolidin-1-ylmethyl)pyrrolidin-2-one;
(5S)-1-{4-[3-((2S)-2-methylpyrrolidin-1-yl)propoxy]phenyl}-5-(pyrrolidin-1-ylmethyl)pyrrolidin-2-one;
(5S)-1-{4-[3-((2R)-2-methylpyrrolidin-1-yl)propoxy]phenyl}-5-(pyrrolidin-1-ylmethyl)pyrrolidin-2-one;
(5S)-1-[4-(3-piperidin-1-ylpropoxy)phenyl]-5-(pyrrolidin-1-ylmethyl)pyrrolidin-2-one;
(5S)-1-{4-[3-(4-isopropylpiperazin-1-yl)propoxy]phenyl}-5-(pyrrolidin-1-ylmethyl)pyrrolidin-2-one;
(5S)-5-[(2-methylpyrrolidin-1-yl)methyl]-1-[4-(3-piperidin-1-ylpropoxy)phenyl]pyrrolidin-2-one;
(−)-(5S)-5-[(2-methylpyrrolidin-1-yl)methyl]-1-[4-(3-piperidin-1-ylpropoxy)phenyl]pyrrolidin-2-one;
(+)-(5S)-5-[(2-methylpyrrolidin-1-yl)methyl]-1-[4-(3-piperidin-1-ylpropoxy)phenyl]pyrrolidin-2-one;
2-{4-[3-(2-methylpiperidin-1-yl)propoxy]phenyl}-2-azaspiro[4.5]decan-3-one;
7-benzyl-2-{4-[3-(2-methylpyrrolidin-1-yl)propoxy]phenyl}-2,7-diazaspiro[4.4]nonan-3-one;
4-(hydroxymethyl)-1-{4-[3-(2-methylpyrrolidin-1-yl)propoxy]phenyl}pyrrolidin-2-one;
4-(2-hydroxyethyl)-1-{4-[3-(2-methylpyrrolidin-1-yl)propoxy]phenyl}pyrrolidin-2-one;
(5S)-5-[(4aR,8aS)-octahydroisoquinolin-2(1H)-ylmethyl]-1-[4-(3-piperidin-1-ylpropoxy)phenyl]pyrrolidin-2-one;
(5S)-5-[(4aR,8aS)-octahydroisoquinolin-2(1H)-ylmethyl]-1-{4-[3-(2-methylpyrrolidin-1-yl)propoxy]phenyl}pyrrolidin-2-one;
7-acetyl-2-{4-[3-(2-methylpyrrolidin-1-yl)propoxy]phenyl}-2,7-diazaspiro[4.4]nonan-3-one;
N-(cyclohexylmethyl)-N-[((2S)-1-{4-[3-(2-methylpyrrolidin-1-yl)propoxy]phenyl}-5-oxopyrrolidin-2-yl)methyl]cyclopropanecarboxamide;
(5S)-5-(morpholin-4-ylmethyl)-1-(4-{3-[(2S)-2-(pyrrolidin-1-ylmethyl)pyrrolidin-1-yl]propoxy}phenyl)pyrrolidin-2-one;

(5S)-1-(4-{3-[(2R)-2-methylpyrrolidin-1-yl]
  propoxy}phenyl)-5-(pyrrolidin-1-ylmethyl)pyrrolidin-2-
  one;
(5S)-5-{[(2-fluorophenyl)amino]methyl}-1-{4-[3-(2-meth-
  ylpyrrolidin-1-yl)propoxy]phenyl}pyrrolidin-2-one;
(5S)-5-{[(3-fluorophenyl)amino]methyl}-1-{4-[3-(2-meth-
  ylpyrrolidin-1-yl)propoxy]phenyl}pyrrolidin-2-one;
(5S)-5-{[(2,4-difluorophenyl)amino]methyl}-1-{4-[3-(2-
  methylpyrrolidin-1-yl)propoxy]phenyl}pyrrolidin-2-one;
(5S)-5-{[(3-methoxyphenyl)amino]methyl}-1-{4-[3-(2-me-
  thylpyrrolidin-1-yl)propoxy]phenyl}pyrrolidin-2-one;
(5S)-1-{4-[3-(2-methylpyrrolidin-1-yl)propoxy]phenyl}-5-
  ({[4-(trifluoromethyl)phenyl]amino}methyl)pyrrolidin-
  2-one;
3-{4-[3-(2-methylpyrrolidin-1-yl)propoxy]phenyl}-4-(pyr-
  rolidin-1-ylmethyl)-1,3-oxazolidin-2-one;
(5S)-1-{4-[3-(2-methylpyrrolidin-1-yl)propoxy]phenyl}-5-
  (piperidin-1-ylmethyl)pyrrolidine-2-thione;
(5S)-5-[(4-fluorophenoxy)methyl]-1-{4-[3-(2-methylpyrro-
  lidin-1-yl)propoxy]phenyl}pyrrolidin-2-one;
(5S)-5-{[(4-methylphenyl)amino]methyl}-1-{4-[3-(2-meth-
  ylpyrrolidin-1-yl)propoxy]phenyl}pyrrolidin-2-one;
(5S)-5-{[(3,4-difluorophenyl)amino]methyl}-1-{4-[3-(2-
  methylpyrrolidin-1-yl)propoxy]phenyl}pyrrolidin-2-one;
(5S)-5-[(2,6-dimethylmorpholin-4-yl)methyl]-1-{4-[3-(2-
  methylpyrrolidin-1-yl)propoxy]phenyl}pyrrolidin-2-one;
(5S)-1-{4-[3-(2-methylpyrrolidin-1-yl)propoxy]phenyl}-5-
  (thiomorpholin-4-ylmethyl)pyrrolidin-2-one;
(5S)-5-{[(3,5-difluorophenyl)amino]methyl}-1-{4-[3-(2-
  methylpyrrolidin-1-yl)propoxy]phenyl}pyrrolidin-2-one;
(5S)-5-[(4,4-difluoropiperidin-1-yl)methyl]-1-{4-[3-(2-me-
  thylpyrrolidin-1-yl)propoxy]phenyl}pyrrolidin-2-one;
(5S)-1-{4-[3-(2-methylpyrrolidin-1-yl)propoxy]phenyl}-5-
  {[(2,2,2-trifluoroethyl)amino]methyl}pyrrolidin-2-one;
(5S)-5-[(3,4-difluorophenoxy)methyl]-1-{4-[3-(2-meth-
  ylpyrrolidin-1-yl)propoxy]phenyl}pyrrolidin-2-one;
(5S)-5-[(1,3-benzodioxol-5-ylamino)methyl]-1-{4-[3-(2-
  methylpyrrolidin-1-yl)propoxy]phenyl}pyrrolidin-2-one;
(5S)-5-{[(4-fluorophenyl)(methyl)amino]methyl}-1-{4-[3-
  (2-methylpyrrolidin-1-yl)propoxy]phenyl}pyrrolidin-2-
  one;
4-(4-chlorobenzyl)-3-{4-[3-(2-methylpyrrolidin-1-yl)pro-
  poxy]phenyl}-1,3-oxazolidin-2-one;
(4R)-4-(cyclohexylmethyl)-3-{4-[3-(2-methylpyrrolidin-1-
  yl)propoxy]phenyl}-1,3-oxazolidin-2-one;
(5S)-5-{[cis-2,6-dimethylmorpholin-4-yl]methyl}-1-{4-[3-
  (2-methylpyrrolidin-1-yl)propoxy]phenyl}pyrrolidin-2-
  one;
(4R)-4-{[cis-2,6-dimethylmorpholin-4-yl]methyl}-3-{4-[3-
  (2-methylpyrrolidin-1-yl)propoxy]phenyl}-1,3-oxazoli-
  din-2-one;
(5S)-5-[(1,1-dioxidothiomorpholin-4-yl)methyl]-1-{4-[3-
  (2-methylpyrrolidin-1-yl)propoxy]phenyl}pyrrolidin-2-
  one;
(4R)-3-{4-[3-(2-methylpyrrolidin-1-yl)propoxy]phenyl}-4-
  (piperidin-1-ylmethyl)-1,3-oxazolidin-2-one;
(4R)-4-[(4,4-difluoropiperidin-1-yl)methyl]-3-{4-[3-(2-me-
  thylpyrrolidin-1-yl)propoxy]phenyl}-1,3-oxazolidin-2-
  one;
(4R)-3-{4-[3-(2-methylpyrrolidin-1-yl)propoxy]phenyl}-4-
  phenyl-1,3-oxazolidin-2-one;
(4R)-4-{[(3,4-difluorophenyl)amino]methyl}-3-{4-[3-(2-
  methylpyrrolidin-1-yl)propoxy]phenyl}-1,3-oxazolidin-
  2-one;
(5S)-5-[(4aR,8aS)-octahydroisoquinolin-2(1H)-ylmethyl]-
  1-{4-[3-(1-azaspiro[4.4]non-1-yl)propoxy]
  phenyl}pyrrolidin-2-one;
(5S)-1-{4-[4-(2-methylpyrrolidin-1-yl)butoxy]phenyl}-5-
  (piperidin-1-ylmethyl)pyrrolidin-2-one;
(5S)-3,3-dimethyl-1-{4-[3-(2-methylpyrrolidin-1-yl)pro-
  poxy]phenyl}-5-(piperidin-1-ylmethyl)pyrrolidin-2-one;
(5S)-5-[(cis-2,6-dimethylmorpholin-4-yl)methyl]-3,3-dim-
  ethyl-1-{4-[3-(2-methylpyrrolidin-1-yl)propoxy]
  phenyl}pyrrolidin-2-one;
(5S)-5-[(4,4-difluoropiperidin-1-yl)methyl]-3,3-dimethyl-1-
  {4-[3-(2-methylpyrrolidin-1-yl)propoxy]
  phenyl}pyrrolidin-2-one;
(5S)-5-[(dibenzylamino)methyl]-1-{4-[3-(2-methylpyrroli-
  din-1-yl)propoxy]phenyl}pyrrolidin-2-one;
(5S)-5-(aminomethyl)-1-{4-[3-(2-methylpyrrolidin-1-yl)
  propoxy]phenyl}pyrrolidin-2-one;
N-[((2S)-1-{4-[3-(2-methylpyrrolidin-1-yl)propoxy]phe-
  nyl}-5-oxopyrrolidin-2-yl)methyl]acetamide;
1-{4-[3-(4-methylpiperidin-1-yl)propoxy]phenyl}-5-(pip-
  eridin-1-ylmethyl)pyrrolidin-2-one;
1-{4-[3-(3,5-dimethylpiperidin-1-yl)propoxy]phenyl}-5-
  (piperidin-1-ylmethyl)pyrrolidin-2-one;
1-[4-(3-octahydroquinolin-1(2H)-ylpropoxy)phenyl]-5-(pi-
  peridin-1-ylmethyl)pyrrolidin-2-one;
1-{4-[3-(3,5-dimethylpiperidin-1-yl)propoxy]-3-fluorophe-
  nyl}-5-(piperidin-1-ylmethyl)pyrrolidin-2-one;
1-{4-[3-(2-azaspiro[5.5]undec-2-yl)propoxy]-3-fluorophe-
  nyl}-5-(piperidin-1-ylmethyl)pyrrolidin-2-one;
1-{4-[3-(3,5-dimethylpiperidin-1-yl)propoxy]-2-fluorophe-
  nyl}-5-(piperidin-1-ylmethyl)pyrrolidin-2-one;
1-{3,5-difluoro-4-[3-(4-methylpiperidin-1-yl)propoxy]phe-
  nyl}-5-(piperidin-1-ylmethyl)pyrrolidin-2-one;
1-{4-[3-(2-azaspiro[5.5]undec-2-yl)propoxy]-3,5-difluo-
  rophenyl}-5-(piperidin-1-ylmethyl)pyrrolidin-2-one;
1-{4-[3-(3,5-dimethylpiperidin-1-yl)propoxy]-3-meth-
  ylphenyl}-5-(piperidin-1-ylmethyl)pyrrolidin-2-one;
1-{4-[3-(4-benzylpiperidin-1-yl)propoxy]phenyl}-5-(pip-
  eridin-1-ylmethyl)pyrrolidin-2-one;
1-{3-fluoro-4-[3-(3-phenylpiperidin-1-yl)propoxy]phenyl}-
  5-(piperidin-1-ylmethyl)pyrrolidin-2-one;
1-{4-[3-(1-azaspiro[4.4]non-1-yl)propoxy]phenyl}-5-(pip-
  eridin-1-ylmethyl)pyrrolidin-2-one;
1-{3-fluoro-4-[3-(2-methylpyrrolidin-1-yl)propoxy]phe-
  nyl}-5-(piperidin-1-ylmethyl)pyrrolidin-2-one;
1-{4-[3-(1-azaspiro[4.4]non-1-yl)propoxy]-3-fluorophe-
  nyl}-5-(piperidin-1-ylmethyl)pyrrolidin-2-one;
1-{3,5-difluoro-4-[3-(2-methylpyrrolidin-1-yl)propoxy]
  phenyl}-5-(piperidin-1-ylmethyl)pyrrolidin-2-one;
1-{3-methyl-4-[3-(2-methylpyrrolidin-1-yl)propoxy]phe-
  nyl}-5-(piperidin-1-ylmethyl)pyrrolidin-2-one;
1-{4-[3-(1-azaspiro[4.4]non-1-yl)propoxy]-3-methylphe-
  nyl}-5-(piperidin-1-ylmethyl)pyrrolidin-2-one;
1-(4-{3-[2-(hydroxymethyl)pyrrolidin-1-yl]propoxy}-3-
  methylphenyl)-5-(piperidin-1-ylmethyl)pyrrolidin-2-one;
1-[4-(3-azepan-1-ylpropoxy)phenyl]-5-(piperidin-1-ylm-
  ethyl)pyrrolidin-2-one;
1-[4-(3-azepan-1-ylpropoxy)-3-fluorophenyl]-5-(piperidin-
  1-ylmethyl)pyrrolidin-2-one;
1-[4-(3-azocan-1-ylpropoxy)-3-fluorophenyl]-5-(piperidin-
  1-ylmethyl)pyrrolidin-2-one;
1-[4-(3-azepan-1-ylpropoxy)-2-methoxyphenyl]-5-(piperi-
  din-1-ylmethyl)pyrrolidin-2-one;
5-[(4,4-difluoropiperidin-1-yl)methyl]-1-{4-[3-(3,5-dimeth-
  ylpiperidin-1-yl)propoxy]phenyl}pyrrolidin-2-one;
5-[(4,4-difluoropiperidin-1-yl)methyl]-1-{4-[3-(3,5-dimeth-
  ylpiperidin-1-yl)propoxy]-3-methylphenyl}pyrrolidin-2-
  one;

5-[(4,4-difluoropiperidin-1-yl)methyl]-1-{3-methyl-4-[3-(2-methylpyrrolidin-1-yl)propoxy]phenyl}pyrrolidin-2-one; and (5S)-1-{6-[3-(2-methylpyrrolidin-1-yl)propoxy]pyridin-3-yl}-5-(piperidin-1-ylmethyl)pyrrolidin-2-one.

Advantageously, the present invention relates to a compound of formula (I) selected from the groups consisting of:

(5S)-5-{[(cyclohexylmethyl)amino]methyl}-1-{4-[3-(2-methylpyrrolidin-1-yl)propoxy]phenyl}pyrrolidin-2-one;

(5S)-5-{[(cyclopropylmethyl)(propyl)amino]methyl}-1-[4-(3-piperidin-1-ylpropoxy)phenyl]pyrrolidin-2-one;

(5S)-5-[(cyclobutylamino)methyl]-1-{4-[3-(2-methylpyrrolidin-1-yl)propoxy]phenyl}pyrrolidin-2-one;

(5S)-5-[(cyclopentylamino)methyl]-1-{4-[3-(2-methylpyrrolidin-1-yl)propoxy]phenyl}pyrrolidin-2-one;

(5S)-5-[(cyclopentylamino)methyl]-1-[4-(3-piperidin-1-ylpropoxy)phenyl]pyrrolidin-2-one;

(5S)-5-[(diethylamino)methyl]-1-{4-[3-(2-methylpyrrolidin-1-yl)propoxy]phenyl}pyrrolidin-2-one;

(5S)-5-(anilinomethyl)-1-{4-[3-(2-methylpyrrolidin-1-yl)propoxy]phenyl}pyrrolidin-2-one;

(5S)-5-{[(4-fluorophenyl)amino]methyl}-1-{4-[3-(2-methylpyrrolidin-1-yl)propoxy]phenyl}pyrrolidin-2-one;

(5S)-5-(azepan-1-ylmethyl)-1-{4-[3-(2-methylpyrrolidin-1-yl)propoxy]phenyl}pyrrolidin-2-one;

(4R)-4-benzyl-3-{4-[3-(2-methylpyrrolidin-1-yl)propoxy]phenyl}-1,3-oxazolidin-2-one;

(5S)-1-{4-[3-(2-methylpyrrolidin-1-yl)propoxy]phenyl}-5-(morpholin-4-ylmethyl)pyrrolidin-2-one;

(5S)-5-[(4-isopropylpiperazin-1-yl)methyl]-1-{4-[3-(2-methylpyrrolidin-1-yl)propoxy]phenyl}pyrrolidin-2-one;

(5S)-1-{4-[3-(2-methylpyrrolidin-1-yl)propoxy]phenyl}-5-(piperidin-1-ylmethyl)pyrrolidin-2-one;

(5S)-5-(piperidin-1-ylmethyl)-1-[4-(3-piperidin-1-ylpropoxy)phenyl]pyrrolidin-2-one;

(5S)-5-[(2,6-dimethylpiperidin-1-yl)methyl]-1-[4-(3-piperidin-1-ylpropoxy)phenyl]pyrrolidin-2-one;

(5S)-5-[(2,6-dimethylpiperidin-1-yl)methyl]-1-{4-[3-(2-methylpyrrolidin-1-yl)propoxy]phenyl}pyrrolidin-2-one;

(5S)-5-[(2-methylpiperidin-1-yl)methyl]-1-[4-(3-piperidin-1-ylpropoxy)phenyl]pyrrolidin-2-one;

(5S)-5-[(2-methylpiperidin-1-yl)methyl]-1-{4-[3-(2-methylpyrrolidin-1-yl)propoxy]phenyl}pyrrolidin-2-one;

(5S)-5-[(4-methylpiperidin-1-yl)methyl]-1-{4-[3-(2-methylpyrrolidin-1-yl)propoxy]phenyl}pyrrolidin-2-one;

(5S)-5-[(4-methylpiperidin-1-yl)methyl]-1-[4-(3-piperidin-1-ylpropoxy)phenyl]pyrrolidin-2-one;

(5S)-1-{4-[3-(2-methylpyrrolidin-1-yl)propoxy]phenyl}-5-(pyrrolidin-1-ylmethyl)pyrrolidin-2-one;

(5S)-1-{4-[3-((2R)-2-methylpyrrolidin-1-yl)propoxy]phenyl}-5-(pyrrolidin-1-ylmethyl)pyrrolidin-2-one;

(5S)-1-{4-[3-((2S)-2-methylpyrrolidin-1-yl)propoxy]phenyl}-5-(pyrrolidin-1-ylmethyl)pyrrolidin-2-one;

(5S)-1-[4-(3-piperidin-1-ylpropoxy)phenyl]-5-(pyrrolidin-1-ylmethyl)pyrrolidin-2-one;

(+)-(5S)-5-[(2-methylpyrrolidin-1-yl)methyl]-1-[4-(3-piperidin-1-ylpropoxy)phenyl]pyrrolidin-2-one;

(5S)-1-(4-{3-[(2R)-2-methylpyrrolidin-1-yl]propoxy}phenyl)-5-(pyrrolidin-1-ylmethyl)pyrrolidin-2-one;

(5S)-5-{[(2,4-difluorophenyl)amino]methyl}-1-{4-[3-(2-methylpyrrolidin-1-yl)propoxy]phenyl}pyrrolidin-2-one;

3-{4-[3-(2-methylpyrrolidin-1-yl)propoxy]phenyl}-4-(pyrrolidin-1-ylmethyl)-1,3-oxazolidin-2-one;

(5S)-5-{[(3,4-difluorophenyl)amino]methyl}-1-{4-[3-(2-methylpyrrolidin-1-yl)propoxy]phenyl}pyrrolidin-2-one;

(5S)-1-{4-[3-(2-methylpyrrolidin-1-yl)propoxy]phenyl}-5-(thiomorpholin-4-ylmethyl)pyrrolidin-2-one;

(5S)-5-[(4,4-difluoropiperidin-1-yl)methyl]-1-{4-[3-(2-methylpyrrolidin-1-yl)propoxy]phenyl}pyrrolidin-2-one;

(5S)-5-[(3,4-difluorophenoxy)methyl]-1-{4-[3-(2-methylpyrrolidin-1-yl)propoxy]phenyl}pyrrolidin-2-one;

(4R)-4-(cyclohexylmethyl)-3-{4-[3-(2-methylpyrrolidin-1-yl)propoxy]phenyl}-1,3-oxazolidin-2-one;

(4R)-4-{[(2R,6S)cis-2,6-dimethylmorpholin-4-yl]methyl}-3-{4-[3-(2-methylpyrrolidin-1-yl)propoxy]phenyl}-1,3-oxazolidin-2-one;

(5S)-5-[(1,1-dioxidothiomorpholin-4-yl)methyl]-1-{4-[3-(2-methylpyrrolidin-1-yl)propoxy]phenyl}pyrrolidin-2-one;

(4R)-3-{4-[3-(2-methylpyrrolidin-1-yl)propoxy]phenyl}-4-(piperidin-1-ylmethyl)-1,3-oxazolidin-2-one;

(4R)-4-[(4,4-difluoropiperidin-1-yl)methyl]-3-{4-[3-(2-methylpyrrolidin-1-yl)propoxy]phenyl}-1,3-oxazolidin-2-one;

(4R)-4-{[(3,4-difluorophenyl)amino]methyl}-3-{4-[3-(2-methylpyrrolidin-1-yl)propoxy]phenyl}-1,3-oxazolidin-2-one;

(5S)-1-{4-[4-(2-methylpyrrolidin-1-yl)butoxy]phenyl}-5-(piperidin-1-ylmethyl)pyrrolidin-2-one;

(5S)-3,3-dimethyl-1-{4-[3-(2-methylpyrrolidin-1-yl)propoxy]phenyl}-5-(piperidin-1-ylmethyl)pyrrolidin-2-one;

(5S)-5-[(4,4-difluoropiperidin-1-yl)methyl]-3,3-dimethyl-1-{4-[3-(2-methylpyrrolidin-1-yl)propoxy]phenyl}pyrrolidin-2-one;

1-{4-[3-(3,5-dimethylpiperidin-1-yl)propoxy]phenyl}-5-(piperidin-1-ylmethyl)pyrrolidin-2-one;

1-{3,5-difluoro-4-[3-(2-methylpyrrolidin-1-yl)propoxy]phenyl}-5-(piperidin-1-ylmethyl)pyrrolidin-2-one;

1-[4-(3-azepan-1-ylpropoxy)phenyl]-5-(piperidin-1-ylmethyl)pyrrolidin-2-one; and (5S)-1-{6-[3-(2-methylpyrrolidin-1-yl)propoxy]pyridin-3-yl}-5-(piperidin-1-ylmethyl)pyrrolidin-2-one.

The "pharmaceutically acceptable salts" according to the invention include therapeutically active, non-toxic acid salt forms which the compounds of formula (I) are able to form.

The acid addition salt form of a compound of formula (I) that occurs in its free form as a base can be obtained by treating the free base with an appropriate acid such as an inorganic acid, for example, a hydrochloric, hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic, and the like.

Conversely said salt forms can be converted into the free forms by treatment with an appropriate base.

Compounds of the formula (I) and their salts can be in the form of a solvate, which is included within the scope of the present invention. Such solvates include for example hydrates, alcoholates and the like.

Many of the compounds of formula (I) and some of their intermediates have at least one stereogenic center in their structure. This stereogenic center may be present in a R or a S configuration, said R and S notation is used in correspondence with the rules described in Pure Appl. Chem. 1976, 45, 11-30.

The invention also relates to all stereoisomeric forms such as enantiomeric and diastereoisomeric forms of the compounds of formula (I) or mixtures thereof (including all possible mixtures of stereoisomers).

With respect to the present invention reference to a compound or compounds is intended to encompass that compound in each of its possible isomeric forms and mixtures thereof, unless the particular isomeric form is referred to specifically.

Compounds according to the present invention may exist in different polymorphic forms. Although not explicitly indicated in the above formula, such forms are included within the scope of the present invention.

The invention also includes within its scope pro-drug forms of the compounds of formula (I) and its various subscopes and sub-groups.

The term "prodrug" as used herein includes compound forms which are rapidly transformed in vivo to the parent compound according to the invention, for example, by hydrolysis in blood. Prodrugs are compounds bearing groups which are removed by biotransformation prior to exhibiting their pharmacological action. Such groups include moieties which are readily cleaved in vivo from the compound bearing it, which compound after cleavage remains or becomes pharmacologically active. Metabolically cleavable groups form a class of groups well known to practitioners of the art. They include, but are not limited to such groups as alkanoyl (i.e. acetyl, propionyl, butyryl, and the like), unsubstituted and substituted carbocyclic aroyl (such as benzoyl, substituted benzoyl and 1- and 2-naphthoyl), alkoxycarbonyl (such as ethoxycarbonyl), trialklysilyl (such as trimethyl- and triethylsilyl), monoesters formed with dicarboxylic acids (such as succinyl), phosphate, sulfate, sulfonate, sulfonyl, sulfinyl and the like. The compounds bearing the metabolically cleavable groups have the advantage that they may exhibit improved bioavailability as a result of enhanced solubility and/or rate of absorption conferred upon the parent compound by virtue of the presence of the metabolically cleavable group. T. Higuchi and V. Stella, "Pro-drugs as Novel Delivery System", Vol. 14 of the A.C.S. Symposium Series; "Bioreversible Carriers in Drug Design", ed. Edward B. Roche, American Pharmaceutical Association and Pergamon Press, 1987.

Compounds of formula (I) according to the invention may be prepared according to conventional methods known to the person skilled in the art of synthetic organic chemistry.

A. According to one embodiment, some compounds having the general formula (I) may be prepared by reaction of a compound of formula (II) with a compound of formula (III) according to the following equation:

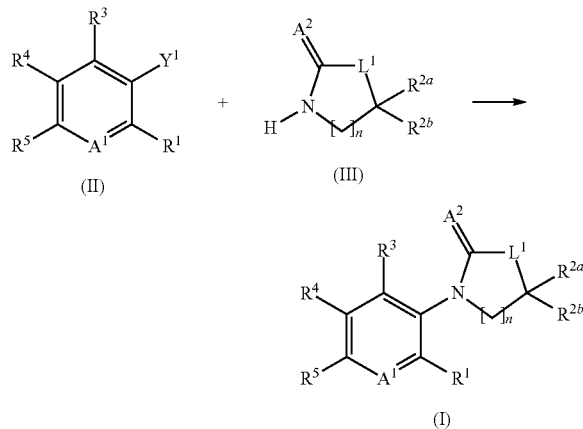

wherein $R^1$ is hydrogen; $R^3$ is hydrogen, fluorine or chlorine; $Y^1$ is iodine or bromine; and $R^{2a}$, $R^{2b}$, $R^4$, $R^5$, $A^1$, $A^2$ and $L^1$ have the same definitions as described above for compounds of formula I.

This reaction may be carried out using a catalyst such as copper iodide or palladium acetate, associated with a ligand such as 1,2-diamine (e.g. trans-1,2-diamineocyclohexane), a phosphine (e.g. 1,1'-bis(diphenylphosphino)ferrocene or 2-(dicyclohexylphosphino)-2'-(N,N-dimethylamino)-biphenyl) or an amino acid (e.g. glycine), in a solvent (such as dioxane, tetrahydrofuran, dimethylformamide or toluene), in the presence of a base (such as potassium phosphate or sodium tert-butylate), at a temperature ranging from 25° C. to 120° C. and under an inert atmosphere (argon or nitrogen).

Alternatively, this reaction may be performed according to the methodology described by Klapars A. et al. in J. Am. Chem. Soc. 2002, 124, 7421.

Compounds of formula (II) may be commercially available or prepared according to any one of the following methods.

(A.1) Compounds of formula (II) wherein $A^1$ is CH; $R^4$ is —O—(CH$_2$)$_t$—NR$^{7a}$R$^{7b}$; $R^5$ is hydrogen, hydroxy or $C_{1-4}$ alkoxy; and $R^1$, $R^3$ and y1 have the same definitions as described above, may be prepared by reaction of a compound of formula (IV) with an amine of formula HNR$^{7a}$R$^{7b}$ according to the following equation:

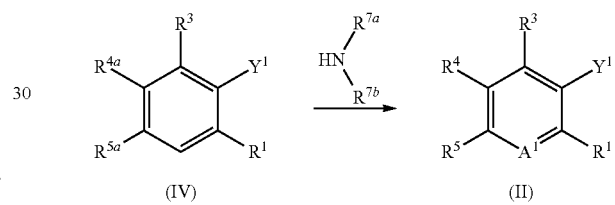

wherein $R^{4a}$ is —O—(CH$_2$)$_t$—Cl and $R^{5a}$ is hydrogen, hydroxy or $C_{1-4}$ alkoxy, t, $R^{7a}$ and $R^{7b}$ having the same definitions as described above for compounds of formula (I).

This reaction may be carried out in the presence of a base such as triethylamine or potassium carbonate, in acetonitrile or acetone as solvent, or according to any conventional method known to the man skilled in the art.

(A.2) Similarly, compounds of formula (II) wherein $A^1$ is CH; $R^4$ is hydrogen, halogen, $C_{1-4}$ alkyl, $C_{1-4}$ alkoxy or hydroxy; $R^5$ is —O—(CH$_2$)$_w$—NR$^{8a}$R$^{8b}$; and $R^1$, $R^3$ and $Y^1$ have the same definitions as described above, may be prepared by reaction of a compound of formula (IV) with an amine of formula HNR$^{8a}$R$^{8b}$ according to the following equation:

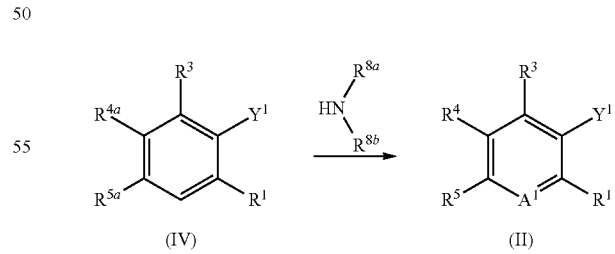

wherein $R^{4a}$ is hydrogen, fluorine, chlorine, $C_{1-4}$ alkyl, $C_{1-4}$ alkoxy or hydroxy, $R^{5a}$ is —O—(CH$_2$)$_w$—Cl, w, $R^{8a}$ and $R^{8b}$ having the same definitions as described above for compounds of formula I.

Compounds of formula (IV) may be commercially available or may be prepared according to any conventional method known to the person skilled in the art.

(A.3) Compounds of formula (II) wherein $A^1$ is N; $R^1$ is hydrogen; $R^3$ is hydrogen, $C_{1-4}$ alkyl or $C_{1-4}$ alkoxy; $R^4$ is $-O-(CH_2)_t-NR^{7a}R^{7b}$; and $R^5$ is hydrogen or $C_{1-4}$ alkoxy, may be prepared by reaction of a compound of formula (V) with an alcohol of formula $HO-(CH_2)_t-NR^{7a}R^{7b}$ according to the following equation:

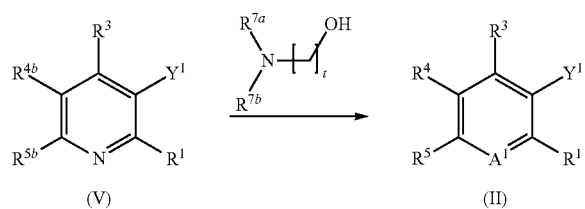

wherein $R^{4b}$ is a halogen, preferably bromine or iodine, $R^{5b}$ is hydrogen or $C_{1-4}$ alkoxy, and t, $R^{7a}$ and $R^{7b}$ are as defined above for compounds of formula (I).

This reaction may be performed in the presence of a base, such as potassium tert-butylate, cesium carbonate or sodium hydride, in a solvent, such as dimethylformamide or tetrahydrofuran, in the presence of a palladium- or a copper-based catalyst, according to method described by Penning et al. in J. Med. Chem. 2000, 43, 721.

(A.4) Similarly, compounds of formula (II) wherein $A^1$ is N; $R^1$ is hydrogen; $R^3$ is hydrogen, $C_{1-4}$ alkyl or $C_{1-4}$ alkoxy; $R^4$ is hydrogen, $C_{1-4}$ alkyl or $C_{1-4}$ alkoxy; and $R^5$ is $-O-(CH_2)_w-NR^{8a}R^{8b}$, may be prepared by reaction of a compound of formula (V) wherein $R^{4b}$ is hydrogen, $C_{1-4}$ alkyl or $C_{1-4}$ alkoxy and $R^{5b}$ is a fluorine, chlorine or bromine, with an alcohol of formula $HO-(CH_2)_w-NR^{8a}R^{8b}$, w, $R^{8a}$ and $R^{8b}$ having the same definitions as described above for compounds of formula (I).

The reaction may be carried out in the presence of a base, for example potassium tert-butylate in a solvent, for example tetrahydrofuran, at a temperature ranging from 25° C. to 120° C., or according to the method described by Westland, R. D. et al. in J. Med. Chem. 1973, 16, 319.

Compounds of formula (V) are commercially available or may be prepared according to conventional methods known to the person skilled in the art.

Compounds of formula (III) may be commercially available or prepared according to any one of the following methods.

(A.5) Compounds of formula (III) wherein $R^{2a}$ is $-(CH_2)_r-NR^{6a}R^{6b}$ and $R^{2b}$ is hydrogen may be obtained by the reaction of a compound of formula (VI) with an amine of formula $HNR^{6a}R^{6b}$ according to the equation:

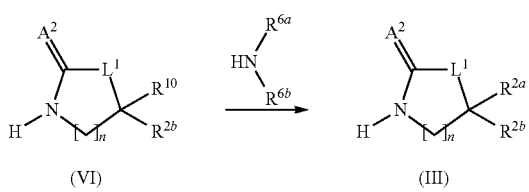

wherein $R^{10}$ is $-(CH_2)_r-R^{11}$, $R^{11}$ is a leaving group and $L^1$, $A^2$, $R^{6a}$ and $R^{6b}$ have the same definitions as described above for compounds of formula (I).

The term "leaving group", as used herein, has the same meaning by the person skilled in the art as defined in "Advanced Organic Chemistry: reactions, mechanisms and structure—Third Edition by Jerry March, John Wiley and Sons Ed.; 1985 page 179".

Examples of leaving groups are sulfonates, for example methylsulfonate, and halogens, for example chlorine, bromine or iodine.

The term "sulfonate", as used herein, represents a group of formula $-O-SO_2-R^e$ wherein $R^e$ is $C_{1-4}$ alkyl or aryl as defined above in the specifications.

This reaction may be carried out according to the method described by Kenda, B. et al. in J. Med. Chem. 2004, 47, 530, or according to any conventional method known to the person skilled in the art.

Amines of formula $HNR^{6a}R^{6b}$ may be commercially available or may be prepared according to any conventional method known to the person skilled in the art.

(A.6) Compounds of formula (III) wherein $R^{2a}$ is $-(CH_2)_r-OH$, r being equal to 1 or 2, and $R^{2b}$ is hydrogen may be obtained by reduction of a compound of formula (VI) wherein $R^{10}$ is $-(CH_2)_{r-1}-COOR^{12}$, $R^{12}$ being a hydrogen or a $C_{1-4}$ alkyl. This reduction may be carried out according to any conventional method known to the person skilled in the art.

(A.7) Compounds of formula (III) wherein $R^{2a}$ is $-(CH_2)_r-R^{13}$, $R^{13}$ being an aryl, a heteroaryl or a $C_{1-8}$ alkyl optionally substituted by an aryl, may be prepared by reaction of a compound of formula (VI) with an organometallic reagent of formula $R^{13}MgX^i$ or $(R^{13})_2CuLi$ according to the following equation:

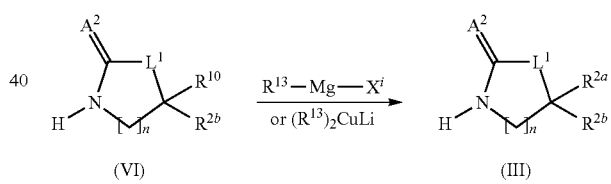

wherein $R^{10}$ is $-(CH_2)_r-R^{11}$, $X^i$ is chlorine, bromine or iodine, and $R^{13}$ is an aryl group, a heteroaryl group or a $C_{1-8}$ alkyl optionally substituted by an aryl group, $R^{11}$, $R^{2b}$, $L^1$ and $A^2$ being as defined here above in the specification.

This reaction may be carried out according to the method described by Occhiato, E. G. et al. in J. Org. Chem. 2005, 70, 4542, or according to any other conventional method known to the person skilled in the art.

(A.8) Compounds of formula (III) wherein $R^{2a}$ and $R^{2b}$ are linked together to form a $C_{2-6}$ alkylene, one methylene being replaced by a nitrogen atom, said nitrogen atom being substituted by a $C_{1-8}$ alkyl, an arylalkyl or an acyl, may be prepared according to the methods described in Cignarella, G. et al. in J. Heterocycl. Chem. 1993, 30, 1357; by Smith, Paul W. et al. in J. Med. Chem. 1995, 38, 3772; or according to any conventional method known to the person skilled in the art.

(A.9) Compounds of formula (III) wherein $A^2$ is O and $L^1$ is $-(O)_v-(CR^{9a}R^{9b})_m-(CH_2)_z-$ and v=1, may be obtained by cyclisation of the corresponding amino-alcohol of formula (VII) according to the following equation:

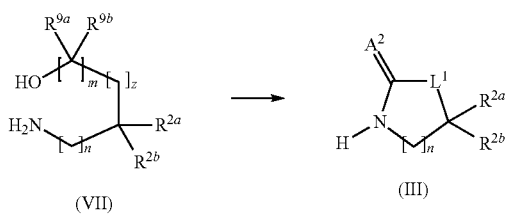

(VII) → (III)

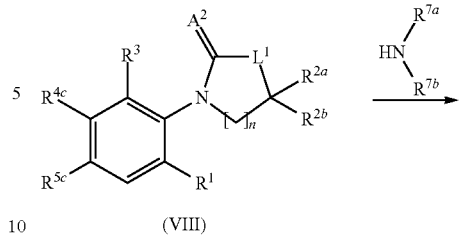

(VIII)

(I)

wherein $R^{4c}$ is —O—$(CH_2)_t$—Cl and $R^{5c}$ is hydrogen or $C_{1-4}$ alkoxy, and t, $R^{7a}$ and $R^{7b}$ have the same definitions as described above for compounds of formula (I).

This reaction may be carried out in the presence of a base, such as triethylamine or potassium carbonate, in for example acetonitrile or acetone as solvent. This reaction may be also performed according to any conventional method known to the person skilled in the art.

Compounds of formula (VIII) wherein $R^{4c}$ is —O—$(CH_2)_t$—Cl and $R^{5c}$ is hydrogen or $C_{1-4}$ alkoxy may be prepared by reaction of a compound of formula (VIII) wherein $R^{4c}$ is a hydroxy with a di-haloalkane of formula Cl—$(CH_2)_t$—Br according to the following equation:

This reaction may be performed in the presence of carbonic acid bis-trichloromethyl ester (or triphosgene) according to the method described by Ding, K. et al. in Tetrahedron Lett. 2004, 45, 1027; or in the presence of carbonic acid diethyl ester according to the method described by Tomioka, K. in Tetrahedron 1993, 49, 1891; or according to any other conventional method known to the person skilled in the art. Compounds of formula (VII) are commercially available or may be prepared according to any conventional method known to the person skilled in the art.

(A.10) Compounds of formula (III) wherein $A^2$ is O and $L^1$ is —$(O)_v$—$(CR^{9a}R^{9b})_m$—$(CH_2)_z$— and v=0, and m=1, may be obtained using the procedure described by Davies, S. B. et al. in Tetrahedron Asym. 2002, 13, 647.

(A.11) Compounds of formula (III) wherein $A^2$ is O and $L^1$ is —$(O)_v$—$(CR^{9a}R^{9b})_m$—$(CH_2)_z$— and v=0, $R^{2a}$ and $R^{2b}$ being as defined in general formula (I), may be obtained by cyclisation of the corresponding amino-acid or an amino-ester of formula (VIIa), wherein R is hydrogen or a $C_{1-4}$ alkyl, according to the following equation:

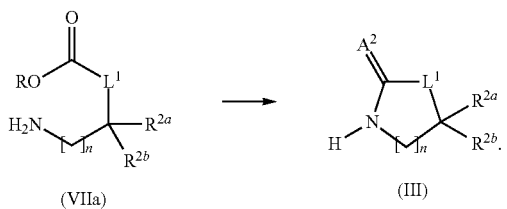

(VIIa) → (III)

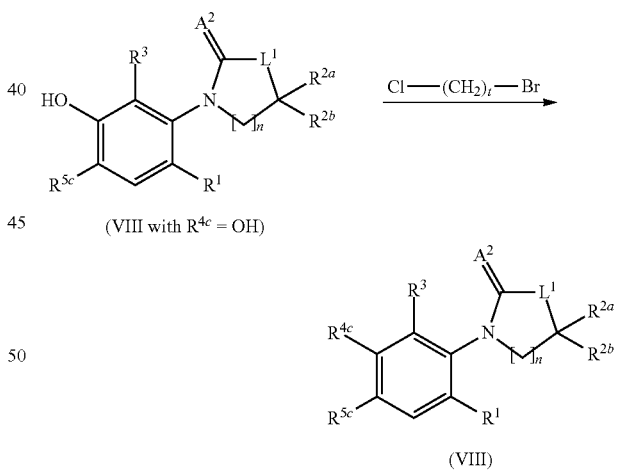

(VIII with $R^{4c}$ = OH)

(VIII)

This reaction may be carried out in the presence of a base, for example potassium carbonate, in a solvent, for example acetone or acetonitrile, at a temperature ranging from 50° C. to 100° C., according to the method described by Walsh et al. in J. Med. Chem. 1989, 32, 105.

Similarly, compounds of formula (I) wherein $A^1$ is CH, $R^5$ is —O—$(CH_2)_w$—$NR^{8a}R^{8b}$ and $R^4$ is hydrogen, halogen, $C_{1-4}$ alkyl or $C_{1-4}$ alkoxy, and $R^1$, $R^{2a}$, $R^{2b}$, $L^1$, $A^2$ and $R^3$ have the same definitions as described above for compounds of formula (I), may be prepared according to the following equation:

This reaction may be performed according to the method described by Lopez-Garcia, M. et al. in J. Org. Chem. 2003, 2, 648, or according to any other conventional method known to the person skilled in the art.

Compounds of formula (VIIa) are commercially available or may be prepared from the corresponding nitro-ester by hydrogenolysis of the nitro group according to any conventional method known to the person skilled in the art.

B. According to another embodiment, some compounds of general formula (I) wherein $A^1$ is CH, $R^4$ is —O—$(CH_2)_t$—$NR^{7a}R^{7b}$, $R^5$ is hydrogen or $C_{1-4}$ alkoxy, and $R^1$, $R^{2a}$, $R^{2b}$, $L^1$, $A^2$ and $R^3$ have the same definitions as described above in the specification for compounds of formula (I), may be prepared by reaction of a compound of formula (VIII) with an amine of formula $HNR^{7a}R^{7b}$ according to the following equation:

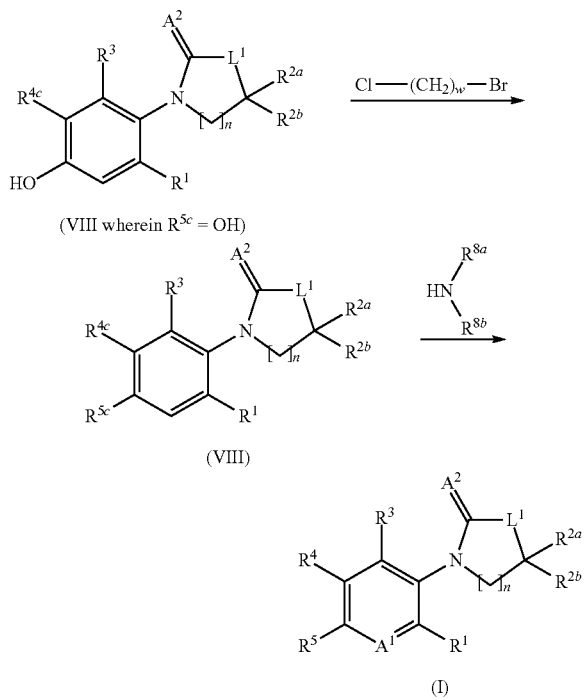

wherein $R^{4c}$ is hydrogen, halogen, $C_{1-4}$ alkyl or $C_{1-4}$ alkoxy and $R^{5c}$ is —O—$(CH_2)_w$—Cl, and w, $R^{8a}$ and $R^{8b}$ have the same definitions as described above for compounds of formula (I).

C. According to another embodiment, some compounds having the general formula (I) wherein $A^1$ is N, $R^1$ is hydrogen, $R^3$ is hydrogen, $C_{1-4}$ alkyl or $C_{1-4}$ alkoxy, $R^4$ is —O—$(CH_2)_t$—$NR^{7a}R^{7b}$ and $R^5$ is hydrogen or $C_{1-4}$ alkoxy, may be prepared by reaction of a compound of formula (IX) with an alcohol of formula HO—$(CH_2)_t$—$NR^{7a}R^{7b}$ according to the following equation:

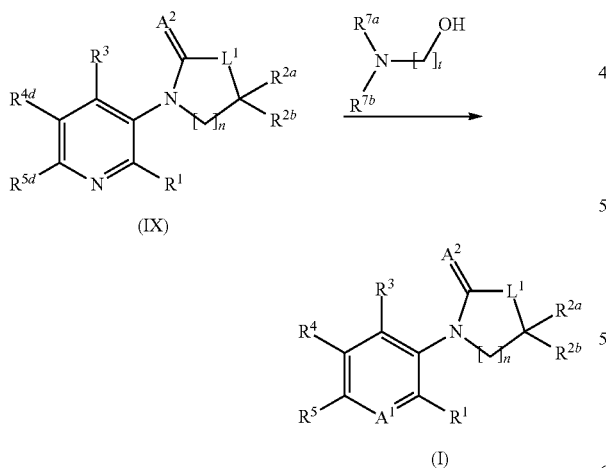

wherein $R^{4d}$ is a halogen, preferably bromine or iodine, and $R^{5d}$ is hydrogen or a $C_{1-4}$ alkoxy, and t, $R^{7a}$ and $R^{7b}$ have the same definitions as described above for compounds of formula I.

This reaction may be performed in the presence of a base, for example potassium tert-butylate, cesium carbonate or sodium hydride, in a solvent, for example dimethylformamide or tetrahydrofuran, in the presence of a palladium- or a copper-based catalyst, according to methods described by Penning et al. in J. Med. Chem. 2000, 43, 721.

Similarly, compounds of formula (I) wherein $A^1$ is N, $R^1$ is hydrogen, $R^3$ is hydrogen, $C_{1-4}$ alkyl or $C_{1-4}$ alkoxy, $R^4$ is hydrogen, halogen, $C_{1-4}$ alkyl or $C_{1-4}$ alkoxy, and $R^5$ is —O—$(CH_2)_w$—$NR^{8a}R^{8b}$, may be prepared by reaction of a compound of formula (IX) wherein $R^{4d}$ is hydrogen, halogen, $C_{1-4}$ alkyl or $C_{1-4}$ alkoxy, and $R^{5d}$ is a halogen, preferably fluorine, chlorine or bromine, with an alcohol of formula HO—$(CH_2)_w$—$NR^{8a}R^{8b}$, w, $R^{8a}$ and $R^{8b}$ having the same definitions as described above for compounds of formula (I).

This reaction may be carried out in the presence of a base, for example potassium tert-butylate in a solvent, for example tetrahydrofuran, at a temperature ranging from 25° C. to 120° C., or according to the methods described by Westland, R. D. et al. in J. Med. Chem. 1973, 16, 319 and by Penning et al. in J. Med. Chem. 2000, 43, 721.

D. According to another embodiment, some compounds of general formula (I) wherein $R^{2a}$ is $C_{1-8}$ alkyl substituted by a hydroxy may be prepared from the corresponding compound of formula (X)

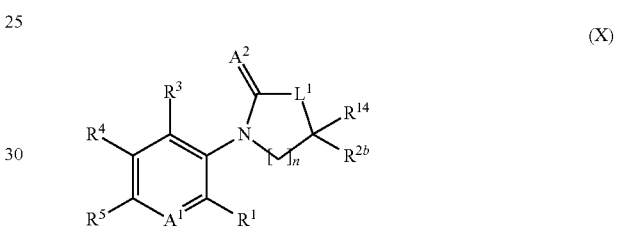

wherein $R^1$, $R^3$, $R^{2b}$, $R^4$, $R^5$, and $A^2$ are as defined above in the specification, and $R^{14}$ is —$COOR^{15}$ or a $C_{1-7}$ alkyl substituted by —$COOR^{15}$, $R^{15}$ being hydrogen or $C_{1-4}$ alkyl, according to the method described by Kenda, B. et al. in J. Med. Chem. 2004, 47, 530, or to any other conventional method known to the person skilled in the art.

In a particular embodiment, some compounds of formula (I) wherein $R^{2a}$ is —$(CH_2)_r$—OH, r being equal to 1 or 2, $R^{2b}$ is hydrogen, $R^1$ is hydrogen or fluorine, and $R^3$ is hydrogen, fluorine or chlorine, may be obtained by reduction of a compound of formula (X)

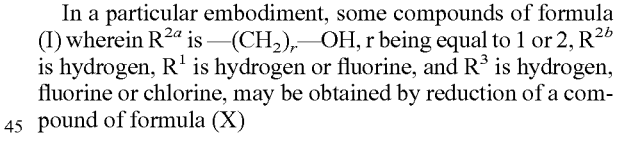

wherein $R^{14}$ is —$(CH_2)_{r-1}$—$COOR^{15}$, $R^{15}$ being an hydrogen or a $C_{1-4}$ alkyl. This reduction may be carried out using a reducing agent, for example lithium borohydride, in a solvent, for example tetrahydrofuran or methanol, at a temperature ranging from 25° C. to 80° C., or according to the method described by Xi, N. et al. in Bioorg. Med. Chem. Lett. 2004, 14, 2905, or according to any conventional method known to the person skilled in the art.

Compounds of formula (X) may be prepared according to the method described in paragraph A for compounds of formula (I).

Compounds of formula (X) wherein r is equal to 1 may also be prepared by reaction of a compound of formula (II), wherein $Y^1$ is $NH_2$, and $R^1$, $R^3$, $R^4$ and $R^5$ are as defined above in the specification, with a compound of formula (XI) wherein $R^{16}$ is hydrogen or $C_{1-4}$ alkyl, according to the following equation:

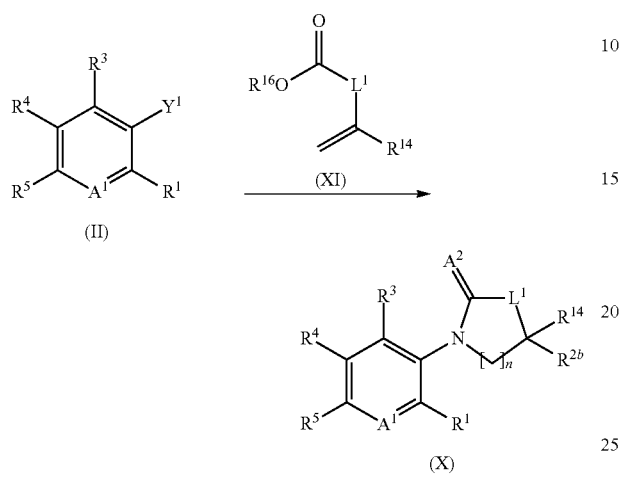

or according to any conventional method known to the person skilled in the art.

E. According to another embodiment, some compounds of formula (I) wherein $A^2$ is O, $L^1$ is $-(O)_v-(CR^{9a}R^{9b})_m-(CH_2)_z-$ and v=1, may be obtained by cyclisation of the corresponding amino-alcohol of formula (XII), wherein $R^1$, $R^3$, $R^{2a}$, $R^{2b}$, $R^4$, $R^5$, $R^{9a}$ and $R^{9b}$ are as defined above in the specification, according to the following equation:

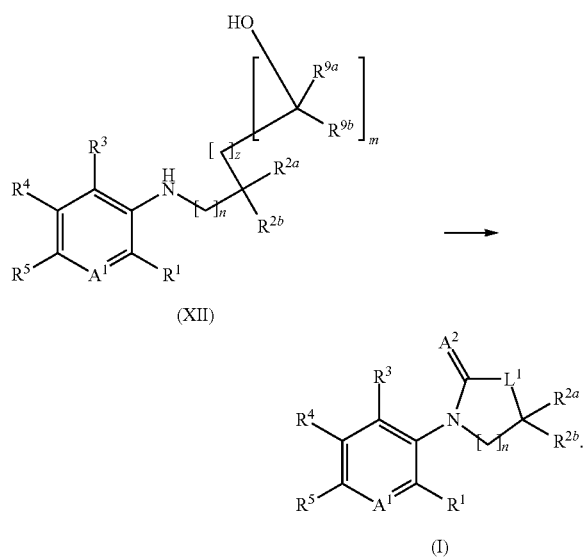

This reaction may be performed in the presence of carbonic acid bis-trichloromethyl ester (or triphosgene) according to the method described by Ding, K. et al. in Tetrahedron Lett. 2004, 45, 1027; or according to any other conventional method known to the person skilled in the art.

Compounds of formula (XII) wherein $R^1$, $R^3$ and $R^4$ are different from halogen, may be obtained by reaction of a compound of formula (II) with a compound of formula (XIII), according to the following equation

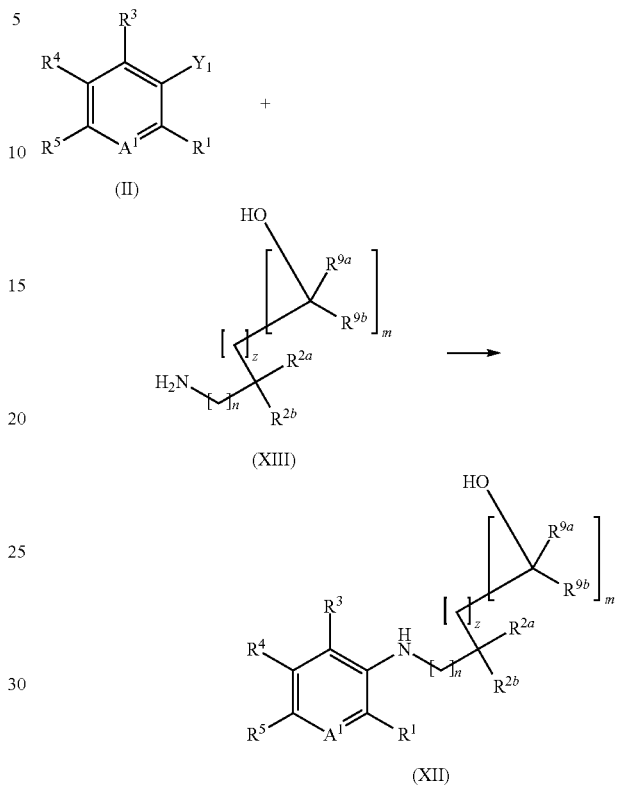

wherein $Y^1$ is a halogen, preferably iodine or bromine.

This reaction may be performed as described by Wolfe, J. P. et al. in J. Org. Chem. 2000, 65, 1158, or according to any other conventional method known to the person skilled in the art.

Compounds of formula (XIII) are commercially available or may be prepared according to any conventional method known to the person skilled in the art.

F. According to another embodiment, some compounds of general formula (I) may be prepared by functional group transformation.

(F.1) Compounds of formula (I) wherein $R^{2a}$ is $-(CH_2)_r-NR^{6a}R^{6b}$, $R^{6a}$ is $C_{1-8}$ alkyl, aryl, arylalkyl or acyl, and $R^{6b}$ is $C_{1-8}$ alkyl may be prepared by alkylation of the corresponding compound of formula (I) wherein $R^{6b}$ is hydrogen according to any conventional method known to the person skilled in the art.

(F.2) Compounds of formula (I) wherein $A^2$ is S may be prepared from the corresponding compound of formula (I) wherein $A^2$ is O according to any conventional method known to the person skilled in the art. For example, this transformation may be achieved by reacting said compound of formula (I) with 2,4-bis(4-methoxyphenyl)-1,3,2,4-dithiadiphosphetane in a solvent, for example chloroform, or a mixture of solvents, for example chloroform or toluene, at a temperature ranging from 80 to 120° C.

(F.3) Compounds of formula (I) wherein $R^{2a}$ is carboxy or $C_{1-6}$-alkyl carboxy may be prepared by hydrolysis of the corresponding compound of formula (I) wherein $R^{2a}$ is alkoxycarbonyl or $C_{1-6}$-alkyl alkoxycarbonyl according to any conventional method known to the person skilled in the art.

(F.4) Compounds of formula (I) wherein $R^{2a}$ is aminocarbonyl or $C_{1-6}$ alkyl aminocarbonyl may be prepared by coupling an amino group with a compound of formula (I) wherein $R^{2a}$ is carboxy or $C_{1-6}$-alkyl carboxy according to any conventional method known to the person skilled in the art.

(F.5) Compounds of formula (I) wherein $R^{2a}$ is —$NH_2$ or $C_{1-6}$-alkyl substituted by $NH_2$ may be prepared by hydrogenolysis of the corresponding compound of formula (I) wherein $R^{2a}$ is —$N(CH_2\text{-Ph})_2$ or $C_{1-6}$-alkyl substituted by —$N(CH_2\text{-Ph})_2$ using, for example, hydrogen atmosphere in the presence of palladium charcoal, or according to any conventional method known to the person skilled in the art.

(F.6) Compounds of formula (I) wherein $R^{2a}$ is an acylamino or $C_{1-6}$-alkyl acylamino may be prepared by reaction of an acyl chloride, or a carboxylic acid, with a compound of formula (I) wherein $R^{2a}$ is an amino group or a $C_{1-6}$-alkyl amino, according to any conventional method known to the person skilled in the art.

(F.7) Compounds of formula (I) wherein $R^{2a}$ is $C_{1-6}$ alkyl ureido may be obtained from the corresponding compound of formula (I) wherein $R^{2a}$ is a $C_{1-6}$-alkyl amino, for example by reaction with triphosgene and a second amino group according to any conventional method known to the person skilled in the art.

G. According to another embodiment, some compounds of general formula (I) wherein $R^{2a}$ is —$(CH_2)_r$—$NR^{6a}R^{6b}$ may be prepared from the corresponding compound of formula (X) wherein $R^{14}$ is —$(CH_2)_r$—Cl, according to any conventional method known to the person skilled in the art.

In a particular embodiment, the present invention relates to compounds of formula (III), geometrical isomers, enantiomers, diastereoisomers, pharmaceutically acceptable salts and all possible mixtures thereof,

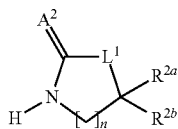

(III)

wherein
$A^2$ is an oxygen or a sulfur;
$R^{2a}$ is $(CH_2)_r$—$NR^{6a}R^{6b}$;
$R^{2b}$ is hydrogen;
or $R^{2a}$ and $R^{2b}$ are linked together to form a $C_{2-6}$ alkylene, one methylene being optionally replaced by a nitrogen atom, said nitrogen atom being optionally substituted by a $C_{1-6}$-alkyl aryl or an acyl;
$L^1$ is $(O)_v$—$(CR^{9a}R^{9b})_m$—$(CH_2)_z$;
$R^{6a}$ is hydrogen, $C_{1-8}$ alkyl, $C_{1-6}$-alkyl cycloalkyl, $C_{3-8}$ cycloalkyl, acyl, aryl or $C_{1-6}$-alkyl aryl;
$R^{6b}$ is hydrogen, $C_{1-4}$ alkyl, $C_{1-6}$-alkyl cycloalkyl or $C_{1-6}$-alkyl aryl;
or $R^{6a}$ and $R^{6b}$ are linked together to form a $C_{3-6}$ alkylene, each methylene of the alkylene being optionally substituted by one or two halogen, or by one or two $C_{1-4}$ alkyl, optionally linked together to form with the carbon to which they are attached a $C_{3-8}$ cycloalkyl; or one methylene thereof being linked to a second methylene thereof to form a $C_{3-6}$ alkylene; or one methylene being optionally replaced by sulfur dioxide, an oxygen or a nitrogen atom, said nitrogen atom being optionally substituted by a $C_{1-8}$ alkyl or $C_{3-8}$ cycloalkyl;
$R^{9a}$ is hydrogen or unsubstituted $C_{1-4}$ alkyl;
$R^{9b}$ is unsubstituted $C_{1-4}$ alkyl;

n is an integer equal to 0 or 1;
r is an integer equal to 1 or 2;
v and m are independently an integer equal to 0 or 1;
z is an integer comprised between 0 and 3;
and at least one of m and z is different from 0.
Preferably, $A^2$ is oxygen.

In another particular embodiment, the present invention relates to a compound of formula (X), geometrical isomers, enantiomers, diastereoisomers, pharmaceutically acceptable salts and all possible mixtures thereof,

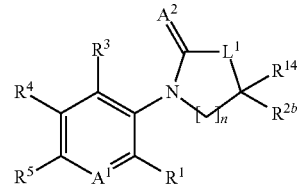

(X)

wherein
$A^1$ is CH, C-halogen or N;
$A^2$ is oxygen or sulfur;
$R^1$ is hydrogen;
$R^{2b}$ is hydrogen;
$R^3$ is hydrogen, halogen or $C_{1-4}$ alkoxy;
$R^4$ is hydrogen, halogen, $C_{1-4}$ alkyl, $C_{1-4}$ alkoxy or —O—$(CH_2)_t$—$NR^{7a}R^{7b}$;
$R^5$ is hydrogen or —O—$(CH_2)_w$—$NR^{8a}R^{8b}$;
$L^1$ is —$(O)_v$—$(CR^{9a}R^{9b})_m$—$(CH_2)_z$;
$R^{7a}$ and $R^{7b}$ are linked together to form a $C_{3-6}$ alkylene, each methylene of the alkylene being optionally substituted by one or two $C_{1-4}$ alkyl;
$R^{8a}$ and $R^{8b}$ are linked together to form a $C_{3-6}$ alkylene, each methylene of the alkylene being optionally substituted by one or two $C_{1-4}$ alkyl optionally linked together to form with the carbon to which they are attached a $C_{3-8}$ cycloalkyl, by $C_{1-6}$ alkyl hydroxy, by aryl or by $C_{1-6}$ alkyl aryl; or one methylene thereof being linked to a second methylene thereof to form a $C_{3-6}$ alkylene; or one methylene of the alkylene being optionally replaced by a nitrogen, said nitrogen being substituted by a $C_{1-4}$ alkyl or $C_{3-8}$ cycloalkyl;
$R^{9a}$ is hydrogen or an unsubstituted $C_{1-4}$ alkyl;
$R^{9b}$ is an unsubstituted $C_{1-4}$ alkyl;
$R^{14}$ is —$(CH_2)_r$—Cl, —$COOR^{15}$ or $C_{1-7}$ alkyl substituted by —$COOR^{15}$;
$R^{15}$ is hydrogen or $C_{1-4}$ alkyl;
n is an integer equal to 0 or 1;
r is an integer equal to 1 or 2;
t and w are independently an integer comprised between 2 and 4;
v and m are independently an integer equal to 0 or 1;
z is an integer comprised between 0 and 3;
provided that
at least one of m and z is different from 0; and that
$R^4$ is —O—$(CH_2)_t$—$NR^{7a}R^{7b}$, when $R^5$ is hydrogen; and
$R^5$ is —O—$(CH_2)_w$—$NR^{8a}R^{8b}$, when $R^4$ is hydrogen, halogen, $C_{1-4}$ alkyl or $C_{1-4}$ alkoxy.

Unless otherwise specified, preferred R groups, $A^1$, $A^2$ and $L^1$ in compounds of formula (III) and (X) are as defined for compounds of general formula (I).

In a further aspect, the present invention relates to the use of a compound of formula (III) or (X) for the synthesis of a compound of formula (I).

In a particular embodiment, the present invention relates to synthetic intermediates selected from the group consisting of:
1-(4-chlorobutoxy)-4-iodobenzene;
1-bromo-4-(3-chloropropoxy)-2-fluorobenzene;
5-bromo-2-(3-chloropropoxy)-1,3-difluorobenzene;
4-bromo-1-(3-chloropropoxy)-2-methylbenzene;
1-[3-(4-iodophenoxy)propyl]-2-methylpyrrolidine;
1-[3-(4-iodophenoxy)propyl]-2-methylpiperidine;
1-[3-(4-iodophenoxy)propyl]-4-isopropylpiperazine;
1-cyclopentyl-4-[3-(4-iodophenoxy)propyl]piperazine;
1-[2-(4-iodophenoxy)ethyl]-2-methylpyrrolidine;
1-[3-(3-bromophenoxy)propyl]-2-methylpyrrolidine;
1-[3-(4-iodophenoxy)propyl]-2-(pyrrolidin-1-ylmethyl)pyrrolidine;
1-[4-(4-iodophenoxy)butyl]-2-methylpyrrolidine;
1-[3-(4-iodophenoxy)propyl]-1-azaspiro[4.4]nonane;
1-[3-(4-bromophenoxy)propyl]-3,5-dimethylpiperidine;
1-[3-(4-bromophenoxy)propyl]decahydroquinoline;
1-[3-(4-bromo-2-fluorophenoxy)propyl]-3,5-dimethylpiperidine;
2-[3-(4-bromo-2-fluorophenoxy)propyl]-2-azaspiro[5.5]undecane;
1-[3-(4-bromo-3-fluorophenoxy)propyl]-3,5-dimethylpiperidine;
1-[3-(4-bromo-2,6-difluorophenoxy)propyl]-4-methylpiperidine;
2-[3-(4-bromo-2,6-difluorophenoxy)propyl]-2-azaspiro[5.5]undecane;
1-[3-(4-bromo-2-methylphenoxy)propyl]-3,5-dimethylpiperidine;
4-benzyl-1-[3-(4-bromophenoxy)propyl]piperidine;
1-[3-(4-bromo-2-fluorophenoxy)propyl]-3-phenylpiperidine;
1-[3-(4-bromophenoxy)propyl]-1-azaspiro[4.4]nonane;
1-[3-(4-bromo-2-fluorophenoxy)propyl]-2-methylpyrrolidine;
1-[3-(4-bromo-2-fluorophenoxy)propyl]-1-azaspiro[4.4]nonane;
1-[3-(4-bromo-2,6-difluorophenoxy)propyl]-2-methylpyrrolidine;
1-[3-(4-bromo-2-methylphenoxy)propyl]-2-methylpyrrolidine;
1-[3-(4-bromo-2-methylphenoxy)propyl]-1-azaspiro[4.4]nonane;
{1-[3-(4-bromo-2-methylphenoxy)propyl]pyrrolidin-2-yl}methanol;
1-[3-(4-bromophenoxy)propyl]azepane;
1-[3-(4-bromo-2-fluorophenoxy)propyl]azepane;
1-[3-(4-bromo-2-fluorophenoxy)propyl]azocane;
1-[3-(4-bromo-3-methoxyphenoxy)propyl]azepane;
(5S)-5-(piperidin-1-ylmethyl)pyrrolidin-2-one;
(5R)-5-(piperidin-1-ylmethyl)pyrrolidin-2-one;
(5S)-5-[(2-methylpiperidin-1-yl)methyl]pyrrolidin-2-one;
(5S)-5-[(2,6-dimethylpiperidin-1-yl)methyl]pyrrolidin-2-one;
(5S)-5-[(4-methylpiperidin-1-yl)methyl]pyrrolidin-2-one;
(5S)-5-[(2-methylpyrrolidin-1-yl)methyl]pyrrolidin-2-one;
(5S)-5-{[(2R)-2-methylpyrrolidin-1-yl]methyl}pyrrolidin-2-one;
(5S)-5-{[(2S)-2-methylpyrrolidin-1-yl]methyl}pyrrolidin-2-one;
(5S)-5-(pyrrolidin-1-ylmethyl)pyrrolidin-2-one;
(5S)-5-(azepan-1-ylmethyl)pyrrolidin-2-one;
(5S)-5-[(4-cyclopentylpiperazin-1-yl)methyl]pyrrolidin-2-one;
(5S)-5-{[4-(cyclohexylmethyl)piperazin-1-yl]methyl}pyrrolidin-2-one;
(5S)-5-[(4-isopropylpiperazin-1-yl)methyl]pyrrolidin-2-one;
(5S)-5-{[(cyclopropylmethyl)amino]methyl}pyrrolidin-2-one;
(5S)-5-{[(cyclohexylmethyl)amino]methyl}pyrrolidin-2-one;
(5S)-5-[(cyclobutylamino)methyl]pyrrolidin-2-one;
(5S)-5-[(cyclopentylamino)methyl]pyrrolidin-2-one;
(5S)-5-[(cyclohexylamino)methyl]pyrrolidin-2-one;
(5S)-5-{[(cyclopropylmethyl)(propyl)amino]methyl}pyrrolidin-2-one;
(5S)-5-{[(4-fluorobenzyl)amino]methyl}pyrrolidin-2-one;
(5S)-5-(anilinomethyl)pyrrolidin-2-one;
(5S)-5-{[(4-fluorophenyl)amino]methyl}pyrrolidin-2-one;
(5S)-5-{[(2-fluorophenyl)amino]methyl}pyrrolidin-2-one;
(5S)-5-{[(3-fluorophenyl)amino]methyl}pyrrolidin-2-one;
(5S)-5-{[(2,4-difluorophenyl)amino]methyl}pyrrolidin-2-one;
(5S)-5-{[(3-methoxyphenyl)amino]methyl}pyrrolidin-2-one;
(5S)-5-({[4-(trifluoromethyl)phenyl]amino}methyl)pyrrolidin-2-one;
(5S)-5-[(4-fluorophenoxy)methyl]pyrrolidin-2-one;
(5S)-5-{[(4-methylphenyl)amino]methyl}pyrrolidin-2-one;
(5S)-5-{[(3,4-difluorophenyl)amino]methyl}pyrrolidin-2-one;
(5S)-5-{[(3,5-difluorophenyl)amino]methyl}pyrrolidin-2-one;
(5S)-5-[(3,4-difluorophenoxy)methyl]pyrrolidin-2-one;
(5S)-5-[(1,3-benzodioxol-5-ylamino)methyl]pyrrolidin-2-one;
(5S)-5-{[(4-fluorophenyl)(methyl)amino]methyl}pyrrolidin-2-one;
(5S)-5-(thiomorpholin-4-ylmethyl)pyrrolidin-2-one;
(5S)-5-[(4,4-difluoropiperidin-1-yl)methyl]pyrrolidin-2-one;
(5S)-5-{[(2,2,2-trifluoroethyl)amino]methyl}pyrrolidin-2-one;
(5S)-5-[(4aS,8aS)-octahydroisoquinolin-2(1H)-ylmethyl]pyrrolidin-2-one;
(5S)-5-{[cis-2,6-dimethylmorpholin-4-yl]methyl}pyrrolidin-2-one;
(4R)-4-{[cis-2,6-dimethylmorpholin-4-yl]methyl}-1,3-oxazolidin-2-one;
(4R)-4-(piperidin-1-ylmethyl)-1,3-oxazolidin-2-one;
(4R)-4-[(4,4-difluoropiperidin-1-yl)methyl]-1,3-oxazolidin-2-one;
(4R)-4-[(dibenzylamino)methyl]-1,3-oxazolidin-2-one;
(4R)-4-{[(3,4-difluorophenyl)amino]methyl}-1,3-oxazolidin-2-one;
(4S)-4-(piperidin-1-ylmethyl)azetidin-2-one;
7-benzyl-2,7-diazaspiro[4.4]nonan-3-one;
4-(pyrrolidin-1-ylmethyl)-1,3-oxazolidin-2-one;
4-(4-chlorobenzyl)-1,3-oxazolidin-2-one;
(5S)-5-[(1,1-dioxidothiomorpholin-4-yl)methyl]pyrrolidin-2-one;
(5S)-3,3-dimethyl-5-(piperidin-1-ylmethyl)pyrrolidin-2-one;
(5R)-5-{[cis-2,6-dimethylmorpholin-4-yl]methyl}-3,3-dimethylpyrrolidin-2-one;
(5R)-5-[(4,4-difluoropiperidin-1-yl)methyl]-3,3-dimethylpyrrolidin-2-one;
[(2S)-4-oxoazetidin-2-yl]methyl-4-methylbenzenesulfonate;
methyl [1-benzyl-3-(nitromethyl)pyrrolidin-3-yl]acetate;
methyl 1-[4-(3-chloropropoxy)phenyl]-5-oxopyrrolidine-3-carboxylate;

methyl 1-{4-[3-(2-methylpyrrolidin-1-yl)propoxy]phenyl}-5-oxopyrrolidine-3-carboxylate;
ethyl (1-{4-[3-(2-methylpyrrolidin-1-yl)propoxy]phenyl}-5-oxopyrrolidin-3-yl)acetate;
4-(chloromethyl)-1-{4-[3-(2-methylpyrrolidin-1-yl)propoxy]phenyl}pyrrolidin-2-one;
4-(2-chloroethyl)-1-{4-[3-(2-methylpyrrolidin-1-yl)propoxy]phenyl}pyrrolidin-2-one;
2-{4-[3-(2-methylpyrrolidin-1-yl)propoxy]phenyl}-2,7-diazaspiro[4.4]nonan-3-one; and
(5S)-1-(6-chloropyridin-3-yl)-5-(piperidin-1-ylmethyl)pyrrolidin-2-one.

Particularly, the present invention relates to synthetic intermediates selected from the group consisting of:
(5S)-5-(piperidin-1-ylmethyl)pyrrolidin-2-one;
(5R)-5-(piperidin-1-ylmethyl)pyrrolidin-2-one;
(5S)-5-[(2-methylpiperidin-1-yl)methyl]pyrrolidin-2-one;
(5S)-5-[(2,6-dimethylpiperidin-1-yl)methyl]pyrrolidin-2-one;
(5S)-5-[(4-methylpiperidin-1-yl)methyl]pyrrolidin-2-one;
(5S)-5-[(2-methylpyrrolidin-1-yl)methyl]pyrrolidin-2-one;
(5S)-5-{[(2R)-2-methylpyrrolidin-1-yl]methyl}pyrrolidin-2-one;
(5S)-5-{[(2S)-2-methylpyrrolidin-1-yl]methyl}pyrrolidin-2-one;
(5S)-5-(pyrrolidin-1-ylmethyl)pyrrolidin-2-one;
(5S)-5-(azepan-1-ylmethyl)pyrrolidin-2-one;
(5S)-5-[(4-cyclopentylpiperazin-1-yl)methyl]pyrrolidin-2-one;
(5S)-5-{[4-(cyclohexylmethyl)piperazin-1-yl]methyl}pyrrolidin-2-one;
(5S)-5-[(4-isopropylpiperazin-1-yl)methyl]pyrrolidin-2-one;
(5S)-5-{[(cyclopropylmethyl)amino]methyl}pyrrolidin-2-one;
(5S)-5-{[(cyclohexylmethyl)amino]methyl}pyrrolidin-2-one;
(5S)-5-[(cyclobutylamino)methyl]pyrrolidin-2-one;
(5S)-5-[(cyclopentylamino)methyl]pyrrolidin-2-one;
(5S)-5-[(cyclohexylamino)methyl]pyrrolidin-2-one;
(5S)-5-{[(cyclopropylmethyl)(propyl)amino]methyl}pyrrolidin-2-one;
(5S)-5-{[(4-fluorobenzyl)amino]methyl}pyrrolidin-2-one;
(5S)-5-(anilinomethyl)pyrrolidin-2-one;
(5S)-5-{[(4-fluorophenyl)amino]methyl}pyrrolidin-2-one;
(5S)-5-{[(2-fluorophenyl)amino]methyl}pyrrolidin-2-one;
(5S)-5-{[(3-fluorophenyl)amino]methyl}pyrrolidin-2-one;
(5S)-5-{[(2,4-difluorophenyl)amino]methyl}pyrrolidin-2-one;
(5S)-5-{[(3-methoxyphenyl)amino]methyl}pyrrolidin-2-one;
(5S)-5-({[4-(trifluoromethyl)phenyl]amino}methyl)pyrrolidin-2-one;
(5S)-5-[(4-fluorophenoxy)methyl]pyrrolidin-2-one;
(5S)-5-{[(4-methylphenyl)amino]methyl}pyrrolidin-2-one;
(5S)-5-{[(3,4-difluorophenyl)amino]methyl}pyrrolidin-2-one;
(5S)-5-{[(3,5-difluorophenyl)amino]methyl}pyrrolidin-2-one;
(5S)-5-[(3,4-difluorophenoxy)methyl]pyrrolidin-2-one;
(5S)-5-[(1,3-benzodioxol-5-ylamino)methyl]pyrrolidin-2-one;
(5S)-5-{[(4-fluorophenyl)(methyl)amino]methyl}pyrrolidin-2-one;
(5S)-5-(thiomorpholin-4-ylmethyl)pyrrolidin-2-one;
(5S)-5-[(4,4-difluoropiperidin-1-yl)methyl]pyrrolidin-2-one;
(5S)-5-{[(2,2,2-trifluoroethyl)amino]methyl}pyrrolidin-2-one;
(5S)-5-[(4aS,8aS)-octahydroisoquinolin-2(1H)-ylmethyl]pyrrolidin-2-one;
(5S)-5-{[cis-2,6-dimethylmorpholin-4-yl]methyl}pyrrolidin-2-one;
(4R)-4-{[cis-2,6-dimethylmorpholin-4-yl]methyl}-1,3-oxazolidin-2-one;
(4R)-4-(piperidin-1-ylmethyl)-1,3-oxazolidin-2-one;
(4R)-4-[(4,4-difluoropiperidin-1-yl)methyl]-1,3-oxazolidin-2-one;
(4R)-4-[(dibenzylamino)methyl]-1,3-oxazolidin-2-one;
(4R)-4-{[(3,4-difluorophenyl)amino]methyl}-1,3-oxazolidin-2-one;
(4S)-4-(piperidin-1-ylmethyl)azetidin-2-one;
7-benzyl-2,7-diazaspiro[4.4]nonan-3-one;
4-(pyrrolidin-1-ylmethyl)-1,3-oxazolidin-2-one;
4-(4-chlorobenzyl)-1,3-oxazolidin-2-one;
(5S)-5-[(1,1-dioxidothiomorpholin-4-yl)methyl]pyrrolidin-2-one;
(5S)-3,3-dimethyl-5-(piperidin-1-ylmethyl)pyrrolidin-2-one;
(5R)-5-{[cis-2,6-dimethylmorpholin-4-yl]methyl}-3,3-dimethylpyrrolidin-2-one;
(5R)-5-[(4,4-difluoropiperidin-1-yl)methyl]-3,3-dimethylpyrrolidin-2-one;
[(2S)-4-oxoazetidin-2-yl]methyl-4-methylbenzenesulfonate;
methyl [1-benzyl-3-(nitromethyl)pyrrolidin-3-yl]acetate;
methyl 1-[4-(3-chloropropoxy)phenyl]-5-oxopyrrolidine-3-carboxylate;
methyl 1-{4-[3-(2-methylpyrrolidin-1-yl)propoxy]phenyl}-5-oxopyrrolidine-3-carboxylate;
ethyl (1-{4-[3-(2-methylpyrrolidin-1-yl)propoxy]phenyl}-5-oxopyrrolidin-3-yl)acetate;
4-(chloromethyl)-1-{4-[3-(2-methylpyrrolidin-1-yl)propoxy]phenyl}pyrrolidin-2-one;
4-(2-chloroethyl)-1-{4-[3-(2-methylpyrrolidin-1-yl)propoxy]phenyl}pyrrolidin-2-one;
2-{4-[3-(2-methylpyrrolidin-1-yl)propoxy]phenyl}-2,7-diazaspiro[4.4]nonan-3-one; and
(5S)-1-(6-chloropyridin-3-yl)-5-(piperidin-1-ylmethyl)pyrrolidin-2-one.

It has now been found that compounds of formula (I) according to the present invention and their pharmaceutically acceptable salts are useful in a variety of medical disorders.

For example, the compounds according to the invention are useful for the treatment and prevention of diseases or pathological conditions of the central nervous system including mild-cognitive impairments, Alzheimer's disease, learning and memory disorders, cognitive disorders, attention deficit disorder, attention-deficit hyperactivity disorder, Parkinson's disease, schizophrenia, dementia, depression, epilepsy, seizures, convulsions, sleep/wake and arousal/vigilance disorders such as hypersomnia and narcolepsy, and/or obesity.

Furthermore, compounds according to the invention alone or in combination with an antiepileptic drug (AED) may be useful in the treatment of epilepsy, seizure or convulsions. It is known from literature that the combination of $H_3$-receptor ligands with an AED may produce additive synergistic effects on efficacy with reduced side-effects such as decreased vigilance, sedation or cognitive problems.

Furthermore, compounds of general formula (I) alone or in combination with a histamine $H_1$ antagonist may also be used for the treatment of upper airway allergic disorders.

In a particular embodiment of the present invention, compounds of general formula (I), alone or in combination with muscarinic receptor ligands and particularly with a muscarinic $M_2$ antagonist, may be useful for the treatment of cognitive disorders, Alzheimer's disease, and attention-deficit hyperactivity disorder.

Particularly, compounds of general formula (I) displaying NO-donor properties, alone or in combination with a nitric oxide (NO) releasing agent may be useful in the treatment of cognitive dysfunctions.

Compounds of general formula (I) may also be used in the treatment and prevention of multiple sclerosis (MS).

Usually, compounds of general formula (I) may be used in the treatment and prevention of all types of cognitive-related disorders.

In one embodiment, compounds of general formula (I) may be used for the treatment and prevention of cognitive dysfunctions in diseases such as mild cognitive impairment, dementia, Alzheimer's disease, Parkinson's disease, Down's syndrome as well as for the treatment of attention-deficit hyperactivity disorder.

In another embodiment, compounds of general formula (I) may also be used for the treatment and prevention of psychotic disorders, such as schizophrenia; or for the treatment of eating disorders, such as obesity; or for the treatment of inflammation and pain disorders; or for the treatment of anxiety, stress and depression; or for the treatment of cardiovascular disorders, for example, myocardial infarction; or for the treatment and prevention of multiple sclerosis (MS).

Pain disorders include neuropathic pain, such as associated with diabetic neuropathy, post-herpetic neuralgia; trigeminal neuralgia, posttraumatic peripheral neuropathy, phantom limb pain, with cancer and neuropathies induced by treatment with antineoplastic agents, pain due to nerve damage associated with demyelinating disease such as multiple sclerosis, neuropathy associated with HIV, post-operative pain; corneal pain, obstetrics pain (pain relief during delivery or after caesarean section), visceral pain, inflammatory pain such as associated to rheumatoid arthritis; low-back pain/sciatica; carpal tunnel syndrome, allodynic pain such as fibromyalgia; chronic pain associated with Complex Regional Pain Syndrome (CRPS) and chronic muscle pain such as, yet not limited to, that associated with back spasm.

In a particular embodiment, compounds of formula (I) may be used for the treatment and prevention neuropathic pain.

In one embodiment, compounds of formula (I) according to the present invention may be used as a medicament.

In a further embodiment, the present invention concerns the use of a compound of formula (I) or a pharmaceutically acceptable salt thereof or of a pharmaceutical composition comprising an effective amount of said compound for the manufacture of a medicament for the treatment and prevention of mild-cognitive impairment, Alzheimer's disease, learning and memory disorders, attention-deficit hyperactivity disorder, Parkinson's disease, schizophrenia, dementia, depression, epilepsy, seizures, convulsions, sleep/wake disorders, cognitive dysfunctions, narcolepsy, hypersomnia, obesity, upper airway allergic disorders, Down's syndrome, anxiety, stress, cardiovascular disorders, inflammation, pain disorders or multiple sclerosis.

In another embodiment, the present invention concerns the use of a compound of formula (I) or a pharmaceutically acceptable salt thereof or a pharmaceutical composition comprising an effective amount of said compound for the manufacture of a medicament for the treatment of cognitive dysfunctions in diseases such as mild cognitive impairment, dementia, Alzheimer's disease, Parkinson's disease, Down's syndrome as well as for the treatment of attention-deficit hyperactivity disorder.

In a particular embodiment, the present invention concerns the use of a compound of formula (I) or a pharmaceutically acceptable salt thereof or a pharmaceutical composition comprising an effective amount of said compound for the manufacture of a medicament for the treatment of neuropathic pain.

The methods of the invention comprise administration to a mammal (preferably human) suffering from above mentioned conditions or disorders, of a compound according to the invention in an amount sufficient to alleviate or prevent the disorder or condition.

The compound is conveniently administered in any suitable unit dosage form, including but not limited to one containing 3 to 3000 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "cognitive disorders" as used herein refers to disturbances of cognition, which encompasses perception, learning and reasoning or in other terms the physiological (mental/neuronal) process of selectively acquiring, storing, and recalling information.

The term "attention-deficit hyperactivity disorder" (ADHD) as used herein refers to a problem with inattentiveness, over-activity, impulsivity, or a combination of these. For these problems to be diagnosed as ADHD, they must be out of the normal range for the child's age and development. The term "attention-deficit disorder" (ADD) is also commonly used for the same disorder.

The term "Alzheimer's disease" (AD) as used herein refers to a progressive, neurodegenerative disease characterized in the brain by abnormal clumps (amyloid plaques) and tangled bundles of fibers (neurofibrillary tangles) composed of misplaced proteins. Age is the most important risk factor for AD; the number of people with the disease doubles every 5 years beyond age 65. Three genes have been discovered that cause early onset (familial) AD. Other genetic mutations that cause excessive accumulation of amyloid protein are associated with age-related (sporadic) AD. Symptoms of AD include memory loss, language deterioration, impaired ability to mentally manipulate visual information, poor judgment, confusion, restlessness, and mood swings. Eventually AD destroys cognition, personality, and the ability to function. The early symptoms of AD, which include forgetfulness and loss of concentration, are often missed because they resemble natural signs of aging.

The term "Parkinson's disease" (PD) as used herein refers to a group of conditions called motor system disorders, which are the result of the loss of dopamine-producing brain cells. The four primary symptoms of PD are tremor, or trembling in hands, arms, legs, jaw, and face; rigidity, or stiffness of the limbs and trunk; bradykinesia, or slowness of movement; and postural instability, or impaired balance and coordination. As these symptoms become more pronounced, patients may have difficulty walking, talking, or completing other simple tasks. PD usually affects people over the age of 50. Early symptoms of PD are subtle and occur gradually. In some people the disease progresses more quickly than in others. As the disease progresses, the shaking, or tremor, which affects the majority of PD patients may begin to interfere with daily activities. Other symptoms may include depression and other emotional changes; difficulty in swallowing, chewing, and speaking; urinary problems or constipation; skin problems; and sleep disruptions.

The term "Down's syndrome" as used herein refers to a chromosome abnormality, usually due to an extra copy of the $21^{st}$ chromosome. This syndrome, usually but not always results in mental retardation and other conditions. The term "mental retardation" refers to a below-average general intellectual function with associated deficits in adaptive behavior that occurs before age 18.

The term "mild-cognitive impairment" as used herein refers to a transitional stage of cognitive impairment between normal aging and early Alzheimer's disease. It refers particularly to a clinical state of individuals who are memory impaired but are otherwise functioning well and do not meet clinical criteria for dementia.

The term "obesity" as used herein refers to a body mass index (BMI) which is greater than 30 kg/m$^2$.

The term "dementia" as used herein refers to a group of symptoms involving progressive impairment of brain function. American Geriatrics Society refers to dementia as a condition of declining mental abilities, especially memory. The person will have problems doing things he or she used to be able to do, like keep the check book, drive a car safely, or plan a meal. He or she will often have problems finding the right words and may become confused when given too many things to do at once. The person with dementia may also change in personality, becoming aggressive, paranoid, or depressed.

The term "schizophrenia" as used herein refers to a group of psychotic disorders characterized by disturbances in thought, perception, attention, affect, behavior, and communication that last longer than 6 months. It is a disease that makes it difficult for a person to tell the difference between real and unreal experiences, to think logically, to have normal emotional responses to others, and to behave normally in social situations.

The term "anxiety" as used herein refers to a feeling of apprehension or fear. Anxiety is often accompanied by physical symptoms, including twitching or trembling, muscle tension, headaches, sweating, dry mouth, difficulty swallowing and/or abdominal pain.

The term "narcolepsy" as used herein refers to a sleep disorder associated with uncontrollable sleepiness and frequent daytime sleeping.

The term "depression" as used herein refers to a disturbance of mood and is characterized by a loss of interest or pleasure in normal everyday activities. People who are depressed may feel "down in the dumps" for weeks, months, or even years at a time. Some of the following symptoms may be symptoms of depression: persistent sad, anxious, or "empty" mood; feelings of hopelessness, pessimism; feelings of guilt, worthlessness, helplessness; loss of interest or pleasure in hobbies and activities that were once enjoyed, including sex; decreased energy, fatigue, being "slowed down"; difficulty concentrating, remembering, making decisions; insomnia, early-morning awakening, or oversleeping; appetite and/or weight loss or overeating and weight gain; thoughts of death or suicide; suicide attempts; restlessness, irritability; persistent physical symptoms that do not respond to treatment, such as headaches, digestive disorders, and chronic pain.

The term "epilepsy" as used herein refers a brain disorder in which clusters of nerve cells, or neurons, in the brain sometimes signal abnormally. In epilepsy, the normal pattern of neuronal activity becomes disturbed, causing strange sensations, emotions, and behavior or sometimes convulsions, muscle spasms, and loss of consciousness. Epilepsy is a disorder with many possible causes. Anything that disturbs the normal pattern of neuron activity—from illness to brain damage to abnormal brain development—can lead to seizures. Epilepsy may develop because of an abnormality in brain wiring, an imbalance of nerve signaling chemicals called neurotransmitters, or some combination of these factors. Having a seizure does not necessarily mean that a person has epilepsy. Only when a person has had two or more seizures is he or she considered to have epilepsy.

The term "seizure" as used herein refers to a transient alteration of behaviour due to the disordered, synchronous, and rhythmic firing of populations of brain neurones.

The term "migraine" as used herein means a disorder characterised by recurrent attacks of headache that vary widely in intensity, frequency, and duration. The pain of a migraine headache is often described as an intense pulsing or throbbing pain in one area of the head. It is often accompanied by extreme sensitivity to light and sound, nausea, and vomiting. Some individuals can predict the onset of a migraine because it is preceded by an "aura," visual disturbances that appear as flashing lights, zig-zag lines or a temporary loss of vision. People with migraine tend to have recurring attacks triggered by a lack of food or sleep, exposure to light or hormonal irregularities (only in women). Anxiety, stress, or relaxation after stress can also be triggers. For many years, scientists believed that migraines were linked to the dilation and constriction of blood vessels in the head. Investigators now believe that migraine is caused by inherited abnormalities in genes that control the activities of certain cell populations in the brain. The International Headache Society (IHS, 1988) classifies migraine with aura (classical migraine) and migraine without aura (common migraine) as the major types of migraine.

The term "multiple sclerosis" (MS) as used herein is a chronic disease of the central nervous system in which gradual destruction of myelin occurs in patches throughout the brain or spinal cord or both, interfering with the nerve pathways. As more and more nerves are affected, a patient experiences a progressive interference with functions that are controlled by the nervous system such as vision, speech, walking, writing, and memory.

The term "neuropathic pain" as used herein refers to a pathological form of pain due to lesion or disease of the nervous system, either occurring following injury to the central nervous system (central pain, e.g., post-stroke, after spinal cord injury, phantom limb pain following amputation) or caused by damage to the peripheral nervous system, such as to one or more peripheral nerves (e.g., painful peripheral neuropathy due to nerve compression or neuroma formation, trigeminal neuralgia, postherpetic neuralgia, diabetic neuropathy). Neuropathic pain may originate from a dysfunction in a single peripheral nerve (mononeuropathy) or in several (polyneuropathy, as in diabetic polyneuropathy). Neuropathic pain, which is typically experienced as abnormal pain, may be spontaneous or evoked, and consists of dysesthesias, such as intense, electrical shock-like, well-localized burning pain, often with a superimposed sharp, lancinating component. Such a pain may radiate in a pattern indicative of a dermatome or peripheral nerve territory. Other hallmark sensations include hyperalgesia (exaggerated pain response to normally painful stimuli) and allodynia (pain from a nonnoxious stimulus). Several types of neuropathy, which may share some underlying pathogenic mechanisms, have been distinguished. The 3 major syndromes are: 1. Diabetic painful polyneuropathy (symmetrical, distal lower limb sensory disturbances with autonomic, but little motor involvement); 2. Postherpetic Neuralgia (chronic painful condition, in which burning and jabbing pain persists for longer than a month in the dermatome of the skin eruptions of a prior Herpes Zoster infection, such as a thoracic dermatome); and 3. Trigeminal Neuralgia or "tic douloureux" (paroxysms of intense, stabbing unilateral pain in the distribution of the mandibular and maxillary divisions of the Vth cranial nerve. Trigger zones are face, lips or gums).

Activity in any of the above-mentioned indications can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner. Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the total weight of the composition.

For the preferred oral compositions, the daily dosage is in the range 3 to 3000 milligrams (mg) of compounds of formula (I).

In compositions for parenteral administration, the quantity of compound of formula (I) present is at least 0.5% by weight and can be up to 33% by weight with respect to the total weight of the composition. For the preferred parenteral compositions, the dosage unit is in the range 3 mg to 3000 mg of compounds of formula (I).

The daily dose can fall within a wide range of dosage units of compound of formula (I) and is generally in the range 3 to 3000 mg. However, it should be understood that the specific doses can be adapted to particular cases depending on the individual requirements, at the physician's discretion.

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

Unless specified otherwise in the examples, characterization of the compounds is performed according to the following methods:

NMR spectra are recorded on a BRUKER AC 250 Fourier Transform NMR Spectrometer fitted with an Aspect 3000 computer and a 5 mm $^1H/^{13}C$ dual probehead or BRUKER DRX 400 FT NMR fitted with a SG Indigo$^2$ computer and a 5 mm inverse geometry $^1H/^{13}C/^{15}N$ triple probehead. The compound is studied in $d_6$-dimethylsulfoxide (or $d_3$-chloroform) solution at a probe temperature of 313 K or 300 K and at a concentration of 20 mg/ml. The instrument is locked on the deuterium signal of $d_6$-dimethylsulfoxide (or $d_3$-chloroform). Chemical shifts are given in ppm downfield from TMS (tetramethylsilane) taken as internal standard.

HPLC analyses are performed using one of the following systems:

an Agilent 1100 series HPLC system mounted with an INERTSIL ODS 3 C18, DP 5 µm, 250×4.6 mm column. The gradient runs from 100% solvent A (acetonitrile, water, phosphoric acid (5/95/0.001, v/v/v)) to 100% solvent B (acetonitrile, water, phosphoric acid (95/5/0.001, v/v/v)) in 6 min with a hold at 100% B of 4 min. The flow rate is set at 2.5 ml/min. The chromatography is carried out at 35° C.

a HP 1090 series HPLC system mounted with a HPLC Waters Symmetry C18, 250×4.6 mm column. The gradient runs from 100% solvent A (methanol, water, phosphoric acid (15/85/0.001M, v/v/M)) to 100% solvent B (methanol, water, phosphoric acid (85/15/0.001M, v/v/M)) in 10 min with a hold at 100% B of 10 min. The flow rate is set at 1 ml/min. The chromatography is carried out at 40° C.

Mass spectrometric measurements in LC/MS mode are performed as follows:

HPLC Conditions

Analyses are performed using a WATERS Alliance HPLC system mounted with an INERTSIL ODS 3, DP 5 µm, 250× 4.6 mm column.

The gradient runs from 100% solvent A (acetonitrile, water, trifluoroacetic acid (10/90/0.1, v/v/v)) to 100% solvent B (acetonitrile, water, trifluoroacetic acid (90/10/0.1, v/v/v))

in 7 min with a hold at 100% B of 4 min. The flow rate is set at 2.5 ml/min and a split of 1/25 is used just before API source.

MS Conditions

Samples are dissolved in acetonitrile/water, 70/30, v/v at the concentration of about 250 μg/ml. API spectra (+ or −) are performed using a FINNIGAN LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN TSQ 700 tandem quadrupole mass spectrometer. The source temperature is set at 150° C.

Mass spectrometric measurements on a TSQ 700 tandem quadrupole mass spectrometer (Finnigan MAT) in GC/MS mode are performed with a gas chromatograph model 3400 (Varian) fitted with a split/splitless injector and a DB-5MS fused-silica column (15 m×0.25 mm I.D., 1 μm) from J&W Scientific. Helium (purity 99.999%) is used as carrier gas. The injector (CTC A200S autosampler) and the transfer line operate at 290 and 250° C., respectively. Sample (1 μl) is injected in splitless mode and the oven temperature is programmed as follows: 50° C. for 5 min., increasing to 280° C. (23° C./min) and holding for 10 min. The TSQ 700 spectrometer operates in electron impact (EI) or chemical ionization (CI/CH$_4$) mode (mass range 33-800, scan time 1.00 sec). The source temperature is set at 150° C.

Specific rotation is recorded on a Perkin-Elmer 341 polarimeter. The angle of rotation is recorded at 25° C. on 1% solutions in methanol, at 589 nm.

Melting points are determined on a Büchi 535 or 545 Tottoli-type fusionometer, and are not corrected, or by the onset temperature on a Perkin Elmer DSC 7.

Preparative chromatographic separations are performed on silicagel 60 Merck, particle size 15-40 μm, reference 1.15111.9025, using Novasep axial compression columns (80 mm i.d.), flow rates between 70 and 150 ml/min. Amount of silicagel and solvent mixtures as described in individual procedures.

Preparative Chiral Chromatographic separations are performed on a DAICEL Chiralpak AD 20 μm, 100*500 mm column using an in-house build instrument with various mixtures of lower alcohols and C5 to C8 linear, branched or cyclic alkanes at ±350 ml/min. Solvent mixtures as described in individual procedures.

EXAMPLE 1

Synthesis of (5S)-1-{4-[3-(2-methylpyrrolidin-1-yl)propoxyl]phenyl}-5-(piperidin-1-ylmethyl)pyrrolidin-2-one 48

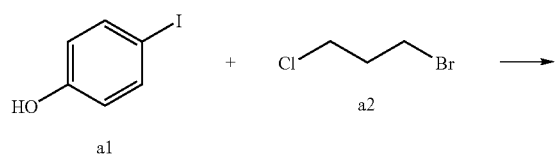

-continued

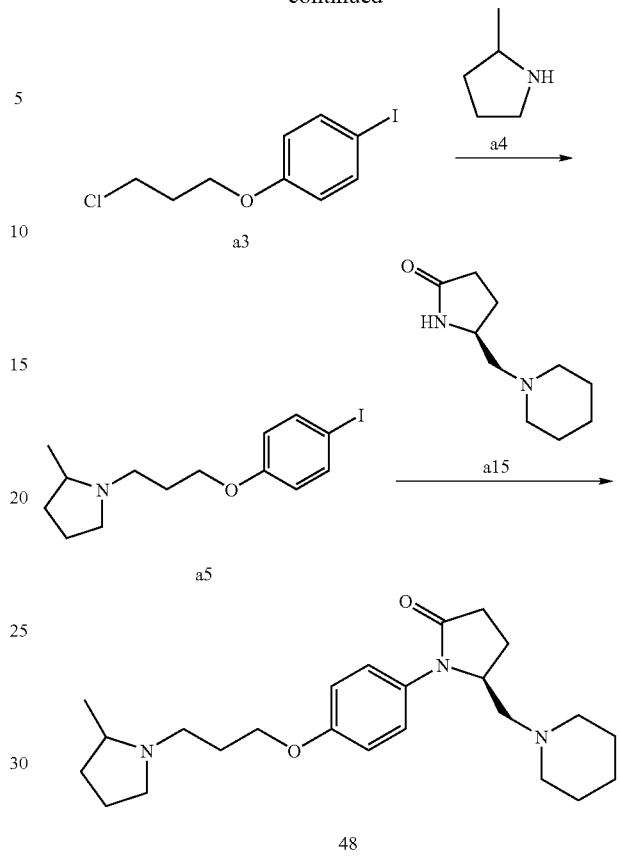

1.1 Synthesis of 1-(3-chloropropoxy)-4-iodobenzene a3

Potassium carbonate (6.3 g, 45.4 mmol, 2 eq) is added to a solution of 4-iodophenol a1 (5 g, 22.7 mmol, 1 eq) in acetone (200 ml) then 1-bromo-3-chloropropane a2 (2.2 ml, 22.7 mmol, 1 eq) is added and the mixture is heated at reflux overnight. The solvent is then removed in vacuo, and the residue is dissolved into dichloromethane. The organic layer is washed twice with a saturated solution of aqueous ammonium chloride then the aqueous layer is extracted with dichloromethane. The organic layers are dried over magnesium sulfate and concentrated in vacuo to give 6.6 g of 1-(3-chloropropoxy)-4-iodobenzene a3 as a colorless oil.

Yield: 98%.

GC-MS (M$^+$.): 296/297.

1-(4-chlorobutoxy)-4-iodobenzene a52 may be obtained according to the same method.

GC-MS (M$^+$.): 310/312.

1.2 Synthesis of 1-[3-(4-iodophenoxy)propyl]-2-methylpyrrolidine a5

2-methylpyrrolidine a4 (2 g, 23 mmol, 2 eq) is added into a suspension of 1-(3-chloropropoxy)-4-iodobenzene a3 (3.48 g, 11.7 mmol, 1 eq), potassium carbonate (3.24 g, 23 mmol, 2 eq) and sodium iodide (0.035 g, 0.23 mmol, 0.02 eq) in acetonitrile (120 ml), and the mixture is heated at reflux overnight. The solvent is then removed in vacuo, and the residue is dissolved in ethyl acetate. The organic layer is washed twice with a saturated solution of aqueous sodium hydrogenocarbonate, dried over magnesium sulfate, and concentrated in vacuo to give 3.65 g of a yellow oil. This oil is purified by chromatography over silicagel (dichloromethane/methanol/ammonia:98/2/0.2) to afford 2.57 g of 1-[3-(4-iodophenoxy)propyl]-2-methylpyrrolidine a5 as a yellow oil.

Yield: 80%.

LC-MS (MH$^+$): 346.

The following compounds may be synthesized according to the same method:

| | | |
|---|---|---|
| a6 | 1-[3-(4-iodophenoxy)propyl]piperidine | LC-MS (MH$^+$): 346 |
| a7 | 1-[3-(4-iodophenoxy)propyl]-2-methyl-piperidine | LC-MS (MH$^+$): 360 |
| a8 | 1-[3-(4-iodophenoxy)propyl]-4-isopropylpiperazine | LC-MS (MH$^+$): 389 |
| a9 | 1-cyclopentyl-4-[3-(4-iodophenoxy)-propyl]piperazine | LC-MS (MH$^+$): 415 |
| a10 | 1-[2-(4-iodophenoxy)ethyl]piperidine | LC-MS (MH$^+$): 332 |
| a11 | 1-[2-(4-iodophenoxy)ethyl]-2-methylpyrrolidine | LC-MS (MH$^+$): 332 |
| a12 | 1-[3-(3-bromophenoxy)propyl]-2-methylpyrrolidine | LC-MS (MH$^+$): 298/300 |
| a61 | 1-[3-(4-iodophenoxy)propyl]-2-(pyrrolidin-1-ylmethyl)pyrrolidine | LC-MS (MH$^+$): 415 |
| a62 | 1-[4-(4-iodophenoxy)butyl]-2-methylpyrrolidine | LC-MS (MH$^+$): 360 |
| a63 | 1-[3-(4-iodophenoxy)propyl]-1-azaspiro[4.4]nonane | LC-MS (MH$^+$): 386 |
| a64 | (2R)-1-[3-(4-iodophenoxy)propyl]-2-methylpyrrolidine | LC-MS (MH+): 346 |

1.3 Synthesis of pyrrolidin-2-one derivatives of formula (III)

1.3.1 Synthesis of (5S)-5-(piperidin-1-ylmethyl)pyrrolidin-2-one a15

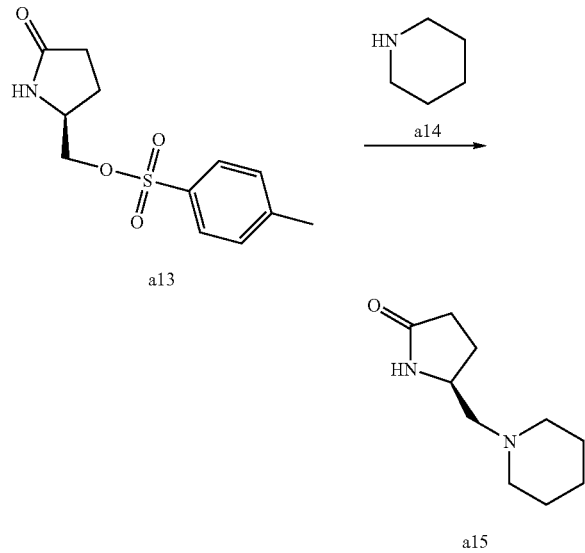

Piperidine a14 (0.7 g, 8.3 mmol, 1.5 eq) is added to a suspension of [(2S)-5-oxopyrrolidin-2-yl]methyl 4-methylbenzenesulfonate a13 (1.5 g, 5.56 mmol, 1 eq) and potassium carbonate (1.5 g, 11.1 mmol, 2 eq) in acetonitrile (50 ml), and the mixture is stirred at reflux overnight. Potassium carbonate is filtered and the solvent is removed in vacuo. The residue is dissolved in a minimum of dichloromethane, then the organic layer is sonicated and heated to precipitate a white solid which is filtered. The liquid phase is concentrated in vacuo to give 1 g of (5S)-5-(piperidin-1-ylmethyl)pyrrolidin-2-one a15 as a yellow oil.

Yield: 100%.

LC-MS (MH$^+$): 183.

The following compounds may be synthesized in a suitable solvent according to the same method:

| | | |
|---|---|---|
| a16 | (5R)-5-(piperidin-1-ylmethyl)-pyrrolidin-2-one | LC-MS (MH$^+$): 183 |
| a17 | (5S)-5-[(2-methylpiperidin-1-yl)-methyl]pyrrolidin-2-one | LC-MS (MH$^+$): 197 |
| a18 | (5S)-5-[(2,6-dimethylpiperidin-1-yl)-methyl]pyrrolidin-2-one | LC-MS (MH$^+$): 211 |
| a19 | (5S)-5-[(4-methylpiperidin-1-yl)methyl]-pyrrolidin-2-one | LC-MS (MH$^+$): 169 |
| a20 | (5S)-5-[(2-methylpyrrolidin-1-yl)methyl]-pyrrolidin-2-one | LC-MS (MH$^+$): 183 |
| a21 | (5S)-5-[(2-methylpyrrolidin-1-yl)methyl]-pyrrolidin-2-one, diastereoisomer A | LC-MS (MH$^+$): 183 |
| a22 | (5S)-5-[(2-methylpyrrolidin-1-yl)methyl]-pyrrolidin-2-one, diastereoisomer B | LC-MS (MH$^+$): 183 |
| a23 | (5S)-5-(pyrrolidin-1-ylmethyl)pyrrolidin-2-one | LC-MS (MH$^+$): 169 |
| a24 | (5S)-5-(azepan-1-ylmethyl)pyrrolidin-2-one | LC-MS (MH$^+$): 197 |
| a25 | (5S)-5-(morpholin-4-ylmethyl)pyrrolidin-2-one | LC-MS (MH$^+$): 185 |
| a26 | (5S)-5-[(4-cyclopentylpiperazin-1-yl)-methyl]pyrrolidin-2-one | LC-MS (MH$^+$): 252 |
| a27 | (5S)-5-{[4-(cyclohexylmethyl)piperazin-1-yl]methyl}pyrrolidin-2-one | LC-MS (MH$^+$): 280 |
| a28 | (5S)-5-[(4-isopropylpiperazin-1-yl)methyl]-pyrrolidin-2-one | LC-MS (MH$^+$): 226 |
| a29 | (5S)-5-{[(cyclopropylmethyl)amino]methyl}-pyrrolidin-2-one | LC-MS (MH$^+$): 169 |
| a30 | (5S)-5-{[(cyclohexylmethyl)amino]methyl}-pyrrolidin-2-one | LC-MS (MH$^+$): 211 |
| a31 | (5S)-5-[(cyclobutylamino)methyl]-pyrrolidin-2-one | LC-MS (MH$^+$): 169 |
| a32 | (5S)-5-[(cyclopentylamino)methyl]-pyrrolidin-2-one | LC-MS (MH$^+$): 183 |
| a33 | (5S)-5-[(cyclohexylamino)methyl]-pyrrolidin-2-one | LC-MS (MH$^+$): 197 |
| a34 | (5S)-5-[(diethylamino)methyl]pyrrolidin-2-one | LC-MS (MH$^+$): 171 |
| a35 | (5S)-5-{[(cyclopropylmethyl)(propyl)-amino]methyl}pyrrolidin-2-one | LC-MS (MH$^+$): 211 |
| a36 | (5S)-5-{[(4-fluorobenzyl)amino]methyl}-pyrrolidin-2-one | LC-MS (MH$^+$): 223 |
| a37 | (5S)-5-(anilinomethyl)pyrrolidin-2-one | LC-MS (MH$^+$): 191 |
| a38 | (5S)-5-{[(4-fluorophenyl)amino]methyl}-pyrrolidin-2-one | LC-MS (MH$^+$): 209 |
| a65 | (5S)-5-{[(2-fluorophenyl)amino]methyl}-pyrrolidin-2-one | LC-MS (MH$^+$): 209 |
| a66 | (5S)-5-{[(3-fluorophenyl)amino]methyl}-pyrrolidin-2-one | LC-MS (MH$^+$): 209 |
| a67 | (5S)-5-{[(2,4-difluorophenyl)amino]methyl}-pyrrolidin-2-one | LC-MS (MH$^+$): 227 |
| a68 | (5S)-5-{[(3-methoxyphenyl)amino]methyl}-pyrrolidin-2-one | LC-MS (MH$^+$): 221 |
| a69 | (5S)-5-({[4-(trifluoromethyl)phenyl]amino}-methyl)pyrrolidin-2-one | LC-MS (MH$^+$): 259 |
| a70 | (5S)-5-[(4-fluorophenoxy)methyl]-pyrrolidin-2-one | LC-MS (MH$^+$): 210 |
| a71 | (5S)-5-{[(4-methylphenyl)amino]methyl}-opyrrolidin-2-ne | LC-MS (MH$^+$): 205 |
| a72 | (5S)-5-{[(3,4-difluorophenyl)amino]methyl}-pyrrolidin-2-one | LC-MS (MH$^+$): 227 |
| a73 | (5S)-5-{[(3,5-difluorophenyl)amino]methyl}-pyrrolidin-2-one | LC-MS (MH$^+$): 227 |
| a74 | (5S)-5-[(3,4-difluorophenoxy)methyl]-pyrrolidin-2-one | LC-MS (MH$^+$): 228 |
| a75 | (5S)-5-[(1,3-benzodioxol-5-ylamino)-methyl]pyrrolidin-2-one | LC-MS (MH$^+$): 235 |
| a76 | (5S)-5-{[(4-fluorophenyl)(methyl)amino]-methyl}pyrrolidin-2-one | LC-MS (MH$^+$): 223 |
| a77 | (5S)-5-(thiomorpholin-4-ylmethyl)-pyrrolidin-2-one | LC-MS (MH$^+$): 245 |

| | | |
|---|---|---|
| a78 | (5S)-5-[(4,4-difluoropiperidin-1-yl)methyl]-pyrrolidin-2-one | LC-MS (MH+): 219 |
| a79 | (5S)-5-{[(2,2,2-trifluoroethyl)amino]methyl}-pyrrolidin-2-one | LC-MS (MH+): 197 |
| a80 | (5S)-5-[(4aS,8aS)-octahydroisoquinolin-2(1H)-ylmethyl]pyrrolidin-2-one | LC-MS (MH+): 237 |
| a81 | (5S)-5-[(2,6-dimethylmorpholin-4-yl)-methyl]pyrrolidin-2-one | LC-MS (MH+): 401 |
| a82 | (5S)-5-{[cis-2,6-dimethylmorpholin-4-yl]methyl}pyrrolidin-2-one | LC-MS (MH+): 401 |
| a83 | (4R)-4-{[cis-2,6-dimethylmorpholin-4-yl]methyl}-1,3-oxazolidin-2-one | LC-MS (MH+): 215 |
| a84 | (4R)-4-(piperidin-1-ylmethyl)-1,3-oxazolidin-2-one | LC-MS (MH+): 185 |
| a85 | (4R)-4-[(4,4-difluoropiperidin-1-yl)methyl]-1,3-oxazolidin-2-one | LC-MS (MH+): 212 |
| a86 | (4R)-4-[(dibenzylamino)methyl]-1,3-oxazolidin-2-one | LC-MS (MH+): 295 |
| a87 | (4R)-4-{[(3,4-difluorophenyl)amino]methyl}-1,3-oxazolidin-2-one | LC-MS (MH+): 229 |

Compounds a21 and a22 are obtained from compound a20 by chromatography on silicagel (dichloromethane/methanol/ammonia 95/4.5/0.5).

1.3.2 Synthesis of 4-(piperidin-1-ylmethyl)azetidin-2-one a42

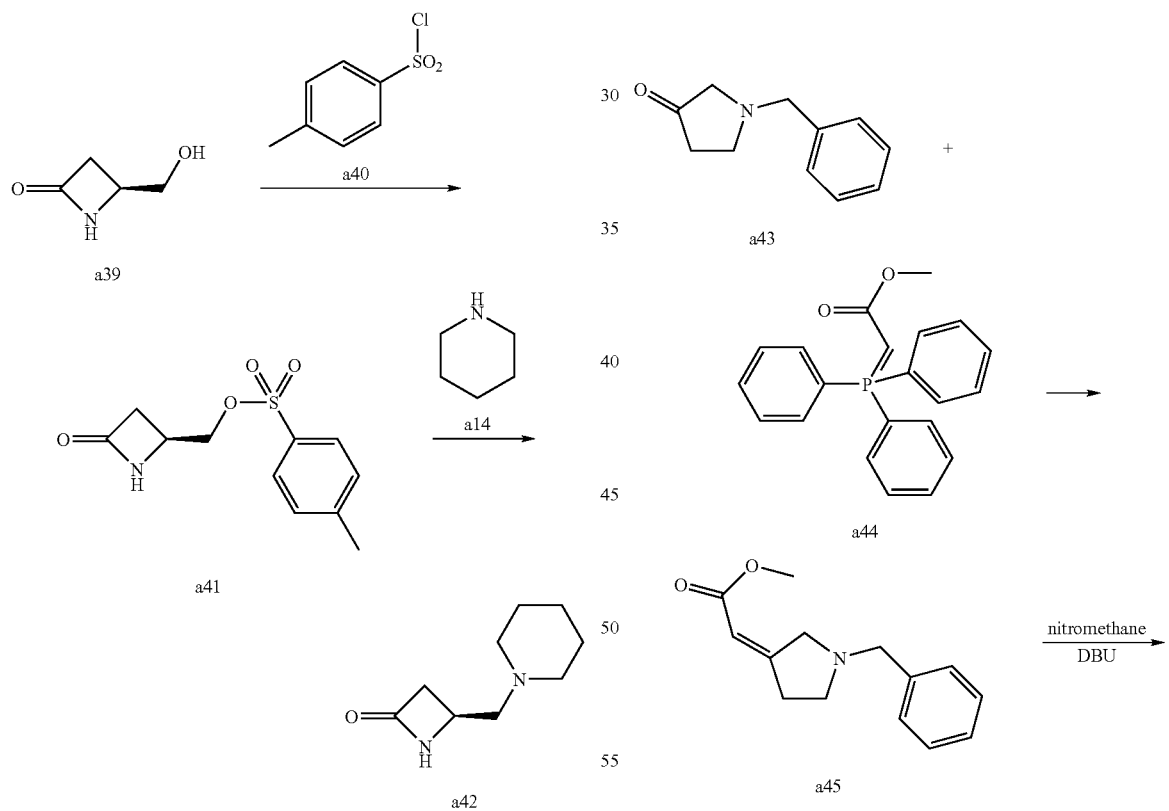

1.3.2.a. Synthesis of [(2S)-4-oxoazetidin-2-yl]methyl 4-methylbenzenesulfonate a41

(4S)-4-(hydroxymethyl)azetidin-2-one a39 (0.41 g, 4.6 mmol, 1 eq) and N-methylimidazole (1.1 ml, 14 mmol, 3.5 eq) are dissolved in dimethylformamide (5 ml) at 0° C. A solution of p-toluenesulfonyl chloride a40 (0.85 g, 4.4 mmol, 4 eq) in dimethylformamide (1 ml) is added dropwise. After 2 h, diethyl ether and water are added. The organic phase is separated, dried over magnesium sulfate and concentrated under reduced pressure to give 0.27 g of crude [(2S)-4-oxoazetidin-2-yl]methyl 4-methylbenzenesulfonate a41.

Yield: 26%.

LC-MS (MH+): 256.

1.3.2.b. Synthesis of (4S)-4-(piperidin-1-ylmethyl)azetidin-2-one a42

A mixture of [(2S)-4-oxoazetidin-2-yl]methyl 4-methylbenzenesulfonate a41 (0.23 g, 0.9 mol, 1 eq), potassium carbonate (0.25 g, 1.8 mmol, 2 eq) and piperidine a14 (0.15 ml, 1.5 mmol, 1.6 eq) is refluxed in acetonitrile (5 ml) for 4 h. The reaction mixture is then concentrated and the residue is taken up in ether, filtered and concentrated to give 0.17 g of (4S)-4-(piperidin-1-ylmethyl)azetidin-2-one a42.

Yield: 100%.

LC-MS (MH+): 169.

1.3.3. Synthesis of 7-benzyl-2,7-diazaspiro[4.4]nonan-3-one a47

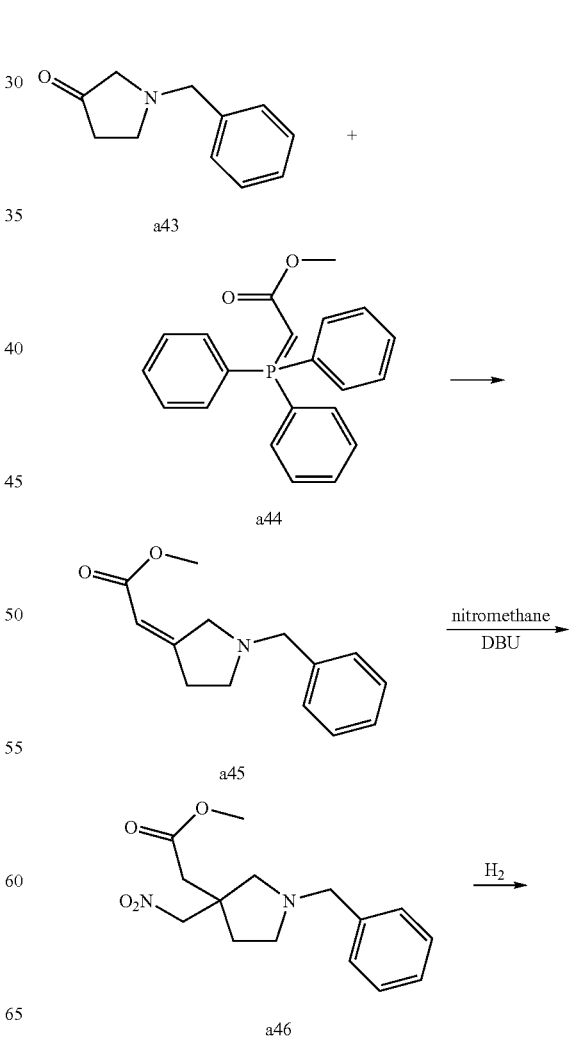

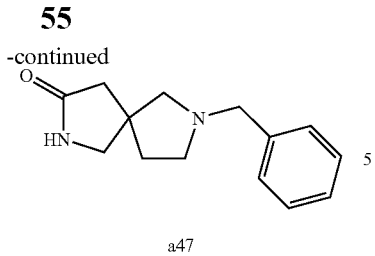

a47

1.3.3.a. Synthesis of methyl (1-benzylpyrrolidin-3-ylidene)acetate a45

1-benzylpyrrolidin-3-one a43 (8.75 g, 50 mmol, 1 eq) is dissolved in toluene (100 ml). Methyl (triphenylphosphoranylidene)acetate a44 (18.4 g, 55 mmol, 1.1 eq) is added and the mixture is refluxed for 60 h. The cold suspension is then filtered and the filtrate is concentrated to dryness. The crude product is purified by chromatography over silicagel (ethyl acetate/hexane 10/90) to afford 7.2 g of pure methyl (1-benzylpyrrolidin-3-ylidene)acetate a45.

Yield: 61%.
LC-MS (MH⁺): 232.

1.3.3.b. Synthesis of methyl [1-benzyl-3-(nitromethyl)pyrrolidin-3-yl]acetate a46

A solution of methyl (1-benzylpyrrolidin-3-ylidene)acetate a45 (3 g, 1.2 mmol, 1 eq), 1,8-diazabicyclo[5.4.0]undec-7-ene (DBU, 0.7 g, 4.6 mmol, 3.8 eq) in nitromethane (30 ml) is refluxed for 30 h. The solution is concentrated in vacuum and the resulting oil is purified by chromatography over silicagel (ethyl acetate/hexane 30/70) to afford 3.7 g of methyl [1-benzyl-3-(nitromethyl)pyrrolidin-3-yl]acetate a46 as a black oil.

Yield: 100%.
LC-MS (MH⁺): 293.

1.3.3.c. Synthesis of 7-benzyl-2,7-diazaspiro[4.4]nonan-3-one a47

A suspension of methyl [1-benzyl-3-(nitromethyl)pyrrolidin-3-yl]acetate a46 (3.3 g, 1.1 mmol, 1 eq) and Raney nickel (1 g of a 50% slurry in water) in ethanol (200 ml) is shaken in a Parr bottle at 30° C. for 24 h, under a hydrogen pressure of 40 psi. The reaction mixture is then filtered through Celite and the filtrate is concentrated to afford 1.8 g of 7-benzyl-2,7-diazaspiro[4.4]nonan-3-one a47 as a brown oil.

Yield: 60%.
LC-MS (MH⁺): 231.

1.3.4. Synthesis of substantially optically pure (4R)- and (4S)-4-propylpyrrolidin-2-one a59 and a60

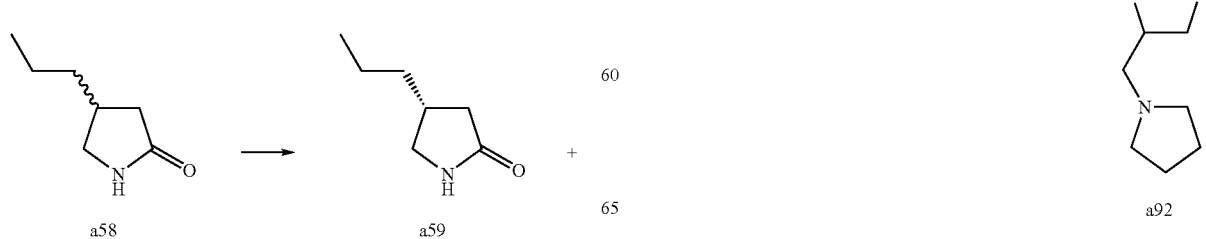

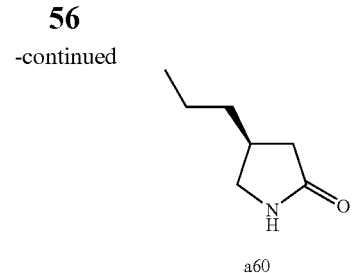

a60

343 g of 4-propylpyrrolidin-2-one a58 are separated by liquid chromatography on a CHIRALPAK® AD column (100×500 mm; propanol/ethanol/hexane/DEA 8/2/90/0.1) to afford 146.0 g of (4R)-4-propylpyrrolidin-2-one a59 and 150.4 g of (4S)-4-propylpyrrolidin-2-one a60.

(4R)-4-propylpyrrolidin-2-one a59

Yield: 42.5%.
Chiral HPLC (n-propanol/ethanol:80/20): retention time=7.81 minutes.
α$_D$: +2.33°.

(4S)-4-propylpyrrolidin-2-one a60

Yield: 43%.
Chiral HPLC (n-propanol/ethanol:80/20): retention time=6.65 minutes.
α$_D$: −2.16°.

1.3.5. Synthesis of 4-(pyrrolidin-1-ylmethyl)-1,3-oxazolidin-2-one a92

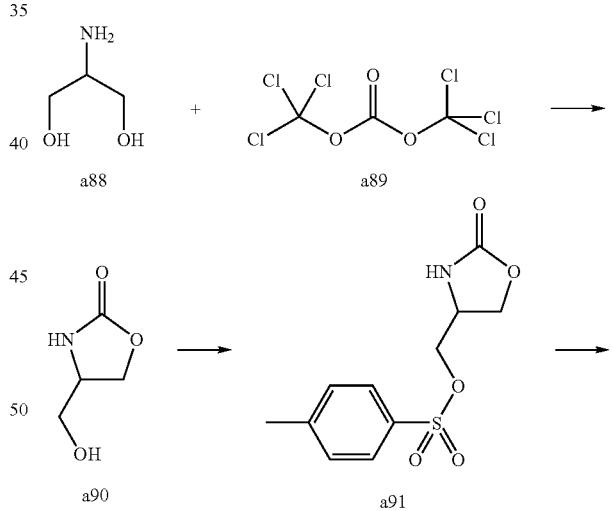

1.3.5.a. Synthesis of 4-(hydroxymethyl)-1,3-oxazolidin-2-one a90

Sodium carbonate (4.23 g, 339 mmol, 3.35 eq) is added to a solution of 2-aminopropane-1,3-diol a88 (1.04 g, 11.4 mmol, 1 eq) in water (18 ml) then triphosgene a89 (1.13 g, 3.8 mmol, 0.33 eq) is added by portions and the mixture is stirred at room temperature for 4 hours. The aqueous mixture is washed with dichloromethane (2×10 ml) and treated with a 1 N solution of hydrochloric acid. Ethanol is then added and the solvents are removed in vacuo. The residual white solid is taken up in hot ethanol, cooled, filtered, and dried in vacuo to afford 4-(hydroxymethyl)-1,3-oxazolidin-2-one a90.

Yield: 98%.

LC-MS (MH$^+$): 118.

1.3.5.b. Synthesis of (2-oxo-1,3-oxazolidin-4-yl)methyl 4-methylbenzenesulfonate a91

N-methylimidazole (360 ml, 4.5 mmol, 1.5 eq) is added to a cooled suspension of 4-(hydroxymethyl)-1,3-oxazolidin-2-one a90 (0.35 g, 3 mmol, 1 eq) in dichloromethane (20 ml). p-Toluenesulfonyl chloride a40 (0.63 g, 3.3 mmol, 1.1 eq) in dichloromethane (5 ml) is then added, dropwise. The mixture is stirred at 0° C. for 5 hours then at room temperature for 24 hours. The mixture is then quenched under vigorous stirring with 0.5 ml of water and taken up in chloroform (100 ml). The organic phase is washed with a saturated aqueous solution of sodium hydrogenocarbonate (2×25 ml), with a 1N solution of hydrochloric acid (2×25 ml), with brine, and is dried over magnesium sulfate. The organic layer is concentrated in vacuo to afford 0.61 g of (2-oxo-1,3-oxazolidin-4-yl)methyl 4-methylbenzenesulfonate a91 as a white solid.

Yield: 75%.

LC-MS (MH$^+$): 272.

1.3.5.c. Synthesis of 4-(pyrrolidin-1-ylmethyl)-1,3-oxazolidin-2-one a92

Potassium carbonate (0.62 g, 4.5 mmol, 2 eq) and pyrrolidine (0.28 ml, 3.37 mmol, 1.5 eq) are added to a solution of (2-oxo-1,3-oxazolidin-4-yl)methyl 4-methylbenzenesulfonate a91 (0.62 g, 2.25 mmol, 1 eq) in acetonitrile (22 ml). The mixture is heated at reflux overnight. After cooling, the mixture is filtered and the solid is washed with acetonitrile. The acetonitrile phases are concentrated in vacuo. The residue is taken up in dichloromethane, heated, filtered and washed with dichloromethane. The dichloromethane phases are concentrated in vacuo to give 0.35 g of 4-(pyrrolidin-1-ylmethyl)-1,3-oxazolidin-2-one a92 as a yellow oil.

Yield: 92%.

LC-MS (MH$^+$): 171.

1.3.6. Synthesis of 4-(4-chlorobenzyl)-1,3-oxazolidin-2-one a94

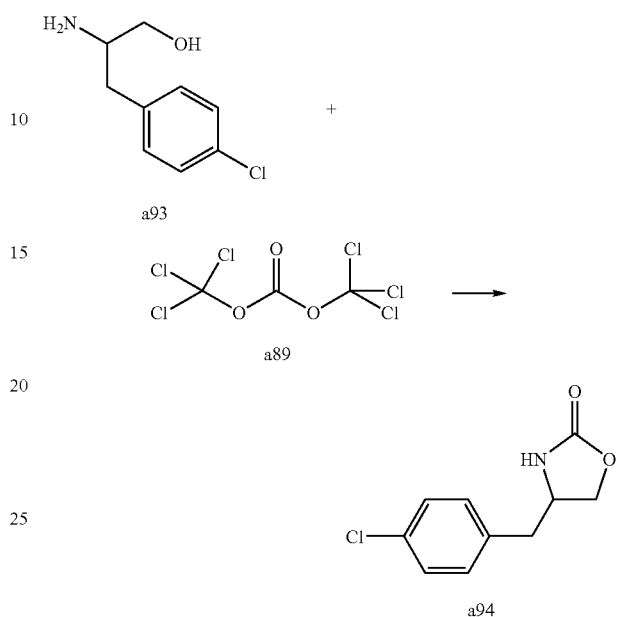

Diisopropylethylamine (0.78 ml, 4.5 mmol, 2.25 eq) is added to a solution of 2-amino-3-(4-chlorophenyl)propan-1-ol a93 (0.37 g, 2 mmol, 1 eq) in dichloromethane (75 ml). The mixture is cooled (ice bath) and triphosgene a89 (0.30 g, 1 mmol, 0.5 eq) is added. The mixture is stirred overnight at room temperature, washed with water, with 0.1 N aqueous hydrochloric acid, dried over magnesium sulfate and concentrated in vacuo to give 0.47 g of 4-(4-chlorobenzyl)-1,3-oxazolidin-2-one a94 as a yellow oil. This oil is used in the next step without any further purification.

Yield: 100%.

LC-MS (MH$^+$): 212/214.

(4R)-4-(cyclohexylmethyl)-1,3-oxazolidin-2-one a95 (LC-MS (MH$^+$): 184) may be synthesized according to the same method.

1.3.7. Synthesis of (5S)-5-[(1,1-dioxidothiomorpholin-4-yl)methyl]pyrrolidin-2-one a96

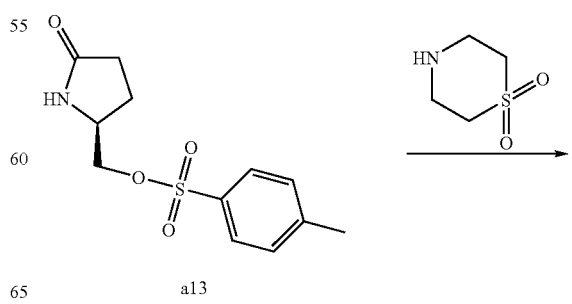

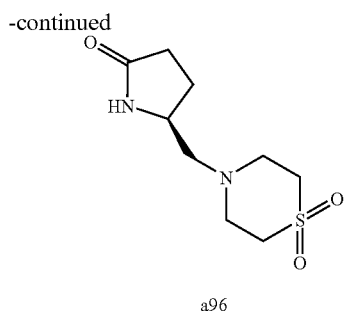

a96

Diisopropylethylamine (1.19 g, 9.19 mmol, 1.5 eq) and [(2S)-5-oxopyrrolidin-2-yl]methyl 4-methylbenzenesulfonate a13 (2.48 g, 9.19 mmol, 1.5 eq) are added to a solution of thiomorpholine 1,1-dioxide (1.24 g at 66% of purity, 6.07 mmol, 1 eq) in acetonitrile (14 ml). The mixture is heated under microwave irradiation at 150° C. for 6.25 hours. The residue is then taken up in water and extracted with dichloromethane (3×50 ml). The organic layers are washed with brine, dried over magnesium sulfate and concentrated in vacuo to give 0.45 g of yellow solid. The aqueous phase is then brought to pH~12 with sodium hydroxide (pellets) and extracted with dichloromethane (3×40 ml). The organics layers are washed with brine, dried over magnesium sulfate and concentrated in vacuo to afford another batch of 0.85 g of an orange oil. The two residues are combined and purified by chromatography over silicagel (dichloromethane/methanol/ammonia 96/4/0.4) to afford 0.24 g of (5S)-5-[(1,1-dioxidothiomorpholin-4-yl)methyl]pyrrolidin-2-one a96.

Yield: 17%.

LC-MS (MH+): 233.

1.3.8 Synthesis of (5S)-3,3-dimethyl-5-(piperidin-1-ylmethyl)pyrrolidin-2-one a98

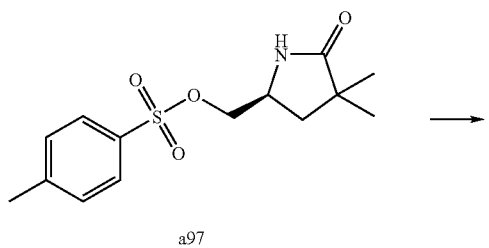

a97

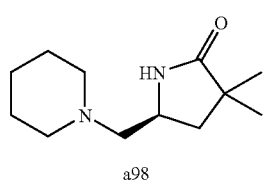

a98

[(2S)-4,4-dimethyl-5-oxopyrrolidin-2-yl]methyl 4-methylbenzenesulfonate a97 (3.8 g, 20.74 mmol, 1 eq) is obtained from (S)-5-hydroxymethyl-pyrrolidine-2-one using the procedure described in Davies S. G. and D. J. Dixon in Tetrahedron Asymmetry (2002), 13, 647-658.

A solution of [(2S)-4,4-dimethyl-5-oxopyrrolidin-2-yl] methyl 4-methylbenzenesulfonate a97 (3.8 g, 20.74 mmol, 1 eq) and piperidine (4.1 ml, 41.47 mmol, 2 eq) in acetonitrile (62 ml) is heated at 90° C. overnight. The mixture is concentrated in vacuo and the residue is taken up in dichloromethane (100 ml). This organic phase is washed with a saturated solution of sodium bicarbonate, dried over magnesium sulfate and concentrated in vacuo to give 2.7 g of brown solid. The residue is purified by chromatography over silicagel (dichloromethane/methanol/ammonia 97:3:0.3) to afford 1.9 g of (5S)-3,3-dimethyl-5-(piperidin-1-ylmethyl)pyrrolidin-2-one a98 as a beige solid.

Yield: 43%.

LC-MS (MH+): 211.

The following compounds may be synthesized according to the same method:

| | | |
|---|---|---|
| a99 | (5R)-5-{[(2R,6S)-2,6-dimethylmorpholin-4-yl]methyl}-3,3-dimethylpyrrolidin-2-one | LC-MS (MH+): 241 |
| a100 | (5R)-5-[(4,4-difluoropiperidin-1-yl)methyl]-3,3-dimethylpyrrolidin-2-one | LC-MS (MH+): 247 |

1.4 Synthesis of (5S)-1-{4-[3-(2-methylpyrrolidin-1-yl)propoxyl]phenyl}-5-(piperidin-1-ylmethyl)pyrrolidin-2-one 48

A suspension of 1-[3-(4-iodophenoxy)propyl]-2-methylpyrrolidine a5 (0.245 g, 0.71 mmol, 1 eq) in dioxan (4 ml), potassium phosphate (0.3 g, 1.42 mmol, 2 eq), copper iodide (0.001 g, 0.007 mmol, 1 mol %), trans-1,2-diaminocyclohexane (0.008 g, 0.07 mmol, 10 mol %) and (5S)-5-(piperidin-1-ylmethyl)pyrrolidin-2-one a15 (0.155 g, 0.85 mmol, 1.2 eq) is placed in a sealed tube under argon atmosphere and heated at 110° C. until reaction completion. The mixture is diluted with dichloromethane and is washed twice with a solution of 1 M sodium hydroxide. The organic layer is dried over magnesium sulfate and concentrated in vacuo to give 279 mg of a brown oil. This oil is purified by chromatography on silicagel (dichloromethane/ethanol/ammonia 95/5/0.5) to afford 130 mg of (5S)-1-{4-[3-(2-methylpyrrolidin-1-yl)propoxyl]phenyl}-5-(piperidin-1-ylmethyl)pyrrolidin-2-one 48 as a pink oil.

Yield: 46%.

LC-MS (MH+): 400.

Compounds 1, 2, 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 35, 36, 37, 38, 39, 40, 41, 42, 43, 46, 48, 49, 50, 51, 52, 53, 54, 55, 56, 57, 58, 59, 60, 61, 62, 63, 64, 65, 66, 67, 68, 69, 70, 71, 74, 75, 78, 79, 80, 81, 82, 83, 84, 85, 87, 88, 89, 90, 91, 92, 93, 94, 95, 96, 97, 98, 99, 100, 101, 102, 103, 104, 105, 106, 107, 108, 109, 110, 111 and 112 may be synthesized according to the same method.

EXAMPLE 2

Synthesis of (5S)-5-{[(cyclohexylmethyl)(cyclopropylmethyl)amino]methyl}-1-{4-[3-(2-methylpyrrolidin-1-yl)propoxy]phenyl}pyrrolidin-2-one 3

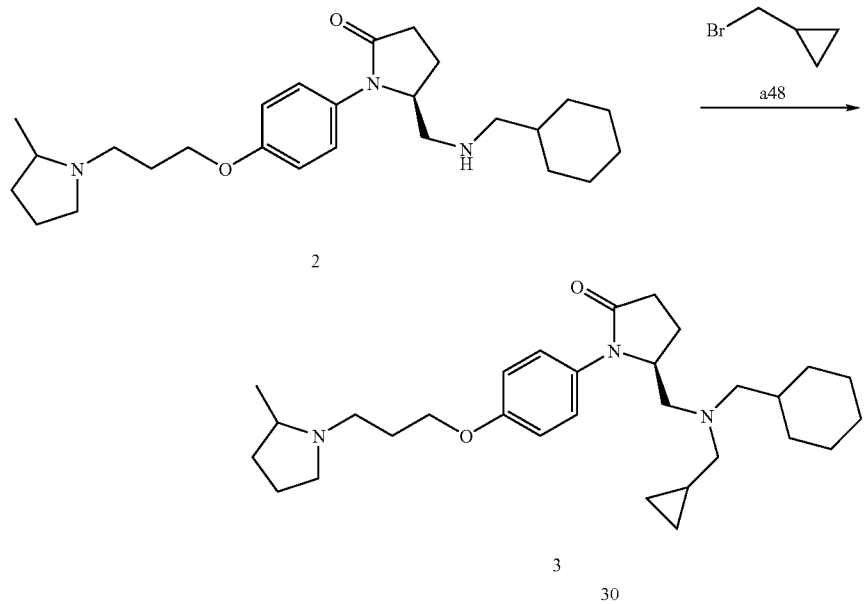

(Bromomethyl)cyclopropane a48 (47 μl, 0.48 mmol, 2.1 eq) is added to a solution of (5S)-5-{[(cyclohexylmethyl)amino]methyl}-1-[4-(3-piperidin-1-ylpropoxy)phenyl]pyrrolidin-2-one 2 in acetonitrile (4 ml), then cesium carbonate (150 mg, 0.46 mmol, 2 eq) and potassium iodide (8 mg, 0.05 mmol, 0.2 eq) are added and the mixture is heated at 50° C. for 24 h. The precipitate is filtered and the solvent is removed in vacuo. The residue is dissolved into dichloromethane and washed with a saturated solution of aqueous ammonium chloride. The aqueous layer is then extracted with dichloromethane, the organic layers are dried over magnesium sulfate and concentrated in vacuo to give 109 mg of a yellow oil. This oil is purified by chromatography over silicagel (dichloromethane/methanol/ammonia 92/8/0.8) to obtain 47 mg of (5S)-5-{[(cyclohexylmethyl)(cyclopropylmethyl)amino]methyl}-1-{4-[3-(2-methylpyrrolidin-1-yl)propoxy]phenyl}pyrrolidin-2-one 3 as a yellow oil.

Yield: 42%.

LC-MS (MH$^+$): 482.

EXAMPLE 3

Synthesis of (5S)-5-(azepan-1-ylmethyl)-1-{4-[3-(2-methylpyrrolidin-1-yl)propoxy]phenyl}pyrrolidine-2-thione 21

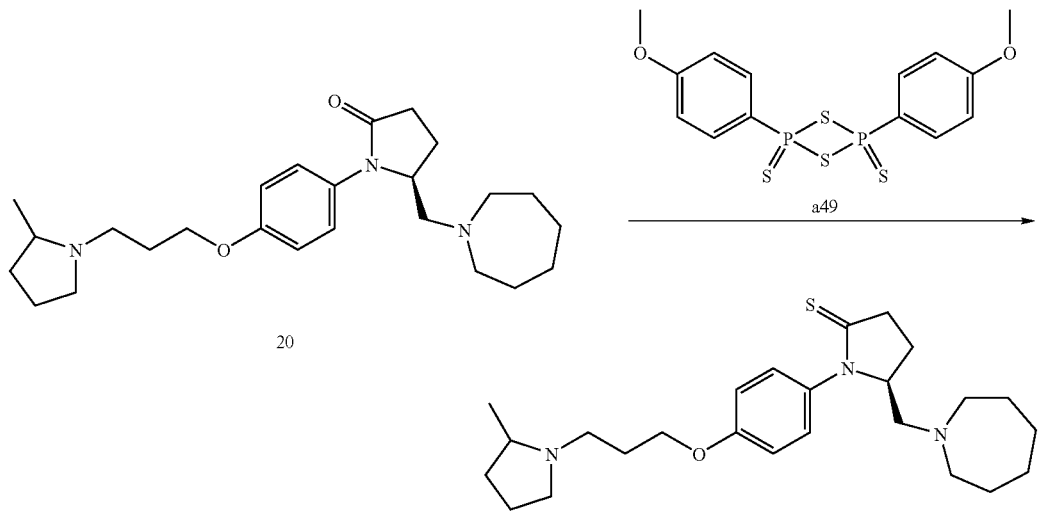

(5S)-5-(azepan-1-ylmethyl)-1-{4-[3-(2-methylpyrrolidin-1-yl)propoxy]phenyl}pyrrolidin-2-one 20 (0.1 g, 0.24 mmol, 1 eq) is dissolved in chloroform (5 ml) and 2,4-bis(4-methoxyphenyl)-1,3,2,4-dithiadiphosphetane 2,4-disulfide a49 (Lawesson's reagent, 0.05 g, 0.12 mmol, 0.5 eq) is added. Toluene (5 ml) is added and the mixture is refluxed for 6 h. Water is then added, and after phase separation, the organic layer is dried over magnesium sulfate and concentrated to give 0.2 g of crude material. Purification by chromatography over silicagel (dichloromethane/methanol/ammonia 94/6/0.6) affords 0.05 g of pure (5S)-5-(azepan-1-ylmethyl)-1-{4-[3-(2-methylpyrrolidin-1-yl)propoxy]phenyl}pyrrolidine-2-thione 21.

Yield: 35%.

LC-MS (MH$^+$): 430.

(5S)-1-{4-[3-(2-methylpyrrolidin-1-yl)propoxy]phenyl}-5-(piperidin-1-ylmethyl)pyrrolidine-2-thione 86 may be synthesized according to the same method.

EXAMPLE 4

Synthesis of 4-[(4-cyclopentylpiperazin-1-yl)methyl]-1-{4-[3-(2-methylpyrrolidin-1-yl)propoxy]phenyl}pyrrolidin-2-one 44

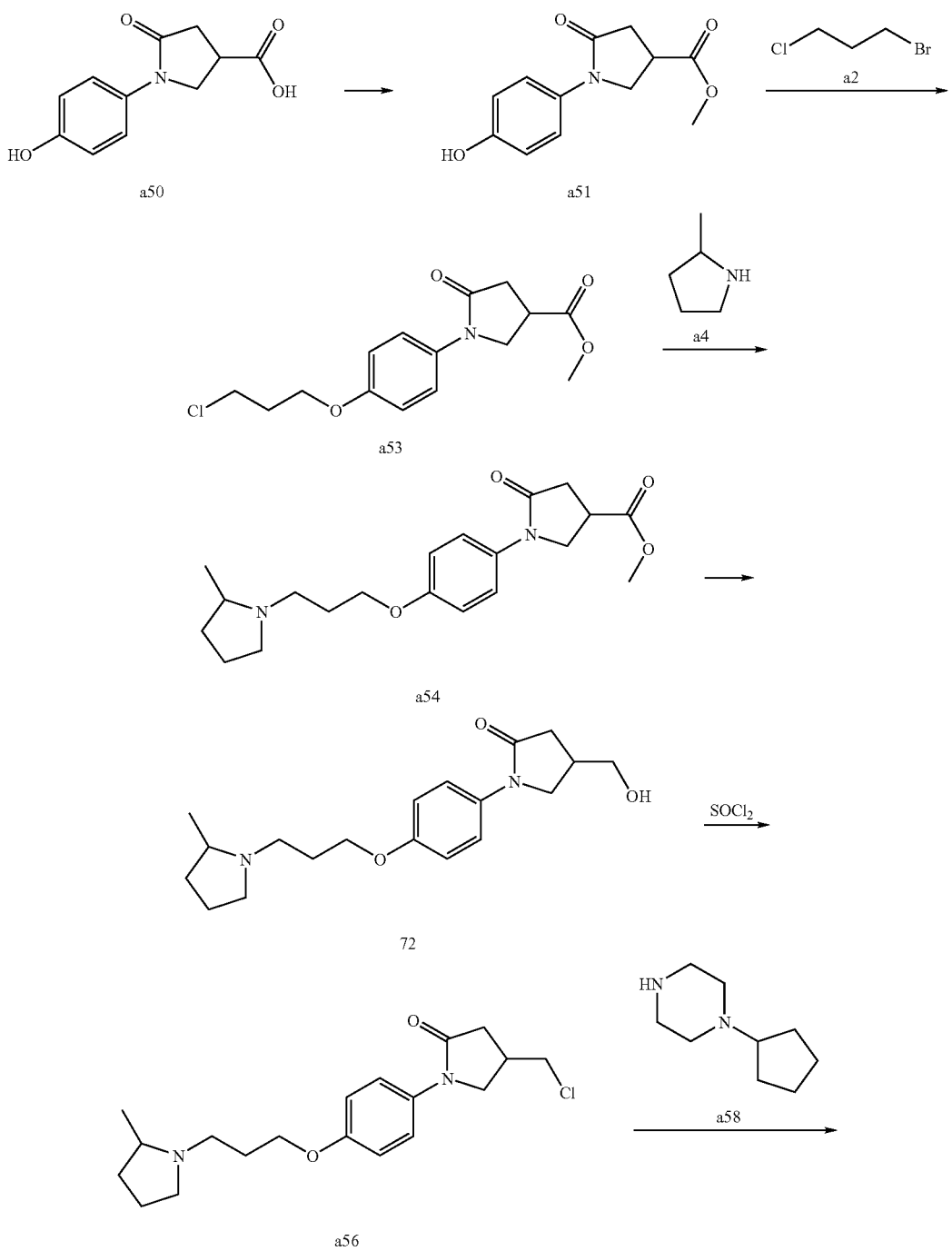

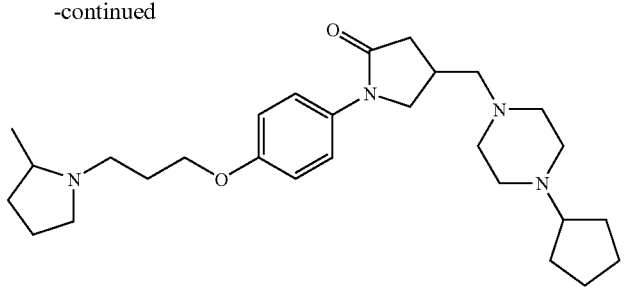

44

4.1 Synthesis of methyl 1-(4-hydroxyphenyl)-5-oxopyrrolidine-3-carboxylate a51

A catalytic amount of concentrated sulfuric acid is added to a solution of 1-(4-hydroxyphenyl)-5-oxopyrrolidine-3-carboxylic acid a50 (3.7 g, 16.7 mmol, 1 eq) in methanol (100 ml) and the mixture is heated at reflux overnight. The solvent is then removed under vacuum, and the residue is dissolved into ethyl acetate. The organic layer is washed with a saturated solution of aqueous sodium hydrogenocarbonate, dried over magnesium sulfate and concentrated under vacuum to afford 3.5 g of methyl 1-(4-hydroxyphenyl)-5-oxopyrrolidine-3-carboxylate a51.

Yield: 89%.
LC-MS (MH$^+$): 236.

4.2 Synthesis of methyl 1-[4-(3-chloropropoxy)phenyl]-5-oxopyrrolidine-3-carboxylate a53

A mixture of methyl 1-(4-hydroxyphenyl)-5-oxopyrrolidine-3-carboxylate a51 (3.48 g, 14.8 mmol, 1 eq), potassium carbonate (4 g, 29.6 mmol, 2 eq) and 1-bromo-3-chloropropane a2 (1.6 ml, 16.2 mmol, 1.1 eq) in acetone (80 ml) is stirred at reflux overnight. The mixture is concentrated under vacuum then the residue is dissolved in ethyl acetate, and washed with a saturated solution of aqueous sodium hydrogenocarbonate. The organic layer is dried over magnesium sulfate and concentrated under vacuum to give 2.3 g of methyl 1-[4-(3-chloropropoxy)phenyl]-5-oxopyrrolidine-3-carboxylate a53 as a yellow oil.

Yield: 50%.
LC-MS (MH$^+$): 312/314.

4.3 Synthesis of methyl 1-{4-[3-(2-methylpyrrolidin-1-yl)propoxy]phenyl}-5-oxopyrrolidine-3-carboxylate a54

2-methylpyrrolidine a4 (0.66 g, 7.76 mmol, 1.1 eq) is added to a suspension of methyl 1-[4-(3-chloropropoxy)phenyl]-5-oxopyrrolidine-3-carboxylate a53 (2.2 g, 7.05 mmol, 1 eq), potassium carbonate (1.94 g, 14.1 mmol, 2 eq) and sodium iodide (0.2 g, 1.41 mmol, 0.2 eq) in acetonitrile (70 ml). The mixture is stirred at reflux for 1 to 2 days. Potassium carbonate is filtered away and the solvent is removed under vacuum. The residue is dissolved in ethyl acetate, and washed with a solution of aqueous sodium hydrogenocarbonate. The organic layer is dried over magnesium sulfate and concentrated under vacuum to give 2.6 g of a black oil. This oil is purified by chromatography over silicagel (dichloromethane/methanol/ammonia 97/3/0.3) to afford 1.2 g of methyl 1-{4-[3-(2-methylpyrrolidin-1-yl)propoxy]phenyl}-5-oxopyrrolidine-3-carboxylate a54 as a yellow oil.

Yield: 48%.
LC-MS (MH$^+$): 361.

Ethyl (1-{4-[3-(2-methylpyrrolidin-1-yl)propoxy]phenyl}-5-oxopyrrolidin-3-yl)acetate a55 may be synthesized according to the same method. Compound a55 has been obtained from 1-[3-(4-iodophenoxy)propyl]-2-methylpyrrolidine a5 and ethyl (5-oxopyrrolidin-3-yl)acetate according to conditions described in example 1.3.

LC-MS (MH$^+$): 389.

4.4 Synthesis of 4-(hydroxymethyl)-1-{4-[3-(2-methylpyrrolidin-1-yl)propoxy]phenyl}pyrrolidin-2-one 72

Lithium borohydride (0.1 g, 4.92 mmol, 1.8 eq) is added to a solution of methyl 1-{4-[3-(2-methylpyrrolidin-1-yl)propoxy]phenyl}-5-oxopyrrolidine-3-carboxylate a54 (0.99 g, 2.73 mmol, 1 eq) in tetrahydrofuran (20 ml) and methanol (0.35 ml). The mixture is stirred at 75° C. for 1 h, then cooled to 0° C. and a solution of 1 M hydrochloric acid is added. A solution of 2M sodium hydroxide is then added to reach a pH of 10. The aqueous layer is extracted twice with ethyl acetate, then the organic layers are dried over magnesium sulfate, and concentrated under vacuum to give 0.79 g of 4-(hydroxymethyl)-1-{4-[3-(2-methylpyrrolidin-1-yl)propoxy]phenyl}pyrrolidin-2-one 72 as a colorless oil.

Yield: 88%
LC-MS (MH$^+$): 333.

4-(2-hydroxyethyl)-1-{4-[3-(2-methylpyrrolidin-1-yl)propoxy]phenyl}pyrrolidin-2-one 73 may be synthesized according to the same method.

LC-MS (MH$^+$): 347.

4.5 Synthesis of 4-(chloromethyl)-1-{4-[3-(2-methylpyrrolidin-1-yl)propoxy]phenyl}pyrrolidin-2-one a56

Thionyl chloride (0.24 ml, 3.25 mmol, 1.5 eq) is added into a cold solution of 4-(hydroxymethyl)-1-{4-[3-(2-methylpyrrolidin-1-yl)propoxy]phenyl}pyrrolidin-2-one 72 (0.78 g, 2.16 mmol, 1 eq) and triethylamine (0.3 ml, 2.16 mmol, 1 eq) in dichloromethane (30 ml). The mixture is warmed to room temperature and stirred overnight. The solution is washed once with water and once with a saturated solution of aqueous sodium chloride. The organic layer is dried over magnesium sulfate and concentrated under vacuum to give 0.54 g of 4-(chloromethyl)-1-{4-[3-(2-methylpyrrolidin-1-yl)propoxy]phenyl}pyrrolidin-2-one a56 as a dark-red oil.

Yield: 71%.
LC-MS (MH$^+$): 351/353.

4-(2-chloroethyl)-1-{4-[3-(2-methylpyrrolidin-1-yl)propoxy]phenyl}pyrrolidin-2-one a57 is synthesized according to the same method.

LC-MS (MH+): 365/367.

4.6 Synthesis of 4-[(4-cyclopentylpiperazin-1-yl)methyl]-1-{4-[3-(2-methylpyrrolidin-1-yl)propoxy]phenyl}pyrrolidin-2-one 44

A mixture of 4-(chloromethyl)-1-{4-[3-(2-methylpyrrolidin-1-yl)propoxy]phenyl}pyrrolidin-2-one a56 (0.26 g, 0.74 mmol, 1 eq), potassium carbonate (0.4 g, 2.96 mmol, 4 eq), 1-cyclopentylpiperazine a58 (0.34 g, 2.22 mmol, 3 eq) and a catalytic amount of sodium iodide in acetonitrile (20 ml) is stirred at reflux for 4 days. Potassium carbonate is filtered and the mixture is concentrated under vacuum, then the residue is dissolved in ethyl acetate, and washed twice with a saturated solution of aqueous sodium hydrogenocarbonate. The organic layer is dried over magnesium sulfate and concentrated under vacuum to give 0.17 g of crude material. This product is purified by chromatography over silicagel (dichloromethane/methanol/ammonia 94/6/0.6) to afford 0.052 g of 4-[(4-cyclopentylpiperazin-1-yl)methyl]-1-{4-[3-(2-methylpyrrolidin-1-yl)propoxy]phenyl}pyrrolidin-2-one 44 as an orange oil.

Yield: 15%.

LC-MS (MH+): 469.

Compounds 45 and 47 may be synthesized according to the same method.

EXAMPLE 5

Synthesis of 7-acetyl-2-{4-[3-(2-methylpyrrolidin-1-yl)propoxy]phenyl}-2,7-diazaspiro[4.4]nonan-3-one 76

5.1 Synthesis of 2-{4-[3-(2-methylpyrrolidin-1-yl)propoxy]phenyl}-2,7-diazaspiro[4.4]nonan-3-one a101

To a solution of 7-benzyl-2-{4-[3-(2-methylpyrrolidin-1-yl)propoxy]phenyl}-2,7-diazaspiro[4.4]nonan-3-one 71 (0.65 g, 1.45 mmol, 1 eq) in methanol (25 ml) is added palladium 10% on charcoal (0.169 g) and 5 N aqueous hydrochloric acid (0.5 ml, 2.5 mmol, 1.72 eq). The mixture is stirred overnight under hydrogen pressure (40 psi) and at room temperature. Fresh catalyst is then added, and the mixture is stirred under hydrogen at 60° C. for a further five-hour period. The mixture is filtered and concentrated to give 0.89 g of crude material that is purified by chromatography over silicagel to affors 0.5 g of 2-{4-[3-(2-methylpyrrolidin-1-yl)propoxy]phenyl}-2,7-diazaspiro[4.4]nonan-3-one a101.

Yield: 96%.

LC-MS (MH+): 358.

5.2 Synthesis of 7-acetyl-2-{4-[3-(2-methylpyrrolidin-1-yl)propoxy]phenyl}-2,7-diazaspiro[4.4]nonan-3-one 76

To a solution of 2-{4-[3-(2-methylpyrrolidin-1-yl)propoxy]phenyl}-2,7-diazaspiro[4.4]nonan-3-one a101 (0.17 g, 0.47 mmol, 1 eq) in dichloromethane (10 ml) is added triethylamine (0.1 ml, 0.07 g, 0.72 mmol, 1.5 eq) and a solution of acetyl chloride (0.045 g, 0.57 mmol, 1.2 eq) in dichloromethane (1 ml). The mixture is stirred at room temperature for 1 hour and washed with water and brine, dried over magnesium sulfate and concentrated in vacuo to give 0.14 g of crude material. The residue is purified by chromatography over silicagel (dichloromethane/methanol/ammonia 95:5:0.5) to afford 0.023 g of 7-acetyl-2-{4-[3-(2-methylpyrrolidin-1-yl)propoxy]phenyl}-2,7-diazaspiro[4.4]nonan-3-one 76.

Yield: 12%.

LC-MS (MH+): 400.

EXAMPLE 6

Synthesis of N-(cyclohexylmethyl)-N-[((2S)-1-{4-[3-(2-methylpyrrolidin-1-yl)propoxy]phenyl}-5-oxopyrrolidin-2-yl)methyl]cyclopropanecarboxamide 77

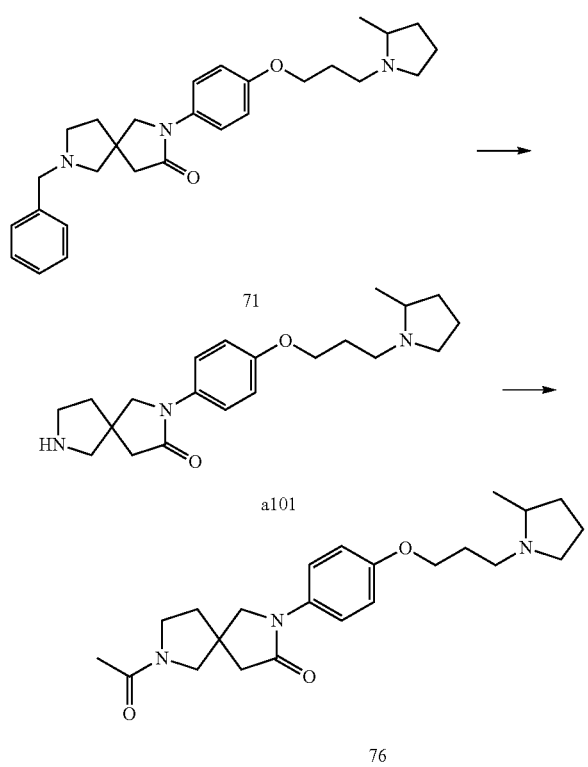

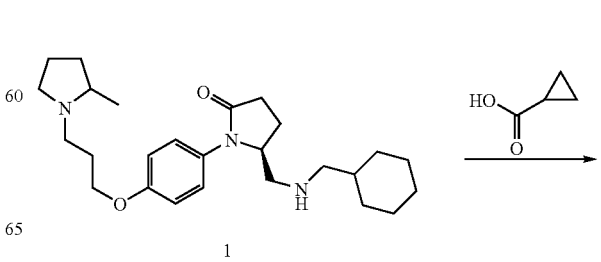

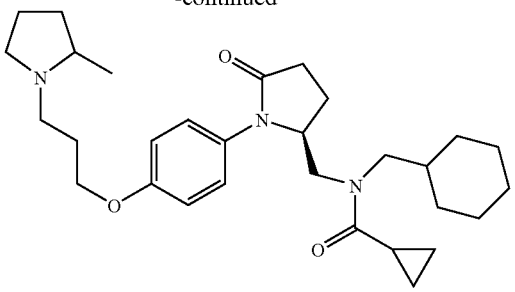

77

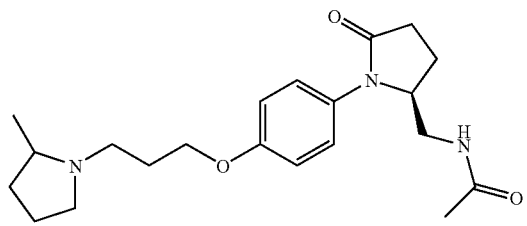

114

Triethylamine (0.13 ml, 0.93 mmol, 2 eq) is added to a solution of cyclopropanecarboxylic acid (40 mg, 0.47 mmol, 1 eq) and ((5S)-5-{[(cyclohexylmethyl)amino]methyl}-1-{4-[3-(2-methylpyrrolidin-1-yl)propoxy]phenyl}pyrrolidin-2-one 1 (200 mg, 0.47 mmol, 1 eq) in dichloromethane (5 ml). The mixture is cooled with an ice bath. 1-Hydroxybenzotriazole (12 mg, 0.093 mmol, 0.2 eq), and 1-(3-dimethylaminopropyl)-3-ethylcarbodiimide hydrochloride (99 mg, 0.52 mmol, 1.1 eq) are added. The mixture is stirred at room temperature for 5 hours, washed with water and brine, dried over magnesium sulfate and concentrated in vacuo to give 0.246 g of yellow oil that is purified by chromatography over silicagel (dichloromethane/methanol/ammonia 96/4/0.4) to afford 0.135 g of N-(cyclohexylmethyl)-N-[((2S)-1-{4-[3-(2-methylpyrrolidin-1-yl)propoxy]phenyl}-5-oxopyrrolidin-2-yl)methyl]cyclopropanecarboxamide 77 as a yellow lacquer.

Yield: 58%.

LC-MS (MH$^+$): 496.

EXAMPLE 7

Synthesis of N-[((2S)-1-{4-[3-(2-methylpyrrolidin-1-yl)propoxy]phenyl}-5-oxopyrrolidin-2-yl)methyl]acetamide 114

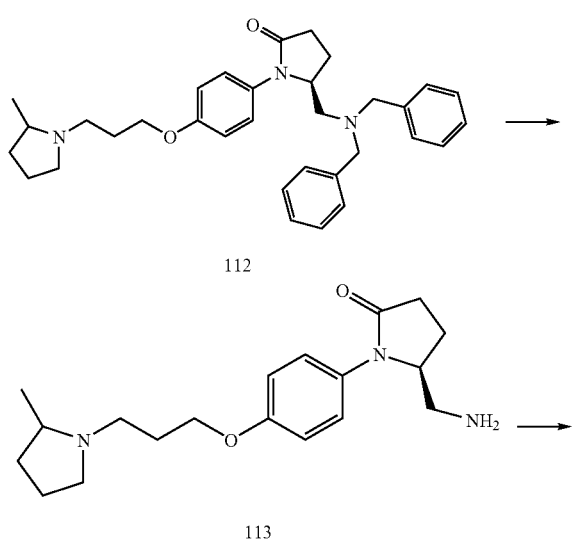

7.1 Synthesis of (5S)-5-(aminomethyl)-1-{4-[3-(2-methylpyrrolidin-1-yl)propoxy]phenyl}pyrrolidin-2-one 113

Palladium hydroxide on charcoal is added to a solution of (5S)-5-[(dibenzylamino)methyl]-1-{4-[3-(2-methylpyrrolidin-1-yl)propoxy]phenyl}pyrrolidin-2-one 112 (0.377 g, 0.74 mmol, 1 eq) in methanol (10 ml). The mixture is shaken overnight at room temperature under hydrogen atmosphere (45 psi). The mixture is filtered over celite and concentrated under vacuum. The residue is taken up in a mixture of methanol (10 ml) and 4 drops of aqueous 5 N hydrochloric acid. Palladium hydroxide on charcoal is added and the mixture is shaken again overnight at room temperature under hydrogen atmosphere (45 psi). The mixture is filtered over celite and concentrated under vacuum to give 0.245 g of (5S)-5-(aminomethyl)-1-{4-[3-(2-methylpyrrolidin-1-yl)propoxy]phenyl}pyrrolidin-2-one 113 as a yellow oil.

Yield: 100%.

LC-MS (MH$^+$): 332.

7.2 Synthesis of N-[((2S)-1-{4-[3-(2-methylpyrrolidin-1-yl)propoxy]phenyl}-5-oxopyrrolidin-2-yl)methyl]acetamide 114

Acetyl chloride (0.51 ml, 0.72 mmol, 1.2 eq) is added to a cooled (ice bath) solution of (5S)-5-(aminomethyl)-1-{4-[3-(2-methylpyrrolidin-1-yl)propoxy]phenyl}pyrrolidin-2-one 113 (0.2 g, 0.6 mmol, 1 eq) in dichloromethane (12 ml). The mixture is stirred 2 hours at room temperature, washed with a saturated solution of sodium bicarbonate and with brine, dried over magnesium sulfate and concentrated under vacuum to give 0.158 g of yellow oil. The crude material is purified by two chromatographies over silicagel (first one: gradient dichloromethane/methanol/ammonia 100:0:0 to 88:12:1.2; second one: dichloromethane/methanol/ammonia 80:20:2).

Yield: 22%.

LC-MS (MH$^+$): 374.

EXAMPLE 8

Synthesis of 1-{4-[3-(4-methylpiperidin-1-yl)propoxy]phenyl}-5-(piperidin-1-ylmethyl)pyrrolidin-2-one bis(trifluoroacetate) 115

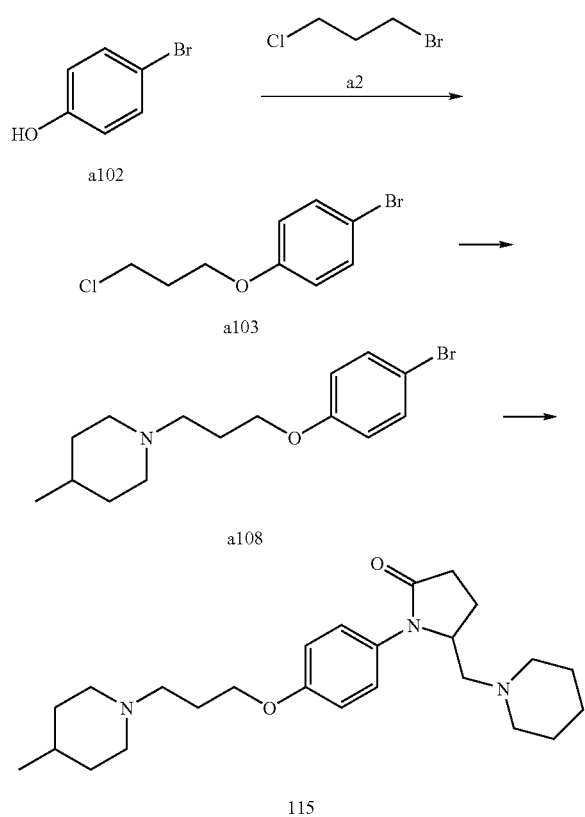

8.1 Synthesis of 1-bromo-4-(3-chloropropoxy)benzene a103

To a solution of 4-bromophenol a102 (0.934 g, 5.4 mmol, 1 eq) and potassium carbonate (1.493 g, 10.8 mmol, 2 eq) in acetone (40 ml) is added 1-bromo-3-chloropropane a2 (0.8 ml, 1.27 g, 8.08 mmol, 1.5 eq). The mixture is stirred at 65° C. overnight. 1-Bromo-3-chloropropane a2 (0.1 eq) is added and the mixture is stirred at 65° C. for another 2 hours. The reaction mixture is filtered, washed with acetone and concentrated in vacuo to give 1.4 g of crude 1-bromo-4-(3-chloropropoxy)benzene a103 which is used directly in the next step, without any purification

GC-MS (M$^+$.): 248/250/252.

The following compounds may be synthesized according to the same method:

| a104 | 4-bromo-1-(3-chloropropoxy)-2-fluorobenzene | GC-MS(M$^+$·): 266/268/270 |
|---|---|---|
| a105 | 1-bromo-4-(3-chloropropoxy)-2-fluorobenzene | GC-MS(M$^+$·): 266/268/270 |
| a106 | 5-bromo-2-(3-chloropropoxy)-1,3-difluorobenzene | GC-MS(M$^+$·): 284/286/288 |
| a107 | 4-bromo-1-(3-chloropropoxy)-2-methylbenzene | GC-MS(M$^+$·): 262/264/266 |

8.2 Synthesis of 1-[3-(4-bromophenoxy)propyl]-4-methylpiperidine a108

A 1.08 M solution of 4-methylpiperidine (0.25 ml, 0.27 mmol, 2 eq) in dimethylformamide is added to a suspension of 1-bromo-4-(3-chloropropoxy)benzene a103 (0.035 g, 0.135 mmol, 1 eq), supported carbonate (Argonaute, 0.095 g, 0.27 mmol, 2 eq) and sodium iodide (0.4 mg, 0.003 mmol, 0.01 eq) in dimethylformamide (0.2 ml). The mixture is stirred at 80° C. overnight, filtered, washed with dimethylformamide and concentrated in vacuo. Crude 1-[3-(4-bromophenoxy)propyl]-4-methylpiperidine a108 is used directly in the next step without any further purification.

The following compounds may be synthesized according to the same method and are used directly in the next step without any further purification:

| a109 | 1-[3-(4-bromophenoxy)propyl]-3,5-dimethylpiperidine |
|---|---|
| a110 | 1-[3-(4-bromophenoxy)propyl]decahydroquinoline |
| a111 | 1-[3-(4-bromo-2-fluorophenoxy)propyl]-3,5-dimethylpiperidine |
| a112 | 2-[3-(4-bromo-2-fluorophenoxy)propyl]-2-azaspiro[5.5]undecane |
| a113 | 1-[3-(4-bromo-3-fluorophenoxy)propyl]-3,5-dimethylpiperidine |
| a114 | 1-[3-(4-bromo-2,6-difluorophenoxy)propyl]-4-methylpiperidine |
| a115 | 2-[3-(4-bromo-2,6-difluorophenoxy)propyl]-2-azaspiro[5.5]undecane |
| a116 | 1-[3-(4-bromo-2-methylphenoxy)propyl]-3,5-dimethylpiperidine |
| a117 | 4-benzyl-1-[3-(4-bromophenoxy)propyl]piperidine |
| a118 | 1-[3-(4-bromo-2-fluorophenoxy)propyl]-3-phenylpiperidine |
| a119 | 1-[3-(4-bromophenoxy)propyl]-1-azaspiro[4.4]nonane |
| a120 | 1-[3-(4-bromo-2-fluorophenoxy)propyl]-2-methylpyrrolidine |
| a121 | 1-[3-(4-bromo-2-fluorophenoxy)propyl]-1-azaspiro[4.4]nonane |
| a122 | 1-[3-(4-bromo-2,6-difluorophenoxy)propyl]-2-methylpyrrolidine |
| a123 | 1-[3-(4-bromo-2-methylphenoxy)propyl]-2-methylpyrrolidine |
| a124 | 1-[3-(4-bromo-2-methylphenoxy)propyl]-1-azaspiro[4.4]nonane |
| a125 | {1-[3-(4-bromo-2-methylphenoxy)propyl]pyrrolidin-2-yl}methanol |
| a126 | 1-[3-(4-bromophenoxy)propyl]azepane |
| a127 | 1-[3-(4-bromo-2-fluorophenoxy)propyl]azepane |
| a128 | 1-[3-(4-bromo-2-fluorophenoxy)propyl]azocane |
| a129 | 1-[3-(4-bromo-3-methoxyphenoxy)propyl]azepane |

8.3 Synthesis of 1-{4-[3-(4-methylpiperidin-1-yl)propoxy]phenyl}-5-(piperidin-1-ylmethyl)pyrrolidin-2-one bis(trifluoroacetate) 115

A 0.45 M solution of 1-[3-(4-bromophenoxy)propyl]-4-methylpiperidine a108 (0.067 mmol, 1 eq) in dimethylformamide (0.15 ml), cesium carbonate (44 mg, 0.13 mmol, 2 eq), a 0.263 M solution of rac-trans-N,N'-dimethylcyclohexane-1,2-diamine (0.005 mmol, 0.08 eq) in dimethylformamide (0.02 ml), and copper iodide (1.33 mg, 0.007 mmol, 0.1 eq) are added to a 0.53 M solution of (5S)-5-(piperidin-1-ylmethyl)pyrrolidin-2-one a15 (0.08 mmol, 1.2 eq) in dimethylformamide (0.15 ml). The mixture is stirred at 99° C. overnight, filtered and concentrated. The residue is dissolved in dimethylformamide (0.3 ml). Cesium carbonate (44 mg, 0.13 mmol, 2 eq), a 6.7 M solution of N,N'-dimethyl-ethane-1,2-diamine (0.13 mmol, 2 eq) in dimethylformamide (0.02 ml), and copper iodide (6 mg, 0.018 mmol, 0.3 eq) are added. The mixture is stirred at 99° C. overnight, filtered, washed with dimethylformamide and concentrated in vacuo. The crude material is purified by reverse phase chromatography (C18 column, acetonitrile/water/trifluoroacetic acid, gradient) to afford 2.7 mg of 1-{4-[3-(4-methylpiperidin-1-yl)propoxy]phenyl}-5-(piperidin-1-ylmethyl)pyrrolidin-2-one bis(trifluoroacetate) 115.

Yield: 10%.

LC-MS (MH$^+$): 414.

Compounds 116, 117, 118, 119, 120, 121, 122, 123, 124, 125, 126, 127, 128, 129, 130, 131, 132, 133, 134, 135, 136, 137, 138 and 139 may be synthesized according to the same method.

EXAMPLE 9

Synthesis of (5S)-1-{6-[3-(2-methylpyrrolidin-1-yl)propoxy]pyridin-3-yl}-5-(piperidin-1-ylmethyl)pyrrolidin-2-one 140

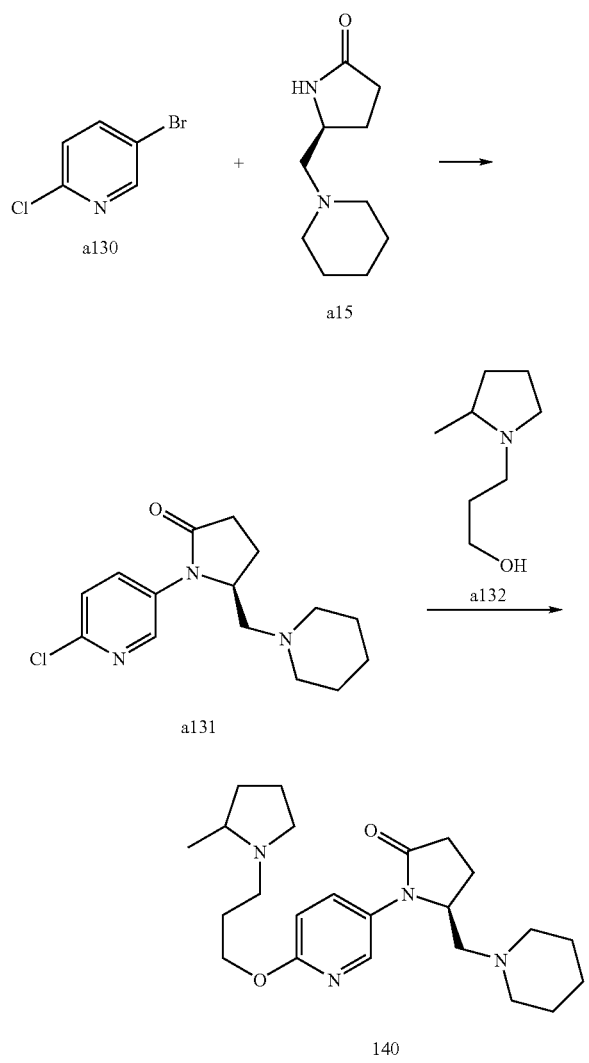

9.1 Synthesis of (5S)-1-(6-chloropyridin-3-yl)-5-(piperidin-1-ylmethyl)pyrrolidin-2-one a131

A suspension of 5-bromo-2-chloropyridine a130 (0.75 g, 3.9 mmol, 1 eq), (5S)-5-(piperidin-1-ylmethyl)pyrrolidin-2-one a15 (0.85 g, 4.67 mmol, 1.2 eq), cesium carbonate (1.78 g, 5.46 mmol, 1.4 eq), Xanphos (0.17 g, 0.29 mmol, 0.075 eq), and tris(dibenzylideneacetone) dipalladium (0) (89 mg, 0.097 mmol, 0.025 eq) in dioxane (25 ml) is stirred under an argon atmosphere in a sealed tube for 12 h at 100° C. The mixture is left to cool to room temperature and filtered through a pad of Celite. The solid is washed with ethyl acetate and the resulting soluble fractions are combined and concentrated to dryness. The residue is taken up in ethyl acetate and washed twice with a saturated aqueous solution of sodium hydrogenocarbonate. The organic phase is then dried over magnesium sulfate and concentrated to afford 1.4 g of crude mixture. Purification by chromatography over silicagel (dichloromethane/methanol/ammonia gradient) affords 0.5 g of (5S)-1-(6-chloropyridin-3-yl)-5-(piperidin-1-ylmethyl)pyrrolidin-2-one a131.
Yield: 44%.
LC-MS (MH$^+$): 294/296.

9.2 Synthesis of (5S)-1-{6-[3-(2-methylpyrrolidin-1-yl)propoxy]pyridin-3-yl}-5-(piperidin-1-ylmethyl)pyrrolidin-2-one 140

A suspension of (5S)-1-(6-chloropyridin-3-yl)-5-(piperidin-1-ylmethyl)pyrrolidin-2-one a131 (0.51 g, 1.73 mmol, 1 eq), 3-(2-methylpyrrolidin-1-yl)propan-1-ol a132 (0.3 g, 2.08 mmol, 1.2 eq), sodium hydride (60% dispersion in oil, 0.138 g, 3.46 mmol, 2 eq), Xanphos (0.05 g, 0.17 mmol, 0.09 eq), and tris(dibenzylideneacetone) dipalladium (0) (0.08 g, 0.086 mmol, 0.05 eq) in toluene (20 ml) is stirred under an argon atmosphere at 110° C. for 48 hours in a sealed tube. The reaction mixture is concentrated and the residue is taken up in ethyl acetate. The solution is washed twice with a saturated aqueous solution of sodium hydrogenocarbonate, dried over magnesium sulfate and concentrated. The residue is purified by chromatography over silicagel (dichloromethane/methanol/ammonia gradient) to yield 142 mg of (5S)-1-{6-[3-(2-methylpyrrolidin-1-yl)propoxy]pyridin-3-yl}-5-(piperidin-1-ylmethyl)pyrrolidin-2-one 140.
Yield: 21%.
LC-MS (MH$^+$): 401.

Table I gives characteristics of some compounds of general formula (I). Said table indicates the stereochemical information in the columns headed "configuration": the second column indicates whether a compound has no stereogenic center (achiral), is a pure enantiomer (pure), a racemate (rac) or is a mixture of two stereoisomers, possibly in unequal proportions (mixture); the first column contains the stereochemical assignment for the recognized center, following the IUPAC numbering used in the "IUPAC name" column. A number alone indicates the existence of both configurations at that center. A number followed by 'R' or 'S' indicates the known absolute configuration at that center. A number followed by '!' indicates the existence of only one but unknown absolute configuration at that center. The letter (A, B) in front is a way of distinguishing the various enantiomers of the same structure.

Table I indicates also the type and stoechiometry of salt, which was synthesized (if not the free base), the IUPAC name of the compound, the ion peak observed in mass spectrometry, the $^1$H NMR description and the optical rotation in the case of enantiomerically pure compounds. The expression "enantiomerically pure" as used herein refers to compounds which have an enantiomeric excess (ee) greater than 95%.

TABLE I

| n° | Configuration | | IUPAC Name | MH+ (M+.) | alphaD | 1H NMR (CDCl3 unless otherwise specified) δH (ppm) |
|---|---|---|---|---|---|---|
| 1 | 5S,2 | mixture | (5S)-5-{[(cyclohexylmethyl)amino]methyl}-1-{4-[3-(2-methylpyrrolidin-1-yl)propoxy]phenyl}pyrrolidin-2-one | 428 | | 0.80 (m, 3 H), 1.09 (d, 6.04 Hz, 3 H), 1.29 (m, 6 H), 1.95 (m, 16 H), 2.51 (m, 1 H), 2.65 (m, 3 H), 2.96 (dt, 11.82, 7.95 Hz, 1 H), 3.17 (td, 8.80, 2.70 Hz, 1 H), 4.02 (m, 2 H), 4.20 (dd, 7.80, 4.65 Hz, 1 H), 6.92 (m, 2 H), 7.24 (m, 2 H) |
| 2 | 5S | pure | (5S)-5-{[(cyclohexylmethyl)amino]methyl}-1-[4-(3-piperidin-1-ylpropoxy)phenyl]pyrrolidin-2-one | 428 | −15.2 | 0.80 (m, 2 H), 1.23 (m, 5 H), 1.45 (m, 2 H), 1.62 (m, 9 H), 1.99 (m, 3 H), 2.31 (m, 3 H), 2.47 (m, 7 H), 2.65 (m, 3 H), 4.00 (t, 6.31 Hz, 2 H), 4.19 (dd, 8.08, 4.80 Hz, 1 H), 6.91 (d, 8.84 Hz, 2 H), 7.24 (d, 9.09 Hz, 2 H) |
| 3 | 5S,2 | mixture | (5S)-5-{[(cyclohexylmethyl)(cyclopropylmethyl)amino]methyl}-1-{4-[3-(2-methylpyrrolidin-1-yl)propoxy]phenyl}pyrrolidin-2-one | 482 | | 0.00 (m, 2 H), 0.42 (m, 2 H), 0.76 (m, 3 H), 1.10 (d, 6.04 Hz, 3 H), 1.18 (m, 3 H), 1.31 (m, 1 H), 1.43 (m, 1 H), 1.81 (m, 10 H), 2.21 (m, 9 H), 2.52 (m, 4 H), 2.97 (m, 1 H), 3.18 (dd, 10.06, 2.52 Hz, 1 H), 4.00 (m, 2 H), 4.13 (m, 1 H), 6.88 (d, 9.05 Hz, 2 H), 7.27 (s, 2 H) |
| 5 | 5S | pure | (5S)-5-{[(cyclopropylmethyl)(propyl)amino]methyl}-1-[4-(3-piperidin-1-ylpropoxy)phenyl]pyrrolidin-2-one | 428 | −42.7 | 0.01 (m, 3 H), 0.44 (m, 2 H), 0.75 (m, 1 H), 0.85 (t, 7.32 Hz, 3 H), 1.41 (m, 4 H), 1.59 (m, 4 H), 1.70 (s, 1 H), 1.97 (m, 2 H), 2.39 (m, 17 H), 4.00 (t, 6.44 Hz, 2 H), 4.17 (m, 1 H), 6.90 (d, 8.84 Hz, 2 H), 7.28 (s, 2 H) |
| 6 | 2,5S | mixture | (5S)-5-{[(cyclopropylmethyl)(propyl)amino]methyl}-1-{4-[3-(2-methylpyrrolidin-1-yl)propoxy]phenyl}pyrrolidin-2-one | 428 | | 0.01 (m, 3 H), 0.44 (m, 2 H), 0.75 (m, 1 H), 0.85 (t, 7.32 Hz, 3 H), 1.09 (d, 6.06 Hz, 3 H), 1.41 (m, 3 H), 1.73 (m, 1 H), 1.95 (m, 3 H), 2.37 (m, 13 H), 2.97 (m, 1 H), 3.17 (m, 1 H), 4.02 (td, 6.31, 3.41 Hz, 2 H), 4.17 (m, 1 H), 6.90 (d, 9.09 Hz, 2 H), 7.28 (m, 2 H) |
| 7 | 5S | pure | (5S)-5-[(cyclobutylamino)methyl]-1-[4-(3-piperidin-1-ylpropoxy)phenyl]pyrrolidin-2-one | 386 | | 1.24 (t, 6.92 Hz, 1 H), 1.45 (d, 5.79 Hz, 3 H), 1.59 (m, 4 H), 1.72 (m, 1 H), 2.04 (m, 6 H), 2.46 (m, 12 H), 3.12 (m, 1 H), 4.00 (m, 2 H), 4.16 (m, 1 H), 6.92 (m, 2 H), 7.24 (d, 9.05 Hz, 2 H) |
| 8 | 5S,2 | mixture | (5S)-5-[(cyclobutylamino)methyl]-1-{4-[3-(2-methylpyrrolidin-1-yl)propoxy]phenyl}pyrrolidin-2-one | 386 | | 1.09 (t, 5.68 Hz, 5 H), 1.58 (m, 5 H), 2.11 (m, 11 H), 2.55 (m, 4 H), 2.97 (m, 1 H), 3.14 (m, 2 H), 4.03 (d, 2.53 Hz, 2 H), 4.17 (d, 2.02 Hz, 1 H), 6.93 (m, 2 H), 7.25 (m, 2 H) |
| 9 | 2,5S | mixture | (5S)-5-[(cyclohexylamino)methyl]-1-{4-[3-(2-methylpyrrolidin-1-yl)propoxy]phenyl}pyrrolidin-2-one | 414 | | 0.95 (m, 2 H), 1.09 (d, 6.06 Hz, 3 H), 1.17 (m, 3 H), 1.41 (m, 1 H), 1.56 (m, 1 H), 1.71 (m, 6 H), 2.10 (m, 9 H), 2.50 (m, 1 H), 2.67 (m, 3 H), 2.96 (dt, 11.62, 8.05 Hz, 1 H), 3.17 (m, 1 H), 4.02 (m, 2 H), 4.17 (m, 1 H), 6.92 (d, 8.84 Hz, 2 H), 7.24 (d, 8.84 Hz, 2 H) |
| 10 | 5S | pure | (5S)-5-[(cyclohexylamino)methyl]-1-[4-(3-piperidin-1-ylpropoxy)phenyl]pyrrolidin-2-one | 414 | −19.8 | 0.95 (m, 2 H), 1.16 (m, 3 H), 1.45 (m, 2 H), 1.65 (m, 10 H), 1.99 (m, 3 H), 2.27 (m, 2 H), 2.47 (m, 7 H), 2.67 (m, 3 H), 4.00 (t, 6.44 Hz, 2 H), 4.18 (m, 1 H), 6.91 (m, 2 H), 7.24 (m, 2 H) |
| 11 | 2,5S | mixture | (5S)-5-[(cyclopentylamino)methyl]-1-{4-[3-(2-methylpyrrolidin-1-yl)propoxy]phenyl}pyrrolidin-2-one | 400 | | 1.09 (d, 6.06 Hz, 3 H), 1.18 (m, 2 H), 1.60 (m, 10 H), 2.10 (m, 8 H), 2.50 (m, 1 H), 2.64 (m, 3 H), 2.94 (m, 2 H), 3.17 (td, 8.59, 2.65 Hz, 1 H), 4.02 (m, 2 H), 4.18 (m, 1 H), 6.92 (m, 2 H), 7.24 (d, 9.09 Hz, 2 H) |
| 12 | 5S | pure | (5S)-5-[(cyclopentylamino)methyl]-1-[4-(3-piperidin-1-ylpropoxy)phenyl]pyrrolidin-2-one | 400 | −19.3 | 1.18 (m, 2 H), 1.47 (m, 4 H), 1.59 (m, 6 H), 1.70 (m, 2 H), 1.99 (m, 3 H), 2.28 (m, 1 H), 2.47 (m, 7 H), 2.64 (m, 3 H), 2.92 (t, 6.44 Hz, 1 H), 4.00 (t, 6.44 Hz, 2 H), 4.18 (m, 1 H), 6.91 (m, 2 H), 7.24 (m, 2 H) |
| 13 | 5S,2 | mixture | (5S)-5-[(diethylamino)methyl]-1-{4-[3-(2-methylpyrrolidin-1-yl)propoxy]phenyl}pyrrolidin-2-one | 388 | | 0.94 (t, 7.17 Hz, 6 H), 1.09 (d, 6.04 Hz, 3 H), 1.43 (m, 1 H), 1.73 (m, 3 H), 2.06 (m, 6 H), 2.40 (m, 9 H), 2.63 (m, 1 H), 2.97 (m, 1 H), 3.17 (m, 1 H), 4.01 (m, 2 H), 4.16 (m, 1 H), 6.91 (d, 8.80 Hz, 2 H), 7.28 (m, 2 H) |
| 14 | 2,5S | mixture | (5S)-5-(anilinomethyl)-1-{4-[3-(2-methylpyrrolidin-1-yl)propoxy]phenyl}pyrrolidin-2-one | 408 | | 1.09 (d, 5.81 Hz, 3 H), 1.42 (m, 1 H), 1.73 (m, 3 H), 2.12 (m, 8 H), 2.60 (m, 2 H), 2.97 (dt, 11.62, 8.08 Hz, 1 H), 3.18 (m, 2 H), 3.32 (m, 1 H), 3.51 (t, 6.19 Hz, 1 H), 4.02 (m, 2 H), 4.35 (m, 1 H), 6.49 (d, 8.08 Hz, 2 H), 6.71 (t, 7.32 Hz, 1 H), 6.93 (d, 8.84 Hz, 2 H), 7.14 (m, 2 H), 7.24 (s, 1 H) |
| 15 | 5S | pure | (5S)-5-(anilinomethyl)-1-[4-(3-piperidin-1-ylpropoxy)phenyl]pyrrolidin-2-one | 408 | −20.2 | 1.44 (d, 4.04 Hz, 2 H), 1.59 (m, 4 H), 1.78 (m, 1 H), 2.00 (m, 3 H), 2.50 (m, 9 H), 3.19 (m, 1 H), 3.32 (m, 1 H), 3.52 (s, 1 H), 4.00 (t, 5.94 Hz, 2 H), 4.35 (m, 1 H), 6.49 (d, 7.58 Hz, 2 H), 6.71 (t, 7.32 Hz, 1 H), 6.93 (d, 7.58 Hz, 2 H), 7.14 (t, 7.20 Hz, 2 H), 7.24 (s, 1 H) |
| 16 | 5S,2 | mixture | (5S)-5-{[(4-fluorobenzyl)amino]methyl}-1-{4-[3-(2-methylpyrrolidin-1-yl)propoxy]phenyl}pyrrolidin-2-one | 440 | | 0.00 (s, 4 H), 1.02 (d, 6.04 Hz, 4 H), 1.35 (s, 2 H), 1.93 (m, 5 H), 2.53 (m, 4 H), 2.89 (m, 1 H), 3.10 (m, 1 H), 3.57 (s, 2 H), 3.95 (td, 6.29, 2.39 Hz, 2 H), 4.13 (m, 1 H), 6.83 (d, 8.80 Hz, 2 H), 6.89 (t, 8.68 Hz, 2 H), 7.06 (m, 2 H), 7.15 (d, 9.05 Hz, 2 H) |
| 17 | 5S | pure | (5S)-5-{[(4-fluorobenzyl)amino]methyl}-1-[4-(3-piperidin-1-ylpropoxy)phenyl]pyrrolidin-2-one | 440 | −19.4 | 1.45 (d, 5.03 Hz, 2 H), 1.59 (m, 4 H), 2.01 (m, 3 H), 2.27 (m, 1 H), 2.48 (m, 7 H), 2.67 (m, 3 H), 3.64 (s, 2 H), 4.00 (t, 6.41 Hz, 2 H), 4.20 (m, 1 H), 6.89 (d, 9.05 Hz, 2 H), 6.96 (t, 8.55 Hz, 2 H), 7.14 (m, 2 H), 7.21 (d, 9.05 Hz, 2 H) |
| 18 | 5S | pure | (5S)-5-{[(4-fluorophenyl)amino]methyl}-1-[4-(3-piperidin-1-ylpropoxy)phenyl]pyrrolidin-2-one | 426 | −24.2 | 1.45 (m, 2 H), 1.59 (m, 2 H), 1.78 (m, 1 H), 2.01 (m, 3 H), 2.50 (m, 10 H), 3.17 (m, 1 H), 3.25 (m, 1 H), 3.39 (t, 6.19 Hz, 1 H), 4.00 (t, 6.44 Hz, 2 H), 4.34 (m, 1 H), 6.41 (m, 2 H), 6.84 (t, 8.59 Hz, 2 H), 6.92 (d, 9.09 Hz, 2 H), 7.23 (d, 8.84 Hz, 2 H) |

TABLE I-continued

| n° | Configuration | | IUPAC Name | MH+ (M+.) | alphaD | 1H NMR (CDCl3 unless otherwise specified) δH (ppm) |
|---|---|---|---|---|---|---|
| 19 | 5S,2 | mixture | (5S)-5-{[(4-fluorophenyl)amino]methyl}-1-{4-[3-(2-methylpyrrolidin-1-yl)propoxy]phenyl}pyrrolidin-2-one | 426 | | 1.02 (d, 6.04 Hz, 3 H), 1.35 (m, 1 H), 1.92 (m, 10 H), 2.54 (m, 2 H), 2.89 (m, 1 H), 3.14 (m, 3 H), 3.32 (m, 1 H), 3.95 (m, 2 H), 4.26 (m, 1 H), 6.34 (m, 2 H), 6.77 (t, 8.68 Hz, 2 H), 6.86 (d, 8.80 Hz, 2 H), 7.17 (d, 8.80 Hz, 2 H) |
| 20 | 2,5S | mixture | (5S)-5-(azepan-1-ylmethyl)-1-{4-[3-(2-methylpyrrolidin-1-yl)propoxy]phenyl}pyrrolidin-2-one | 414 | | 1.09 (d, 6.04 Hz, 3 H), 1.42 (m, 1 H), 1.52 (s, 8 H), 1.73 (m, 2 H), 2.10 (m, 8 H), 2.54 (m, 8 H), 2.96 (m, 1 H), 3.17 (m, 1 H), 4.01 (m, 2 H), 4.15 (m, 1 H), 6.90 (d, 9.05 Hz, 2 H), 7.27 (m, 2 H) |
| 21 | 5S,2 | mixture | (5S)-5-(azepan-1-ylmethyl)-1-{4-[3-(2-methylpyrrolidin-1-yl)propoxy]phenyl}pyrrolidine-2-thione | 430 | | (DMSO): 1.03 (s, 3 H), 1.41 (s, 9 H), 1.67 (m, 2 H), 1.94 (m, 4 H), 2.31 (m, 2 H), 2.47 (d, 5.02 Hz, 4 H), 2.94 (m, 2 H), 3.13 (m, 2 H), 4.04 (t, 6.28 Hz, 2 H), 4.45 (m, 1 H), 6.97 (d, 8.79 Hz, 2 H), 7.29 (d, 8.79 Hz, 2 H) (some signals obscured by solvent) |
| 22 | 4R,2 | mixture | (4R)-4-benzyl-3-{4-[3-(2-methylpyrrolidin-1-yl)propoxy]phenyl}-1,3-oxazolidin-2-one | 395 | | 1.10 (dd, 6.03, 1.00 Hz, 3 H), 1.44 (m, 1 H), 1.73 (m, 3 H), 1.97 (m, 3 H), 2.12 (q, 8.79 Hz, 1 H), 2.21 (m, 1 H), 2.32 (m, 1 H), 2.73 (dd, 13.56, 9.80 Hz, 1 H), 2.98 (dt, 11.80, 8.07 Hz, 1 H), 3.09 (dd, 13.81, 3.14 Hz, 1 H), 3.18 (m, 1 H), 4.05 (m, 2 H), 4.18 (m, 1 H), 4.33 (m, 1 H), 4.54 (m, 1 H), 6.97 (m, 2 H), 7.11 (d, 7.79 Hz, 2 H), 7.29 (m, 2 H), 7.38 (m, 2 H) |
| 23 | 2 | rac | 1-{4-[3-(2-methylpiperidin-1-yl)propoxy]phenyl}pyrrolidin-2-one | 317 | | 1.08 (d, 6.29 Hz, 3 H), 1.30 (m, 2 H), 1.61 (m, 4 H), 1.93 (m, 3 H), 2.16 (m, 3 H), 2.31 (m, 1 H), 2.54 (m, 3 H), 2.86 (m, 2 H), 3.82 (t, 7.04 Hz, 2 H), 3.98 (m, 2 H), 6.89 (d, 9.05 Hz, 2 H), 7.47 (d, 9.05 Hz, 2 H) |
| 24 | 2 | rac | 1-{4-[3-(2-methylpyrrolidin-1-yl)propoxy]phenyl}pyrrolidin-2-one | 303 | | 1.09 (d, 6.04 Hz, 3 H), 1.41 (m, 1 H), 1.73 (m, 2 H), 1.94 (m, 3 H), 2.15 (m, 4 H), 2.29 (m, 1 H), 2.59 (t, 8.17 Hz, 2 H), 2.96 (m, 1 H), 3.17 (td, 8.55, 2.39 Hz, 1 H), 3.82 (t, 6.92 Hz, 2 H), 4.01 (m, 2 H), 6.90 (d, 9.05 Hz, 2 H), 7.47 (d, 9.05 Hz, 2 H) |
| 25 | 2 | rac | 1-{4-[3-(2-methylpyrrolidin-1-yl)propoxy]phenyl}piperidin-2-one | 317 | | 1.09 (d, 6.04 Hz, 3 H), 1.41 (m, 1 H), 1.73 (m, 2 H), 1.94 (m, 7 H), 2.15 (m, 2 H), 2.29 (m, 1 H), 2.54 (m, 2 H), 2.96 (m, 1 H), 3.16 (m, 1 H), 3.59 (m, 2 H), 4.01 (m, 2 H), 6.90 (d, 9.05 Hz, 2 H), 7.13 (d, 9.05 Hz, 2 H) |
| 26 | 2 | rac | 1-{4-[3-(2-methylpyrrolidin-1-yl)propoxy]phenyl}azepan-2-one | 331 | | 1.09 (d, 6.04 Hz, 3 H), 1.42 (m, 1 H), 1.74 (m, 8 H), 1.94 (m, 3 H), 2.19 (m, 3 H), 2.68 (s, 2 H), 2.96 (m, 1 H), 3.17 (m, 1 H), 3.70 (d, 6.54 Hz, 2 H), 4.01 (m, 2 H), 6.88 (d, 9.05 Hz, 2 H), 7.09 (d, 8.80 Hz, 2 H) |
| 27 | 5S | pure | (5S)-5-(hydroxymethyl)-1-[4-(3-piperidin-1-ylpropoxy)phenyl]pyrrolidin-2-one | 333 | −27.1 | 1.52 (d, 5.03 Hz, 2 H), 1.66 (m, 4 H), 1.86 (s, 2 H), 2.04 (m, 2 H), 2.22 (m, 1 H), 2.48 (m, 8 H), 2.75 (m, 1 H), 3.66 (dd, 11.32, 2.64 Hz, 1 H), 3.76 (m, 1 H), 4.07 (t, 6.41 Hz, 2 H), 4.25 (m, 1 H), 6.99 (d, 9.05 Hz, 2 H), 7.33 (m, 2 H) |
| 28 | 5S,2 | mixture | (5S)-5-(hydroxymethyl)-1-{4-[3-(2-methylpyrrolidin-1-yl)propoxy]phenyl}pyrrolidin-2-one | 333 | | 1.52 (d, 5.03 Hz, 2 H), 1.66 (m, 4 H), 1.86 (s, 2 H), 2.04 (m, 2 H), 2.22 (m, 1 H), 2.48 (m, 8 H), 2.75 (m, 1 H), 3.66 (dd, 11.32, 2.64 Hz, 1 H), 3.76 (m, 1 H), 4.07 (t, 6.41 Hz, 2 H), 4.25 (m, 1 H), 6.99 (d, 9.05 Hz, 2 H), 7.33 (m, 2 H) |
| 29 | 4R,2 | mixture | (4R)-4-isopropyl-3-{4-[3-(2-methylpyrrolidin-1-yl)propoxy]phenyl}-1,3-oxazolidin-2-one | 347 | | 0.87 (m, 6 H), 1.09 (d, 6.03 Hz, 3 H), 1.42 (m, 1 H), 1.74 (m, 2 H), 2.06 (m, 6 H), 2.29 (m, 1 H), 2.96 (m, 1 H), 3.17 (t, 8.41 Hz, 1 H), 4.02 (t, 6.15 Hz, 2 H), 4.21 (dd, 8.04, 5.15 Hz, 1 H), 4.31 (m, 1 H), 4.40 (t, 8.67 Hz, 1 H), 6.92 (d, 8.79 Hz, 2 H), 7.30 (m, 2 H) |
| 30 | 5S,2 | mixture | (5S)-1-{4-[3-(2-methylpyrrolidin-1-yl)propoxy]phenyl}-5-(morpholin-4-ylmethyl)pyrrolidin-2-one bis(trifluoroacetate) | 402 | | 1.09 (d, 6.04 Hz, 3 H), 1.42 (m, 1 H), 1.72 (m, 2 H), 2.05 (m, 6 H), 2.40 (m, 9 H), 2.65 (m, 1 H), 2.97 (m, 1 H), 3.17 (m, 1 H), 3.61 (t, 4.65 Hz, 4 H), 4.02 (td, 6.04, 2.96 Hz, 2 H), 4.23 (m, 1 H), 6.90 (m, 2 H), 7.26 (m, 2 H) |
| 31 | 5S,2 | mixture | (5S)-1-{4-[3-(2-methylpyrrolidin-1-yl)propoxy]phenyl}-5-(morpholin-4-ylmethyl)pyrrolidin-2-one | 402 | | 0.79 (m, 2 H), 1.21 (m, 7 H), 2.02 (m, 8 H), 2.41 (m, 6 H), 3.53 (t, 4.53 Hz, 5 H), 3.97 (m, 2 H), 4.16 (m, 1 H), 6.82 (d, 9.05 Hz, 2 H), 7.20 (m, 2 H) |
| 32 | 2,4R | mixture | (4R)-1-{4-[3-(2-methylpiperidin-1-yl)propoxy]phenyl}-4-propylpyrrolidin-2-one | 359 | | 0.95 (t, 7.29 Hz, 3 H), 1.07 (d, 6.29 Hz, 3 H), 1.47 (m, 9 H), 1.91 (m, 3 H), 2.22 (m, 3 H), 2.47 (m, 2 H), 2.70 (dd, 16.60, 8.30 Hz, 1 H), 2.86 (m, 2 H), 3.46 (dd, 9.56, 7.04 Hz, 1 H), 3.87 (m, 1 H), 3.97 (m, 2 H), 6.88 (m, 2 H), 7.46 (m, 2 H) |
| 33 | 4S,2 | mixture | (4S)-1-{4-[3-(2-methylpiperidin-1-yl)propoxy]phenyl}-4-propylpyrrolidin-2-one | 359 | | 0.95 (t, 7.29 Hz, 3 H), 1.07 (d, 6.29 Hz, 3 H), 1.47 (m, 10 H), 1.92 (m, 3 H), 2.22 (m, 3 H), 2.47 (m, 2 H), 2.70 (dd, 16.60, 8.30 Hz, 1 H), 2.86 (m, 2 H), 3.46 (dd, 9.56, 7.04 Hz, 1 H), 3.87 (m, 1 H), 3.97 (m, 2 H), 6.88 (m, 2 H), 7.46 (m, 2 H) |
| 34 | 4R | pure | (4R)-1-[4-(3-piperidin-1-ylpropoxy)phenyl]-4-propylpyrrolidin-2-one | 345 | nt | 0.95 (t, 7.29 Hz, 3 H), 1.48 (m, 10 H), 1.96 (m, 2 H), 2.27 (dd, 16.60, 8.05 Hz, 1 H), 2.43 (m, 7 H), 2.70 (dd, 16.60, 8.30 Hz, 1 H), 3.46 (dd, 9.56, 7.04 Hz, 1 H), 3.87 (m, 1 H), 3.99 (t, 6.41 Hz, 2 H), 6.89 (m, 2 H), 7.46 (m, 2 H) |

TABLE I-continued

| n° | Configuration | | IUPAC Name | MH+ (M+.) | alphaD | 1H NMR (CDCl3 unless otherwise specified) δH (ppm) |
|---|---|---|---|---|---|---|
| 35 | 4 | rac | 1-{4-[3-(4-isopropylpiperazin-1-yl)propoxy]phenyl}-4-propylpyrrolidin-2-one | 388 | | 0.95 (m, 3 H), 1.07 (d, 6.31 Hz, 5 H), 1.38 (m, 2 H), 1.50 (m, 2 H), 1.96 (m, 2 H), 2.27 (m, 2 H), 2.55 (m, 13 H), 3.46 (m, 1 H), 3.86 (m, 1 H), 4.00 (m, 2 H), 6.89 (d, 7.83 Hz, 2 H), 7.46 (d, 7.83 Hz, 2 H) |
| 36 | 4 | rac | 4-(4-chlorophenyl)-3,3-dimethyl-1-[4-(3-piperidin-1-ylpropoxy)phenyl]pyrrolidin-2-one | 441/443 | | 0.84 (s, 3 H), 1.31 (s, 3 H), 1.44 (d, 5.28 Hz, 1 H), 1.58 (m, 4 H), 1.97 (m, 2 H), 2.44 (m, 6 H), 3.32 (t, 7.92 Hz, 1 H), 4.00 (m, 4 H), 6.92 (m, 2 H), 7.18 (d, 8.30 Hz, 2 H), 7.33 (m, 2 H), 7.57 (d, 9.05 Hz, 2 H) |
| 37 | 4 | rac | 4-(4-chlorophenyl)-1-[4-(3-piperidin-1-ylpropoxy)phenyl]pyrrolidin-2-one | 413/415 | | 1.45 (m, 2 H), 1.59 (m, 4 H), 1.96 (m, 2 H), 2.44 (m, 6 H), 2.72 (dd, 16.85, 8.43 Hz, 1 H), 3.00 (dd, 16.85, 8.80 Hz, 1 H), 3.67 (m, 1 H), 3.81 (m, 1 H), 4.00 (t, 6.41 Hz, 2 H), 4.15 (m, 1 H), 6.91 (m, 2 H), 7.23 (m, 2 H), 7.33 (m, 2 H), 7.47 (m, 2 H) |
| 38 | 5 | rac | 5-(4-chlorophenyl)-1-[4-(3-piperidin-1-ylpropoxy)phenyl]piperidin-2-one | 427/429 | | 1.44 (m, 2 H), 1.58 (m, 4 H), 1.95 (m, 2 H), 2.17 (m, 2 H), 2.43 (m, 6 H), 2.69 (m, 2 H), 3.24 (m, 1 H), 3.68 (m, 2 H), 3.99 (t, 6.29 Hz, 2 H), 6.90 (m, 2 H), 7.15 (m, 2 H), 7.22 (m, 2 H), 7.31 (m, 2 H) |
| 39 | 4 | rac | 4-(4-chlorophenyl)-1-{4-[3-(4-isopropylpiperazin-1-yl)propoxy]phenyl}pyrrolidin-2-one | 456 | | 1.05 (d, 6.57 Hz, 6 H), 1.97 (m, 2 H), 2.62 (m, 12 H), 3.00 (m, 1 H), 3.68 (m, 1 H), 3.81 (m, 1 H), 4.00 (t, 6.31 Hz, 2 H), 4.15 (m, 1 H), 6.90 (m, 2 H), 7.22 (m, 2 H), 7.33 (m, 2 H), 7.48 (m, 2 H) |
| 40 | 5 | rac | 5-(4-chlorophenyl)-1-{4-[3-(4-isopropylpiperazin-1-yl)propoxy]phenyl}piperidin-2-one | 470 | | 0.84 (t, 11.49 Hz, 2 H), 1.19 (m, 3 H), 1.43 (m, 3 H), 1.59 (m, 4 H), 1.70 (m, 4 H), 1.96 (m, 2 H), 2.07 (d, 7.07 Hz, 2 H), 2.40 (m, 8 H), 2.64 (m, 1 H), 3.99 (t, 6.31 Hz, 2 H), 4.21 (m, 1 H), 6.89 (d, 8.84 Hz, 2 H), 7.26 (m, 2 H) |
| 41 | 5S | pure | (5S)-5-{[4-(cyclohexylmethyl)piperazin-1-yl]methyl}-1-[4-(3-piperidin-1-ylpropoxy)phenyl]pyrrolidin-2-one | 497 | −15.3 | 0.84 (t, 11.49 Hz, 2 H), 1.18 (m, 3 H), 1.43 (m, 3 H), 1.69 (m, 11 H), 2.00 (m, 5 H), 2.39 (m, 17 H), 2.64 (m, 1 H), 3.99 (t, 6.31 Hz, 2 H), 4.21 (m, 1 H), 6.89 (d, 8.84 Hz, 2 H), 7.26 (m, 2 H) |
| 42 | 5S,2 | mixture | (5S)-5-[(4-cyclopentylpiperazin-1-yl)methyl]-1-{4-[3-(2-methylpyrrolidin-1-yl)propoxy]phenyl}pyrrolidin-2-one | 469 | | 1.11 (d, 6.06 Hz, 3 H), 2.01 (m, 32 H), 2.98 (m, 1 H), 3.19 (m, 1 H), 4.02 (m, 2 H), 4.22 (m, 1 H), 6.90 (d, 8.59 Hz, 2 H), 7.27 (d, 8.59 Hz, 2 H) |
| 43 | 5S | pure | (5S)-5-[(4-cyclopentylpiperazin-1-yl)methyl]-1-[4-(3-piperidin-1-ylpropoxy)phenyl]pyrrolidin-2-one | 469 | −17.2 | 1.52 (m, 12 H), 1.82 (m, 2 H), 2.02 (m, 4 H), 2.40 (m, 18 H), 2.65 (m, 1 H), 4.00 (t, 6.31 Hz, 2 H), 4.22 (m, 1 H), 6.89 (d, 8.84 Hz, 2 H), 7.27 (m, 2 H) |
| 44 | 4,2 | mixture | 4-[(4-cyclopentylpiperazin-1-yl)methyl]-1-{4-[3-(2-methylpyrrolidin-1-yl)propoxy]phenyl}pyrrolidin-2-one | 469 | | 1.09 (d, 6.04 Hz, 3 H), 1.40 (dd, 2.77, 1.76 Hz, 3 H), 1.54 (m, 2 H), 1.84 (m, 10 H), 2.14 (m, 2 H), 2.49 (m, 14 H), 2.97 (m, 1 H), 3.17 (m, 1 H), 3.52 (m, 1 H), 3.84 (m, 1 H), 4.05 (t, 6.16 Hz, 2 H), 6.95 (m, 2 H), 7.24 (m, 2 H) |
| 45 | 4,2 | mixture | 4-[2-(4-cyclopentylpiperazin-1-yl)ethyl]-1-{4-[3-(2-methylpyrrolidin-1-yl)propoxy]phenyl}pyrrolidin-2-one | 483 | | 1.09 (d, 6.04 Hz, 3 H), 1.40 (m, 3 H), 1.54 (m, 2 H), 1.70 (m, 6 H), 1.91 (m, 6 H), 2.34 (m, 15 H), 2.72 (dd, 16.60, 8.55 Hz, 1 H), 2.96 (m, 1 H), 3.17 (td, 8.55, 2.64 Hz, 1 H), 3.50 (dd, 9.31, 7.29 Hz, 1 H), 3.89 (m, 1 H), 4.01 (m, 2 H), 6.89 (d, 9.05 Hz, 2 H), 7.45 (d, 9.05 Hz, 2 H) |
| 46 | 2,5S | mixture | (5S)-5-[(4-isopropylpiperazin-1-yl)methyl]-1-{4-[3-(2-methylpyrrolidin-1-yl)propoxy]phenyl}pyrrolidin-2-one | 443 | | 1.01 (d, 6.54 Hz, 6 H), 1.09 (d, 6.04 Hz, 3 H), 1.42 (m, 1 H), 2.18 (m, 22 H), 2.97 (m, 1 H), 3.18 (m, 1 H), 3.75 (m, 1 H), 4.01 (m, 2 H), 4.22 (m, 1 H), 6.90 (m, 2 H), 7.27 (m, 2 H) |
| 47 | 2,4 | mixture | 1-{4-[3-(2-methylpyrrolidin-1-yl)propoxy]phenyl}-4-(2-piperidin-1-ylethyl)pyrrolidin-2-one | 414 | | 1.10 (d, 6.04 Hz, 3 H), 1.45 (m, 3 H), 1.58 (m, 4 H), 1.74 (m, 4 H), 1.96 (m, 3 H), 2.31 (m, 12 H), 2.71 (dd, 16.60, 8.30 Hz, 1 H), 2.98 (m, 1 H), 3.19 (m, 1 H), 3.50 (dd, 9.31, 7.17 Hz, 1 H), 3.89 (m, 1 H), 4.01 (m, 2 H), 6.89 (m, 2 H), 7.46 (m, 2 H) |
| 48 | 5S,2 | mixture | (5S)-1-{4-[3-(2-methylpyrrolidin-1-yl)propoxy]phenyl}-5-(piperidin-1-ylmethyl)pyrrolidin-2-one | 400 | | 1.09 (d, 6.04 Hz, 3 H), 1.43 (m, 7 H), 2.09 (m, 19 H), 2.65 (m, 1 H), 2.97 (m, 1 H), 3.17 (td, 8.55, 2.58 Hz, 1 H), 4.01 (m, 2 H), 4.21 (m, 1 H), 6.90 (m, 2 H), 7.28 (m, 2 H) |
| 49 | 5S | pure | (5S)-5-(piperidin-1-ylmethyl)-1-[4-(3-piperidin-1-ylpropoxy)phenyl]pyrrolidin-2-one | 400 | nt | (DMSO): 1.36 (m, 8 H), 1.50 (m, 4 H), 1.89 (m, 3 H), 2.29 (m, 14 H), 2.58 (m, 1 H), 3.99 (t, 6.44 Hz, 2 H), 4.34 (m, 1 H), 6.92 (d, 9.09 Hz, 2 H), 7.34 (d, 9.09 Hz, 2 H) |
| 50 | 4S | pure | (4S)-4-(piperidin-1-ylmethyl)-1-[4-(3-piperidin-1-ylpropoxy)phenyl]azetidin-2-one | 386 | +2.4 | (DMSO): 1.40 (m, 4 H), 1.50 (m, 8 H), 1.85 (m, 2 H), 2.44 (m, 7.83 Hz, 1 H), 2.51 (m, 1 H), 2.61 (dd, 16.67, 8.08 Hz, 1 H), 3.12 (m, 1 H), 3.65 (dd, 9.85, 6.57 Hz, 1 H), 3.87 (m, 1 H), 3.98 (t, 6.44 Hz, 2 H), 6.92 (d, 9.09 Hz, 2 H), 7.54 (d, 9.09 Hz, 2 H) (some signals obscured by solvent) |
| 51 | 5S | pure | (5S)-1-[4-(2-piperidin-1-ylethoxy)phenyl]-5-(piperidin-1-ylmethyl)pyrrolidin-2-one | 386 | −21 | 1.37 (d, 5.53 Hz, 2 H), 1.47 (m, 7 H), 1.61 (m, 2 H), 2.06 (m, 3 H), 2.38 (m, 13 H), 2.64 (m, 1 H), 2.76 (t, 6.15 Hz, 2 H), 4.10 (t, 6.03 Hz, 2 H), 4.21 (m, 1 H), 6.90 (m, 2 H), 7.28 (m, 2 H) |
| 52 | 5S,2 | mixture | (5S)-1-{4-[2-(2-methylpyrrolidin-1-yl)ethoxy]phenyl}-5-(piperidin-1-ylmethyl)pyrrolidin-2-one | 386 | | 1.17 (d, 6.04 Hz, 3 H), 1.39 (d, 5.03 Hz, 2 H), 1.50 (d, 4.53 Hz, 5 H), 1.92 (m, 2 H), 2.49 (m, 13 H), 3.25 (m, 2 H), 4.13 (m, 2 H), 4.23 (m, 1 H), 6.92 (d, 8.80 Hz, 2 H), 7.30 (m, 2 H) |
| 53 | 5R | pure | (5R)-5-(piperidin-1-ylmethyl)-1-[4-(3-piperidin-1-ylpropoxy)phenyl]pyrrolidin-2-one | 400 | +16.14 | 1.42 (m, 6 H), 1.58 (m, 3 H), 1.71 (s, 2 H), 2.00 (m, 3 H), 2.38 (m, 15 H), 2.64 (m, 1 H), 3.99 (m, 2 H), 4.21 (m, 1 H), 6.89 (d, 8.30 Hz, 2 H), 7.27 (m, 2 H) |

TABLE I-continued

| n° | Configuration | | IUPAC Name | MH+ (M+.) | alphaD | 1H NMR (CDCl3 unless otherwise specified) δH (ppm) |
|---|---|---|---|---|---|---|
| 54 | 5S,2 | mixture | (5S)-1-{3-[3-(2-methylpyrrolidin-1-yl)propoxy]phenyl}-5-(piperidin-1-ylmethyl)pyrrolidin-2-one | 414 | | 1.10 (d, 6.06 Hz, 3 H), 1.44 (m, 6 H), 1.74 (m, 2 H), 2.20 (m, 16 H), 2.68 (m, 1 H), 2.97 (m, 1 H), 3.18 (td, 8.59, 2.46 Hz, 1 H), 4.03 (m, 2 H), 4.29 (m, 1 H), 6.73 (dd, 8.08, 2.15 Hz, 1 H), 6.98 (d, 8.08 Hz, 1 H), 7.11 (t, 2.15 Hz, 1 H), 7.25 (d, 8.84 Hz, 1 H) |
| 55 | 5S | pure | (5S)-1-{4-[3-(4-cyclopentylpiperazin-1-yl)propoxy]phenyl}-5-(piperidin-1-ylmethyl)pyrrolidin-2-one | 469 | nt | (DMSO): 1.43 (m, 13 H), 1.79 (m, 5 H), 2.30 (m, 18 H), 3.98 (t, 6.29 Hz, 2 H), 4.33 (m, 1 H), 6.91 (d, 9.05 Hz, 2 H), 7.33 (d, 9.05 Hz, 2 H) (some signals obscured by solvent) |
| 56 | 5S,2,6 | mixture | (5S)-5-[(2,6-dimethylpiperidin-1-yl)methyl]-1-[4-(3-piperidin-1-ylpropoxy)phenyl]pyrrolidin-2-one | 428 | | 1.01 (dd, 11.11, 6.57 Hz, 6 H), 1.30 (m, 8 H), 1.59 (m, 3 H), 1.97 (m, 2 H), 2.39 (m, 15 H), 4.00 (t, 6.44 Hz, 2 H), 4.12 (m, 1 H), 6.90 (d, 8.84 Hz, 2 H), 7.22 (d, 8.84 Hz, 2 H) |
| 57 | 2,5S,2,6 | mixture | (5S)-5-[(2,6-dimethylpiperidin-1-yl)methyl]-1-{4-[3-(2-methylpyrrolidin-1-yl)propoxy]phenyl}pyrrolidin-2-one | 428 | | 1.01 (dd, 9.35, 6.57 Hz, 7 H), 1.30 (m, 6 H), 1.71 (m, 4 H), 2.25 (m, 17 H), 2.99 (m, 1 H), 3.20 (t, 8.46 Hz, 1 H), 4.03 (m, 2 H), 4.12 (m, 1 H), 6.91 (d, 7.32 Hz, 2 H), 7.22 (m, 2 H) |
| 58 | 5S,2 | mixture | (5S)-5-[(2-methylpiperidin-1-yl)methyl]-1-[4-(3-piperidin-1-ylpropoxy)phenyl]pyrrolidin-2-one | 414 | | 0.89 (d, 6.31 Hz, 1 H), 1.00 (m, 2 H), 1.23 (m, 2 H), 1.54 (m, 10 H), 2.19 (m, 15 H), 2.69 (m, 3 H), 4.00 (t, 6.44 Hz, 2 H), 4.17 (m, 1 H), 6.89 (d, 8.84 Hz, 2 H), 7.28 (m, 2 H) |
| 59 | 2,5S,2 | mixture | (5S)-5-[(2-methylpiperidin-1-yl)methyl]-1-{4-[3-(2-methylpyrrolidin-1-yl)propoxy]phenyl}pyrrolidin-2-one | 414 | | 0.89 (d, 6.31 Hz, 1 H), 0.97 (d, 6.06 Hz, 2 H), 1.09 (d, 6.06 Hz, 3 H), 1.22 (m, 2 H), 1.86 (m, 18 H), 2.47 (m, 1 H), 2.69 (m, 3 H), 2.97 (m, 1 H), 3.18 (td, 8.59, 2.59 Hz, 1 H), 4.02 (m, 2 H), 4.17 (m, 1 H), 6.90 (d, 8.84 Hz, 2 H), 7.28 (m, 2 H) |
| 60 | 5S,2 | mixture | (5S)-5-[(4-methylpiperidin-1-yl)methyl]-1-{4-[3-(2-methylpyrrolidin-1-yl)propoxy]phenyl}pyrrolidin-2-one | 414 | | 0.88 (d, 6.31 Hz, 3 H), 1.14 (m, 5 H), 1.48 (m, 3 H), 2.10 (m, 16 H), 2.65 (m, 2 H), 2.76 (d, 11.11 Hz, 1 H), 2.99 (m, 1 H), 3.20 (m, 1 H), 4.02 (m, 2 H), 4.21 (m, 1 H), 6.90 (d, 8.84 Hz, 2 H), 7.28 (m, 2 H) |
| 61 | 5S | pure | (5S)-5-[(4-methylpiperidin-1-yl)methyl]-1-[4-(3-piperidin-1-ylpropoxy)phenyl]pyrrolidin-2-one | 414 | −19.6 | 0.88 (d, 6.31 Hz, 3 H), 1.15 (m, 2 H), 1.44 (d, 4.55 Hz, 2 H), 1.57 (m, 6 H), 1.96 (m, 6 H), 2.39 (m, 10 H), 2.64 (m, 2 H), 2.76 (d, 10.86 Hz, 1 H), 3.99 (t, 6.31 Hz, 2 H), 4.20 (m, 1 H), 6.89 (d, 8.59 Hz, 2 H), 7.27 (d, 8.59 Hz, 2 H) |
| 62 | 5S,2 | mixture | (5S)-1-{4-[3-(2-methylpyrrolidin-1-yl)propoxy]phenyl}-5-(pyrrolidin-1-ylmethyl)pyrrolidin-2-one | 386 | | 1.09 (d, 6.06 Hz, 3 H), 1.39 (m, 1 H), 1.75 (m, 6 H), 1.95 (m, 3 H), 2.15 (m, 3 H), 2.31 (m, 2 H), 2.50 (m, 7 H), 2.64 (m, 1 H), 2.97 (m, 1 H), 3.17 (td, 8.59, 2.53 Hz, 1 H), 4.02 (m, 2 H), 4.22 (m, 1 H), 6.90 (d, 9.09 Hz, 2H), 7.28 (m, 2 H) |
| 63 | 5S,2S | pure | (5S)-1-{4-[3-((2S)-2-methylpyrrolidin-1-yl)propoxy]phenyl}-5-(pyrrolidin-1-ylmethyl)pyrrolidin-2-one | 386 | nt | 1.09 (d, 6.04 Hz, 3 H), 1.42 (m, 1 H), 1.69 (m, 6 H), 1.95 (m, 3 H), 2.22 (m, 5 H), 2.49 (m, 7 H), 2.64 (m, 1 H), 2.97 (m, 1 H), 3.17 (td, 8.55, 2.45 Hz, 1 H), 4.02 (m, 2 H), 4.22 (m, 1 H), 6.90 (d, 8.80 Hz, 2 H), 7.28 (m, 2 H) |
| 64 | 5S,2R | pure | (5S)-1-{4-[3-((2R)-2-methylpyrrolidin-1-yl)propoxy]phenyl}-5-(pyrrolidin-1-ylmethyl)pyrrolidin-2-one | 386 | nt | 1.09 (d, 6.04 Hz, 3 H), 1.43 (m, 1 H), 1.73 (m, 6 H), 1.95 (m, 3 H), 2.15 (m, 3 H), 2.31 (m, 2 H), 2.49 (m, 7 H), 2.64 (m, 1 H), 2.96 (m, 1 H), 3.17 (m, 1 H), 4.02 (m, 2 H), 4.21 (m, 1 H), 6.90 (d, 8.80 Hz, 2 H), 7.29 (d Hz, 2 H) |
| 65 | 5S | pure | (5S)-1-[4-(3-piperidin-1-ylpropoxy)phenyl]-5-(pyrrolidin-1-ylmethyl)pyrrolidin-2-one | 386 | −23.7 | 1.45 (m, 2 H), 1.59 (m, 4 H), 1.72 (s, 4 H), 1.97 (m, 3 H), 2.11 (m, 1 H), 2.43 (m, 14 H), 2.64 (m, 1 H), 4.00 (t, 6.31 Hz, 2 H), 4.22 (m, 1 H), 6.90 (d, 8.84 Hz, 2 H), 7.27 (m, 2 H) |
| 66 | 5S | pure | (5S)-1-{4-[3-(4-isopropylpiperazin-1-yl)propoxy]phenyl}-5-(pyrrolidin-1-ylmethyl)pyrrolidin-2-one | 429 | −17 | 1.17 (d, 6.54 Hz, 6 H), 1.73 (s, 4 H), 1.98 (m, 3 H), 2.11 (m, 1 H), 2.34 (m, 1 H), 2.63 (m, 19 H), 4.00 (t, 6.29 Hz, 2 H), 4.23 (m, 1 H), 6.89 (d, 8.80 Hz, 2 H), 7.28 (m, 2 H) |
| 67 | 2,5S | mixture | (5S)-5-[(2-methylpyrrolidin-1-yl)methyl]-1-[4-(3-piperidin-1-ylpropoxy)phenyl]pyrrolidin-2-one | 400 | | 1.00 (m, 3 H), 1.41 (m, 3 H), 1.70 (m, 6 H), 2.05 (m, 4 H), 2.37 (m, 11 H), 2.65 (m, 2 H), 3.09 (m, 1 H), 4.00 (t, 6.41 Hz, 2 H), 4.22 (m, 1 H), 6.90 (dd, 8.80, 2.14 Hz, 2 H), 7.30 (t, 8.93 Hz, 2 H) |
| 68 | A-2!,5S | pure | (−)-(5S)-5-[(2-methylpyrrolidin-1-yl)methyl]-1-[4-(3-piperidin-1-ylpropoxy)phenyl]pyrrolidin-2-one bis(trifluoroacetate) | 400 | −20.5 | (DMSO): 1.30 (d, 6.31 Hz, 3 H), 1.39 (m, 1 H), 1.64 (m, 4 H), 1.99 (m, 9 H), 2.40 (m, 2 H), 2.68 (m, 1 H), 2.91 (m, 4 H), 3.19 (m, 2 H), 3.35 (m, 1 H), 3.49 (m, 3 H), 3.77 (m, 1 H), 4.05 (t, 6.06 Hz, 3 H), 4.75 (m, 11 H), 6.98 (d, 9.09 Hz, 2 H), 7.38 (d, 9.09 Hz, 2 H) (some signals obscured by solvent) |
| 69 | B-2!,5S | pure | (+)-(5S)-5-[(2-methylpyrrolidin-1-yl)methyl]1-[4-(3-piperidin-1-ylpropoxy)phenyl]pyrrolidin-2-one | 400 | +14.68 | 0.96 (d, 5.81 Hz, 3 H), 1.30 (m, 1 H), 1.45 (d, 4.80 Hz, 2 H), 1.64 (m, 6 H), 1.80 (m, 1 H), 2.05 (m, 5 H), 2.39 (m, 10 H), 2.67 (m, 1 H), 2.83 (dd, 13.39, 3.41 Hz, 1 H), 3.05 (td, 8.34, 3.03 Hz, 1 H), 4.00 (t, 6.31 Hz, 2 H), 4.24 (m, 1 H), 6.89 (d, 8.84 Hz, 2 H), 7.31 (d, 8.84 Hz, 2 H) |
| 70 | 2 | rac | 2-{4-[3-(2-methylpiperidin-1-yl)propoxy]phenyl}-2-azaspiro[4.5]decan-3-one | 385 | | 1.07 (d, 6.04 Hz, 3 H), 1.29 (m, 2 H), 1.55 (m, 14 H), 1.92 (m, 2 H), 2.17 (td, 11.07, 2.83 Hz, 1 H), 2.29 (m, 1 H), 2.45 (s, 2 H), 2.50 (m, 1 H), 2.85 (m, 2 H), 3.56 (s, 2 H), 3.97 (td, 6.29, 2.64 Hz, 2 H), 6.89 (d, 9.05 Hz, 2 H), 7.47 (d, 9.05 Hz, 2 H) |

TABLE I-continued

| n° | Configuration | | IUPAC Name | MH+ (M+.) | alphaD | 1H NMR (CDCl3 unless otherwise specified) δH (ppm) |
|---|---|---|---|---|---|---|
| 71 | 5,2 | mixture | 7-benzyl-2-{4-[3-(2-methylpyrrolidin-1-yl)propoxy]phenyl}-2,7-diazaspiro[4.4]nonan-3-one | 448 | | 1.34 (d, 6.28 Hz, 3 H), 1.99 (m, 9 H), 2.66 (m, 8 H), 3.19 (m, 1 H), 3.48 (m, 1 H), 3.63 (d, 3.77 Hz, 1 H), 3.74 (m, 2 H), 4.04 (m, 2 H), 6.87 (d, 9.04 Hz, 2 H), 7.24 (m, 1 H), 7.31 (m, 3 H), 7.45 (d, 8.79 Hz, 2 H) |
| 72 | 4,2 | mixture | 4-(hydroxymethyl)-1-{4-[3-(2-methylpyrrolidin-1-yl)propoxy]phenyl}pyrrolidin-2-one | 333 | | 0.99 (dd, 6.04, 1.01 Hz, 3 H), 1.22 (m, 2 H), 1.64 (m, 2 H), 1.86 (m, 3 H), 2.12 (m, 5 H), 2.90 (m, 1 H), 3.05 (m, 1 H), 3.17 (s, 1 H), 3.46 (m, 3 H), 3.72 (m, 1 H), 4.02 (m, 3 H), 6.93 (m, 1 H), 7.06 (d, 8.30 Hz, 1 H), 7.18 (m, 1 H), 7.26 (m, 1 H) |
| 73 | 4,2 | mixture | 4-(2-hydroxyethyl)-1-{4-[3-(2-methylpyrrolidin-1-yl)propoxy]phenyl}pyrrolidin-2-one | 347 | | 1.02 (d, 6.04 Hz, 3 H), 1.19 (s, 4 H), 1.36 (s, 1 H), 1.94 (m, 9 H), 2.57 (m, 1 H), 2.68 (m, 1 H), 2.90 (m, 1 H), 3.11 (m, 1 H), 3.47 (dd, 9.56, 7.04 Hz, 1 H), 3.69 (m, 2 H), 3.86 (m, 1 H), 3.94 (m, 1 H), 6.82 (d, 8.80 Hz, 2 H), 7.39 (d, 8.80 Hz, 2 H) |
| 74 | 5S,8aS, 4aR | pure | (5S)-5-[(4aR,8aS)-octahydroisoquinolin-2(1 H)-ylmethyl]-1-[4-(3-piperidin-1-ylpropoxy)phenyl]pyrrolidin-2-one | 454 | | (DMSO): 0.88 (m, 3 H), 1.17 (m, 4 H), 1.45 (m, 3 H), 1.58 (m, 5 H), 1.68 (m, 2 H), 1.96 (m, 4 H), 2.30 (m, 2 H), 2.48 (m, 3 H), 2.63 (m, 1 H), 2.76 (dd, 32.3, 10.9 Hz, 1 H), 3.99 (t, 6.3 Hz, 2 H), 4.21 (m, 1 H), 6.89 (dd, 8.8, 1.8 Hz, 2 H), 7.27 (dd, 8.3, 2 Hz, 2 H) (some signals obscured by solvent) |
| 75 | 5S,8aS, 4aR,2! | pure | (5S)-5-[(4aR,8aS)-octahydroisoquinolin-2(1 H)-ylmethyl]-1-{4-[3-(2-methylpyrrolidin-1-yl)propoxy]phenyl}pyrrolidin-2-one | 454 | | (DMSO): 0.86 (m, 4 H), 1.09 (dd, 5.8, 1.5 Hz, 4 H), 1.21 (m, 3 H), 1.43 (m, 3 H), 1.56 (m, 2 H), 1.71 (m, 4 H), 2.09 (m, 9 H), 2.47 (m, 2 H), 2.62 (m, 1 H), 2.76 (dd, 32.6, 10.6 Hz, 1 H), 2.96 (m, 1 H), 3.17 (t, 8.6 Hz, 1 H), 4.02 (m, 2 H), 4.21 (m, 1 H), 6.90 (m, 2 H), 7.28 (m, 2 H) (some signals obscured by solvent) |
| 76 | 5,2 | mixture | 7-acetyl-2-{4-[3-(2-methylpyrrolidin-1-yl)propoxy]phenyl}-2,7-diazaspiro[4.4]nonan-3-one | 400 | | (DMSO): 0.99 (d, 6.0 Hz, 3 H), 1.27 (m, 1 H), 1.63 (m, 2 H), 1.85 (m, 3 H), 1.93 (d, 5.3 Hz, 4 H), 2.07 (m, 3 H), 2.25 (m, 1 H), 2.56 (m, 2 H), 2.89 (dt, 11.8, 8.0 Hz, 1 H), 3.06 (m, 1 H), 3.40 (m, 2 H), 3.52 (m, 2 H), 3.75 (m, 2 H), 3.99 (t, 6.3 Hz, 2 H), 6.92 (d, 9.0 Hz, 2 H), 7.51 (t, 8.8 Hz, 2 H) (some signals obscured by solvent) |
| 77 | 2S,2 | mixture | N-(cyclohexylmethyl)-N-[((2S)-1-{4-[3-(2-methylpyrrolidin-1-yl)propoxy]phenyl}-5-oxopyrrolidin-2-yl)methyl]cyclopropanecarboxamide | 496 | | 0.71 (m, 2 H), 0.82 (m, 2 H), 0.94 (m, 2 H), 1.11 (m, 7 H), 1.70 (m, 18 H), 2.23 (m, 5 H), 2.48 (m, 1 H), 2.64 (m, 1 H), 3.02 (m, 3 H), 3.19 (m, 1 H), 3.43 (m, 2 H), 4.01 (d, 1.3 Hz, 2 H), 4.63 (m, 1 H), 6.90 (d, 8.8 Hz, 2 H), 7.38 (d, 8.8 Hz, 2 H) |
| 78 | 2S,5S | pure | (5S)-5-(morpholin-4-ylmethyl)-1-(4-{3-[(2S)-2-(pyrrolidin-1-ylmethyl)pyrrolidin-1-yl]propoxy}phenyl)pyrrolidin-2-one | 471 | | (DMSO): 1.51 (m, 1 H), 1.63 (m, 3 H), 1.87 (m, 2 H), 2.08 (q, 8.8 Hz, 1 H), 2.32 (m, 8 H), 3.02 (m, 1 H), 3.47 (t, 4.3 Hz, 2 H), 4.00 (m, 1 H), 4.37 (m, 1 H), 6.91 (d, 8.8 Hz, 1 H), 7.33 (d, 8.8 Hz, 1 H) (some signals obscured by solvent) |
| 79 | 5S,2R | pure | (5S)-1-(4-{3-[(2R)-2-methylpyrrolidin-1-yl]propoxy}phenyl)-5-(pyrrolidin-1-ylmethyl)pyrrolidin-2-one | 386 | | 1.10 (d, 6.1 Hz, 3 H), 1.43 (m, 1 H), 1.95 (m, 4 H), 2.15 (m, 3 H), 2.33 (m, 2 H), 2.47 (m, 4 H), 2.64 (m, 1 H), 2.97 (m, 1 H), 3.18 (td, 8.6, 2.8 Hz, 1 H), 4.02 (m, 2 H), 4.22 (m, 1 H), 6.90 (d, 8.8 Hz, 2 H), 7.28 (m, 2 H) (some signals obscured by solvent) |
| 80 | 5S,2 | mixture | (5S)-5-{[(2-fluorophenyl)amino]methyl}-1-{4-[3-(2-methylpyrrolidin-1-yl)propoxy]phenyl}pyrrolidin-2-one | 426 | | 1.11 (d, 5.9 Hz, 3 H), 1.46 (m, 1 H), 1.97 (m, 8 H), 2.38 (m, 2 H), 2.61 (m, 2 H), 2.99 (m, 1 H), 3.20 (m, 2 H), 3.34 (m, 1 H), 3.82 (s, 1 H), 4.03 (m, 2 H), 4.37 (d, 2.6 Hz, 1 H), 6.54 (t, 8.1 Hz, 1 H), 6.62 (m, 1 H), 6.93 (d, 8.8 Hz, 4 H), 7.25 (d, 8.8 Hz, 2 H) |
| 81 | 5S,2 | mixture | (5S)-5-{[(3-fluorophenyl)amino]methyl}-1-{4-[3-(2-methylpyrrolidin-1-yl)propoxy]phenyl}pyrrolidin-2-one | 426 | | 1.10 (d, 5.9 Hz, 3 H), 1.43 (m, 1 H), 1.75 (m, 2 H), 1.97 (m, 3 H), 2.18 (m, 2 H), 2.35 (m, 2 H), 2.61 (m, 2 H), 2.98 (m, 1 H), 3.23 (m, 3 H), 3.65 (s, 1 H), 4.02 (m, 2 H), 4.35 (m, 1 H), 6.16 (m, 1 H), 6.23 (m, 1 H), 6.38 (td, 8.1, 1.8 Hz, 1 H), 6.93 (m, 2 H), 7.05 (m, 1 H), 7.24 (m, 2 H) |
| 82 | 5S,2 | mixture | (5S)-5-{[(2,4-difluorophenyl)amino]methyl}-1-{4-[3-(2-methylpyrrolidin-1-yl)propoxy]phenyl}pyrrolidin-2-one | 444 | | 1.11 (d, 5.9 Hz, 3 H), 1.44 (m, 1 H), 1.75 (m, 2 H), 2.08 (m, 6 H), 2.37 (m, 2 H), 2.62 (m, 2 H), 2.99 (m, 1 H), 3.17 (m, 2 H), 3.28 (m, 1 H), 3.61 (s, 1 H), 4.03 (m, 2 H), 4.36 (dd, 5.1, 3.7 Hz, 1 H), 6.44 (td, 9.5, 5.5 Hz, 1 H), 6.72 (m, 1 H), 6.93 (d, 8.8 Hz, 2 H), 7.24 (m, 2 H) |
| 83 | 5S,2 | mixture | (5S)-5-{[(3-methoxyphenyl)amino]methyl}-1-{4-[3-(2-methylpyrrolidin-1-yl)propoxy]phenyl}pyrrolidin-2-one | 438 | | 1.11 (d, 6.0 Hz, 3 H), 1.45 (m, 1 H), 1.75 (m, 3 H), 1.98 (m, 5 H), 2.19 (m, 2 H), 2.34 (m, 2 H), 2.60 (m, 2 H), 2.98 (m, 1 H), 3.18 (m, 2 H), 3.30 (m, 1 H), 3.54 (t, 6.8 Hz, 1 H), 3.74 (s, 3 H), 4.02 (td, 6.0, 2.8 Hz, 2 H), 4.35 (m, 1 H), 6.04 (t, 2.0 Hz, 1 H), 6.11 (dd, 8.0, 2.0 Hz, 1 H), 6.27 (dd, 8.3, 2.3 Hz, 1 H), 6.93 (d, 8.8 Hz, 2 H), 7.04 (t, 8.0 Hz, 1 H), 7.25 (m, 3 H) |
| 84 | 5S,2 | mixture | (5S)-1-{4-[3-(2-methylpyrrolidin-1-yl)propoxy]phenyl}-5-({[4-(trifluoromethyl)phenyl]amino}methyl)pyrrolidin-2-one | 476 | | 1.09 (d, J = 6.0 Hz, 3 H), 1.43 (m, 1 H), 1.74 (m, 3 H), 1.96 (m, 4 H), 2.17 (m, 2 H), 2.35 (m, 2 H), 2.61 (m, 2 H), 2.98 (dt, J = 11.8, 8.0 Hz, 1 H), 3.22 (m, 2 H), 3.35 (m, 1 H), 3.86 (t, J = 6.0 Hz, 1 H), 4.03 (td, J = 6.0, 1.5 Hz, 2 H), 4.36 (m, 1 H), 6.48 (d, J = 8.5 Hz, 2 H), 6.94 (d, J = 8.8 Hz, 2 H), 7.24 (m, 3 H), 7.36 (d, J = 8.5 Hz, 2 H) |

TABLE I-continued

| n° | Configuration | | IUPAC Name | MH+ (M+.) | alphaD | ¹H NMR (CDCl₃ unless otherwise specified) δH (ppm) |
|---|---|---|---|---|---|---|
| 85 | 4,2 | mixture | 3-{4-[3-(2-methylpyrrolidin-1-yl)propoxy]phenyl}-4-(pyrrolidin-1-ylmethyl)-1,3-oxazolidin-2-one | 388 | | 0.87 (m, 1 H), 1.24 (m, 5 H), 1.60 (m, 1 H), 1.77 (m, 3 H), 1.93 (m, 1 H), 2.05 (m, 3 H), 2.49 (m, 5 H), 2.67 (m, 3 H), 3.13 (m, 1 H), 3.40 (s, 1 H), 4.03 (m, 2 H), 4.40 (m, 2 H), 4.53 (m, 1 H), 6.90 (m, 2 H), 7.32 (m, 2 H) |
| 86 | 5S,2 | mixture | (5S)-1-{4-[3-(2-methylpyrrolidin-1-yl)propoxy]phenyl}-5-(piperidin-1-ylmethyl)pyrrolidine-2-thione | 416 | | (DMSO): 1.09 (s, 3 H), 1.30 (m, 8 H), 1.72 (s, 2 H), 1.95 (m, 4 H), 2.16 (d, 5.0 Hz, 2 H), 2.30 (m, 5 H), 2.94 (m, 2 H), 3.13 (m, 3 H), 4.05 (t, 6.0 Hz, 2 H), 4.53 (m, 1 H), 6.98 (d, 9.0 Hz, 2 H), 7.29 (d, 8.8 Hz, 2 H) |
| 87 | 5S,2 | mixture | (5S)-5-[(4-fluorophenoxy)methyl]-1-{4-[3-(2-methylpyrrolidin-1-yl)propoxy]phenyl}pyrrolidin-2-one | 427 | | 1.09 (d, 6.0 Hz, 3 H), 1.42 (m, 1 H), 1.73 (m, 3 H), 1.94 (m, 3 H), 2.21 (m, 3 H), 2.41 (m, 1 H), 2.57 (m, 1 H), 2.78 (m, 1 H), 2.95 (m, 1 H), 3.17 (td, 8.8, 2.3 Hz, 1 H), 3.89 (d, 3.5 Hz, 2 H), 4.00 (td, 6.0, 2.0 Hz, 2 H), 4.36 (m, 1 H), 6.74 (m, 2 H), 6.92 (m, 4 H), 7.21 (d, 8.8 Hz, 2 H) |
| 88 | 5S,2 | mixture | (5S)-5-{[(4-methylphenyl)amino]methyl}-1-{4-[3-(2-methylpyrrolidin-1-yl)propoxy]phenyl}pyrrolidin-2-one | 422 | | 1.09 (d, 6.05 Hz, 3 H), 1.42 (s, 1 H), 1.89 (m, 7 H), 2.22 (s, 4 H), 2.32 (m, 2 H), 2.60 (m, 2 H), 2.97 (m, 1 H), 3.17 (m, 2 H), 3.29 (m, 1 H), 3.38 (t, 6.14 Hz, 1 H), 4.02 (m, 2 H), 4.33 (m, 1 H), 6.42 (d, 8.24 Hz, 2 H), 6.94 (m, 4 H), 7.25 (d, 8.24 Hz, 2 H) |
| 89 | 5S,2 | mixture | (5S)-5-{[(3,4-difluorophenyl)amino]methyl}-1-{4-[3-(2-methylpyrrolidin-1-yl)propoxy]phenyl}pyrrolidin-2-one | 444 | | 1.09 (d, 6.0 Hz, 3 H), 1.43 (dd, 10.8, 6.0 Hz, 1 H), 1.74 (m, 3 H), 1.96 (m, 3 H), 2.15 (m, 2 H), 2.33 (m, 2 H), 2.60 (m, 1 H), 2.97 (dt, 11.8, 8.0 Hz, 1 H), 3.18 (m, 3 H), 3.50 (t, 6.0 Hz, 1 H), 4.02 (td, 6.3, 1.8 Hz, 2 H), 4.33 (dd, 8.3, 4.0 Hz, 1 H), 6.12 (m, 1 H), 6.24 (ddd, 12.5, 6.5, 2.8 Hz, 1 H), 6.91 (m, 3 H), 7.24 (m, 2 H) |
| 90 | 5S,2,2,6 | mixture | (5S)-5-[(2,6-dimethylmorpholin-4-yl)methyl]-1-{4-[3-(2-methylpyrrolidin-1-yl)propoxy]phenyl}pyrrolidin-2-one | 430 | | 1.10 (m, 7 H), 1.20 (m, 1 H), 1.41 (m, 1 H), 2.16 (m, 19 H), 2.96 (dt, 11.72, 8.06 Hz, 1 H), 3.17 (td, 8.61, 2.52 Hz, 1 H), 3.54 (m, 2 H), 4.02 (m, 2 H), 4.23 (m, 1 H), 6.90 (d, 8.79 Hz, 2 H), 7.26 (m, 2 H) |
| 91 | 5S,2 | mixture | (5S)-1-{4-[3-(2-methylpyrrolidin-1-yl)propoxy]phenyl}-5-(thiomorpholin-4-ylmethyl)pyrrolidin-2-one | 418 | | 1.09 (d, 6.05 Hz, 3 H), 1.42 (m, 1 H), 1.73 (m, 2 H), 1.94 (m, 4 H), 2.22 (m, 5 H), 2.57 (m, 11 H), 2.97 (m, 1 H), 3.17 (m, 1 H), 4.02 (m, 2 H), 4.20 (m, 1 H), 6.90 (d, 8.61 Hz, 2 H), 7.25 (d, 8.79 Hz, 2 H) |
| 92 | 5S,2 | mixture | (5S)-5-{[(3,5-difluorophenyl)amino]methyl}-1-{4-[3-(2-methylpyrrolidin-1-yl)propoxy]phenyl}pyrrolidin-2-one | 444 | | 1.09 (d, 6.05 Hz, 3 H), 1.41 (m, 1 H), 1.73 (m, 2 H), 1.95 (m, 4 H), 2.16 (m, 2 H), 2.33 (m, 2 H), 2.59 (m, 2 H), 2.97 (m, 1 H), 3.20 (m, 3 H), 3.80 (t, 5.22 Hz, 1 H), 4.03 (m, 2 H), 4.33 (m, 1 H), 5.95 (d, 7.88 Hz, 2 H), 6.12 (t, 9.07 Hz, 1 H), 6.94 (d, 8.79 Hz, 2 H), 7.22 (d, 8.79 Hz, 2 H) |
| 93 | 5S,2 | mixture | (5S)-5-[(4,4-difluoropiperidin-1-yl)methyl]-1-{4-[3-(2-methylpyrrolidin-1-yl)propoxy]phenyl}pyrrolidin-2-one | 436 | | 1.09 (d, 6.03 Hz, 3 H), 1.42 (m, 1 H), 2.11 (m, 22 H), 2.64 (m, 1 H), 2.96 (dt, 11.80, 8.19 Hz, 1 H), 3.17 (td, 8.79, 2.57 Hz, 1 H), 4.01 (td, 6.28, 2.64 Hz, 2 H), 4.21 (m, 1 H), 6.90 (d, 8.79 Hz, 2 H), 7.25 (d, 8.79 Hz, 2 H) |
| 94 | 5S,2 | mixture | (5S)-1-{4-[3-(2-methylpyrrolidin-1-yl)propoxy]phenyl}-5-{[(2,2,2-trifluoroethyl)amino]methyl}pyrrolidin-2-one | 414 | | 1.09 (d, 6.05 Hz, 3 H), 1.42 (m, 1 H), 2.00 (m, 11 H), 2.59 (m, 2 H), 2.82 (m, 2 H), 3.06 (m, 4 H), 4.02 (m, 2 H), 4.18 (m, 1 H), 6.92 (d, 8.79 Hz, 2 H), 7.22 (d, 8.79 Hz, 2 H) |
| 95 | 5S,2 | mixture | (5S)-5-[(3,4-difluorophenoxy)methyl]-1-{4-[3-(2-methylpyrrolidin-1-yl)propoxy]phenyl}pyrrolidin-2-one | 445 | | 1.08 (d, 6.05 Hz, 3 H), 1.42 (m, 1 H), 1.73 (m, 2 H), 1.94 (m, 3 H), 2.19 (m, 4 H), 2.42 (m, 3 H), 2.58 (m, 1 H), 2.76 (m, 1 H), 2.95 (m, 1 H), 3.16 (m, 1 H), 3.87 (m, 2 H), 4.00 (m, 2 H), 4.37 (m, 1 H), 6.50 (m, 1 H), 6.61 (m, 1 H), 6.89 (d, 8.79 Hz, 2 H), 7.02 (m, 1 H), 7.20 (d, 8.98 Hz, 2 H) |
| 96 | 5S,2 | mixture | (5S)-5-[(1,3-benzodioxol-5-ylamino)methyl]-1-{4-[3-(2-methylpyrrolidin-1-yl)propoxy]phenyl}pyrrolidin-2-one | 452 | | 1.12 (d, 6.05 Hz, 3 H), 1.46 (m, 1 H), 1.88 (m, 7 H), 2.27 (m, 4 H), 2.58 (m, 2 H), 2.99 (m, 1 H), 3.17 (m, 3 H), 4.03 (m, 2 H), 4.33 (m, 1 H), 5.84 (s, 2 H), 5.91 (dd, 8.24, 2.29 Hz, 1 H), 6.11 (d, 2.02 Hz, 1 H), 6.61 (d, 8.24 Hz, 1 H), 6.93 (d, 8.79 Hz, 2 H), 7.24 (d, 8.79 Hz, 2 H) |
| 97 | 5S,2 | mixture | (5S)-5-{[(4-fluorophenyl)(methyl)amino]methyl}-1-{4-[3-(2-methylpyrrolidin-1-yl)propoxy]phenyl}pyrrolidin-2-one | 440 | | 1.09 (d, 6.05 Hz, 3 H), 1.43 (m, 1 H), 1.83 (m, 6 H), 2.22 (m, 4 H), 2.51 (m, 1 H), 2.63 (m, 1 H), 2.78 (s, 3 H), 2.98 (m, 1 H), 3.20 (m, 2 H), 3.47 (dd, 14.84, 4.40 Hz, 1 H), 4.03 (m, 2 H), 4.38 (m, 1 H), 6.49 (m, 2 H), 6.90 (m, 4 H), 7.23 (d, 8.98 Hz, 2 H) |
| 98 | 4,2 | mixture | 4-(4-chlorobenzyl)-3-{4-[3-(2-methylpyrrolidin-1-yl)propoxy]phenyl}-1,3-oxazolidin-2-one | 429/431 | | 1.10 (d, 6.05 Hz, 3 H), 1.43 (m, 1 H), 1.74 (m, 2 H), 1.96 (m, 2 H), 2.16 (m, 2 H), 2.30 (m, 1 H), 2.74 (dd, 13.74, 9.16 Hz, 1 H), 3.00 (m, 2 H), 3.18 (m, 1 H), 4.04 (m, 2 H), 4.13 (m, 1 H), 4.35 (t, 8.52 Hz, 1 H), 4.51 (m, 1 H), 6.96 (m, 1 H), 7.03 (d, 8.24 Hz, 2 H), 7.27 (m, 3 H), 7.35 (m, 2 H) |
| 99 | 4R,2 | mixture | (4R)-4-(cyclohexylmethyl)-3-{4-[3-(2-methylpyrrolidin-1-yl)propoxy]phenyl}-1,3-oxazolidin-2-one | 401 | | 0.92 (m, 2 H), 1.20 (m, 5 H), 1.41 (m, 1 H), 1.56 (d, 6.60 Hz, 3 H), 1.67 (m, 5 H), 1.99 (m, 2 H), 2.24 (m, 3 H), 2.39 (m, 1 H), 2.95 (m, 2 H), 3.20 (m, 1 H), 3.51 (m, 1 H), 4.06 (m, 5 H), 4.37 (m, 1 H), 4.55 (t, 8.24 Hz, 1 H), 6.88 (d, 8.98 Hz, 2 H), 7.28 (m, 2 H) |

TABLE I-continued

| n° | Configuration | | IUPAC Name | MH+ (M+.) | alphaD | 1H NMR (CDCl3 unless otherwise specified) δH (ppm) |
|---|---|---|---|---|---|---|
| 100 | 2,5S, cis-2,6 | mixture | (5S)-5-{[cis-2,6-dimethylmorpholin-4-yl]methyl}-1-{4-[3-(2-methylpyrrolidin-1-yl)propoxy]phenyl}pyrrolidin-2-one | 430 | | 1.10 (m, 9 H), 1.42 (m, 1 H), 1.73 (m, 4 H), 2.11 (m, 9 H), 2.54 (m, 5 H), 2.96 (m, 1 H), 3.17 (m, 1 H), 3.54 (m, 2 H), 4.01 (m, 2 H), 4.23 (m, 1 H), 6.90 (d, 8.61 Hz, 2 H), 7.25 (m, 3 H) |
| 101 | 4R,2, cis-2,6 | mixture | (4R)-4-{[cis-2,6-dimethylmorpholin-4-yl]methyl}-3-{4-[3-(2-methylpyrrolidin-1-yl)propoxy]phenyl}-1,3-oxazolidin-2-one | 432 | | 1.11 (m, 9 H), 1.42 (m, 1 H), 1.73 (m, 3 H), 1.85 (m, 1 H), 1.96 (m, 3 H), 2.12 (d, 8.98 Hz, 1 H), 2.20 (m, 1 H), 2.30 (m, 1 H), 2.45 (dd, 12.82, 8.98 Hz, 1 H), 2.58 (m, 3 H), 2.97 (m, 1 H), 3.17 (td, 8.61, 2.52 Hz, 1 H), 3.58 (m, 2 H), 4.02 (m, 2 H), 4.32 (m, 1 H), 4.40 (m, 1 H), 4.51 (t, 8.24 Hz, 1 H), 6.92 (d, 8.98 Hz, 2 H), 7.30 (d, 8.98 Hz, 2 H) |
| 102 | 2,5S | mixture | (5S)-5-[(1,1-dioxidothiomorpholin-4-yl)methyl]-1-{4-[3-(2-methylpyrrolidin-1-yl)propoxy]phenyl}pyrrolidin-2-one | 450 | | 1.10 (d, 5.86 Hz, 3 H), 1.58 (s, 3 H), 1.74 (m, 2 H), 1.96 (m, 4 H), 2.33 (m, 2 H), 2.55 (m, 2 H), 2.65 (m, 2 H), 2.90 (m, 9 H), 3.18 (m, 1 H), 4.02 (m, 2 H), 4.22 (m, 1 H), 6.91 (d, 8.98 Hz, 2 H), 7.22 (d, 8.98 Hz, 2 H) |
| 103 | 4R,2 | mixture | (4R)-3-{4-[3-(2-methylpyrrolidin-1-yl)propoxy]phenyl}-4-(piperidin-1-ylmethyl)-1,3-oxazolidin-2-one | 402 | | 1.12 (d, 6.05 Hz, 3 H), 1.46 (m, 7 H), 1.76 (m, 2 H), 1.97 (m, 3 H), 2.29 (m, 8 H), 2.55 (m, 1 H), 2.99 (m, 1 H), 3.21 (m, 1 H), 4.02 (m, 2 H), 4.35 (m, 2 H), 4.51 (m, 1 H), 6.90 (d, 8.98 Hz, 2 H), 7.31 (d, 8.98 Hz, 2 H) |
| 104 | 4R,2 | mixture | (4R)-4-[(4,4-difluoropiperidin-1-yl)methyl]-3-{4-[3-(2-methylpyrrolidin-1-yl)propoxy]phenyl}-1,3-oxazolidin-2-one | 438 | | 1.09 (d, 6.05 Hz, 3 H), 1.42 (m, 1 H), 1.73 (m, 3 H), 1.94 (m, 7 H), 2.10 (m, 1 H), 2.19 (m, 1 H), 2.29 (m, 1 H), 2.56 (m, 6 H), 2.96 (m, 1 H), 3.17 (m, 1 H), 4.02 (m, 2 H), 4.30 (m, 1 H), 4.36 (m, 1 H), 4.52 (t, 8.15 Hz, 1 H), 6.92 (m, 2 H), 7.32 (d, 8.98 Hz, 2 H) |
| 105 | 4R,2 | mixture | (4R)-3-{4-[3-(2-methylpyrrolidin-1-yl)propoxy]phenyl}-4-phenyl-1,3-oxazolidin-2-one | 381 | | 1.05 (d, 6.05 Hz, 3 H), 1.40 (m, 1 H), 1.71 (m, 2 H), 1.90 (m, 3 H), 2.11 (m, 2 H), 2.26 (m, 1 H), 2.91 (m, 1 H), 3.13 (m, 1 H), 3.93 (m, 2 H), 4.21 (dd, 8.61, 6.41 Hz, 1 H), 4.76 (t, 8.70 Hz, 1 H), 5.30 (dd, 8.79, 6.32 Hz, 1 H), 6.78 (m, 2 H), 7.22 (m, 2 H), 7.35 (m, 5 H) |
| 106 | 4R,2 | mixture | (4R)-4-{[(3,4-difluorophenyl)amino]methyl}-3-{4-[3-(2-methylpyrrolidin-1-yl)propoxy]phenyl}-1,3-oxazolidin-2-one | 446 | | 1.10 (m, 3 H), 1.43 (m, 1 H), 1.75 (m, 2 H), 1.96 (m, 3 H), 2.17 (m, 2 H), 2.32 (m, 1 H), 2.98 (m, 1 H), 3.18 (m, 1 H), 3.28 (m, 2 H), 3.64 (t, 6.14 Hz, 1 H), 4.03 (m, 2 H), 4.31 (dd, 7.88, 4.31 Hz, 1 H), 4.55 (m, 2 H), 6.18 (m, 1 H), 6.29 (m, 1 H), 6.93 (m, 3 H), 7.28 (m, 3 H) |
| 107 | 5S,8aS, 4aR | pure | (5S)-5-[(4aR,8aS)-octahydroisoquinolin-2(1H)-ylmethyl]-1-{4-[3-(1-azaspiro[4.4]non-1-yl)propoxy]phenyl}pyrrolidin-2-one | 494 | | 0.86 (m, 4 H), 1.58 (m, 25 H), 2.29 (m, 2 H), 2.60 (m, 9 H), 4.02 (t, 6.14 Hz, 2 H), 4.21 (m, 1 H), 6.90 (m, 2 H), 7.28 (m, 2 H) |
| 108 | 5S,2 | mixture | (5S)-1-{4-[4-(2-methylpyrrolidin-1-yl)butoxy]phenyl}-5-(piperidin-1-ylmethyl)pyrrolidin-2-one | 414 | | 1.09 (d, 5.9 Hz, 3 H), 1.37 (dd, 2.8, 2.4 Hz, 2 H), 1.42 (m, 1 H), 1.49 (m, 3 H), 1.68 (m, 2 H), 1.80 (m, 2 H), 1.92 (m, 1 H), 2.07 (m, 2 H), 2.28 (m, 3 H), 2.35 (m, 3 H), 2.40 (d, 3.5 Hz, 1 H), 2.44 (m, 1 H), 2.50 (dd, 9.7, 5.0 Hz, 1 H), 2.64 (m, 1 H), 2.82 (m, 1 H), 3.16 (m, 1 H), 3.96 (m, 2 H), 4.21 (m, 1 H), 6.89 (d, 9.0 Hz, 2 H), 7.27 (m, 6 H) |
| 109 | 5S,2 | mixture | (5S)-3,3-dimethyl-1-{4-[3-(2-methylpyrrolidin-1-yl)propoxy]phenyl}-5-(piperidin-1-ylmethyl)pyrrolidin-2-one | 428 | | 1.10 (d, 5.5 Hz, 3 H), 1.20 (s, 3 H), 1.29 (s, 3 H), 1.37 (d, 5.8 Hz, 2 H), 1.50 (d, 5.0 Hz, 3 H), 1.70 (m, 1 H), 1.78 (dd, 5.3, 2.3 Hz, 1 H), 1.85 (dd, 13.1, 7.0 Hz, 2 H), 1.92 (m, 1 H), 1.99 (m, 2 H), 2.13 (m, 1 H), 2.21 (m, 3 H), 2.27 (m, 2 H), 2.32 (m, 2 H), 2.50 (m, 1 H), 2.97 (m, 1 H), 3.18 (m, 1 H), 4.02 (m, 2 H), 4.15 (m, 1 H), 6.90 (m, 2 H), 7.22 (m, 2 H) |
| 110 | 5S,2, cis-2,6 | mixture | (5S)-5-[(cis-2,6-dimethylmorpholin-4-yl)methyl]-3,3-dimethyl-1-{4-[3-(2-methylpyrrolidin-1-yl)propoxy]phenyl}pyrrolidin-2-one | 458 | | 1.10 (t, 6.1 Hz, 9 H), 1.21 (s, 3 H), 1.30 (s, 3 H), 1.42 (m, 1 H), 1.72 (m, 4 H), 1.84 (m, 2 H), 1.96 (m, 4 H), 2.12 (q, 9.0 Hz, 1 H), 2.20 (m, 3 H), 2.30 (m, 1 H), 2.54 (m, 3 H), 2.97 (m, 1 H), 3.18 (m, 1 H), 3.56 (m, 2 H), 4.01 (m, 2 H), 4.16 (m, 1 H), 6.90 (d, 8.8 Hz, 2 H), 7.20 (d, 8.8 Hz, 2 H) |
| 111 | 5S,2 | mixture | (5S)-5-[(4,4-difluoropiperidin-1-yl)methyl]-3,3-dimethyl-1-{4-[3-(2-methylpyrrolidin-1-yl)propoxy]phenyl}pyrrolidin-2-one | 464 | | 1.11 (d, 5.5 Hz, 3 H), 1.21 (s, 3 H), 1.30 (s, 3 H), 1.71 (m, 1 H), 1.82 (dd, 13.3, 7.0 Hz, 3 H), 1.90 (m, 4 H), 1.99 (m, 2 H), 2.14 (m, 1 H), 2.20 (dd, 12.8, 7.3 Hz, 2 H), 2.33 (dd, 13.1, 8.0 Hz, 2 H), 2.47 (m, 4 H), 2.60 (dd, 12.8, 4.0 Hz, 1 H), 2.97 (m, 1 H), 3.19 (m, 1 H), 4.01 (m, 2 H), 4.13 (m, 1 H), 6.90 (d, 9.0 Hz, 2 H), 7.20 (d, 8.8 Hz, 2 H) |
| 112 | 5S,2 | mixture | (5S)-5-[(dibenzylamino)methyl]-1-{4-[3-(2-methylpyrrolidin-1-yl)propoxy]phenyl}pyrrolidin-2-one | 512 | | 1.11 (d, 6.0 Hz, 3 H), 1.46 (m, 1 H), 1.74 (m, 2 H), 1.90 (m, 2 H), 2.00 (m, 2 H), 2.18 (m, 3 H), 2.32 (m, 3 H), 2.32 (m), 2.41 (dd, 12.8, 10.0 Hz, 1 H), 2.43 (m), 2.56 (dd, 2.8, 3.0 Hz, 1 H), 2.99 (m, 1 H), 3.20 (t, 8.0 Hz, 1 H), 3.40 (d, 13.3 Hz, 2 H), 3.65 (m, 2 H), 4.04 (m, 3 H), 6.86 (d, 8.8 Hz, 2 H), 7.13 (d, 8.8 Hz, 2 H), 7.29 (m, 10 H) |
| 113 | 5S,2 | mixture | (5S)-5-(aminomethyl)-1-{4-[3-(2-methylpyrrolidin-1-yl)propoxy]phenyl}pyrrolidin-2-one | 332 | | (DMSO): 1.16 (d, 6.1 Hz, 3 H), 1.44 (m, 1 H), 1.77 (m, 2 H), 2.03 (m, 3 H), 2.32 (m, 2 H), 2.77 (d, 4.8 Hz, 3 H), 3.15 (m, 3 H), 4.04 (t, 6.1 Hz, 2 H), 4.40 (m, 1 H), 6.97 (d, 8.6 Hz, 2 H), 7.37 (d, 8.8 Hz, 2 H) |

TABLE I-continued

| n° | Configuration | | IUPAC Name | MH+ (M+.) | alphaD | 1H NMR (CDCl3 unless otherwise specified) δH (ppm) |
|---|---|---|---|---|---|---|
| 114 | 2S,2 | mixture | N-[((2S)-1-{4-[3-(2-methylpyrrolidin-1-yl)propoxy]phenyl}-5-oxopyrrolidin-2-yl)methyl]acetamide | 374 | | 1.14 (d, 6.1 Hz, 3 H), 1.47 (m, 1 H), 1.73 (m, 1 H), 1.82 (m, 1 H), 1.88 (s, 3 H), 1.94 (m, 2 H), 2.03 (m, 2 H), 2.20 (m, 1 H), 2.29 (m, 2 H), 2.40 (m, 1 H), 2.56 (m, 2 H), 3.01 (m, 1 H), 3.23 (m, 2 H), 3.57 (ddd, 14.1, 7.0, 4.2 Hz, 1 H), 4.03 (m, 2 H), 4.31 (m, 1 H), 5.47 (m, 1 H), 6.93 (d, 9.0 Hz, 2 H), 7.28 (d, 8.8 Hz, 2 H) |
| 115* | 5 | mixture | 1-{4-[3-(4-methylpiperidin-1-yl)propoxy]phenyl}-5-(piperidin-1-ylmethyl)pyrrolidin-2-one bis(trifluoroacetate) | 414 | | 1.03 (d, 5.8 Hz, 3 H), 1.10 (d, 6.8 Hz, 1 H), 1.68 (m, 2 H), 1.84 (m, 3 H), 2.61 (m, 3 H), 3.02 (m, 1 H), 3.24 (m, 1 H), 3.59 (m, 1 H), 3.73 (m, 1 H), 4.09 (t, 5.5 Hz, 2 H), 4.65 (m, 1 H), 6.87 (m, 2 H), 7.21 (m, 2 H) |
| 116* | 5,3,5 | mixture | 1-{4-[3-(3,5-dimethylpiperidin-1-yl)propoxy]phenyl}-5-(piperidin-1-ylmethyl)pyrrolidin-2-one bis(trifluoroacetate) | 427 | | 0.81 (m), 1.01 (d, 6 H), 1.30 (m, 2 H), 1.84 (m, 2 H), 1.92 (m, 2 H), 2.16 (m, 4 H), 2.28 (m, 2 H), 2.57 (d, 4.5 Hz, 2 H), 2.61 (m, 2 H), 2.80 (d, 1.3 Hz, 5 H), 3.03 (m, 2 H), 3.24 (m, 2 H), 3.60 (m, 4 H), 4.10 (m, 2 H), 4.65 (m, 1 H), 6.87 (d, 9.0 Hz, 2 H), 7.20 (d, 9.0 Hz, 2 H) |
| 117* | 5,8a,4a | mixture | 1-[4-(3-octahydroquinolin-1(2H)-ylpropoxy)phenyl]-5-(piperidin-1-ylmethyl)pyrrolidin-2-one bis(trifluoroacetate) | 453 | | 0.83 (m, 1 H), 1.36 (m, 2 H), 1.51 (d, 14.3 Hz, 1 H), 1.67 (m, 1 H), 1.83 (m, 3 H), 1.97 (m, 2 H), 2.13 (s, 14 H), 2.60 (m, 4 H), 2.79 (m, 1 H), 3.02 (m, 2 H), 3.20 (ddd, 6.0, 3.0, 2.0, 1.0 Hz, 2 H), 3.37 (m, 1 H), 3.60 (m, 2 H), 4.08 (m, 2 H), 4.66 (m, 1 H), 6.88 (d, 8.8 Hz, 2 H), 7.21 (d, 8.5 Hz, 2 H) |
| 118* | 5,3,5 | mixture | 1-{4-[3-(3,5-dimethylpiperidin-1-yl)propoxy]-3-fluorophenyl}-5-(piperidin-1-ylmethyl)pyrrolidin-2-one bis(trifluoroacetate) | 445 | | 0.80 (m, 2 H), 1.00 (m, 6 H), 1.37 (m, 1 H), 1.85 (d, 0.8 Hz, 2 H), 1.93 (m, 2 H), 2.17 (s, 2 H), 2.30 (m, 2 H), 2.69 (s, 9 H), 3.05 (m, 2 H), 3.31 (m, 2 H), 3.62 (m, 4 H), 4.20 (m, 2 H), 4.66 (m, 1 H), 6.92 (m, 1 H), 6.98 (m, 1 H), 7.18 (dd, 12.0, 2.3 Hz, 1 H) (some signals obscured by solvent) |
| 119* | 5 | mixture | 1-{4-[3-(2-azaspiro[5.5]undec-2-yl)propoxy]-3-fluorophenyl}-5-(piperidin-1-ylmethyl)pyrrolidin-2-one bis(trifluoroacetate) | 485 | | 0.83 (m, 1 H), 1.15 (m, 1 H), 1.32 (d, 3.5 Hz, 2 H), 1.39 (m, 2 H), 1.49 (s, 3 H), 1.84 (m, 3 H), 2.28 (m, 2 H), 2.38 (m, 1 H), 2.58 (dd, 15.1, 4.3 Hz, 2 H), 3.06 (m, 2 H), 3.31 (m, 2 H), 3.47 (m, 1 H), 3.63 (m, 2 H), 3.81 (m, 1 H), 4.16 (m, 2 H), 4.68 (m, 1 H), 6.97 (m, 2 H), 7.21 (dd, 11.8, 4.0 Hz, 1 H) (some signals obscured by solvent) |
| 120* | 5,3,5 | mixture | 1-{4-[3-(3,5-dimethylpiperidin-1-yl)propoxy]-2-fluorophenyl}-5-(piperidin-1-ylmethyl)pyrrolidin-2-one bis(trifluoroacetate) | 445 | | 1.00 (d, 5.0 Hz, 6 H), 1.88 (dd, 4 H), 2.17 (m, 3 H), 2.29 (m, 2 H), 2.63 (m, 11 H), 3.05 (m, 2 H), 3.25 (m, 2 H), 3.58 (m, 4 H), 4.09 (t, 5.5 Hz, 2 H), 4.50 (m, 1 H), 6.66 (m, 2 H), 7.15 (t, 9.3 Hz, 1 H) (some signals obscured by solvent) |
| 121* | 5 | mixture | 1-{3,5-difluoro-4-[3-(4-methylpiperidin-1-yl)propoxy]phenyl}-5-(piperidin-1-ylmethyl)pyrrolidin-2-one bis(trifluoroacetate) | 449 | | 1.03 (d, 5.5 Hz, 3 H), 1.67 (d, 1.8 Hz, 1 H), 1.88 (dd, 4 H), 2.21 (d, 5.0 Hz, 2 H), 2.40 (s, 15 H), 2.68 (d, 8.5 Hz, 2 H), 3.09 (m, 1 H), 3.29 (dd, 7.3, 4.8 Hz, 2 H), 3.62 (m, 1 H), 3.73 (d, 12.0 Hz, 2 H), 4.27 (m, 2 H), 4.74 (m, 1 H), 7.07 (m, 2 H) (some signals obscured by solvent) |
| 122* | 5 | mixture | 1-{4-[3-(2-azaspiro[5.5]undec-2-yl)propoxy]-3,5-difluorophenyl}-5-(piperidin-1-ylmethyl)pyrrolidin-2-one bis(trifluoroacetate) | 503 | | 1.32 (m, 2 H), 1.41 (dd, 1.8, 0.5 Hz, 2 H), 1.49 (d, 0.8 Hz, 4 H), 1.68 (dd, 2.8, 1.5 Hz, 1 H), 1.89 (s, 2 H), 2.22 (m, 3 H), 2.40 (m, 1 H), 3.09 (m, 2 H), 3.31 (m, 2 H), 3.44 (s, 1 H), 3.63 (m, 1 H), 3.71 (dd, 4.3, 2.0 Hz, 1 H), 3.79 (m, 1 H), 4.22 (t, 5.8 Hz, 2 H), 4.74 (m, 1 H), 7.05 (s, 1 H), 7.08 (s, 1 H) (some signals obscured by solvent) |
| 123* | 5,3,5 | mixture | 1-{4-[3-(3,5-dimethylpiperidin-1-yl)propoxy]-3-methylphenyl}-5-(piperidin-1-ylmethyl)pyrrolidin-2-one bis(trifluoroacetate) | 441 | | 0.99 (d, 5.3 Hz, 6 H), 1.84 (m, 2 H), 1.92 (m, 2 H), 2.17 (s, 4 H), 2.30 (m, 3 H), 2.61 (d, 3.3 Hz, 1 H), 3.03 (m, 2 H), 3.25 (m, 2 H), 3.60 (m, 3 H), 4.09 (m, 2 H), 4.61 (m, 1 H), 6.77 (d, 8.5 Hz, 1 H), 7.01 (m, 1 H), 7.08 (d, 1.8 Hz, 1 H) (some signals obscured by solvent) |
| 124* | 5 | mixture | 1-{4-[3-(4-benzylpiperidin-1-yl)propoxy]phenyl}-5-(piperidin-1-ylmethyl)pyrrolidin-2-one bis(trifluoroacetate) | 489 | | 1.89 (m, 4 H), 2.07 (s, 1 H), 2.25 (m, 2 H), 3.04 (m, 1 H), 3.24 (m, 1 H), 3.68 (m, 3 H), 4.08 (t, 5.5 Hz, 2 H), 4.64 (m, 1 H), 6.86 (d, 8.8 Hz, 2 H), 7.13 (d, 7.0 Hz, 2 H), 7.20 (d, 8.8 Hz, 2 H), 7.30 (m, 3 H) (some signals obscured by solvent) |
| 125* | 5,3 | mixture | 1-{3-fluoro-4-[3-(3-phenylpiperidin-1-yl)propoxy]phenyl}-5-(piperidin-1-ylmethyl)pyrrolidin-2-one bis(trifluoroacetate) | 493 | | 1.37 (m, 1 H), 1.85 (s, 1 H), 2.04 (d, 3.8 Hz, 14 H), 2.31 (s, 1 H), 2.62 (m, 6 H), 3.02 (m, 2 H), 3.32 (m, 2 H), 3.61 (m, 2 H), 3.84 (m, 2 H), 4.20 (m, 2 H), 4.68 (m, 1 H), 6.95 (m, 2 H), 7.25 (m, 4 H), 7.36 (m, 2 H) |
| 126* | 5 | mixture | 1-{4-[3-(1-azaspiro[4.4]non-1-yl)propoxy]phenyl}-5-(piperidin-1-ylmethyl)pyrrolidin-2-one bis(trifluoroacetate) | 439 | | 1.59 (m, 1 H), 1.84 (m, 4 H), 1.95 (m, 2 H), 2.94 (m, 2 H), 3.03 (s, 1 H), 3.38 (m, 1 H), 3.60 (m, 2 H), 4.00 (m, 1 H), 4.10 (m, 2 H), 4.68 (m, 1 H), 6.90 (m, 2 H), 7.22 (m, 8.0 Hz, 2 H) |
| 127* | 5,2 | mixture | 1-{3-fluoro-4-[3-(2-methylpyrrolidin-1-yl)propoxy]phenyl}-5-(piperidin-1-ylmethyl)pyrrolidin-2-one bis(trifluoroacetate) | 417 | | 1.31 (d, 7.0 Hz, 1 H), 1.55 (d, 6.5 Hz, 3 H), 1.80 (s, 9 H), 2.24 (m, 2 H), 2.39 (m, 2 H), 2.63 (m, 6 H), 2.98 (m, 4 H), 3.23 (m, 1 H), 3.61 (m, 3 H), 4.05 (m, 1 H), 4.19 (m, 2 H), 4.70 (m, 1 H), 6.98 (m, 2 H), 7.23 (s, 1 H) |

TABLE I-continued

| n° | Configuration | | IUPAC Name | MH+ (M+.) | alphaD | 1H NMR (CDCl3 unless otherwise specified) δH (ppm) |
|---|---|---|---|---|---|---|
| 128* | 5 | mixture | 1-{4-[3-(1-azaspiro[4.4]non-1-yl)propoxy]-3-fluorophenyl}-5-(piperidin-1-ylmethyl)pyrrolidin-2-one bis(trifluoroacetate) | 457 | | |
| 129* | 5,2 | mixture | 1-{3,5-difluoro-4-[3-(2-methylpyrrolidin-1-yl)propoxy]phenyl}-5-(piperidin-1-ylmethyl)pyrrolidin-2-one bis(trifluoroacetate) | 435 | | 1.56 (dd, 6.3, 3.0 Hz, 3 H), 2.23 (m, 5 H), 2.71 (m, 3 H), 2.92 (d, 0.8 Hz, 1 H), 3.04 (m, 2 H), 3.10 (m, 1 H), 3.24 (m, 1 H), 3.66 (m, 3 H), 4.00 (d, 1.5 Hz, 1 H), 4.27 (m, 2 H), 4.76 (m, 1 H), 7.08 (m, 2 H) |
| 130* | 5,2 | mixture | 1-{3-methyl-4-[3-(2-methylpyrrolidin-1-yl)propoxy]phenyl}-5-(piperidin-1-ylmethyl)pyrrolidin-2-one bis(trifluoroacetate) | 413 | | 1.55 (dd, 6.5, 1.0 Hz, 3 H), 1.84 (m, 2 H), 2.19 (s, 3 H), 2.26 (m, 2 H), 3.60 (m, 2 H), 4.10 (m, 2 H), 4.63 (dd, 4.0, 3.3 Hz, 1 H), 6.80 (d, 8.5 Hz, 1 H), 7.01 (m, 1 H), 7.10 (m, 1 H) |
| 131* | 5 | mixture | 1-{4-[3-(1-azaspiro[4.4]non-1-yl)propoxy]-3-methylphenyl}-5-(piperidin-1-ylmethyl)pyrrolidin-2-one bis(trifluoroacetate) | 453 | | 1.55 (d, 6.5 Hz, 2 H), 2.05 (s, 1 H), 2.26 (d, 4.8 Hz, 4 H), 2.59 (s, 3 H), 3.03 (s, 1 H), 3.61 (dd, 2.8, 2.8, 1.3, 0.5 Hz, 3 H), 4.20 (d, 4.0 Hz, 2 H), 4.63 (m, 1 H), 6.98 (m, 2 H), 7.26 (s, 1 H) |
| 132* | 5,2 | mixture | 1-(4-{3-[2-(hydroxymethyl)pyrrolidin-1-yl]propoxy}-3-methylphenyl)-5-(piperidin-1-ylmethyl)pyrrolidin-2-one bis(trifluoroacetate) | 429 | | 1.73 (s, 28 H), 2.05 (s, 1 H), 2.19 (s, 3 H), 3.87 (d, 8.5 Hz, 2 H), 4.10 (s, 1 H), 6.79 (d, 8.5 Hz, 1 H), 7.00 (s, 1 H) (some signals obscured by solvent) |
| 133* | 5 | mixture | 1-[4-(3-azepan-1-ylpropoxy)phenyl]-5-(piperidin-1-ylmethyl)pyrrolidin-2-one bis(trifluoroacetate) | 413 | | 1.68 (m, 2 H), 1.83 (dd, 8.3, 2.3 Hz, 4 H), 1.91 (s, 2 H), 2.27 (m, 3 H), 2.39 (s, 12 H), 2.61 (m, 2 H), 3.02 (m, 2 H), 3.32 (m, 2 H), 3.64 (m, 2 H), 4.09 (m, 2 H), 4.65 (m, 1 H), 6.88 (d, 9.0 Hz, 2 H), 7.20 (m, 2 H) |
| 134* | 5 | mixture | 1-[4-(3-azepan-1-ylpropoxy)-3-fluorophenyl]-5-(piperidin-1-ylmethyl)pyrrolidin-2-one bis(trifluoroacetate) | 431 | | 1.69 (m, 2 H), 1.85 (d, 0.8 Hz, 3 H), 1.91 (m, 2 H), 2.29 (s, 2 H), 2.61 (m, 14 H), 3.04 (m, 3 H), 3.36 (d, 6.3 Hz, 2 H), 3.61 (m, 2 H), 3.69 (dd, 5.0, 2.8 Hz, 2 H), 4.19 (m, 2 H), 4.67 (m, 1 H), 6.96 (m, 2 H), 7.19 (dd, 11.8, 2.3 Hz, 1 H) |
| 135* | 5 | mixture | 1-[4-(3-azocan-1-ylpropoxy)-3-fluorophenyl]-5-(piperidin-1-ylmethyl)pyrrolidin-2-one bis(trifluoroacetate) | 445 | | 1.58 (s, 2 H), 1.85 (dd, 3.3, 0.5 Hz, 4 H), 1.96 (s, 3 H), 2.28 (s, 2 H), 2.58 (m, 2 H), 2.75 (d, 0.8 Hz, 13 H), 3.05 (m, 2 H), 3.15 (m, 2 H), 3.36 (q, 6.8 Hz, 2 H), 3.64 (m, 2 H), 4.20 (m, 2 H), 4.66 (m, 1 H), 6.96 (m, 2 H), 7.18 (dd, 12.0, 2.3 Hz, 1 H) |
| 136* | 5 | mixture | 1-[4-(3-azepan-1-ylpropoxy)-2-methoxyphenyl]-5-(piperidin-1-ylmethyl)pyrrolidin-2-one bis(trifluoroacetate) | 443 | | 1.68 (m, 2 H), 1.82 (m, 2 H), 1.94 (s, 11 H), 2.27 (m, 2 H), 2.42 (m, 1 H), 2.60 (m, 4 H), 3.00 (m, 4 H), 3.30 (m, 2 H), 3.50 (m, 1 H), 3.59 (m, 1 H), 3.66 (m, 2 H), 3.80 (s, 3 H), 4.09 (t, 5.8 Hz, 2 H), 4.51 (m, 1 H), 6.47 (m, 2 H), 7.01 (m, 1 H) |
| 137* | 5,3,5 | mixture | 5-[(4,4-difluoropiperidin-1-yl)methyl]-1-{4-[3-(3,5-dimethylpiperidin-1-yl)propoxy]phenyl}pyrrolidin-2-one bis(trifluoroacetate) | 463 | | 0.99 (d, 4.3 Hz, 6 H), 3.07 (m, 3 H), 3.30 (m, 3 H), 3.60 (m, 3 H), 4.10 (s, 2 H), 4.58 (m, 1 H), 6.86 (d, 8.8 Hz, 2 H), 7.18 (d, 8.8 Hz, 2 H) (some signals obscured by solvent) |
| 138* | 5,3,5 | mixture | 5-[(4,4-difluoropiperidin-1-yl)methyl]-1-{4-[3-(3,5-dimethylpiperidin-1-yl)propoxy]-3-methylphenyl}pyrrolidin-2-one bis(trifluoroacetate) | 477 | | 0.99 (d, 5.5 Hz, 6 H), 1.92 (m, 1 H), 2.07 (s, 3 H), 2.17 (s, 5 H), 2.61 (d, 1.5 Hz, 3 H), 3.07 (m, 3 H), 3.25 (m, 3 H), 3.59 (m, 2 H), 4.10 (m, 2 H), 4.55 (m, 1 H), 6.77 (d, 8.5 Hz, 1 H), 6.99 (m, 1 H), 7.06 (d, 2.3 Hz, 1 H) (some signals obscured by solvent) |
| 139* | 5,2 | mixture | 5-[(4,4-difluoropiperidin-1-yl)methyl]-1-{3-methyl-4-[3-(2-methylpyrrolidin-1-yl)propoxy]phenyl}pyrrolidin-2-one bis(trifluoroacetate) | 449 | | 1.55 (d, 6.3 Hz, 3 H), 2.05 (s, 3 H), 2.19 (m, 2 H), 2.60 (m, 2 H), 3.03 (m, 1 H), 3.24 (m, 2 H), 3.59 (m, 2 H), 4.10 (m, 2 H), 4.56 (m, 1 H), 6.79 (m, 1 H), 7.01 (m, 1 H), 7.08 (m, 1 H) (some signals obscured by solvent) |
| 140 | 5S,2 | mixture | (5S)-1-{6-[3-(2-methylpyrrolidin-1-yl)propoxy]pyridin-3-yl}-5-(piperidin-1-ylmethyl)pyrrolidin-2-one | 401 | | 1.09 (d, 5.9 Hz, 3 H), 1.36 (d, 4.6 Hz, 2 H), 1.45 (m, 5 H), 1.73 (m, 2 H), 2.04 (m, 7 H), 2.30 (m, 6 H), 2.47 (m, 2 H), 2.65 (m, 1 H), 2.96 (m, 1 H), 3.18 (m, 1 H), 4.22 (m, 1 H), 4.33 (t, 6.2 Hz, 2 H), 6.74 (d, 8.8 Hz, 1 H), 7.72 (m, 1 H), 8.10 (d, 1.8 Hz, 1 H) |

*configuration not determined, but prepared from (5S)-5-(piperidin-1-ylmethyl)pyrrolidin-2-one or (5S)-5-(4,4-difluoropiperidin-1-ylmethyl)-pyrrolidin-2-one.

EXAMPLE 10

Affinity for the human histamine H3-receptor

Material and Methods

Reagents

Reagents and reference compounds were of analytical grade and obtained from various commercial sources. [3H]-N-α-methylhistamine (80-85 Ci/mmol) and [35S]-GTPγS (1250 Ci/mmol) were purchased from Perkin Elmer (Belgium). Cell culture reagents were purchased from Cambrex (Belgium).

Test and reference compounds were dissolved in 100% DMSO to give a 1 mM stock solution. Final DMSO concentration in the assay did not exceed 1%.

A CHO cell line expressing the human histamine H3 receptor was purchased from Euroscreen S.A. (Belgium).

Cell Culture

Cells were grown in HAM-F12 culture media containing 10% fetal bovine serum, 100 IU/ml penicillin, 100 μg/ml streptomycin, 1% sodium pyruvate and 400 μg/ml of gentamycin. Cells were maintained at 37° C. in a humidified atmosphere composed of 95% air and 5% $CO_2$.

Membrane Preparation

Confluent cells were detached by 10 min incubation at 37° C. in PBS/EDTA 0.02%. The cell suspension was centrifuged at 1,500×g for 10 min at 4° C. The pellet was homogenized in a 15 mM Tris-HCl buffer (pH 7.5) containing 2 mM $MgCl_2$, 0.3 mM EDTA, 1 mM EGTA (buffer A). The crude homogenate was frozen in liquid nitrogen and thawed. DNAse (1 µl/ml) was then added and the homogenate was further incubated for 10 min at 25° C. before being centrifuged at 40,000×g for 25 min at 4° C. The pellet was resuspended in buffer A and washed once more under the same conditions. The final membrane pellet was resuspended, at a protein concentration of 1-3 mg/ml, in a 7.5 mM Tris-HCl buffer (pH 7.5) enriched with 12.5 mM $MgCl_2$, 0.3 mM EDTA, 1 mM EGTA and 250 mM sucrose and stored in liquid nitrogen until used.

Binding Assays

[$^3$H]—N-α-methylhistamine binding assay

Affinity of compounds for human histamine $H_3$ receptors was measured by competition with [$^3$H]—N-α-methylhistamine. This binding assay was performed essentially as described by Lovenberg et al. in Mol. Pharmacol. 1999, 55, 1101-1107 and Tedford et al. in J. Pharmacol. Exper. Ther. 1999, 289, 1160-1168, with minor modifications. Briefly, membranes (20-40 µg proteins) expressing human histamine $H_3$ receptors were incubated at 25° C. in 0.5 ml of a 50 mM Tris-HCl buffer (pH 7.4) containing 2 mM $MgCl_2$, 0.2 nM [$^3$H]-N-α-methylhistamine and increasing concentrations of drugs. The non specific binding (NSB) was defined as the residual binding observed in the presence of 10 µM thioperamide or histamine. Membrane-bound and free radioligand were separated by rapid filtration through glass fiber filters presoaked in 0.1% PEI. Samples and filters were rinsed by at least 6 ml of ice-cold 50 mM Tris-HCl buffer (pH 7.4). The entire filtration procedure did not exceed 10 seconds per sample. Radioactivity trapped onto the filters was counted by liquid scintillation in a β-counter.

[$^{35}$S]-GTPγS binding assay

Stimulation (agonist) or inhibition (inverse agonist) of [$^{35}$S]-GTPγS binding to membrane expressing human histamine $H_3$ receptors was measured as described by Lorenzen et al. in Mol. Pharmacol. 1993, 44, 115-123 with a few modifications. Briefly, membranes (10-20 µg proteins) expressing human $H_3$ histamine receptors were incubated at 25° C. in 0.2 ml of a 50 mM Tris-HCl buffer (pH 7.4) containing 3 mM $MgCl_2$, 50 mM NaCl, 1 µM GDP, 2 µg saponin and increasing concentrations of drugs. After 15 min preincubation, 0.2 nM of [$^{35}$S]-GTPγS were added to the samples. The non specific binding (NSB) was defined as the residual binding observed in the presence of 100 µM Gpp(NH)p. Membrane-bound and free radioligand were separated by rapid filtration through glass fiber filters. Samples and filters were rinsed by at least 6 ml of ice-cold 50 mM Tris-HCl buffer (pH 7.4). The entire filtration procedure did not exceed 10 seconds per sample. Radioactivity trapped onto the filters was counted by liquid scintillation in a β-counter.

Data analysis: Determination of $pIC_{50}/pKi/pEC_{50}/pEC_{50}INV$

Analysis

Raw data are analyzed by non-linear regression using XLfit™ (IDBS, United Kingdom) according to the following generic equation $$B=MIN+[(MAX-MIN)/(1+(((10^x)/(10^{-pX50}))^{nH}))]$$

where:

B is the radioligand bound in the presence of the unlabelled compound (dpm),

MIN is the minimal binding observed (dpm)

MAX is maximal binding observed (dpm),

X is the concentration of unlabelled compound (log M), $pX_{50}$ (−log M) is the concentration of unlabelled compound causing 50% of its maximal effect (inhibition or stimulation of radioligand binding). It stands for $pIC_{50}$ when determining the affinity of a compound for the receptor in binding studies with [$^3$H]-N-α-methylhistamine, for $pEC_{50}$ for compounds stimulating the binding of [$^{35}$S]-GTPγS (agonists) and for $pEC_{50}INV$ for compounds inhibiting the binding of [$^{35}$S]-GTPγS (inverse agonists).

$n_H$ is the Hill coefficient.

pKi is obtained by applying the following equation (Cheng and Prusoff, 1973, Biochem. Pharmacol., 22: 3099-3108):

$$pKi=pIC_{50}+\log(1+L/Kd)$$

where:

pKi is the unlabelled compound equilibrium dissociation constant (−log M),

L is the radioligand concentration (nM),

Kd is the radioligand equilibrium dissociation constant (nM).

Compounds of formula (D) according to the invention showed $pIC_{50}$ values greater than or equal to 6.5 for the histamine $H_3$ receptor.

Compounds of formula (I) according to the invention showed $pEC_{50}INV$ values typically greater than or equal to 7 for the histamine $H_3$ receptor.

EXAMPLE 11

Antagonism Activity: Paced Isolated Guinea Pig Myenteric Plexus-Electric-Field Stimulation Assay Material and Methods Reagents Compounds were synthesized in the Chemistry Department at UCB Pharma (Braine l'Alleud, Belgium). These substances were analytically controlled for purity and composition. Stock solutions ($10^{-2}$ M) and further dilutions were freshly prepared in DMSO (WNR, Leuven, Belgium). All other reagents (R(−)-α-methylhistamine, mepyramine, ranitidine, propranolol, yohimbine and components of the Krebs' solution) were of analytical grade and obtained from conventional commercial sources.

Animals

Four week-old male Dunkin-Hartley guinea pigs (200-300 g) were supplied by Charles River (Sultfeld, Germany). All animals were ordered and used under protocol "orgisol-GP" approved by the UCB Pharma ethical committee. Animals were housed in the UCB animal facility in groups of 12, in stainless steel cages (75×50×30 cm) and allowed to acclimatise for a minimum of one week before inclusion in the study. Room temperature was maintained between 20 and 24° C. with 40 to 70% relative humidity. A light and dark cycle of 12 h was applied. Animals had free access to food and water.

Organ Preparation

The method was adapted from that described by Menkveld et al. in Eur. J. Pharmacol. 1990, 186, 343-347. Longitudinal myenteric plexus was prepared from the isolated guinea pig ileum. Tissues were mounted in 20-ml organ baths containing modified Krebs' solution with $10^{-7}$ M mepyramine, $10^{-5}$ M ranitidine, $10^{-5}$ M propranolol and $10^{-6}$ M yohimbine. The bathing solution was maintained at 37° C. and gassed with 95% $O_2$-5% $CO_2$. Tissues were allowed to equilibrate for a 60-min period under a resting tension of 0.5 g and an electrical field stimulation (pulses of 5-20 V, 1 ms and 0.1 Hz was applied during the whole experiment). Such a stimulation induces stable and reproductive twitch contractions. Isometric contractions were measured by force-displacement transducers coupled to an amplifier connected to a computer system (EMKA Technologies) capable of controlling (i) automatic data acquisition, (ii) bath washout by automatic fluid circulation through electrovalves at predetermined times or signal stability and (iii) automatic dilution/injection of drug in the bath at predetermined times or signal stability.

Protocol

After a 60 min-stabilisation period, tissues were stimulated twice with $10^{-6}$ M R(-)-α-methylhistamine at 30-min interval. After a 60-min incubation period in the presence of solvent or antagonist test compound, a cumulative concentration-response to R(-)-α-methylhistamine was elicited ($10^{-10}$ à $10^{-4}$ M). Only one concentration of antagonist was tested on each tissue.

Data Analysis

An appropriate estimate of interactions between agonist and antagonist can be made by studying the family of curves observed in the absence or presence of increasing antagonist concentrations. The value of each relevant parameter of each concentration-response curve ($pD_2$ and $E_{max}$) was calculated by an iterative computer software (XLfit, IDBS, Guildford, UK) fitting the experimental data to the four parameter logistic equation. Antagonistic activity of the test substance was estimated by the calculation of $pD'_2$ and/or $pA_2$ values according to the methods described by Van Rossum et al. in Arch. Int. Pharmacodyn. Ther. 1963, 143, 299 and/or by Arunlakshana & Schild in Br. J. Pharmacol. 1959, 14, 48.

Results are expressed as the mean±SD. The number of observations is indicated as n.

Compounds of formula (I) according to the invention showed $pA_2$ values greater than or equal to 6.5 for the histamine $H_3$ receptor.

The invention claimed is:

1. A compound of formula (Ia)

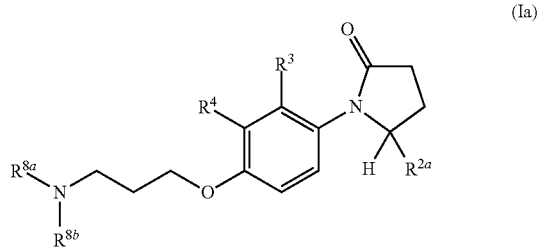

(Ia)

wherein $R^{2a}$ is hydrogen, aryl, $C_{1-6}$ alkoxy, amino, $C_{1-6}$ alkyl, $C_{2-6}$ alkenyl, heteroaryl, $C_{3-8}$ cycloalkyl, 3-8-membered heterocycloalkyl, acyl, $C_{1-6}$-alkyl aryl, $C_{1-6}$-alkyl heteroaryl, $C_{1-6}$-alkyl cycloalkyl, $C_{1-6}$-alkyl heterocycloalkyl, carboxy, alkoxycarbonyl, aminocarbonyl, $C_{1-6}$-alkyl carboxy, $C_{1-6}$-alkyl acyl, $C_{1-6}$-alkyl alkoxy, $C_{1-6}$-alkyl alkoxycarbonyl, $C_{1-6}$-alkyl aminocarbonyl, $C_{1-6}$-alkyl acylamino, acylamino, $C_{1-6}$-alkyl ureido, $C_{1-6}$-alkyl carbamate, $C_{1-6}$-alkyl amino, $C_{3-8}$-cycloalkyl amino, hydroxy, $C_{1-6}$ alkyl hydroxy, halogen or cyano;

$R^3$ is hydrogen, halogen, $C_{1-4}$ alkyl or $C_{1-4}$ alkoxy;

$R^4$ is hydrogen, halogen, $C_{1-4}$ alkyl or $C_{1-4}$ alkoxy; and $R^{8a}$ and $R^{8b}$ are linked together to form with N a 3 to 8 membered heterocycloalkyl.

2. A compound of formula (Ia) according to claim 1 wherein $R^{2a}$ is hydrogen; $C_{1-6}$ alkyl; aryl; $C_{1-6}$-alkyl alkoxy; $C_{1-6}$-alkyl hydroxy; $C_{1-6}$-alkyl aryl or —$(CH_2)_r$—$NR^{6a}R^{6b}$;

$R^3$ is hydrogen, halogen or $C_{1-4}$ alkoxy;

$R^4$ is hydrogen, $C_{1-4}$ alkyl, $C_{1-4}$alkoxy or halogen;

$R^{6a}$ is hydrogen, C1-6 alkyl, $C_{1-6}$-alkyl cycloalkyl, $C_{3-8}$ cycloalkyl, acyl, aryl or $C_{1-6}$-alkyl aryl;

$R^{6b}$ is hydrogen, $C_{1-4}$ alkyl, $C_{1-6}$-alkyl cycloalkyl or $C_{1-6}$-alkyl aryl;

or $R^{6a}$ and $R^{6b}$ are linked together to form a $C_{3-6}$ alkylene, each methylene of the alkylene being optionally substituted by one or two halogen, or by one or two $C_{1-4}$ alkyl, optionally linked together to form with the carbon to which they are attached a $C_{3-8}$ cycloalkyl; or one methylene thereof being linked to a second methylene thereof to form a $C_{3-6}$ alkylene; or one methylene being optionally replaced by sulfur dioxide, an oxygen, a sulfur or a nitrogen atom, said nitrogen atom being optionally substituted by a $C_{1-8}$ alkyl or $C_{3-8}$ cycloalkyl;

$R^{8a}$ and $R^{8b}$ are linked together to form a $C_{3-6}$ alkylene, each methylene of the alkylene being optionally substituted by one or two $C_{1-4}$ alkyl optionally linked together to form with the carbon to which they are attached a $C_{3-8}$ cycloalkyl, by $C_{1-6}$-alkyl hydroxy, $C_{1-6}$-alkyl heterocycloalkyl, by aryl or by $C_{1-6}$-alkyl aryl; or one methylene thereof being linked to a second methylene thereof to form a $C_{3-6}$ alkylene; or one methylene of the alkylene being optionally replaced by a nitrogen, said nitrogen being substituted by a $C_{1-4}$ alkyl or $C_{3-8}$ cycloalkyl; and r is an integer equal to 1 or 2.

3. A compound of formula (Ia) according to claim 1 wherein $R^3$ is hydrogen.

4. A compound of formula (Ia) according to claim 1 wherein $R^4$ is hydrogen or fluorine.

5. A compound of formula (Ia) according to claim 1 wherein $R^{2a}$ is hydrogen, n-propyl, isopropyl, hydroxymethyl, 2-hydroxyethyl, phenyl, benzyl, 4-chlorophenyl, (4-fluorophenoxy)methyl, (3,4-difluorophenoxy)methyl, 4-chlorobenzyl or cyclohexylmethyl.

6. A compound of formula (Ia) according to claim 1 wherein $R^{2a}$ is —$(CH_2)_r$—$NR^{6a}R^{6b}$, wherein r is an integer equal to 1 or 2, $R^{6a}$ is hydrogen, C1-6 alkyl, $C_{1-6}$-alkyl cycloalkyl, $C_{3-8}$ cycloalkyl, acyl, aryl or $C_{1-6}$-alkyl aryl;

$R^{6b}$ is hydrogen, $C_{1-4}$ alkyl, $C_{1-6}$-alkyl cycloalkyl or $C_{1-6}$-alkyl aryl; or $R^{6a}$ and $R^{6b}$ are linked together to form a $C_{3-6}$ alkylene, each methylene of the alkylene being optionally substituted by one or two halogen, or by one or two $C_{1-4}$ alkyl, optionally linked together to form with the carbon to which they are attached a $C_{3-8}$ cycloalkyl; or one methylene thereof being linked to a second methylene thereof to form a $C_{3-6}$ alkylene; or one methylene being optionally replaced by sulfur dioxide, an oxygen, a sulfur or a nitrogen atom, said nitrogen atom being optionally substituted by a $C_{1-8}$ alkyl or $C_{3-8}$ cycloalkyl.

7. A compound of formula (Ia) according to claim 6 wherein r is equal to 1.

8. A compound of formula (Ia) according to claim 7 wherein $R^{6a}$ is hydrogen, ethyl, cyclobutyl, cyclopentyl, cyclohexyl, cyclopropylmethyl, cyclohexylmethyl, 4-fluorobenzyl, phenyl, 4-fluorophenyl, cyclopropylcarbonyl, 2-fluorophenyl, 3-fluorophenyl, 2,4-difluorophenyl, 3-methoxyphenyl, 4-(trifluoromethyl)phenyl, 4-methylphenyl, 3,4-difluorophenyl, 3,5-difluorophenyl, 2,2,2-trifluoroethyl, 1,3-benzodioxol-5-yl, benzyl or acetyl.

9. A compound of formula (Ia) according to claim 6 wherein $R^{6b}$ is hydrogen, methyl, ethyl, n-propyl, cyclopropylmethyl, cyclohexylmethyl or benzyl.

10. A compound of formula (Ia) according to claim 6 wherein $R^{6a}$ and $R^{6b}$ are linked together to form with N a 3-8 membered heterocycloalkyl selected from the group consisting of azepan-1-yl, morpholine-4-yl, 4-(cyclohexylmethyl)piperazin-1-yl, 4-(cyclopentyl)piperazin-1-yl, 4-(isopropyl)piperazin-1-yl, piperidin-1-yl, 2,6-dimethylpiperidin-1-yl, 2-methylpiperidin-1-yl, 4-methylpiperidin-1-yl, pyrrolidin-1-yl, 2-methylpyrrolidin-1-yl, (4aR,8aS)-octahydroisoquinolin-2(1H)-yl, 2,6-dimethylmorpholin-4-yl, cis-2,6-dimethylmorpholine-4-yl, thiomorpholin-4-yl, 4,4-difluoropiperidin-1-yl and 1,1-dioxidothiomorpholin-4-yl.

11. A compound of formula (Ia) according to claim 6 wherein $R^{2a}$ is [(cyclohexylmethyl)amino]methyl, [(cyclohexylmethyl)(cyclopropylmethyl)amino]methyl, [(cyclopropylmethyl)(propyl)amino]methyl, (cyclobutylamino)methyl, (cyclopentylamino)methyl, (cyclohexylamino)methyl, (diethylamino)methyl, anilinomethyl, [(4-fluorobenzyl)amino]methyl, [(4-fluorophenyl)amino]methyl, azepan-1-ylmethyl, morpholin-4-ylmethyl, [4-(cyclohexylmethyl)piperazin-1-yl]methyl, (4-cyclopentylpiperazin-1-yl)methyl, 2-(4-cyclopentylpiperazin-1-yl)ethyl, (4-isopropylpiperazin-1-yl)methyl, 2-piperidin-1-ylethyl, piperidin-1-ylmethyl, (2,6-dimethylpiperidin-1-yl)methyl, (2-methylpiperidin-1-yl)methyl, (4-methylpiperidin-1-yl)methyl, pyrrolidin-1-ylmethyl, 2-methylpyrrolidin-1-yl)methyl, (4aR,8aS)-octahydroisoquinolin-2(1H)-ylmethyl, [(cyclohexylmethyl)(cyclopropylcarbonyl)amino]methyl, [(2-fluorophenyl)amino]methyl, [(3-fluorophenyl)amino]methyl, [(2,4-difluorophenyl)amino]methyl, [(3-methoxyphenyl)amino]methyl, {[4-(trifluoromethyl)phenyl]amino}methyl, [4-(methylphenyl)amino]methyl, [(3,4-difluorophenyl)amino]methyl, (2,6-dimethylmorpholin-4-yl)methyl, thiomorpholin-4-ylmethyl, [(3,5-difluorophenyl)amino]methyl, (4,4-difluoropiperidin-1-yl)methyl, [(2,2,2-trifluoroethyl)amino]methyl, (1,3-benzodioxol-5-ylamino)methyl, [(4-fluorophenyl)methyl)amino]methyl, (cis-2,6-dimethylmorpholin-4-yl)methyl, (1,1-dioxidothiomorpholin-4-yl)methyl, (dibenzylamino)methyl, aminomethyl or (acetylamino)methyl.

12. A compound of formula (Ia) according to claim 1 wherein $R^{8a}$ and $R^{8b}$ are linked together to form with N a 3-8 membered heterocycloalkyl selected from the group consisting of 4-cyclopentylpiperazin-1-yl, 4-isopropylpiperazin-1-yl, piperidin-1-yl, 2-methylpiperidin-1-yl, 2-methylpyrrolidin-1-yl, (2S)-2-methylpyrrolidin-1-yl, (2R)-2-methylpyrrolidin-1-yl, 2-(pyrrolidin-1-ylmethyl)pyrrolidin-1-yl, (2S)-2-(pyrrolidin-1-ylmethyl)pyrroldin-1-yl, 1-azaspiro[4.4]non-1-yl, 4-methylpiperidin-1-yl, 3,5-dimethylpiperidin-1-yl, 3-octahydroquinolin-1(2H)-yl, 2-azaspiro[5.5]undec-2-yl, 4-benzylpiperidin-1-yl, 3-phenylpiperidin-1-yl, 2-(hydroxymethyl)pyrrolidin-1-yl, azepan-1-yl or azocan-1-yl.

13. A compound of formula (Ia) according to claim 1 wherein $R^{8a}$ and $R^{8b}$ are linked together to form with N a 3-8 membered heterocycloalkyl selected from piperidin-1-yl, 2-methylpyrrolidin-1-yl, (2S)-2-methylpyrrolidin-1-yl, (2R)-2-methylpyrrolidin-1-yl, 3,5-dimethylpiperidin-1-yl or azepan-1-yl.

14. A compound of formula (Ia) according to claim 1 selected from the group consisting of (5S)-5-{[(cyclohexylmethyl)amino]methyl}-1-{4-[3-(2-methylpyrrolidin-1-yl)propoxy]phenyl}pyrrolidin-2-one;

(5S)-5-{[(cyclohexylmethyl)amino]methyl}-1-[4-(3-piperidin-1-ylpropoxy)phenyl]pyrrolidin-2-one;

(5S)-5-{[(cyclohexylmethyl)(cyclopropylmethyl)amino]methyl}-1-{4-[3-(2-methylpyrrolidin-1-yl)propoxy]phenyl}pyrrolidin-2-one;

(5S)-5-{[(cyclopropylmethyl)(propyl)amino]methyl}-1-[4-(3-piperidin-1-ylpropoxy)phenyl]pyrrolidin-2-one;

(5S)-5-{[(cyclopropylmethyl)(propyl)amino]methyl}-1-{4-[3-(2-methylpyrrolidin-1-yl)propoxy]phenyl}pyrrolidin-2-one;

(5S)-5-[(cyclobutylamino)methyl]-1-[4-(3-piperidin-1-ylpropoxy)phenyl]pyrrolidin-2-one;

(5S)-5-[(cyclobutylamino)methyl]-1-{4-[3-(2-methylpyrrolidin-1-yl)propoxy]phenyl}pyrrolidin-2-one;

(5S)-5-[(cyclohexylamino)methyl]-1-{4-[3-(2-methylpyrrolidin-1-yl)propoxy]phenyl}pyrrolidin-2-one;

(5S)-5-[(cyclohexylamino)methyl]-1-[4-(3-piperidin-1-ylpropoxy)phenyl]pyrrolidin-2-one;

(5S)-5-[(cyclopentylamino)methyl]-1-{4-[3-(2-methylpyrrolidin-1-yl)propoxy]phenyl}pyrrolidin-2-one;

(5S)-5-[(cyclopentylamino)methyl]-1-[4-(3-piperidin-1-ylpropoxy)phenyl]pyrrolidin-2-one;

(5S)-5-[(diethylamino)methyl]-1-{4-[3-(2-methylpyrrolidin-1-yl)propoxy]phenyl}pyrrolidin-2-one;

(5S)-5-(anilinomethyl)-1-{4-[3-(2-methylpyrrolidin-1-yl)propoxy]phenyl}pyrrolidin-2-one;

(5S)-5-(anilinomethyl)-1-[4-(3-piperidin-1-ylpropoxy)phenyl]pyrrolidin-2-one;

(5S)-5-{[(4-fluorobenzyl)amino]methyl}-1-{4-[3-(2-methylpyrrolidin-1-yl)propoxy]phenyl}pyrrolidin-2-one;

(5S)-5-{[(4-fluorobenzyl)amino]methyl}-1-[4-(3-piperidin-1-ylpropoxy)phenyl]pyrrolidin-2-one;

(5S)-5-{[(4-fluorophenyl)amino]methyl}-1-[4-(3-piperidin-1-ylpropoxy)phenyl]pyrrolidin-2-one;

(5S)-5-{[(4-fluorophenyl)amino]methyl}-1-{4-[3-(2-methylpyrrolidin-1-yl)propoxy]phenyl}pyrrolidin-2-one;

(5S)-5-(azepan-1-ylmethyl)-1-{4-[3-(2-methylpyrrolidin-1-yl)propoxy]phenyl}pyrrolidin-2-one;

(5S)-5-(azepan-1-ylmethyl)-1-{4-[3-(2-methylpyrrolidin-1-yl)propoxy]phenyl}pyrrolidine-2-thione;

(5S)-5-(hydroxymethyl)-1-[4-(3-piperidin-1-ylpropoxy)phenyl]pyrrolidin-2-one;

(5S)-5-(hydroxymethyl)-1-{4-[3-(2-methylpyrrolidin-1-yl)propoxy]phenyl}pyrrolidin-2-one;

(5S)-1-{4-[3-(2-methylpyrrolidin-1-yl)propoxy]phenyl}-5-(morpholin-4-ylmethyl)pyrrolidin-2-one;

(5S)-1-{4-[3-(2-methylpyrrolidin-1-yl)propoxy]phenyl}-5-(morpholin-4-ylmethyl)pyrrolidin-2-one;

5-(4-chlorophenyl)-1-[4-(3-piperidin-1-ylpropoxy)phenyl]pyrrolidin-2-one;

5-(4-chlorophenyl)-1-{4-[3-(4-isopropylpiperazin-1-yl)propoxy]phenyl}piperidin-2-one;

(5S)-5-{[4-(cyclohexylmethyl)piperazin-1-yl]methyl}-1-[4-(3-piperidin-1-ylpropoxy)phenyl]pyrrolidin-2-one;

(5S)-5-[(4-cyclopentylpiperazin-1-yl)methyl]-1-{4-[3-(2-methylpyrrolidin-1-yl)propoxy]phenyl}pyrrolidin-2-one;

(5S)-5-[(4-cyclopentylpiperazin-1-yl)methyl]-1-[4-(3-piperidin-1-ylpropoxy)phenyl]pyrrolidin-2-one;

(5S)-5-[(4-isopropylpiperazin-1-yl)methyl]-1-{4-[3-(2-methylpyrrolidin-1-yl)propoxy]phenyl}pyrrolidin-2-one;

1-{4-[3-(2-methylpyrrolidin-1-yl)propoxy]phenyl}-4-(2-piperidin-1-ylethyl)pyrrolidin-2-one;

(5S)-1-{4-[3-(2-methylpyrrolidin-1-yl)propoxy]phenyl}-5-(piperidin-1-ylmethyl)pyrrolidin-2-one;

(5S)-5-(piperidin-1-ylmethyl)-1-[4-(3-piperidin-1-ylpropoxy)phenyl]pyrrolidin-2-one;

(5R)-5-(piperidin-1-ylmethyl)-1-[4-(3-piperidin-1-ylpropoxy)phenyl]pyrrolidin-2-one;

(5S)-1-{3-[3-(2-methylpyrrolidin-1-yl)propoxy]phenyl}-5-(piperidin-1-ylmethyl)pyrrolidin-2-one;

(5S)-1-{4-[3-(4-cyclopentylpiperazin-1-yl)propoxy]phenyl}-5-(piperidin-1-ylmethyl)pyrrolidin-2-one;
(5S)-5-[(2,6-dimethylpiperidin-1-yl)methyl]-1-[4-(3-piperidin-1-ylpropoxy)phenyl]pyrrolidin-2-one;
(5S)-5-[(2,6-dimethylpiperidin-1-yl)methyl]-1-{4-[3-(2-methylpyrrolidin-1-yl)propoxy]phenyl}pyrrolidin-2-one;
(5S)-5-[(2-methylpiperidin-1-yl)methyl]-1-[4-(3-piperidin-1-ylpropoxy)phenyl]pyrrolidin-2-one;
(5S)-5-[(2-methylpiperidin-1-yl)methyl]-1-{4-[3-(2-methylpyrrolidin-1-yl)propoxy]phenyl}pyrrolidin-2-one;
(5S)-5-[(4-methylpiperidin-1-yl)methyl]-1-{4-[3-(2-methylpyrrolidin-1-yl)propoxy]phenyl}pyrrolidin-2-one;
(5S)-5-[(4-methylpiperidin-1-yl)methyl]-1-[4-(3-piperidin-1-ylpropoxy)phenyl]pyrrolidin-2-one;
(5S)-1-{4-[3-(2-methylpyrrolidin-1-yl)propoxy]phenyl}-5-(pyrrolidin-1-ylmethyl)pyrrolidin-2-one;
(5S)-1-{4-[3-((2S)-2-methylpyrrolidin-1-yl)propoxy]phenyl}-5-(pyrrolidin-1-ylmethyl)pyrrolidin-2-one;
(5S)-1-{4-[3-((2R)-2-methylpyrrolidin-1-yl)propoxy]phenyl}-5-(pyrrolidin-1-ylmethyl)pyrrolidin-2-one;
(5S)-1-[4-(3-piperidin-1-ylpropoxy)phenyl]-5-(pyrrolidin-1-ylmethyl)pyrrolidin-2-one;
(5S)-1-{4-[3-(4-isopropylpiperazin-1-yl)propoxy]phenyl}-5-(pyrrolidin-1-ylmethyl)pyrrolidin-2-one;
(5S)-5-[(2-methylpyrrolidin-1-yl)methyl]-1-[4-(3-piperidin-1-ylpropoxy)phenyl]pyrrolidin-2-one;
(−)-(5S)-5-[(2-methylpyrrolidin-1-yl)methyl]-1-[4-(3-piperidin-1-ylpropoxy)phenyl]pyrrolidin-2-one;
(+)-(5S)-5-[(2-methylpyrrolidin-1-yl)methyl]-1-[4-(3-piperidin-1-ylpropoxy)phenyl]pyrrolidin-2-one;
2-{4-[3-(2-methylpiperidin-1-yl)propoxy]phenyl}-2-azaspiro[4.5]decan-3-one;
(5S)-5-(morpholin-4-ylmethyl)-1-(4-{3-[(2S)-2-(pyrrolidin-1-ylmethyl)pyrrolidin-1-yl]propoxy}phenyl)pyrrolidin-2-one;
(5S)-1-(4-{3-[(2R)-2-methylpyrrolidin-1-yl]propoxy}phenyl)-5-(pyrrolidin-1-ylmethyl)pyrrolidin-2-one;
(5S)-5-{[(2-fluorophenyl)amino]methyl}-1-{4-[3-(2-methylpyrrolidin-1-yl)propoxy]phenyl}pyrrolidin-2-one;
(5S)-5-{[(3-fluorophenyl)amino]methyl}-1-{4-[3-(2-methylpyrrolidin-1-yl)propoxy]phenyl}pyrrolidin-2-one;
(5S)-5-{[(2,4-difluorophenyl)amino]methyl}-1-{4-[3-(2-methylpyrrolidin-1-yl)propoxy]phenyl}pyrrolidin-2-one;
(5S)-5-{[(3-methoxyphenyl)amino]methyl}-1-{4-[3-(2-methylpyrrolidin-1-yl)propoxy]phenyl}pyrrolidin-2-one;
(5S)-1-{4-[3-(2-methylpyrrolidin-1-yl)propoxy]phenyl}-5-({[4-(trifluoromethyl)phenyl]amino}methyl)pyrrolidin-2-one;
(5S)-5-[(4-fluorophenoxy)methyl]-1-{4-[3-(2-methylpyrrolidin-1-yl)propoxy]phenyl}pyrrolidin-2-one;
(5S)-5-{[(4-methylphenyl)amino]methyl}-1-{4-[3-(2-methylpyrrolidin-1-yl)propoxy]phenyl}pyrrolidin-2-one;
(5S)-5-{[(3,4-difluorophenyl)amino]methyl}-1-{4-[3-(2-methylpyrrolidin-1-yl)propoxy]phenyl}pyrrolidin-2-one;
(5S)-5-[(2,6-dimethylmorpholin-4-yl)methyl]-1-{4-[3-(2-methylpyrrolidin-1-yl)propoxy]phenyl}pyrrolidin-2-one;
(5S)-1-{4-[3-(2-methylpyrrolidin-1-yl)propoxy]phenyl}-5-(thiomorpholin-4-ylmethyl)pyrrolidin-2-one;
(5S)-5-{[(3,5-difluorophenyl)amino]methyl}-1-{4-[3-(2-methylpyrrolidin-1-yl)propoxy]phenyl}pyrrolidin-2-one;
(5S)-5-[(4,4-difluoropiperidin-1-yl)methyl]-1-{4-[3-(2-methylpyrrolidin-1-yl)propoxy]phenyl}pyrrolidin-2-one;
(5S)-1-{4-[3-(2-methylpyrrolidin-1-yl)propoxy]phenyl}-5-{[(2,2,2-trifluoroethyl)amino]methyl}pyrrolidin-2-one;
(5S)-5-[(3,4-difluorophenoxy)methyl]-1-{4-[3-(2-methylpyrrolidin-1-yl)propoxy]phenyl}pyrrolidin-2-one;
(5S)-5-[(1,3-benzodioxol-5-ylamino)methyl]-1-{4-[3-(2-methylpyrrolidin-1-yl)propoxy]phenyl}pyrrolidin-2-one;
(5S)-5-{[(4-fluorophenyl)(methyl)amino]methyl}-1-{4-[3-(2-methylpyrrolidin-1-yl)propoxy]phenyl}pyrrolidin-2-one;
(5S)-5-{[cis-2,6-dimethylmorpholin-4-yl]methyl}-1-{4-[3-(2-methylpyrrolidin-1-yl)propoxy]phenyl}pyrrolidin-2-one;
(5S)-5-[(1,1-dioxidothiomorpholin-4-yl)methyl]-1-{4-[3-(2-methylpyrrolidin-1-yl)propoxy]phenyl}pyrrolidin-2-one;
(5S)-5-[(4aR,8aS)-octahydroisoquinolin-2(1H)-ylmethyl]-1-{4-[3-(1-azaspiro[4.4]non-1-yl)propoxy]phenyl}pyrrolidin-2-one;
(5S)-1-{4-[4-(2-methylpyrrolidin-1-yl)butoxy]phenyl}-5-(piperidin-1-ylmethyl)pyrrolidin-2-one;
(5S)-3,3-dimethyl-1-{4-[3-(2-methylpyrrolidin-1-yl)propoxy]phenyl}-5-(piperidin-1-ylmethyl)pyrrolidin-2-one;
(5S)-5-[(dibenzylamino)methyl]-1-{4-[3-(2-methylpyrrolidin-1-yl)propoxy]phenyl}pyrrolidin-2-one;
(5S)-5-(aminomethyl)-1-{4-[3-(2-methylpyrrolidin-1-yl)propoxy]phenyl}pyrrolidin-2-one;
1-{4-[3-(4-methylpiperidin-1-yl)propoxy]phenyl}-5-(piperidin-1-ylmethyl)pyrrolidin-2-one;
1-{4-[3-(3,5-dimethylpiperidin-1-yl)propoxy]phenyl}-5-(piperidin-1-ylmethyl)pyrrolidin-2-one;
1-[4-(3-octahydroquinolin-1(2H)-ylpropoxy)phenyl]-5-(piperidin-1-ylmethyl)pyrrolidin-2-one;
1-{4-[3-(3,5-dimethylpiperidin-1-yl)propoxy]-3-fluorophenyl}-5-(piperidin-1-ylmethyl)pyrrolidin-2-one;
1-{4-[3-(2-azaspiro[5.5]undec-2-yl)propoxy]-3-fluorophenyl}-5-(piperidin-1-ylmethyl)pyrrolidin-2-one;
1-{4-[3-(3,5-dimethylpiperidin-1-yl)propoxy]-2-fluorophenyl}-5-(piperidin-1-ylmethyl)pyrrolidin-2-one;
1-{3,5-difluoro-4-[3-(4-methylpiperidin-1-yl)propoxy]phenyl}-5-(piperidin-1-ylmethyl)pyrrolidin-2-one;
1-{4-[3-(2-azaspiro[5.5]undec-2-yl)propoxy]-3,5-difluorophenyl}-5-(piperidin-1-ylmethyl)pyrrolidin-2-one;
1-{4-[3-(3,5-dimethylpiperidin-1-yl)propoxy]-3-methylphenyl}-5-(piperidin-1-ylmethyl)pyrrolidin-2-one;
1-{4-[3-(4-benzylpiperidin-1-yl)propoxy]phenyl}-5-(piperidin-1-ylmethyl)pyrrolidin-2-one;
1-{3-fluoro-4-[3-(3-phenylpiperidin-1-yl)propoxy]phenyl}-5-(piperidin-1-ylmethyl)pyrrolidin-2-one;
1-{4-[3-(1-azaspiro[4.4]non-1-yl)propoxy]phenyl}-5-(piperidin-1-ylmethyl)pyrrolidin-2-one;
1-{3-fluoro-4-[3-(2-methylpyrrolidin-1-yl)propoxy]phenyl}-5-(piperidin-1-ylmethyl)pyrrolidin-2-one;
1-{4-[3-(1-azaspiro[4.4]non-1-yl)propoxy]-3-fluorophenyl}-5-(piperidin-1-ylmethyl)pyrrolidin-2-one;
1-{3,5-difluoro-4-[3-(2-methylpyrrolidin-1-yl)propoxy]phenyl}-5-(piperidin-1-ylmethyl)pyrrolidin-2-one;
1-{3-methyl-4-[3-(2-methylpyrrolidin-1-yl)propoxy]phenyl}-5-(piperidin-1-ylmethyl)pyrrolidin-2-one;

1-{4-[3-(1-azaspiro[4.4]non-1-yl)propoxy]-3-methylphenyl}-5-(piperidin-1-ylmethyl)pyrrolidin-2-one;

1-(4-{3-[2-(hydroxymethyl)pyrrolidin-1-yl]propoxy}-3-methylphenyl)-5-(piperidin-1-ylmethyl)pyrrolidin-2-one;

1-[4-(3-azepan-1-ylpropoxy)phenyl]-5-(piperidin-1-ylmethyl)pyrrolidin-2-one;

1-[4-(3-azepan-1-ylpropoxy)-3-fluorophenyl]-5-(piperidin-1-ylmethyl)pyrrolidin-2-one;

1-[4-(3-azocan-1-ylpropoxy)-3-fluorophenyl]-5-(piperidin-1-ylmethyl)pyrrolidin-2-one;

1-[4-(3-azepan-1-ylpropoxy)-2-methoxyphenyl]-5-(piperidin-1-ylmethyl)pyrrolidin-2-one;

5-[(4,4-difluoropiperidin-1-yl)methyl]-1-{4-[3-(3,5-dimethylpiperidin-1-yl)propoxy]phenyl}pyrrolidin-2-one;

5-[(4,4-difluoropiperidin-1-yl)methyl]-1-{4-[3-(3,5-dimethylpiperidin-1-yl)propoxy]-3-methylphenyl}pyrrolidin-2-one;

5-[(4,4-difluoropiperidin-1-yl)methyl]-1-{3-methyl-4-[3-(2-methylpyrrolidin-1-yl)propoxy]phenyl}pyrrolidin-2-one; and (5S)-1-{6-[3-(2-methylpyrrolidin-1-yl)propoxy]pyridin-3-yl}-5-(piperidin-1-ylmethyl)pyrrolidin-2-one.

15. A pharmaceutical composition comprising an effective amount of a compound of formula (Ia) according to claim 1 or a pharmaceutically acceptable salt thereof, in combination with a pharmaceutically acceptable diluent or carrier.

16. A compound of formula (Ia) according to claim 1 wherein $R^3$ is hydrogen.

17. A compound of formula (Ia) according to claim 1 wherein $R^4$ is hydrogen or fluorine.

* * * * *